US011229637B2

(12) United States Patent
Arend et al.

(10) Patent No.: US 11,229,637 B2
(45) Date of Patent: *Jan. 25, 2022

(54) NITROGEN-CONTAINING HETEROARYL COMPOUNDS AND METHODS OF USE THEREOF

(71) Applicant: FibroGen, Inc., San Francisco, CA (US)

(72) Inventors: Michael P. Arend, Foster City, CA (US); Lee A. Flippin, Woodside, CA (US); Volkmar Guenzler-Pukall, San Leandro, CA (US); Wen-Bin Ho, Los Altos, CA (US); Eric D. Turtle, Belmont, CA (US); Xiaohui Du, Foster City, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/818,800

(22) Filed: Mar. 13, 2020

(65) Prior Publication Data

US 2021/0060000 A1 Mar. 4, 2021

Related U.S. Application Data

(60) Continuation of application No. 16/109,562, filed on Aug. 22, 2018, now Pat. No. 10,646,482, which is a continuation of application No. 15/133,104, filed on Apr. 19, 2016, now Pat. No. 10,092,558, which is a continuation of application No. 14/284,325, filed on May 21, 2014, now Pat. No. 9,339,527, which is a continuation of application No. 13/912,483, filed on Jun. 7, 2013, now Pat. No. 8,765,956, which is a continuation of application No. 13/599,161, filed on Aug. 30, 2012, now Pat. No. 8,916,585, which is a continuation of application No. 13/186,351, filed on Jul. 19, 2011, now Pat. No. 8,278,325, which is a continuation of application No. 12/015,275, filed on Jan. 16, 2008, now Pat. No. 8,017,625, which is a division of application No. 10/861,082, filed on Jun. 4, 2004, now Pat. No. 7,323,475.

(60) Provisional application No. 60/476,519, filed on Jun. 6, 2003, provisional application No. 60/476,633, filed on Jun. 6, 2003, provisional application No. 60/476,420, filed on Jun. 6, 2003, provisional application No. 60/476,811, filed on Jun. 6, 2003.

(51) Int. Cl.
| | | |
|---|---|---|
| A61K 31/472 | (2006.01) | |
| A61K 31/473 | (2006.01) | |
| C07D 221/08 | (2006.01) | |
| C07D 401/04 | (2006.01) | |
| C07D 401/06 | (2006.01) | |
| C07D 401/12 | (2006.01) | |
| C07D 403/12 | (2006.01) | |
| C07D 217/26 | (2006.01) | |
| A61K 38/18 | (2006.01) | |
| A61K 31/4725 | (2006.01) | |
| C07D 217/24 | (2006.01) | |

(52) U.S. Cl.
CPC .......... *A61K 31/472* (2013.01); *A61K 31/473* (2013.01); *A61K 31/4725* (2013.01); *A61K 38/1816* (2013.01); *C07D 217/26* (2013.01); *C07D 221/08* (2013.01); *C07D 401/04* (2013.01); *C07D 401/06* (2013.01); *C07D 401/12* (2013.01); *C07D 403/12* (2013.01); *C07D 217/24* (2013.01)

(58) Field of Classification Search
None
See application file for complete search history.

(56) References Cited

U.S. PATENT DOCUMENTS

| | | |
|---|---|---|
| 3,989,704 A | 11/1976 | Houlihan et al. |
| 4,036,964 A | 7/1977 | Buckle et al. |
| 4,260,611 A | 4/1981 | Bartmann et al. |
| 4,559,403 A | 12/1985 | Bruderer et al. |
| 4,584,379 A | 4/1986 | Wagner |
| 4,673,682 A | 6/1987 | Konz et al. |
| 4,822,800 A | 4/1989 | Falotico et al. |
| 4,952,588 A | 8/1990 | Glamkowski et al. |
| 4,966,906 A | 10/1990 | Glamkowski et al. |
| 5,620,995 A | 4/1997 | Weidmann et al. |
| 5,658,933 A | 8/1997 | Weidmann et al. |
| 5,719,164 A | 2/1998 | Weidmann et al. |
| 5,726,305 A | 3/1998 | Weidmann et al. |

(Continued)

FOREIGN PATENT DOCUMENTS

| | | |
|---|---|---|
| CA | 2134866 | 5/1995 |
| EP | 0650960 | 5/1995 |

(Continued)

OTHER PUBLICATIONS

Ashizawa et al., Iyaku hin no takei genshou to shouseki no kagaku [Science of polymorphism and crystallization of medicament], Maruzen Planet Co. Ltd., Sep. 20, 2002, pp. 305-317.
Bruick et al., A Conserved Family of Proly-4-Hydroxylases That Modify HIF, *Science*, vol. 294, pp. 1337-1340, (2001).
Cumliffe et al., Novel Inhibitors of Prolyl 4-Hydroxylase 3 Inhibition by the Substrate Analogue N-Oxaloglycine and Its Derivatives, *J. Med. Chem.*, vol. 35, pp. 2652-2658, (1992).
Duro et al., Sintesi Ed Attivita Farmacologica D1 Ammmino-E Dialchilamminoalchilammidi-D1 Derivati Della 3-Carbossi-4-Fenillisochinolina, *Ed. Sc.*, vol. 36, pp. 400-411, (1980) (Abstract in English).

(Continued)

*Primary Examiner* — Zinna Northington Davis
(74) *Attorney, Agent, or Firm* — FibroGen, Inc.; Leanne C. Price

(57) ABSTRACT

The present invention relates to compounds suitable for use in mediating hypoxia inducible factor and for treating erythropoietin-associated conditions by increasing endogenous erythropoietin in vitro and in vivo.

12 Claims, No Drawings

Specification includes a Sequence Listing.

(56) References Cited

U.S. PATENT DOCUMENTS

| | | | |
|---|---|---|---|
| 6,093,730 | A | 7/2000 | Weidmann et al. |
| 6,319,931 | B1 | 11/2001 | Kroemer et al. |
| 6,358,973 | B1 | 3/2002 | Napoletano et al. |
| 6,358,976 | B1 | 3/2002 | Wityak et al. |
| 6,369,053 | B1 | 4/2002 | Yuan et al. |
| 6,762,318 | B2 | 7/2004 | Kodra et al. |
| 6,777,425 | B2 | 8/2004 | Burl et al. |
| 6,903,114 | B2 | 6/2005 | Backstrom et al. |
| 7,208,601 | B2 | 4/2007 | Mjalli et al. |
| 7,323,475 | B2 | 1/2008 | Arend et al. |
| 7,629,357 | B2 | 12/2009 | Arend et al. |
| 7,696,223 | B2 | 4/2010 | Deng et al. |
| 7,863,292 | B2 | 1/2011 | Arend et al. |
| 7,928,120 | B2 | 4/2011 | Arend et al. |
| 8,017,625 | B2 | 9/2011 | Arend et al. |
| 8,168,221 | B2 | 5/2012 | Blyth et al. |
| 8,278,325 | B2 | 10/2012 | Arend et al. |
| 8,318,703 | B2 | 11/2012 | Klaus et al. |
| 8,759,373 | B2 | 6/2014 | Arend et al. |
| 8,765,956 | B2 | 7/2014 | Arend et al. |
| 8,883,823 | B2 | 11/2014 | Witschi et al. |
| 8,916,585 | B2 | 12/2014 | Arend et al. |
| 8,921,389 | B2 | 12/2014 | Ng et al. |
| 9,000,006 | B2 | 4/2015 | Turtle et al. |
| 9,115,085 | B2 | 8/2015 | Witschi et al. |
| 9,149,476 | B2 | 10/2015 | Ho et al. |
| 9,174,976 | B2 | 11/2015 | Arend et al. |
| 9,271,970 | B2 | 3/2016 | Ng et al. |
| 9,339,527 | B2 * | 5/2016 | Arend ............... A61K 31/4725 |
| 9,340,511 | B2 | 5/2016 | Thompson et al. |
| 9,371,288 | B2 | 6/2016 | Witschi et al. |
| 9,387,200 | B2 | 7/2016 | Zhou et al. |
| 9,409,892 | B2 | 8/2016 | Ho et al. |
| 9,617,218 | B2 | 4/2017 | Witschi et al. |
| 9,643,928 | B2 | 5/2017 | Witschi et al. |
| 9,695,170 | B2 | 7/2017 | Danny et al. |
| 9,708,269 | B2 | 7/2017 | Thompson et al. |
| 10,092,558 | B2 | 10/2018 | Arend et al. |
| 10,118,897 | B2 | 11/2018 | Witschi et al. |
| 10,272,078 | B2 | 4/2019 | Witschi et al. |
| 10,765,672 | B2 | 9/2020 | Conca et al. |
| 2003/0153503 | A1 | 8/2003 | Klaus et al. |
| 2003/0176317 | A1 | 9/2003 | Guenzler-Pukall et al. |
| 2004/0204356 | A1 | 10/2004 | Guenzler-Pukall et al. |
| 2004/0235082 | A1 | 11/2004 | Fourney et al. |
| 2005/0020487 | A1 | 1/2005 | Klaus et al. |
| 2006/0178316 | A1 | 8/2006 | Klaus et al. |
| 2006/0178317 | A1 | 8/2006 | Klaus et al. |
| 2006/0183695 | A1 | 8/2006 | Klaus et al. |
| 2006/0199836 | A1 | 9/2006 | Turtle et al. |
| 2006/0217416 | A1 | 9/2006 | Arend et al. |
| 2006/0251638 | A1 | 11/2006 | Guenzler-Pukall et al. |
| 2006/0258660 | A1 | 11/2006 | Guenzler-Pukall et al. |
| 2006/0258702 | A1 | 11/2006 | Guenzler-Pukall et al. |
| 2006/0270699 | A1 | 11/2006 | Guenzler-Pukall et al. |
| 2006/0276477 | A1 | 12/2006 | Klaus et al. |
| 2007/0004627 | A1 | 1/2007 | Seeley et al. |
| 2007/0155784 | A1 | 7/2007 | Arend et al. |
| 2007/0185159 | A1 | 8/2007 | Arend et al. |
| 2007/0292433 | A1 | 12/2007 | Seeley et al. |
| 2007/0293575 | A1 | 12/2007 | Seeley et al. |
| 2007/0298104 | A1 | 12/2007 | Arend et al. |
| 2008/0004309 | A1 | 1/2008 | Deng et al. |
| 2010/0047367 | A1 | 2/2010 | Deng et al. |
| 2010/0172984 | A1 | 7/2010 | Padhi et al. |
| 2010/0303928 | A1 | 12/2010 | Arend et al. |
| 2010/0330199 | A1 | 12/2010 | Zhou et al. |
| 2010/0331400 | A1 | 12/2010 | Ho et al. |
| 2011/0212959 | A1 | 9/2011 | Arend et al. |
| 2011/0305776 | A1 | 12/2011 | Ho et al. |
| 2012/0029011 | A1 | 2/2012 | Arend et al. |
| 2013/0013609 | A1 | 1/2013 | Prahlad et al. |
| 2014/0343094 | A1 | 11/2014 | Arend et al. |
| 2016/0009653 | A1 | 1/2016 | Arend et al. |
| 2016/0120859 | A1 | 5/2016 | Conca et al. |
| 2016/0331741 | A1 | 11/2016 | Witschi et al. |
| 2019/0240213 | A1 | 8/2019 | Arend et al. |
| 2019/0276408 | A1 | 9/2019 | Witschi et al. |
| 2020/0115344 | A1 | 4/2020 | Witschi et al. |

FOREIGN PATENT DOCUMENTS

| | | |
|---|---|---|
| EP | 0650961 | 5/1995 |
| EP | 0911340 | 4/1999 |
| JP | H07-224039 | 8/1995 |
| JP | H07-228571 | 8/1995 |
| JP | H11302257 | 11/1999 |
| JP | 2005-524612 | 8/2005 |
| JP | 2006-514113 | 4/2006 |
| JP | 2006-137763 | 6/2006 |
| JP | 2006-527199 | 11/2006 |
| WO | WO-1996/018616 | 6/1996 |
| WO | WO-2001/058892 | 8/2001 |
| WO | WO-2002/070510 | 9/2002 |
| WO | WO-2002/074249 | 9/2002 |
| WO | WO-2002/074981 | 9/2002 |
| WO | WO-02079193 | 10/2002 |
| WO | WO-2002/100832 | 12/2002 |
| WO | WO-2002/101073 | 12/2002 |
| WO | WO-2003/053997 | 7/2003 |
| WO | WO-2004/052284 | 6/2004 |
| WO | WO-2004/052285 | 6/2004 |
| WO | WO-2004056368 | 7/2004 |
| WO | WO-2004/108121 | 12/2004 |
| WO | WO-2004/108681 | 12/2004 |
| WO | WO-2005/007192 | 1/2005 |
| WO | WO-2005/009962 | 2/2005 |
| WO | WO-2005/011696 | 2/2005 |
| WO | WO-2005/014533 | 2/2005 |
| WO | WO-2005087237 | 9/2005 |
| WO | WO-2006/094292 | 9/2006 |
| WO | WO-2006/133391 | 12/2006 |
| WO | WO-2006/138511 | 12/2006 |
| WO | WO-2007/090068 | 8/2007 |
| WO | WO-2007/097929 | 8/2007 |
| WO | WO-2007/115315 | 10/2007 |
| WO | WO-2007/146425 | 12/2007 |
| WO | WO-2007/146438 | 12/2007 |
| WO | WO-2009/073669 | 6/2009 |
| WO | WO-2009/089547 | 7/2009 |
| WO | WO-2009/100250 | 8/2009 |
| WO | WO-2010/022240 | 2/2010 |
| WO | WO-2010/056767 | 5/2010 |
| WO | WO-2012/097331 | 7/2012 |
| WO | WO-2012/106472 | 8/2012 |
| WO | WO-2013/013609 | 1/2013 |
| WO | WO-2013/134660 | 9/2013 |
| WO | WO-2014/014834 | 1/2014 |
| WO | WO-2014/014835 | 1/2014 |
| WO | WO-2014/116849 | 7/2014 |
| WO | WO-2014/197660 | 12/2014 |

OTHER PUBLICATIONS

Franklin et al., Approaches to the Design of Anti-Fibrotic Drugs, *Biochem. Soc. Trans.*, 19(4):812-815, (1991).

Guo et al., Selective Protection of 2',2'-Difluorodeoxycytidine (Gemcitabine), *J. Org. Chem.*, vol. 64, pp. 8319-8322, (1999).

ICH Harmonised Tripartite Guideline Stability Testing: Photostability Testing of New Drug Substances and Products Q1B, Nov. 6, 1996. (11 pages).

International Preliminary Report on Patentability for International Application No. PCT/US2004/017773 dated Dec. 8, 2005. (9 pages).

Ivan et al., HIFa Targeted for VHL-Mediated Destruction by Proline Hydroxylation: Implications for O2 Sensing, *Science*, 292:464-468, (2001).

Jaakkola et al., Targeting of HIF-alpha to the von Hippel-Lindau Ubiquitylation Complex by O2-Regulated Prolyl Hydroxylation, *Science*, 292(5516):468-472, (2001).

Lando et al., Oxygen-Dependent Regulation of Hypoxia-Inducible Factors by Polyl and Asparaginyl Hydroxylation, *Eur. J. Biochem*, 270:781-790, (2003).

(56) References Cited

OTHER PUBLICATIONS

Matsuoka, M., Kesshou takei No. kiso to ouyou [Basic and application of crystal polymorphism], CMC Publishing Co. Ltd., Oct. 22, 2010, 1st edition of trade edition, pp. 105-117, and 181-191.

Podczeck et al.."Gelatin alternatives and additives," Pharmaceutical Press 2004, pp. 64-66.

Richard et al., Nonhypoxic Pathway Mediates the Induction of Hypoxia-Inducible Factor 1a in Vascular Smooth Muscle Cells, *J. Bio. Chm.*, 275:26765-26771, (2000).

Safran et al., HIF Hydroxylation and the Mammalian Pathway, *J. Clin. Invest.*, 111(6):779-783, (2003).

Sandau et al., Induction of Hypoxia-Inducible-Factor 1 by Nitric Oxide Is Mediated via the P1 3K Pathway, *Biochem. Biophys. Res. Common.*, 278:263-267, (2000).

Sato et al., Stability and Physicochemical Properties of Viracept Tablets, Antibiotics and Chemotherapy, 14(9): 1589-1592, (1998)—English Translation Not Available.

Sodhi et al., MAPK and Akt Act Cooperatively But Independently on Hypoxia Inducible Factor-1 α in rasV12 Unpregulation of VEGF, *Biochem. Biophys. Res. Common.*, 287:292-300, (2001).

Tacchini et al., Hepatocyte Growth Factor Signaling Stimulates Hypoxia Inducible Factor-1 (HIF-1) Activity in HepG2 Hepatoma Cells, *Carcinogenesis*, 22:1363-1371, (2001).

Tonnesen, H.H., "Photodecomposition of Drugs," In: Swarbrick,"Encyclopedia of Pharmaceutical Technology," Third Edition, 2007, Informa Healthcare, New York, pp. 2859-2865.

Written Opinion for International Application No. PCT/US2004/017773, dated Oct. 11, 2004. (8 pages).

Wu et al., Regulatory Perspectives of Type II Prodrug Development and Time-Dependent Toxicity Management: Nonclinical Pharm/Tox Analysis and the Role of Comparative Toxicology, *Toxicology*, 236, pp. 1-6, (2007).

Byrn et al., Pharmaceutical Solids: A Strategic Approach to Regulatory Considerations. Pharmaceutical Research 1995, vol. 12, No. 7, pp. 945-954.

Caira, M.R., Crystalline Polymorphism of Organic Compounds. Topics in Current Chemistry, vol. 198, © Springer Verlag Berlin Heidelberg 1998. 46 pages.

Cross et al., A Whole Output Strategy for Polymorph Screening: Combining Crystal Structure Prediction, Graph Set Analysis, and Targeted Crystallization Experiments in the Case of Diflunisal. Crystal Growth & Design 2003, vol. 3, No. 2, pp. 151-158.

Guillory, J.K., Generation of Polymorphs, Hydrates, Solvates, and Amorphous, Solids. 1999, pp. 183-226.

Hilfiker et al., Polymorphism—integrated approach from high-throughput screening to crystallization optimization. Journal of Thermal Analysis and Calorimetry 2003, vol. 73, pp. 429-440.

Robinson et al., Mucosal Protection by Hypoxia-Inducible Factor Prolyl Hydroxylase Inhibition. Gastroenterology 2008, vol. 134, No. 1, pp. 145-155.

Rosenberger et al., Activation of hypoxia-inducible factors ameliorates hypoxic distal tubular injury in the isolated perfused rat kidney. Nephrol Dial Transplant 2008; 23: pp. 3472-3478.

Suzuki et al., A Facile Synthesis of 1-Oxo-1,2-dihydroisoquinoline-3-carboxylate and 2-Pyridone-6-carboxylate Deriva-tives. Communications 1978, pp. 461-462.

Allam et al., Review Article, Colorants—The Cosmetics For The Pharmaceutical Dosage Forms. International Journal of Pharmacy and Pharmaceutical Sciences 2011, vol. 3, Suppl 3, pp. 13-21.

FDA—Electronic Code of Federal Regulations—Listing of Color Additives in Drugs Part 1 and 2, 2012. 45 pages.

Piechocki et al., Pharmaceutical Photostability and Stabilization Technology 2007, pp. 323-343.

\* cited by examiner

NITROGEN-CONTAINING HETEROARYL COMPOUNDS AND METHODS OF USE THEREOF

CROSS REFERENCE TO RELATED APPLICATIONS

This application is a continuation of U.S. application Ser. No. 16/109,562, filed Aug. 22, 2018, now U.S. Pat. No. 10,646,482, which is a continuation of U.S. application Ser. No. 15/133,104, filed Apr. 19, 2016, now U.S. Pat. No. 10,092,558, which is a continuation of U.S. application Ser. No. 14/284,325, filed May 21, 2014, now U.S. Pat. No. 9,339,527, which is a continuation of U.S. application Ser. No. 13/912,483, filed Jun. 7, 2013, now U.S. Pat. No. 8,765,956, which is a continuation of U.S. application Ser. No. 13/599,161, filed Aug. 30, 2012, now U.S. Pat. No. 8,916,585, which is a continuation of U.S. application Ser. No. 13/186,351, filed Jul. 19, 2011, now U.S. Pat. No. 8,278,325, which is a continuation of U.S. application Ser. No. 12/015,275, filed Jan. 16, 2008, now U.S. Pat. No. 8,017,625, which is a divisional of U.S. application Ser. No. 10/861,082, filed Jun. 4, 2004, now U.S. Pat. No. 7,323,475, which claims the benefit under 35 U.S.C. § 119(e) of U.S. Application Nos. 60/476,811, filed Jun. 6, 2003, 60/476,420, filed Jun. 6, 2003, 60/476,633, filed Jun. 6, 2003, and 60/476,519, filed Jun. 6, 2003, all of which are hereby incorporated by reference in their entireties.

SEQUENCE LISTING

The instant application contains a Sequence Listing which has been filed electronically in ASCII format and is hereby incorporated by reference in its entirety. Said ASCII copy, created on Sep. 20, 2018, is named 19TF-191826-US11_SL.txt and is 1,542 bytes in size.

BACKGROUND OF THE INVENTION

Field of the Invention

The present invention relates to methods and compounds capable of modulating the stability of the alpha subunit of hypoxia inducible factor (HIF) and increasing endogenous erythropoietin, ex vivo and in vivo.

State of the Art

An early response to tissue hypoxia is induction of hypoxia inducible factor (HIF), a basic helix-loop-helix (bHLH) PAS (Per/Arnt/Sim) transcriptional activator that mediates changes in gene expression in response to changes in cellular oxygen concentration. HIF is a heterodimer containing an oxygen-regulated alpha subunit (HIFα) and a constitutively expressed beta subunit (HIFβ), also known as aryl hydrocarbon receptor nuclear transporter (ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus and activates the expression of several genes including glycolytic enzymes, glucose transporter (GLUT)-1, erythropoietin (EPO), and vascular endothelial growth factor (VEGF). (Jiang, et al., (1996) J. Biol. Chem., 271:17771-17778; Iliopoulus, et al., (1996) Proc. Natl. Acad. Sci. USA, 93:10595-10599; Maxwell, et al., (1999), Nature, 399:271-275; Sutter, et al., (2000) Proc. Natl. Acad. Sci. USA, 97:4748-4753; Cockman, et al., (2000) J. Biol. Chem., 275:25733-25741; and Tanimoto, et al., (2000) EMBO. J. 19:4298-4309.)

Levels of HIFα protein are elevated in most cells in response to hypoxia and HIFα is induced in vivo when animals are subjected to anemia or hypoxia. HIFα levels rise within a few hours after the onset of hypoxia and return to baseline under continued hypoxic conditions. HIF has been implicated in numerous cellular and developmental processes including cell proliferation, angiogenesis, and cell cycle arrest. HIFα has also been associated with myocardial acute ischemia and early infarction, pulmonary hypertension, and inflammation. Although HIFα has been associated with tumor growth and metastasis, there is little indication that HIF is directly involved in tumorigenesis. Hypoxic preconditioning, in which a target organ is subjected to brief periods of hypoxia, has been shown to protect both myocardium and brain against hypoxic-ischemic injury. HIFα stabilization is closely associated with ischemia and is induced by preconditioning. (Wang and Semenza, (1993) Proc. Natl. Acad. Sci. USA, 90:4304-4308; Stroka, et al., (2001) FASEB. J., 15:2445-2453; Semenza, et al., (1997) Kidney Int., 51:553-555; Carmeliet, et al., (1998), Nature 394:485-490; Zhong, et al., (1999) Cancer Res., 59:5830-5835; Lee, et al., (2000) N. Engl. J. Med., 343:148-149; Sharp, et al., (2000) J. Cereb. Blood Flow Metab., 20:1011-1032; Semenza, et al., (2000) Adv. Exp. Med. Biol., 475: 123-130; Thornton, et al., (2000) Biochem. J. 350:307-312; Deindl and Schaper, (1998) Mol. Cell. Biochem., 186:43-51; Bergeron, et al., (2000) Ann. Neurol. 48:285-296.)

Several investigators have studied the mechanism of interaction between HIFα and pVHL. An oxygen-dependent degradation domain (ODD) within HIF-1α from residue 401 to 603 was originally identified as sufficient to confer oxygen-dependent instability to chimeric protein constructs. A domain containing a portion of the ODD, from residue 526 to 652, was found to be required for pVHL-dependent degradation. Further, mutation of P564YI to aspartic acids or mutation of $K_{532}$ to arginine within a region conserved among HIFα homologs (residue 556 to 574 in HIF-1a) rendered the full-length HIFα protein stable under normoxic conditions and resistant to pVHL-mediated degradation. (Huang, et al., (1998) Proc. Natl. Acad. Sci. USA, 95:7987-7992; and Tanimoto, et al., (2000) EMBO. J. 19:4298-4309.)

HIFα levels are increased by a number of factors that mimic hypoxia, including iron chelators such as desferrioxamine (DFO) and divalent metal salts such as $CoCl_2$. HIFα levels are increased by angiotensin II, thrombin, and platelet-derived growth factor under normoxic conditions using a mechanism involving reactive oxygen species. Reports have also suggested HIFα is regulated by phosphorylation through pathways involving nitric oxide-activated phosphatidylinositol 3'-kinase (PI3K), hepatocyte growth factor, or mitogen-activated protein kinase. Glycogen-synthase kinase, which is a downstream target of PI3K, directly phosphorylates the HIFα ODD domain. (Richard, et al., (2000) J. Biol. Chem., 275:26765-26771; Sandau, et al., (2000) Biochem. Biophys. Res. Commun. 278:263-267; Tacchini, et al., (2001) Carcinogenesis, 22:1363-1371; and Sodhi, et al., (2001) Biochem. Biophys. Res. Commun., 287:292-300.)

Erythropoietin (EPO), a naturally occurring hormone that is produced in response to HIFα, stimulates the production of red blood cells (erythrocytes), which carry oxygen throughout the body. EPO is normally secreted by the kidneys, and endogenous EPO is increased under conditions of reduced oxygen (hypoxia). All types of anemia are characterized by the blood's reduced capacity to carry oxygen, and thus are associated with similar signs and symptoms, including pallor of the skin and mucous membranes, weakness, dizziness, easy fatigability, and drowsiness, leading to a decrease in quality of life. Subjects with severe cases of anemia show difficulty in breathing and heart abnormalities. Anemia is typically associated with a condition in which the blood is deficient in red blood cells or in hemoglobin.

Common causes of anemia include deficiencies of iron, vitamin $B_{12}$, and folic acid. Anemia can also develop in association with chronic diseases, e.g., in inflammatory disorders, including disorders with consequent inflammatory suppression of marrow, etc. Anemia may be caused by loss of blood, for example, due to accidents, surgery, or gastrointestinal bleeding caused by medications such as aspirin and ibuprofen. Excessive blood loss can also be seen in women with heavy menstrual periods, and in people with stomach ulcers, duodenal ulcers, hemorrhoids, or cancer of the stomach or large intestine, etc.

Various conditions can cause the destruction of erythrocytes (hemolysis), thus leading to anemia. For example, allergic-type reactions to bacterial toxins and various chemical agents such as sulfonamides and benzene can cause hemolysis. Hemolytic anemia is often caused by chemical poisoning, parasites, infection, or sickle-cell anemia. In addition, there are unusual situations in which the body produces antibodies against its own erythrocytes, resulting in hemolysis. Any disease or injury to the bone marrow can cause anemia, since that tissue is the site of erythropoiesis, i.e. erythrocyte synthesis. Irradiation, disease, or various chemical agents can also cause bone marrow destruction, producing aplastic anemia. Cancer patients undergoing chemotherapy often have aplastic anemia. Anemia is also associated with renal dysfunction, the severity of the anemia correlating highly with the extent of the dysfunction. Most patients with renal failure undergoing dialysis suffer from chronic anemia.

In addition to being produced in the kidney, erythropoietin is produced by astrocytes and neurons in the central nervous system (CNS), and EPO and EPO receptors are expressed at capillaries of the brain-periphery interface. Furthermore, systemically administered EPO crosses the blood-brain barrier and reduces neuronal cell loss in response to cerebral and spinal chord ischemia, mechanical trauma, epilepsy, excitotoxins, and neuroinflammation. (Sakanaka, (1998) Proc. Natl. Acad. Sci. USA, 95:4635-4640; Celik, et al., (2002) Proc. Natl. Acad. Sci. USA, 99:2258-2263; Brines, et al., (2000) Proc. Natl. Acad. Sci. USA, 97:10526-10531; Calapai, et al., (2000) Eur. J. Pharmacol., 401:349-356; and Siren, et al., (2001) Proc. Natl. Acad. Sci. USA, 98:4044-404.)

In the late 1980 s, Amgen introduced a genetically engineered EPO for the treatment of anemia in chronic renal failure patients. EPO is also administered to cancer patients undergoing radiation and/or chemotherapy, decreasing the need for blood transfusions. EPO is used to treat anemia associated with HIV infection or azidothymidine (AZT) therapy. Although the market for EPO therapy is increasing, future sales are adversely affected by the high cost of the product. In addition, recombinant EPO therapy requires intravenous administration of EPO one to three times per week for up to twelve weeks, a treatment regimen that limits self-administration and is inconvenient for the patient. Further, human serum EPO shows size heterogeneity due to extensive and varied glycosylation not reproduced in any recombinant human EPO.

Hypoxia, the condition that induces the production of $HIF\alpha$, is a state of reduced oxygen, which can occur when the lungs are compromised or blood flow is reduced. Ischemia, reduction in blood flow, can be caused by the obstruction of an artery or vein by a blood clot (thrombus) or by any foreign circulating matter (embolus), or by a vascular disorder such as atherosclerosis. Reduction in blood flow can have a sudden onset and short duration (acute ischemia), or can have a slow onset with long duration or frequent recurrence (chronic ischemia). Acute ischemia is often associated with regional, irreversible tissue necrosis (an infarct), whereas chronic ischemia is usually associated with transient hypoxic tissue injury. If the decrease in perfusion is prolonged or severe, however, chronic ischemia can also be associated with an infarct. Infarctions commonly occur in the spleen, kidney, lungs, brain, and heart, producing disorders such as intestinal infarction, pulmonary infarction, ischemic stroke, and myocardial infarction.

Pathologic changes in ischemic disorders depend on the duration and severity of ischemia, and on the length of patient survival. Necrosis can be seen within the infarct in the first 24 hours, and an acute inflammatory response develops in the viable tissue adjacent to the infarct with leukocytes migrating into the area of dead tissue. Over succeeding days, there is a gradual breakdown and removal of cells within the infarct by phagocytosis, and replacement with a collagenous or glial scar.

Hypoperfusion or infarction in one organ often affects other organs. For example, ischemia of the lung, caused by, for example, a pulmonary embolism, not only affects the lung, but also puts the heart and other organs, such as the brain, under hypoxic stress. Myocardial infarction, which often involves coronary artery blockage due to thrombosis, arterial wall vasospasms, or viral infection of the heart, can lead to congestive heart failure and systemic hypotension. Secondary complications such as global ischemic encephalopathy can develop if the cardiac arrest is prolonged with continued hypoperfusion. Cerebral ischemia, most commonly caused by vascular occlusion due to atherosclerosis, can range in severity from transient ischemic attacks (TIAs) to cerebral infarction or stroke. While the symptoms of TIAs are temporary and reversible, TIAs tend to recur and are often followed by a stroke.

Occlusive arterial disease includes coronary artery disease, which can lead to myocardial infarction, and peripheral arterial disease, which can affect the abdominal aorta, its major branches, and arteries of the legs. Peripheral arterial disease includes Buerger's disease, Raynaud's disease, and acrocyanosis. Although peripheral arterial disease is commonly caused by atherosclerosis, other major causes include, e.g., diabetes, etc. Complications associated with peripheral arterial disease include severe leg cramps, angina, abnormal heart rhythms, heart failure, heart attack, stroke, and kidney failure.

Ischemic and hypoxic disorders are a major cause of morbidity and mortality. Cardiovascular diseases cause at least 15 million deaths every year and are responsible for 30% of deaths worldwide. Among the various cardiovascular diseases, ischemic heart disease and cerebrovascular diseases cause approximately 17% of deaths. Annually, 1.3 million cases of nonfatal acute myocardial infarction are reported, making the prevalence approximately 600 per 100,000 people. Further, an estimated five million Americans suffer from venous thrombosis every year, and approximately 600,000 of these cases result in pulmonary embolism. About one-third of the pulmonary embolisms end in death, making pulmonary embolism the third most common cause of death in the United States.

Currently, treatment of ischemic and hypoxic disorders is focused on relief of symptoms and treatment of causative disorders. For example, treatments for myocardial infarction include nitroglycerin and analgesics to control pain and relieve the workload of the heart. Other medications, including digoxin, diuretics, amrinone, β-blockers, lipid-lowering agents and angiotensin-converting enzyme inhibitors, are used to stabilize the condition, but none of these therapies directly address the tissue damage produced by the ischemia and hypoxia.

Due to deficiencies in current treatments and in the production and use of recombinant EPO, there remains a need for compounds that are effective in treating erythropoietin-associated conditions such as anemia, including anemia associated with diabetes, ulcers, kidney failure, cancer, infection, dialysis, surgery, and chemotherapy and conditions involving ischemia and hypoxia such as occlusive arterial disease, angina pectoris, intestinal infarctions, pulmonary infarctions, cerebral ischemia, and myocardial infarction. There is also a need for compounds that are effective in the prevention of tissue damage caused by ischemia that occurs due to, e.g., atherosclerosis, diabetes, and pulmonary disorders such as pulmonary embolism and the like. In summary, there is a need in the art for methods and compounds that modulate HIF and/or endogenous erythropoietin (EPO) and can be used to treat and prevent HIF-associated and EPO-associated disorders including conditions involving anemia, ischemia and hypoxia.

SUMMARY OF THE INVENTION

This invention is directed to novel compounds and methods that can modulate hypoxia inducible factor (HIF) and/or endogenous erythropoietin (EPO).

In one of its compound aspects, there is provided compounds represented by formula I:

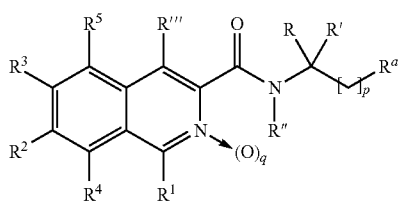

I wherein:
q is zero or one;
p is zero or one;
$R^a$ is —COOH or —$WR^8$; provided that when $R^a$ is —COOH then p is zero and when $R^a$ is —$WR^8$ then p is one;
W is selected from the group consisting of oxygen, —S(O)$_n$— and —$NR^9$— where n is zero, one or two, $R^9$ is selected from the group consisting of hydrogen, alkyl, substituted alkyl, acyl, aryl, substituted aryl, heteroaryl, substituted heteroaryl, heterocyclic and substituted heterocyclic and $R^8$ is selected from the group consisting of hydrogen, alkyl, substituted alkyl, aryl, substituted aryl, heteroaryl, substituted heteroaryl, heterocyclic and substituted heterocyclic, or when W is —$NR^9$— then $R^8$ and $R^9$, together with the nitrogen atom to which they are bound, can be joined to form a heterocyclic or a substituted heterocyclic group, provided that when W is —S(O)$_n$— and n is one or two, then $R^8$ is not hydrogen;

$R^1$ is selected from the group consisting of hydrogen, alkyl, substituted alkyl, alkoxy, substituted alkoxy, amino, substituted amino, aminoacyl, aryl, substituted aryl, halo, heteroaryl, substituted heteroaryl, heterocyclic, substituted heterocyclic, and —$XR^6$ where X is oxygen, —S(O)$_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl or, when X is —$NR^7$—, then $R^7$ and $R^6$, together with the nitrogen atom to which they are bound, can be joined to form a heterocyclic or substituted heterocyclic group;

$R^2$ and $R^3$ are independently selected from the group consisting of hydrogen, alkyl, substituted alkyl, aryl, substituted aryl, heteroaryl, substituted heteroaryl, halo, hydroxy, cyano, —S(O)$_n$—N($R^6$)—$R^6$ where n is 0, 1, or 2, —$NR^6C(O)NR^6R^6$, —$XR^6$ where X is oxygen, —S(O)$_n$— or —$NR^7$— where n is zero, one or two, each $R^6$ is independently selected from the group consisting of hydrogen, alkyl, substituted alkyl, aryl, substituted aryl, cycloalkyl, substituted cycloalkyl, heteroaryl, substituted heteroaryl, heterocyclic and substituted heterocyclic provided that when X is —SO— or —SO$_2$—, then $R^6$ is not hydrogen, and $R^7$ is selected from the group consisting of hydrogen, alkyl, aryl, or $R^2$, $R^3$ together with the carbon atom pendent thereto, form an aryl substituted aryl, heteroaryl, or substituted heteroaryl;

$R^4$ and $R^5$ are independently selected from the group consisting of hydrogen, halo, alkyl, substituted alkyl, alkoxy, substituted alkoxy, aryl, substituted aryl, heteroaryl, substituted heteroaryl and —$XR^6$ where X is oxygen, —S(O)$_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl or, when X is —$NR^7$—, then $R^7$ and $R^6$, together with the nitrogen atom to which they are bound, can be joined to form a heterocyclic or substituted heterocyclic group;

R is selected from the group consisting of hydrogen, deuterium and methyl;

R' is selected from the group consisting of hydrogen, deuterium, alkyl and substituted alkyl; alternatively, R and R' and the carbon pendent thereto can be joined to form cycloalkyl, substituted cycloalkyl, heterocyclic or substituted heterocyclic group;

R" is selected from the group consisting of hydrogen and alkyl or R" together with R' and the nitrogen pendent thereto can be joined to form a heterocyclic or substituted heterocyclic group;

R'" is selected from the group consisting of hydroxy, alkoxy, substituted alkoxy, acyloxy, cycloalkoxy, substituted cycloalkoxy, aryloxy, substituted aryloxy, heteroaryloxy, substituted heteroaryloxy, aryl, —S(O)$_n$—$R^{10}$ wherein $R^{10}$ is selected from the group consisting of alkyl, substituted alkyl, cycloalkyl, substituted cycloalkyl, aryl, substituted aryl, heteroaryl and substituted heteroaryl and n is zero, one or two;

and pharmaceutically acceptable salts, esters and prodrugs thereof;

with the proviso that when R, R' and R" are hydrogen and q is zero, and $R^a$ is either —COOH (p is zero) or —$WR^8$ (p is one) and W is oxygen and $R^8$ is hydrogen then at least one of the following occurs:

1) $R^1$ is fluoro, bromo, iodo, alkyl, substituted alkyl, alkoxy, aminoacyl, substituted alkoxy, aryl, substituted aryl, heteroaryl, substituted heteroaryl, heterocyclic, substituted heterocyclic, and —$XR^6$ where X is oxygen, —$S(O)_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl; or 2) $R^2$ is substituted alkyl, aryl, substituted aryl, heteroaryl, substituted heteroaryl, fluoro, bromo, iodo, cyano, —$XR^6$ where X is oxygen, —$S(O)_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl provided that:

a) when $R^2$ is substituted alkyl such a substituent does not include trifluoromethyl;

b) —$XR^6$ is not alkoxy; and c) when —$XR^6$ is substituted alkoxy such a substituent does not include benzyl or benzyl substituted by a substituent selected from the group consisting of ($C_1$-$C_5$) alkyl and ($C_1$-$C_5$) alkoxy or does not include a fluoroalkoxy substituent of the formula:

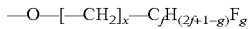

where x is zero or one; f is an integer of from 1 to 5; and g is an integer of from 1 to (2f+1); or 3) $R^3$ is substituted alkyl, aryl, substituted aryl, heteroaryl, substituted heteroaryl, bromo, iodo, —$XR^6$ where X is oxygen, —$S(O)_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl provided that:

a) when $R^3$ is substituted alkyl such a substituent does not include trifluoromethyl;

b) —$XR^6$ is not alkoxy; and c) when —$XR^6$ is substituted alkoxy such a substituent does not include benzyl or benzyl substituted by a substituent selected from the group consisting of ($C_1$-$C_5$) alkyl and ($C_1$-$C_5$) alkoxy or does not include a fluoroalkoxy substituent of the formula:

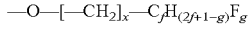

where x is zero or one; f is an integer of from 1 to 5; and g is an integer of from 1 to (2f+1); or 4) $R^4$ is iodo, substituted alkyl, aryl, substituted aryl, heteroaryl, substituted heteroaryl, —$XR^6$ where X is oxygen, —$S(O)_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl provided that:

a) when $R^4$ is substituted alkyl such a substituent does not include trifluoromethyl;

b) —$XR^6$ is not alkoxy; and c) when —$XR^6$ is substituted alkoxy such a substituent does not include a fluoroalkoxy substituent of the formula:

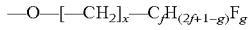

where x is zero or one; f is an integer of from 1 to 5; and g is an integer of from 1 to (2f+1); or 5) $R^5$ is iodo, substituted alkyl, aryl, substituted aryl, heteroaryl, substituted heteroaryl, —$XR^6$ where X is oxygen, —$S(O)_n$— or —$NR^7$— where n is zero, one or two, $R^6$ is selected from the group consisting of alkyl, substituted alkyl, aryl, substituted aryl, heteroaryl, substituted heteroaryl, heterocyclic and substituted heterocyclic, and $R^7$ is hydrogen, alkyl or aryl provided that:

a) when $R^5$ is substituted alkyl such a substituent does not include trifluoromethyl;

b) —$XR^6$ is not alkoxy; and c) when —$XR^6$ is substituted alkoxy such a substituent does not include a fluoroalkoxy substituent of the formula:

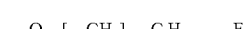

where x is zero or one; f is an integer of from 1 to 5; and g is an integer of from 1 to (2f+1);

and with the further following proviso:

that when $R^1$, $R^3$, $R^4$, and $R^5$ are hydrogen, then $R^2$ is not bromo.

In an alternative embodiment, the compounds of formula I are represented by formula IA:

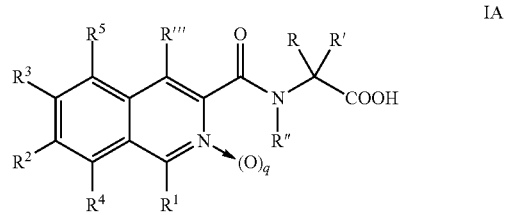

wherein $R^1$, $R^2$, $R^3$, $R^4$, $R^5$, R, R', R", R''' and q are as defined above; and pharmaceutically acceptable salts, esters, prodrugs thereof.

In an another alternative embodiment, the compounds of formula I are represented by the formula IB:

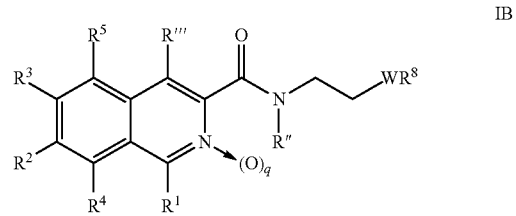

wherein $R^1$, $R^2$, $R^3$, $R^4$, $R^5$, R", R''', $WR^8$ and q are as defined above; and pharmaceutically acceptable salts, esters, prodrugs thereof.

In an another alternative embodiment, the invention is directed to compounds represented by the formula IC:

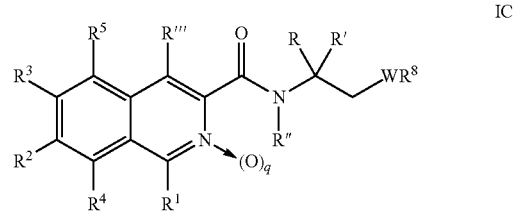

wherein $R^1$, $R^2$, $R^3$, $R^4$, $R^5$, R, R', R", R''', $WR^8$ and q are as defined above; and pharmaceutically acceptable salts, esters, prodrugs thereof.

In yet another alternative embodiment, the invention is directed to compounds represented by the formula ID:

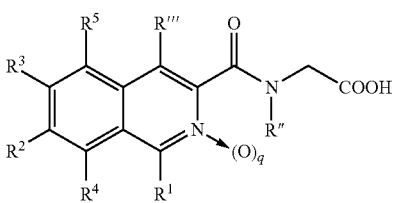

wherein $R^1$, $R^2$, $R^3$, $R^4$, $R^5$, R, R', R", R''' and q are as defined above; and pharmaceutically acceptable salts, esters, prodrugs thereof.

In other embodiments, the invention is directed to compounds represented by the formulae IIA, IIB, IIC, and IID, wherein said formulae are defined below.

Preferred Embodiments

In compounds of formulae I, IA, IB, IC, and ID, preferably $R^1$ is selected from the group consisting of hydrogen, alkyl, substituted alkyl, halo, alkoxy, aryloxy, substituted aryloxy, substituted aryl, alkylthio, aminoacyl, aryl, substituted amino, heteroaryl, heteroaryloxy, —$S(O)_n$-aryl, —$S(O)_n$-substituted aryl, —$S(O)_n$-heteroaryl, and —$S(O)_n$-substituted heteroaryl, where n is zero, one or two.

More preferably, $R^1$ is selected from the group consisting of:
(3-methoxyphenyl)sulfanyl;
(4-chlorophenyl)sulfanyl;
(4-methylphenyl)sulfanyl;
2-fluorophenoxy;
2-methoxyphenoxy;
(2-methoxyphenyl)sulfanyl
3-fluorophenoxy;
3-methoxyphenoxy;
4-(methylcarbonylamino)phenoxy;
4-(methyl sulfonamido)phenoxy;
4-fluorophenoxy;
4-methoxyphenoxy;
4-methoxyphenylsulfanyl;
4-methylphenyl;
bromo;
chloro;
dimethylaminomethyl;
ethoxy;
ethyl sulfanyl;
hydrogen;
isopropyl;
methoxy;
methoxymethyl;
methyl;
N,N-dimethylaminocarbonyl;
naphth-2-yloxy;
naphthylsulfanyl;
phenoxy;
phenyl;
phenylamino;
phenylsulfinyl;
phenylsulfanyl;
pyridin-2-yloxy;
pyridin-2-yl; and
pyridin-2-ylsulfanyl.

In compounds of formulae I, IA, IB, IC and ID, $R^2$ is preferably selected from the group consisting of substituted amino, aryloxy, substituted aryloxy, alkoxy, substituted alkoxy, halo, hydrogen, alkyl, substituted alkyl, aryl, —$S(O)_n$-aryl, —$S(O)_n$-substituted aryl, —$S(O)_n$-cycloalkyl, where n is zero, one or two, aminocarbonylamino, heteroaryloxy, and cycloalkyloxy.

More preferably, $R^2$ is selected from the group consisting of:
(4-methoxy)phenylsulfonylamino;
2,6-dimethylphenoxy;
3,4-difluorophenoxy;
3,5-difluorophenoxy;
3-chloro-4-fluorophenoxy;
3-methoxy-4-fluorophenoxy;
3-methoxy-5-fluorophenoxy;
4-(methyl sulfonamido)phenoxy;
4-(phenyl sulfonamido)phenoxy;
4-$CF_3$—O-phenoxy;
4-$CF_3$-phenoxy;
4-chlorophenoxy;
4-fluorophenoxy;
4-(4-fluorophenoxy)phenoxy;
4-methoxyphenoxy;
4-nitrophenoxy;
benzyloxy;
bromo;
butoxy;
$CF_3$;
chloro;
cyclohexyloxy;
cyclohexylsulfanyl;
cyclohexylsulfonyl;
fluoro;
hydrogen;
iodo;
isopropoxy;
methyl;
phenoxy;
phenyl;
phenylsulfanyl;
phenylsulfinyl;
phenyl sulfonyl;
phenylurea;
pyridin-1-ylsulfanyl;
pyridin-3-yloxy; and
pyridin-4-ylsulfanyl.

In compounds of formulae I, IA, IB, IC, and ID, $R^3$ is preferably selected from the group consisting of: substituted aryloxy, substituted alkoxy, alkoxy, substituted alkyl, alkyl, amino, cycloalkyloxy, hydrogen, halo, aryl, —$S(O)_n$-aryl, —$S(O)_n$-substituted aryl, —$S(O)_n$-heteroaryl, and —$S(O)_n$-substituted heteroaryl, where n is zero, one or two, aminocarbonylamino, and heteroaryloxy.

More preferably, $R^3$ is selected from the group consisting of:
amino;
(4-methyl)phenylsulfonylaminophenoxy;
3,4-difluorophenoxy;
3,5-difluorophenoxy;
3-fluoro-5-methoxy-phenoxy;
3-chloro-4-fluorophenoxy
4-$CF_3$—O-phenoxy;
4-$CF_3$-phenoxy;
4-chlorophenoxy;
4-fluorophenoxy;
4-(4-fluorophenoxy)phenoxy;
4-methoxyphenoxy;
benzyloxy;
bromo;

butoxy;
$CF_3$;
chloro;
cyclohexyloxy;
hydrogen;
iodo;
isopropoxy;
phenoxy;
phenyl;
phenylsulfanyl;
phenyl sulfonyl;
phenylsulfinyl;
phenylurea;
pyridin-1-ylsulfanyl;
pyridin-3-yloxy; and
pyridin-4-ylsulfanyl.

Alternatively, $R^2$ and $R^3$, combined with the carbon atoms pendent thereto, are joined to form an aryl group. Preferably, the aryl group is phenyl.

In compounds of formulae I, IA, IB, IC, and ID, $R^4$ is preferably selected from the group consisting of: substituted arylthio, halo, hydrogen, substituted alkyl and aryl.

More preferably, $R^4$ is selected from the group consisting of:
4-chlorophenyl sulfanyl;
chloro;
hydrogen;
methoxymethyl; and
phenyl.

In compounds of formulae I, IA, IB, IC, and ID, $R^5$ is preferably hydrogen or aryl. More preferably $R^5$ is hydrogen or phenyl.

In compounds of formulae I, IA and IC, R is preferably selected from the group consisting of hydrogen, deuterium, aryl and alkyl. More preferably R is selected from the group consisting of phenyl, hydrogen, deuterium and methyl.

In compounds of formulae I, IA and IC, R' is selected from the group consisting of preferably hydrogen, deuterium, alkyl, substituted alkyl, and substituted amino. More preferably, R' is selected from the group consisting of:
4-aminobutyl;
4-hydroxybenzyl;
benzyl;
carboxylmethyl;
deuterium;
hydroxymethyl;
imidazol-4-ylmethyl;
isopropyl;
methyl; and
propyl.

Alternatively, R, R' and the carbon atom pendent thereto join to form a cycloalkyl and more preferably cyclopropyl.

In compounds of formulae I, IA, and IC, R" is preferably hydrogen, alkyl or substituted alkyl. More preferably, R" is hydrogen, methyl or carboxylmethyl (—$CH_2C(O)OH$). Alternatively, R', R" and the carbon atom and nitrogen atom respectively pendent thereto join to form a heterocyclic group and more preferably pyrrolidinyl.

In compounds of formulae I, IA, IB, IC, and ID, preferably R''' is selected from the group consisting of hydrogen, hydroxy, alkoxy, substituted alkoxy, cycloalkoxy, substituted cycloalkoxy, thiol, acyloxy and aryl. Preferably, R''' is selected from the group consisting of:
hydroxy;
benzyloxy;
ethoxy;
thiol;
methoxy;
methylcarbonyloxy; and
phenyl.

In compounds of formulae I, IB, and IC, $WR^8$ is preferably selected from the group consisting of amino, substituted amino, aminoacyl, hydroxy, and alkoxy. More preferably, $WR^8$ is selected from the group consisting of:
amino;
dimethylamino;
hydroxy;
methoxy; and
methylcarbonylamino.

Representative compounds for this application are presented in Tables A-D, wherein said table letter corresponds to formula letter (i.e., representative compounds of formula IA are in Table A).

TABLE A

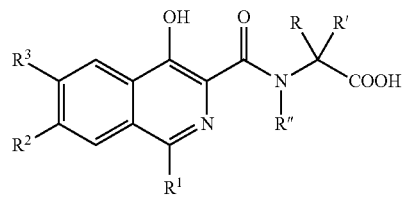

| No. | $R^1$ | $R^2$ | $R^3$ | R | R' | R" |
|---|---|---|---|---|---|---|
| 1 | Cl | H | benzyloxy | H | methyl | H |
| 2 | Cl | H | H | H | hydroxymethyl | H |
| 3 | Cl | H | H | H | hydroxymethyl | H |
| 4 | Cl | H | isopropoxy | H | hydroxymethyl | H |
| 5 | Cl | H | isopropoxy | H | hydroxymethyl | H |
| 6 | Cl | isopropoxy | H | H | hydroxymethyl | H |
| 7 | Cl | isopropoxy | H | H | hydroxymethyl | H |
| 8 | Cl | H | H | methyl | methyl | H |
| 9 | Cl | H | isopropoxy | methyl | methyl | H |
| 10 | Cl | H | H | H | imidazol-4-ylmethyl | H |
| 11 | Cl | H | H | H | imidazol-4-ylmethyl | H |
| 12 | Cl | H | H | H | isopropyl | H |
| 13 | Cl | H | H | H | isopropyl | H |

TABLE A-continued

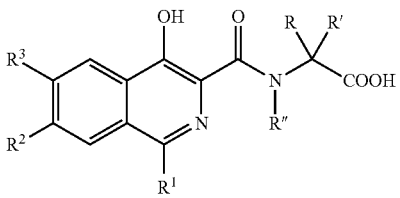

| No. | R¹ | R² | R³ | R | R' | R" |
|---|---|---|---|---|---|---|
| 14 | Cl | H | isopropoxy | H | isopropyl | H |
| 15 | Cl | H | isopropoxy | H | isopropyl | H |
| 16 | Cl | isopropoxy | H | H | isopropyl | H |
| 17 | Cl | isopropoxy | H | H | isopropyl | H |
| 18 | Cl | H | benzyloxy | H | isopropyl | H |
| 19 | Cl | H | H | H | benzyl | H |
| 20 | Cl | H | H | H | benzyl | H |
| 21 | Cl | H | isopropoxy | H | benzyl | H |
| 22 | Cl | H | isopropoxy | H | benzyl | H |
| 23 | Cl | isopropoxy | H | H | benzyl | H |
| 24 | Cl | isopropoxy | H | H | benzyl | H |
| 25 | Cl | H | H | H | 4-hydroxybenzyl | H |
| 26 | Cl | H | H | H | 4-hydroxybenzyl | H |
| 27 | Cl | H | isopropoxy | H | 4-hydroxybenzyl | H |
| 28 | Cl | H | isopropoxy | H | 4-hydroxybenzyl | H |
| 29 | Cl | isopropoxy | H | H | 4-hydroxybenzyl | H |
| 30 | Cl | isopropoxy | H | H | 4-hydroxybenzyl | H |
| 31 | Cl | H | isopropoxy | H | propyl | H |
| 32 | Cl | H | isopropoxy | H | propyl | H |
| 33 | Cl | H | H | H | R' and R" and the carbon and nitrogen atom respectively pendent to which R" is attached join to form a pyrrolidinyl | — |
| 34 | Cl | H | H | H | R' and R" and the carbon and nitrogen atom respectively pendent to which R" is attached join to form a pyrrolidinyl | — |
| 35 | Cl | H | isopropoxy | H | R' and R" and the carbon and nitrogen atom respectively pendent to which R" is attached join to form a pyrrolidinyl | — |
| 36 | Cl | H | isopropoxy | H | R' and R" and the carbon and nitrogen atom respectively pendent to which R" is attached join to form a pyrrolidinyl | — |
| 37 | Cl | H | H | H | 4-aminobutyl | H |
| 38 | Cl | H | H | H | 4-aminobutyl | H |
| 39 | Cl | H | isopropoxy | H | 4-aminobutyl | H |
| 40 | Cl | H | isopropoxy | H | 4-aminobutyl | H |
| 41 | Cl | isopropoxy | H | H | 4-aminobutyl | H |
| 42 | Cl | isopropoxy | H | H | 4-aminobutyl | H |
| 43 | Cl | H | H | H | carboxylmethyl | H |

TABLE A-continued

| No. | R¹ | R² | R³ | R | R' | R" |
|---|---|---|---|---|---|---|
| 44 | Cl | H | H | H | carboxylmethyl | H |
| 45 | Cl | H | isopropoxy | H | carboxylmethyl | H |
| 46 | Cl | H | isopropoxy | H | carboxylmethyl | H |
| 47 | Cl | isopropoxy | H | H | carboxylmethyl | H |
| 48 | Cl | H | H | — | R, R' together with the carbon to which they are attached join to form cyclopropyl | H |
| 49 | Cl | H | isopropoxy | — | R, R' together with the carbon to which they are attached join to form cyclopropyl | H |
| 50 | Cl | H | H | D | D | H |
| 51 | Cl | H | benzyloxy | H | methyl | H |
| 52 | Cl | benzyloxy | H | H | methyl | H |
| 53 | Cl | benzyloxy | H | H | methyl | H |
| 54 | Cl | H | H | H | methyl | H |
| 55 | Cl | H | H | H | methyl | H |
| 56 | Cl | H | isopropoxy | H | methyl | H |
| 57 | Cl | H | isopropoxy | H | methyl | H |
| 58 | Cl | isopropoxy | H | H | methyl | H |
| 59 | Cl | isopropoxy | H | H | methyl | H |
| 60 | H | 4-chlorophenoxy | H | H | methyl | H |
| 61 | H | H | 4-chlorophenoxy | H | methyl | H |
| 62 | H | 3,4-difluorophenoxy | H | H | methyl | H |
| 63 | H | phenyl sulfanyl | H | H | methyl | H |
| 64 | H | phenyl sulfanyl | H | H | methyl | H |
| 65 | H | phenoxy | H | H | methyl | H |
| 66 | H | 4-methoxyphenoxy | H | H | methyl | H |
| 67 | H | phenylsulfonyl | H | H | methyl | H |
| 68 | methoxymethyl | phenoxy | H | H | methyl | H |
| 69 | methoxymethyl | phenoxy | H | H | methyl | H |
| 70 | H | phenoxy | H | H | methyl | H |
| 71 | 4-chlorophenyl sulfanyl | H | H | H | methyl | H |
| 72 | 4-chlorophenyl sulfanyl | H | H | H | methyl | H |
| 73 | H | 3-methoxy-4-fluorophenoxy | H | H | methyl | H |
| 74 | H | cyclohexyloxy | H | H | methyl | H |
| 75 | methyl | 4-fluorophenoxy | H | H | methyl | H |
| 76 | H | 4-fluorophenoxy | H | H | methyl | H |
| 77 | methyl | phenoxy | H | H | methyl | H |
| 78 | methyl | phenyl sulfanyl | H | H | methyl | H |
| 79 | H | 4-trifluoromethyl-phenoxy | H | H | methyl | H |

TABLE B

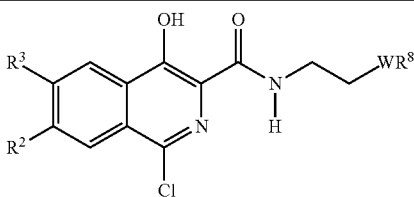

| No. | R² | R³ | WR⁸ |
|---|---|---|---|
| 1 | H | H | methoxy |
| 2 | isopropoxy | H | amino |
| 3 | H | isopropoxy | methoxy |
| 4 | H | H | amino |
| 5 | H | H | hydroxy |
| 6 | H | isopropoxy | hydroxy |
| 7 | H | H | dimethylamino |
| 8 | H | H | methylcarbonylamino |
| 9 | H | isopropoxy | amino |
| 10 | H | isopropoxy | dimethylamino |
| 11 | isopropoxy | H | methoxy |
| 12 | isopropoxy | H | dimethylamino |
| 13 | isopropoxy | H | hydroxy |

TABLE C

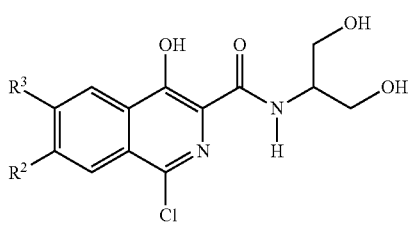

| No. | R² | R³ |
|---|---|---|
| 1 | isopropoxy | H |
| 2 | H | isopropoxy |
| 3 | H | H |

TABLE D

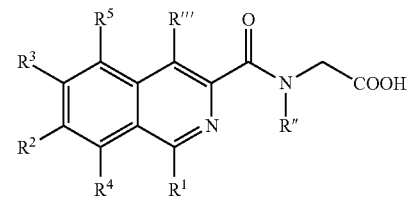

| No. | R¹ | R² | R³ | R⁴ | R⁵ | R″ | R‴ |
|---|---|---|---|---|---|---|---|
| 1 | Br | 2,6-di(CH₃)phenyloxy | H | H | H | H | OH |
| 2 | Br | butoxy | H | H | H | H | OH |
| 3 | Br | phenoxy | H | H | H | H | OH |
| 4 | Cl | Br | H | H | H | H | OH |
| 5 | Br | Cl | H | H | H | H | OH |
| 6 | Cl | I | H | H | H | H | OH |
| 7 | Cl | H | I | H | H | H | OH |
| 8 | Cl | phenoxy | H | H | H | H | OH |
| 9 | Cl | phenylsulfanyl | H | H | H | H | OH |
| 10 | Br | —CF₃ | H | H | H | H | OH |
| 11 | Br | H | phenoxy | H | H | H | OH |
| 12 | Cl | H | H | phenyl | H | H | OH |
| 13 | Cl | 2,6-di(CH₃)phenyloxy | H | H | H | H | OH |
| 14 | Br | H | CF₃ | H | H | H | OH |
| 15 | Br | Br | H | H | H | H | OH |
| 16 | Br | phenylsulfanyl | H | H | H | H | OH |
| 17 | Cl | H | phenylsulfanyl | H | H | H | OH |
| 18 | 4-methoxyphenyl-sulfanyl | H | H | H | H | H | OH |
| 19 | Br | H | H | phenyl | H | H | OH |
| 20 | Cl | phenyl | H | H | H | H | OH |
| 21 | Br | H | H | H | H | H | OH |
| 22 | Br | methyl | H | H | H | H | OH |
| 23 | Br | H | butoxy | H | H | H | OH |
| 24 | Br | H | Cl | H | H | H | OH |
| 25 | Cl | H | phenoxy | H | H | H | OH |
| 26 | Br | H | phenoxy | H | H | H | OH |
| 27 | H | I | H | H | H | H | OH |
| 28 | Br | phenyl | H | H | H | H | OH |
| 29 | Br | H | phenyl | H | H | H | OH |
| 30 | ethyl sulfanyl | H | H | H | H | H | OH |
| 31 | phenoxy | H | H | H | H | H | OH |
| 32 | H | H | phenyl | H | H | H | OH |
| 33 | Br | H | H | H | phenyl | H | OH |

TABLE D-continued

| No. | R¹ | R² | R³ | R⁴ | R⁵ | R'' | R''' |
|---|---|---|---|---|---|---|---|
| 34 | Br | F | H | H | H | H | OH |
| 35 | H | 2,6-di(CH₃) phenyloxy | H | H | H | H | OH |
| 36 | Cl | H | phenyl | H | H | H | OH |
| 37 | H | phenoxy | H | H | H | H | OH |
| 38 | H | phenylsulfanyl | H | H | H | H | OH |
| 39 | H | phenyl | H | H | H | H | OH |
| 40 | H | H | phenoxy | H | H | H | OH |
| 41 | H | H | phenylsulfanyl | H | H | H | OH |
| 42 | H | H | H | phenyl | H | H | OH |
| 43 | Cl | H | H | H | phenyl | H | OH |
| 44 | H | H | H | H | phenyl | H | OH |
| 45 | Cl | F | H | H | H | H | OH |
| 46 | H | F | H | H | H | H | OH |
| 47 | H | H | Br | H | H | H | OH |
| 48 | H | R²/R³ = phenyl | — | H | H | H | OH |
| 49 | Br | H | benzyloxy | H | H | methyl | OH |
| 50 | Cl | H | H | H | H | methyl | OH |
| 51 | Cl | H | isopropoxy | H | H | methyl | OH |
| 52 | Cl | isopropoxy | H | H | H | methyl | OH |
| 53 | Cl | H | H | H | H | CH₂COOH | OH |
| 54 | Cl | H | isopropoxy | H | H | CH₂COOH | OH |
| 55 | naphth-2-yloxy | H | H | H | H | H | OH |
| 56 | pyridin-3-yloxy | H | H | H | H | H | OH |
| 57 | 4-methoxy phenoxy | H | H | H | H | H | OH |
| 58 | 3-methoxy phenoxy | H | H | H | H | H | OH |
| 59 | 3-fluorophenoxy | H | H | H | H | H | OH |
| 60 | 4-fluorophenoxy | H | H | H | H | H | OH |
| 61 | 2-fluorophenoxy | H | H | H | H | H | OH |
| 62 | 2-methoxy phenoxy | H | H | H | H | H | OH |
| 63 | 4-(methyl carbonyl amino) phenoxy | H | H | H | H | H | OH |
| 64 | 4-(methyl sulfonamido) phenoxy | H | H | H | H | H | OH |
| 65 | phenyl amino | H | H | H | H | H | OH |
| 66 | H | H | pyridin-3-yloxy | H | H | H | OH |
| 67 | H | pyridin-3-yloxy | H | H | H | H | OH |
| 68 | Cl | H | H | H | H | H | methoxy |
| 69 | Cl | H | H | H | H | H | ethoxy |
| 70 | methoxy | H | H | H | H | H | OH |
| 71 | ethoxy | H | H | H | H | H | OH |
| 72 | phenyl | H | H | H | H | H | methyl-carbonyloxy |
| 73 | phenyl | H | H | H | H | H | OH |
| 74 | ethoxy | H | H | H | H | H | phenyl |
| 75 | Cl | H | H | H | H | H | phenyl |
| 76 | H | H | H | H | H | H | phenyl |
| 77 | methyl | H | H | H | H | H | OH |
| 78 | methoxy methyl | H | H | H | H | H | OH |
| 79 | N,N-dimethyl amino carbonyl | H | H | H | H | H | OH |
| 80 | methyl | H | phenoxy | H | H | H | OH |
| 81 | methyl | phenoxy | H | H | H | H | OH |
| 82 | methyl | phenoxy | H | H | H | H | benzyloxy |
| 83 | methyl | phenoxy | H | H | H | H | ethoxy |

TABLE D-continued

| No. | R¹ | R² | R³ | R⁴ | R⁵ | R'' | R''' |
|---|---|---|---|---|---|---|---|
| 84 | N,N-dimethyl amino carbonyl | phenoxy | H | H | H | H | OH |
| 85 | methoxy methyl | phenoxy | H | H | H | H | OH |
| 86 | 4-methyl phenyl | H | H | H | H | H | OH |
| 87 | methyl | 4-fluoro phenoxy | H | H | H | H | OH |
| 88 | Cl | 4-methoxy phenoxy | H | H | H | H | OH |
| 89 | H | 4-methoxy phenoxy | H | H | H | H | OH |
| 90 | Cl | H | 4-methoxy-phenoxy | H | H | H | OH |
| 91 | H | H | 4-methoxy-phenoxy | H | H | H | OH |
| 92 | Cl | 4-CF₃-phenoxy | H | H | H | H | OH |
| 93 | H | 4-CF₃-phenoxy | H | H | H | H | OH |
| 94 | Cl | H | 4-CF₃-phenoxy | H | H | H | OH |
| 95 | H | H | 4-CF₃-phenoxy | H | H | H | OH |
| 96 | Cl | 4-fluorophenoxy | H | H | H | H | OH |
| 97 | H | 4-fluorophenoxy | H | H | H | H | OH |
| 98 | Cl | H | 4-fluoro-phenoxy | H | H | H | OH |
| 99 | H | H | 4-fluoro-phenoxy | H | H | H | OH |
| 100 | H | pyridin-4-yl sulfanyl | H | H | H | H | OH |
| 101 | H | H | pyridin-4-yl sulfanyl | H | H | H | OH |
| 102 | H | phenylsulfinyl | H | H | H | H | OH |
| 103 | H | phenylsulfonyl | H | H | H | H | OH |
| 104 | H | H | phenyl sulfinyl | H | H | H | OH |
| 105 | H | H | phenyl sulfonyl | H | H | H | OH |
| 106 | H | H | amino | H | H | H | OH |
| 107 | H | (4-methoxy) phenylsulfonyl amino | H | H | H | H | OH |
| 108 | H | phenylurea | H | H | H | H | OH |
| 109 | H | H | phenylurea | H | H | H | OH |
| 110 | phenyl sulfanyl | H | H | H | H | H | OH |
| 111 | (4-chloro phenyl) sulfanyl | H | H | H | H | H | OH |
| 112 | (4-methyl phenyl) sulfanyl | H | H | H | H | H | OH |
| 113 | pyridin-2-ylsulfanyl | H | H | H | H | H | OH |
| 114 | (3-methoxy phenyl) sulfanyl | H | H | H | H | H | OH |
| 115 | 2-methoxy phenyl sulfanyl | H | H | H | H | H | OH |
| 116 | naphthyl sulfanyl | H | H | H | H | H | OH |
| 117 | phenyl sulfinyl | H | H | H | H | H | OH |
| 118 | phenyl sulfonyl | H | H | H | H | H | OH |
| 119 | H | pyridin-2-yl sulfanyl | H | H | H | H | OH |
| 120 | H | H | pyridin-2-yl sulfanyl | H | H | H | OH |
| 121 | Cl | phenoxy | phenoxy | H | H | H | OH |

TABLE D-continued

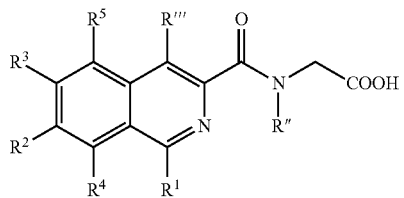

| No. | R¹ | R² | R³ | R⁴ | R⁵ | R″ | R‴ |
|---|---|---|---|---|---|---|---|
| 122 | H | phenoxy | phenoxy | H | H | H | OH |
| 123 | H | H | (4-methyl)phenyl SO₂—NH-phenoxy | H | H | H | OH |
| 124 | H | 4-nitrophenoxy | H | H | H | H | OH |
| 125 | H | phenoxy | H | H | H | H | thiol |
| 126 | H | CF₃ | H | H | H | H | thiol |
| 127 | H | 4-(phenylsulfonamido) phenoxy | H | H | H | H | OH |
| 128 | H | 4-(methylsulfonamido) phenoxy | H | H | H | H | OH |
| 129 | H | 4-chlorophenoxy | H | H | H | H | OH |
| 130 | H | H | 4-chlorophenoxy | H | H | H | OH |
| 131 | H | H | 3-fluoro-5-methoxyphenoxy | H | H | H | OH |
| 132 | H | 3-methoxy-5-fluorophenoxy | H | H | H | H | OH |
| 133 | H | 3,4-difluorophenoxy | H | H | H | H | OH |
| 134 | H | H | 3,4-difluorophenoxy | H | H | H | OH |
| 135 | H | 4-CF₃-O-phenoxy | H | H | H | H | OH |
| 136 | H | H | 4-CF₃—O-phenoxy | H | H | H | OH |
| 137 | H | 3,5-difluorophenoxy | H | H | H | H | OH |
| 138 | H | H | 3,5-difluorophenoxy | H | H | H | OH |
| 139 | H | 4-(4-fluorophenoxy)phenoxy | H | H | H | H | OH |
| 140 | H | H | 4-(4-fluorophenoxy)phenoxy | H | H | H | OH |
| 141 | H | 3-chloro-4-fluorophenoxy | H | H | H | H | OH |
| 142 | H | H | 3-chloro-4-fluorophenoxy | H | H | H | OH |
| 143 | methyl | 4-chlorophenoxy | H | H | H | H | OH |
| 144 | methyl | H | 4-chlorophenoxy | H | H | H | OH |
| 145 | methyl | 3,5-difluorophenoxy | H | H | H | H | OH |
| 146 | methyl | 4-methoxy phenoxy | H | H | H | H | OH |
| 147 | methyl | H | 4-methoxyphenoxy | H | H | H | OH |
| 148 | H | H | cyclohexyloxy | H | H | H | OH |
| 149 | H | cyclohexyloxy | H | H | H | H | |
| 150 | methyl | cyclohexyloxy | H | H | H | H | OH |
| 151 | H | cyclohexyl sulfanyl | H | H | H | H | OH |
| 152 | H | cyclohexyl sulfonyl | H | H | H | H | OH |
| 153 | isopropyl | H | H | H | H | H | OH |
| 154 | pyridin-2-yl | H | H | H | H | H | OH |
| 155 | ethyl | phenoxy | H | H | H | H | OH |
| 156 | dimethyl amino methyl | phenylsulfanyl | H | H | H | H | OH |
| 157 | methyl | phenylsulfanyl | H | H | H | H | OH |
| 158 | methyl | 4-trifluoromethyl phenoxy | H | H | H | H | OH |

Compounds included within the scope of this invention include, for example, those set forth below:

{[4-Hydroxy-1-(naphthalen-2-yloxy)-isoquinoline-3-carbonyl]-amino}-acetic acid;
{[4-Hydroxy-1-(pyridin-3-yloxy)-isoquinoline-3-carbonyl]-amino}-acetic acid;
{[4-Hydroxy-1-(4-methoxy-phenoxy)-isoquinoline-3-carbonyl]-amino}-acetic acid;
{[4-Hydroxy-1-(3-methoxy-phenoxy)-isoquinoline-3-carbonyl]-amino}-acetic acid;
{[1-(3-Fluoro-phenoxy)-4-hydroxy-isoquinoline-3-carbonyl]-amino}-acetic acid;
{[1-(4-Fluoro-phenoxy)-4-hydroxy-isoquinoline-3-carbonyl]-amino}-acetic acid;
{[1-(2-Fluoro-phenoxy)-4-hydroxy-isoquinoline-3-carbonyl]-amino}-acetic acid;
{[4-Hydroxy-1-(2-methoxy-phenoxy)-isoquinoline-3-carbonyl]-amino}-acetic acid;
{[1-(4-Acetylamino-phenoxy)-4-hydroxy-isoquinoline-3-carbonyl]-amino}-acetic acid;
{[4-Hydroxy-1-(4-methanesulfonylamino-phenoxy)-isoquinoline-3-carbonyl]-amino}-acetic acid;
[(4-Hydroxy-1-phenylamino-isoquinoline-3-carbonyl)-amino]-acetic acid;
{[4-Hydroxy-6-(pyridin-3-yloxy)-isoquinoline-3-carbonyl]-amino}-acetic acid;
{[4-Hydroxy-7-(pyridin-3-yloxy)-isoquinoline-3-carbonyl]-amino}-acetic acid;
[(1-Chloro-4-methoxy-isoquinoline-3-carbonyl)-amino]-acetic acid;
[(1-Chloro-4-ethoxy-isoquinoline-3-carbonyl)-amino]-acetic acid;
[(4-Hydroxy-1-methoxy-isoquinoline-3-carbonyl)-amino]-acetic acid;
[(1-Ethoxy-4-hydroxy-isoquinoline-3-carbonyl)-amino]-acetic acid;
[(4-Acetoxy-1-phenyl-isoquinoline-3-carbonyl)-amino]-acetic acid;
[(4-Hydroxy-1-phenyl-isoquinoline-3-carbonyl)-amino]-acetic acid;
[(1-Ethoxy-4-phenyl-isoquinoline-3-carbonyl)-amino]-acetic acid;
[(1-Chloro-4-phenyl-isoquinoline-3-carbonyl)-amino]-acetic acid;
[(4-Phenyl-isoquinoline-3-carbonyl)-amino]-acetic acid;
[(4-Hydroxy-1-methyl-isoquinoline-3-carbonyl)-amino]-acetic acid;
[(4-Hydroxy-1-methoxymethyl-isoquinoline-3-carbonyl)-amino]-acetic acid;
[(1-Dimethylcarbamoyl-4-hydroxy-isoquinoline-3-carbonyl)-amino]-acetic acid;
[(4-Hydroxy-1-methyl-6-phenoxy-isoquinoline-3-carbonyl)-amino]-acetic acid;
[(4-Hydroxy-1-methyl-7-phenoxy-isoquinoline-3-carbonyl)-amino]-acetic acid;
[(4-Benzyloxy-1-methyl-7-phenoxy-isoquinoline-3-carbonyl)-amino]-acetic acid;
[(4-Ethoxy-1-methyl-7-phenoxy-isoquinoline-3-carbonyl)-amino]-acetic acid;
[(1-Dimethylcarbamoyl-4-hydroxy-7-phenoxy-isoquinoline-3-carbonyl)-amino]-acetic acid;
[(4-Hydroxy-1-methoxymethyl-7-phenoxy-isoquinoline-3-carbonyl)-amino]-acetic acid;
[(4-Hydroxy-1-p-tolyl-isoquinoline-3-carbonyl)-amino]-acetic acid;
{[7-(4-Fluoro-phenoxy)-4-hydroxy-1-methyl-isoquinoline-3-carbonyl]-amino}-acetic acid;
{[1-Chloro-4-hydroxy-7-(4-methoxy-phenoxy)-isoquinoline-3-carbonyl]-amino}-acetic acid;
{[4-Hydroxy-7-(4-methoxy-phenoxy)-isoquinoline-3-carbonyl]-amino}-acetic acid;
{[1-Chloro-4-hydroxy-6-(4-methoxy-phenoxy)-isoquinoline-3-carbonyl]-amino}-acetic acid;
{[4-Hydroxy-6-(4-methoxy-phenoxy)-isoquinoline-3-carbonyl]-amino}-acetic acid;
{[1-Chloro-4-hydroxy-7-(4-trifluoromethyl-phenoxy)-isoquinoline-3-carbonyl]-amino}-acetic acid;
{[4-Hydroxy-7-(4-trifluoromethyl-phenoxy)-isoquinoline-3-carbonyl]-amino}-acetic acid;
{[1-Chloro-4-hydroxy-6-(4-trifluoromethyl-phenoxy)-isoquinoline-3-carbonyl]-amino}-acetic acid;
{[4-Hydroxy-6-(4-trifluoromethyl-phenoxy)-isoquinoline-3-carbonyl]-amino}-acetic acid;
{[1-Chloro-7-(4-fluoro-phenoxy)-4-hydroxy-isoquinoline-3-carbonyl]-amino}-acetic acid;
{[7-(4-Fluoro-phenoxy)-4-hydroxy-isoquinoline-3-carbonyl]-amino}-acetic acid;
{[1-Chloro-6-(4-fluoro-phenoxy)-4-hydroxy-isoquinoline-3-carbonyl]-amino}-acetic acid;
{[6-(4-Fluoro-phenoxy)-4-hydroxy-isoquinoline-3-carbonyl]-amino}-acetic acid;
{[4-Hydroxy-7-(pyridin-4-yl sulfanyl)-isoquinoline-3-carbonyl]-amino}-acetic acid;
{[4-Hydroxy-6-(pyridin-4-yl sulfanyl)-isoquinoline-3-carbonyl]-amino}-acetic acid;
[(7-Benzenesulfinyl-4-hydroxy-isoquinoline-3-carbonyl)-amino]-acetic acid;
[(7-Benzenesulfonyl-4-hydroxy-isoquinoline-3-carbonyl)-amino]-acetic acid;
[(6-Benzenesulfinyl-4-hydroxy-isoquinoline-3-carbonyl)-amino]-acetic acid;
[(6-Benzenesulfonyl-4-hydroxy-isoquinoline-3-carbonyl)-amino]-acetic acid;
[(6-Amino-4-hydroxy-isoquinoline-3-carbonyl)-amino]-acetic acid;
{[4-Hydroxy-7-(4-methoxy-benzenesulfonylamino)-isoquinoline-3-carbonyl]-amino}-acetic acid;
{[4-Hydroxy-7-(3-phenyl-ureido)-isoquinoline-3-carbonyl]-amino}-acetic acid;
{[4-Hydroxy-6-(3-phenyl-ureido)-isoquinoline-3-carbonyl]-amino}-acetic acid;
[(4-Hydroxy-1-phenyl sulfanyl-isoquinoline-3-carbonyl)-amino]-acetic acid;
{[1-(4-Chloro-phenylsulfanyl)-4-hydroxy-isoquinoline-3-carbonyl]-amino}-acetic acid;
[(4-Hydroxy-1-p-tolylsulfanyl-isoquinoline-3-carbonyl)-amino]-acetic acid;
{[4-Hydroxy-1-(pyridin-2-ylsulfanyl)-isoquinoline-3-carbonyl]-amino}-acetic acid;
{[4-Hydroxy-1-(3-methoxy-phenyl sulfanyl)-isoquinoline-3-carbonyl]-amino}-acetic acid;
{[4-Hydroxy-1-(2-methoxy-phenyl sulfanyl)-isoquinoline-3-carbonyl]-amino}-acetic acid;
{[4-Hydroxy-1-(naphthalen-2-ylsulfanyl)-isoquinoline-3-carbonyl]-amino}-acetic acid;
[(1-Benzenesulfinyl-4-hydroxy-isoquinoline-3-carbonyl)-amino]-acetic acid;
[(1-Benzenesulfonyl-4-hydroxy-isoquinoline-3-carbonyl)-amino]-acetic acid;
{[4-Hydroxy-7-(pyridin-2-yl sulfanyl)-isoquinoline-3-carbonyl]-amino}-acetic acid;
{[4-Hydroxy-6-(pyridin-2-yl sulfanyl)-isoquinoline-3-carbonyl]-amino}-acetic acid;

[(1-Chloro-4-hydroxy-6,7-diphenoxy-isoquinoline-3-carbonyl)-amino]-acetic acid;
[(4-Hydroxy-6,7-diphenoxy-isoquinoline-3-carbonyl)-amino]-acetic acid;
({4-Hydroxy-7-[4-(toluene-4-sulfonylamino)-phenoxy]-isoquinoline-3-carbonyl}-amino)-acetic acid;
{[4-Hydroxy-7-(4-nitro-phenoxy)-isoquinoline-3-carbonyl]-amino}-acetic acid;
[(4-Mercapto-7-phenoxy-isoquinoline-3-carbonyl)-amino]-acetic acid;
[(4-Mercapto-7-trifluoromethyl-isoquinoline-3-carbonyl)-amino]-acetic acid;
{[7-(4-Benzenesulfonylamino-phenoxy)-4-hydroxy-isoquinoline-3-carbonyl]-amino}-acetic acid;
{[4-Hydroxy-7-(4-methanesulfonylamino-phenoxy)-isoquinoline-3-carbonyl]-amino}-acetic acid;
{[7-(4-Chloro-phenoxy)-4-hydroxy-isoquinoline-3-carbonyl]-amino}-acetic acid;
{[6-(4-Chloro-phenoxy)-4-hydroxy-isoquinoline-3-carbonyl]-amino}-acetic acid;
{[6-(3-Fluoro-5-methoxy-phenoxy)-4-hydroxy-isoquinoline-3-carbonyl]-amino}-acetic acid;
{[7-(3-Fluoro-5-methoxy-phenoxy)-4-hydroxy-isoquinoline-3-carbonyl]-amino}-acetic acid;
{[7-(3,4-Difluoro-phenoxy)-4-hydroxy-isoquinoline-3-carbonyl]-amino}-acetic acid;
{[6-(3,4-Difluoro-phenoxy)-4-hydroxy-isoquinoline-3-carbonyl]-amino}-acetic acid;
{[4-Hydroxy-7-(4-trifluoromethoxy-phenoxy)-isoquinoline-3-carbonyl]-amino}-acetic acid;
{[4-Hydroxy-6-(4-trifluoromethoxy-phenoxy)-isoquinoline-3-carbonyl]-amino}-acetic acid;
2-(S)-{[7-(4-Chloro-phenoxy)-4-hydroxy-isoquinoline-3-carbonyl]-amino}-propionic acid;
2-(S)-{[6-(4-Chloro-phenoxy)-4-hydroxy-isoquinoline-3-carbonyl]-amino}-propionic acid;
2-{[7-(3,4-Difluoro-phenoxy)-4-hydroxy-isoquinoline-3-carbonyl]-amino}-propionic acid;
2-(S)-[(4-Hydroxy-7-phenylsulfanyl-isoquinoline-3-carbonyl)-amino]-propionic acid.,
2-(R)-[(4-Hydroxy-7-phenylsulfanyl-isoquinoline-3-carbonyl)-amino]-propionic acid;
2-(R)-[(4-Hydroxy-7-phenoxy-isoquinoline-3-carbonyl)-amino]-propionic acid;
2-(S)-{[4-Hydroxy-7-(4-methoxy-phenoxy)-isoquinoline-3-carbonyl]-amino}-propionic acid;
2-(S)-[(7-Benzenesulfonyl-4-hydroxy-isoquinoline-3-carbonyl)-amino]-propionic acid;
(R)-2-[(4-Hydroxy-1-methoxymethyl-7-phenoxy-isoquinoline-3-carbonyl)-amino]-propionic acid;
(S)-2-[(4-Hydroxy-1-methoxymethyl-7-phenoxy-isoquinoline-3-carbonyl)-amino]-propionic acid;
(S)-2-[(4-Mercapto-7-phenoxy-isoquinoline-3-carbonyl)-amino]-propionic acid;
(S)-2-{[1-(4-Chloro-phenylsulfanyl)-4-hydroxy-isoquinoline-3-carbonyl]-amino}-propionic acid;
(R)-2-{[1-(4-Chloro-phenylsulfanyl)-4-hydroxy-isoquinoline-3-carbonyl]-amino}-propionic acid;
[(4-Hydroxy-7-phenyl sulfanyl-isoquinoline-3-carbonyl)-amino]-acetic acid;
[(4-Hydroxy-6-phenyl sulfanyl-isoquinoline-3-carbonyl)-amino]-acetic acid;
[(1-Chloro-4-hydroxy-7-phenylsulfanyl-isoquinoline-3-carbonyl)-amino]-acetic acid;
[(1-Chloro-4-hydroxy-6-phenylsulfanyl-isoquinoline-3-carbonyl)-amino]-acetic acid;
[(1-Bromo-4-hydroxy-7-phenylsulfanyl-isoquinoline-3-carbonyl)-amino]-acetic acid;
[(1-Bromo-4-hydroxy-6-phenylsulfanyl-isoquinoline-3-carbonyl)-amino]-acetic acid;
[(4-Hydroxy-7-phenoxy-isoquinoline-3-carbonyl)-amino]-acetic acid;
[(4-Hydroxy-6-phenoxy-isoquinoline-3-carbonyl)-amino]-acetic acid;
[(1-Chloro-4-hydroxy-7-phenoxy-isoquinoline-3-carbonyl)-amino]-acetic acid;
[(1-Chloro-4-hydroxy-6-phenoxy-isoquinoline-3-carbonyl)-amino]-acetic acid;
[(1-Bromo-4-hydroxy-7-phenoxy-isoquinoline-3-carbonyl)-amino]-acetic acid;
[(1-Bromo-4-hydroxy-6-phenoxy-isoquinoline-3-carbonyl)-amino]-acetic acid;
{[7-(2,6-Dimethyl-phenoxy)-4-hydroxy-isoquinoline-3-carbonyl]-amino}-acetic acid;
{[1-Chloro-7-(2,6-dimethyl-phenoxy)-4-hydroxy-isoquinoline-3-carbonyl]-amino}-acetic acid;
{[1-Bromo-7-(2,6-dimethyl-phenoxy)-4-hydroxy-isoquinoline-3-carbonyl]-amino}-acetic acid;
[(1-Bromo-7-chloro-4-hydroxy-isoquinoline-3-carbonyl)-amino]-acetic acid;
[(1-Bromo-6-chloro-4-hydroxy-isoquinoline-3-carbonyl)-amino]-acetic acid;
[(1-Bromo-4-hydroxy-7-trifluoromethyl-isoquinoline-3-carbonyl)-amino]-acetic acid;
[(1-Bromo-4-hydroxy-6-trifluoromethyl-isoquinoline-3-carbonyl)-amino]-acetic acid;
[(4-Hydroxy-1-phenoxy-isoquinoline-3-carbonyl)-amino]-acetic acid;
[(1,7-dibromo-4-hydroxy-isoquinoline-3-carbonyl)-amino]-acetic acid;
[(7-Bromo-1-chloro-4-hydroxy-isoquinoline-3-carbonyl)-amino]-acetic acid;
[(6-Bromo-4-hydroxy-isoquinoline-3-carbonyl)-amino]-acetic acid;
[(1-Bromo-7-fluoro-4-hydroxy-isoquinoline-3-carbonyl)-amino]-acetic acid;
[(7-Fluoro-4-hydroxy-isoquinoline-3-carbonyl)-amino]-acetic acid;
[(1-Chloro-7-fluoro-4-hydroxy-isoquinoline-3-carbonyl)-amino]-acetic acid;
[(1-Chloro-4-hydroxy-benzo[g]isoquinoline-3-carbonyl)-amino]-acetic acid;
[(1-Bromo-4-hydroxy-isoquinoline-3-carbonyl)-amino]-acetic acid;
[(4-Hydroxy-6-phenyl-isoquinoline-3-carbonyl)-amino]-acetic acid;
[(4-Hydroxy-7-phenyl-isoquinoline-3-carbonyl)-amino]-acetic acid;
[(1-Chloro-4-hydroxy-6-phenyl-isoquinoline-3-carbonyl)-amino]-acetic acid;
[(1-Chloro-4-hydroxy-7-phenyl-isoquinoline-3-carbonyl)-amino]-acetic acid;
[(1-Bromo-4-hydroxy-6-phenyl-isoquinoline-3-carbonyl)-amino]-acetic acid;
[(1-Bromo-4-hydroxy-7-phenyl-isoquinoline-3-carbonyl)-amino]-acetic acid;
[(4-Hydroxy-5-phenyl-isoquinoline-3-carbonyl)-amino]-acetic acid;
[(4-Hydroxy-8-phenyl-isoquinoline-3-carbonyl)-amino]-acetic acid;
[(1-Chloro-4-hydroxy-5-phenyl-isoquinoline-3-carbonyl)-amino]-acetic acid;

[(1-Chloro-4-hydroxy-8-phenyl-isoquinoline-3-carbonyl)-amino]-acetic acid;
[(1-Bromo-4-hydroxy-5-phenyl-isoquinoline-3-carbonyl)-amino]-acetic acid;
[(1-Bromo-4-hydroxy-8-phenyl-isoquinoline-3-carbonyl)-amino]-acetic acid;
[(1-Ethylsulfanyl-4-hydroxy-isoquinoline-3-carbonyl)-amino]-acetic acid;
{[4-Hydroxy-1-(4-methoxy-phenyl sulfanyl)-isoquinoline-3-carbonyl]-amino}-acetic acid;
[(1-Chloro-4-hydroxy-7-iodo-isoquinoline-3-carbonyl)-amino]-acetic acid;
[(1-Chloro-4-hydroxy-6-iodo-isoquinoline-3-carbonyl)-amino]-acetic acid;
[(4-Hydroxy-7-iodo-isoquinoline-3-carbonyl)-amino]-acetic acid;
[(1-Bromo-4-hydroxy-7-methyl-isoquinoline-3-carbonyl)-amino]-acetic acid;
[(1-Bromo-7-butoxy-4-hydroxy-isoquinoline-3-carbonyl)-amino]-acetic acid;
[(1-Bromo-6-butoxy-4-hydroxy-isoquinoline-3-carbonyl)-amino]-acetic acid;
[(6-Benzyloxy-1-chloro-4-hydroxy-isoquinoline-3-carbonyl)-methyl-amino]-acetic acid;
[(1-Chloro-4-hydroxy-isoquinoline-3-carbonyl)-methyl-amino]-acetic acid;
[(1-Chloro-4-hydroxy-6-isopropoxy-isoquinoline-3-carbonyl)-methyl-amino]-acetic acid;
[(1-Chloro-4-hydroxy-7-isopropoxy-isoquinoline-3-carbonyl)-methyl-amino]-acetic acid;
[Carboxymethyl-(1-chloro-4-hydroxy-isoquinoline-3-carbonyl)-amino]-acetic acid;
[Carboxymethyl-(1-chloro-4-hydroxy-6-isopropoxy-isoquinoline-3-carbonyl)-amino]-acetic acid;
1-Chloro-4-hydroxy-isoquinoline-3-carboxylic acid (2-amino-ethyl)-amide (trifluoro-acetic acid salt);
1-Chloro-4-hydroxy-isoquinoline-3-carboxylic acid (2-methoxy-ethyl)-amide;
1-Chloro-4-hydroxy-isoquinoline-3-carboxylic acid (2-hydroxy-ethyl)-amide;
1-Chloro-4-hydroxy-isoquinoline-3-carboxylic acid (2-dimethylamino-ethyl)-amide;
1-Chloro-4-hydroxy-isoquinoline-3-carboxylic acid (2-acetylamino-ethyl)-amide;
1-Chloro-4-hydroxy-6-isopropoxy-isoquinoline-3-carboxylic acid (2-hydroxy-ethyl)-amide;
1-Chloro-4-hydroxy-6-isopropoxy-isoquinoline-3-carboxylic acid (2-methoxy-ethyl)-amide;
1-Chloro-4-hydroxy-6-isopropoxy-isoquinoline-3-carboxylic acid (2-amino-ethyl)-amide (trifluoro-acetic acid salt);
1-Chloro-4-hydroxy-6-isopropoxy-isoquinoline-3-carboxylic acid (2-dimethylamino-ethyl)-amide;
1-Chloro-4-hydroxy-7-isopropoxy-isoquinoline-3-carboxylic acid (2-amino-ethyl)-amide (trifluoro-acetic acid salt);
1-Chloro-4-hydroxy-7-isopropoxy-isoquinoline-3-carboxylic acid (2-methoxy-ethyl)-amide;
1-Chloro-4-hydroxy-7-isopropoxy-isoquinoline-3-carboxylic acid (2-dimethylamino-ethyl)-amide;
1-Chloro-4-hydroxy-7-isopropoxy-isoquinoline-3-carboxylic acid (2-hydroxy-ethyl)-amide;
(S)-2-[(6-Benzyloxy-1-chloro-4-hydroxy-isoquinoline-3-carbonyl)-amino]-propionic acid;
(R)-2-[(1-Chloro-4-hydroxy-isoquinoline-3-carbonyl)-amino]-3-hydroxy-propionic acid;
(S)-2-[(1-Chloro-4-hydroxy-isoquinoline-3-carbonyl)-amino]-3-hydroxy-propionic acid;
(R)-2-[(1-Chloro-4-hydroxy-6-isopropoxy-isoquinoline-3-carbonyl)-amino]-3-hydroxy-propionic acid;
(S)-2-[(1-Chloro-4-hydroxy-6-isopropoxy-isoquinoline-3-carbonyl)-amino]-3-hydroxy-propionic acid;
(R)-2-[(1-Chloro-4-hydroxy-7-isopropoxy-isoquinoline-3-carbonyl)-amino]-3-hydroxy-propionic acid;
(S)-2-[(1-Chloro-4-hydroxy-7-isopropoxy-isoquinoline-3-carbonyl)-amino]-3-hydroxy-propionic acid;
2-[(1-Chloro-4-hydroxy-isoquinoline-3-carbonyl)-amino]-2-methyl-propionic acid;
2-[(1-Chloro-4-hydroxy-6-isopropoxy-isoquinoline-3-carbonyl)-amino]-2-methyl-propionic acid;
(R)-2-[(1-Chloro-4-hydroxy-isoquinoline-3-carbonyl)-amino]-3-(1H-imidazol-4-yl)-propionic acid (trifluoroacetic acid salt);
(S)-2-[(1-Chloro-4-hydroxy-isoquinoline-3-carbonyl)-amino]-3-(1H-imidazol-4-yl)-propionic acid (trifluoroacetic acid salt);
(R)-2-[(1-Chloro-4-hydroxy-isoquinoline-3-carbonyl)-amino]-3-methyl-butyric acid;
(S)-2-[(1-Chloro-4-hydroxy-isoquinoline-3-carbonyl)-amino]-3-methyl-butyric acid;
(R)-2-[(1-Chloro-4-hydroxy-6-isopropoxy-isoquinoline-3-carbonyl)-amino]-3-methyl-butyric acid;
(S)-2-[(1-Chloro-4-hydroxy-6-isopropoxy-isoquinoline-3-carbonyl)-amino]-3-methyl-butyric acid;
(R)-2-[(1-Chloro-4-hydroxy-7-isopropoxy-isoquinoline-3-carbonyl)-amino]-3-methyl-butyric acid;
(S)-2-[(1-Chloro-4-hydroxy-7-isopropoxy-isoquinoline-3-carbonyl)-amino]-3-methyl-butyric acid;
(S)-2-[(6-Benzyloxy-1-chloro-4-hydroxy-isoquinoline-3-carbonyl)-amino]-3-methyl-butyric acid;
(R)-2-[(1-Chloro-4-hydroxy-isoquinoline-3-carbonyl)-amino]-3-phenyl-propionic acid;
(S)-2-[(1-Chloro-4-hydroxy-isoquinoline-3-carbonyl)-amino]-3-phenyl-propionic acid;
(R)-2-[(1-Chloro-4-hydroxy-6-isopropoxy-isoquinoline-3-carbonyl)-amino]-3-phenyl-propionic acid;
(S)-2-[(1-Chloro-4-hydroxy-6-isopropoxy-isoquinoline-3-carbonyl)-amino]-3-phenyl-propionic acid;
(R)-2-[(1-Chloro-4-hydroxy-7-isopropoxy-isoquinoline-3-carbonyl)-amino]-3-phenyl-propionic acid;
(S)-2-[(1-Chloro-4-hydroxy-7-isopropoxy-isoquinoline-3-carbonyl)-amino]-3-phenyl-propionic acid;
(R)-2-[(1-Chloro-4-hydroxy-isoquinoline-3-carbonyl)-amino]-3-(4-hydroxy-phenyl)-propionic acid;
(S)-2-[(1-Chloro-4-hydroxy-isoquinoline-3-carbonyl)-amino]-3-(4-hydroxy-phenyl)-propionic acid;
(R)-2-[(1-Chloro-4-hydroxy-6-isopropoxy-isoquinoline-3-carbonyl)-amino]-3-(4-hydroxy-phenyl)-propionic acid;
(S)-2-[(1-Chloro-4-hydroxy-6-isopropoxy-isoquinoline-3-carbonyl)-amino]-3-(4-hydroxy-phenyl)-propionic acid;
(R)-2-[(1-Chloro-4-hydroxy-7-isopropoxy-isoquinoline-3-carbonyl)-amino]-3-(4-hydroxy-phenyl)-propionic acid;
(S)-2-[(1-Chloro-4-hydroxy-7-isopropoxy-isoquinoline-3-carbonyl)-amino]-3-(4-hydroxy-phenyl)-propionic acid;
(R)-2-[(1-Chloro-4-hydroxy-6-isopropoxy-isoquinoline-3-carbonyl)-amino]-pentanoic acid;
(S)-2-[(1-Chloro-4-hydroxy-6-isopropoxy-isoquinoline-3-carbonyl)-amino]-pentanoic acid;
(R)-1-(1-Chloro-4-hydroxy-isoquinoline-3-carbonyl)-pyrrolidine-2-carboxylic acid;
(S)-1-(1-Chloro-4-hydroxy-isoquinoline-3-carbonyl)-pyrrolidine-2-carboxylic acid;

(R)-1-(1-Chloro-4-hydroxy-6-isopropoxy-isoquinoline-3-carbonyl)-pyrrolidine-2-carboxylic acid;
(S)-1-(1-Chloro-4-hydroxy-6-isopropoxy-isoquinoline-3-carbonyl)-pyrrolidine-2-carboxylic acid;
(R)-6-Amino-2-[(1-chloro-4-hydroxy-isoquinoline-3-carbonyl)-amino]-hexanoic acid (trifluoro-acetic acid salt);
(S)-6-Amino-2-[(1-chloro-4-hydroxy-isoquinoline-3-carbonyl)-amino]-hexanoic acid (trifluoro-acetic acid salt);
(R)-6-Amino-2-[(1-chloro-4-hydroxy-6-isopropoxy-isoquinoline-3-carbonyl)-amino]-hexanoic acid; trifluoroacetic acid salt;
(S)-6-Amino-2-[(1-chloro-4-hydroxy-6-isopropoxy-isoquinoline-3-carbonyl)-amino]-hexanoic acid (trifluoro-acetic acid salt);
(R)-6-Amino-2-[(1-chloro-4-hydroxy-7-isopropoxy-isoquinoline-3-carbonyl)-amino]-hexanoic acid; trifluoroacetic acid salt;
(S)-6-Amino-2-[(1-chloro-4-hydroxy-7-isopropoxy-isoquinoline-3-carbonyl)-amino]-hexanoic acid (trifluoro-acetic acid salt);
(R)-2-[(1-Chloro-4-hydroxy-isoquinoline-3-carbonyl)-amino]-succinic acid;
(S)-2-[(1-Chloro-4-hydroxy-isoquinoline-3-carbonyl)-amino]-succinic acid;
(R)-2-[(1-Chloro-4-hydroxy-6-isopropoxy-isoquinoline-3-carbonyl)-amino]-succinic acid;
(S)-2-[(1-Chloro-4-hydroxy-6-isopropoxy-isoquinoline-3-carbonyl)-amino]-succinic acid;
(R)-2-[(1-Chloro-4-hydroxy-7-isopropoxy-isoquinoline-3-carbonyl)-amino]-succinic acid;
1-[(1-Chloro-4-hydroxy-isoquinoline-3-carbonyl)-amino]-cyclopropanecarboxylic acid;
1-[(1-Chloro-4-hydroxy-6-isopropoxy-isoquinoline-3-carbonyl)-amino]-cyclopropanecarboxylic acid;
Dideutero-[(1-chloro-4-hydroxy-isoquinoline-3-carbonyl)-amino]-acetic acid;
(R)-2-[(6-Benzyloxy-1-chloro-4-hydroxy-isoquinoline-3-carbonyl)-amino]-propionic acid;
(S)-2-[(7-Benzyloxy-1-chloro-4-hydroxy-isoquinoline-3-carbonyl)-amino]-propionic acid;
(R)-2-[(7-Benzyloxy-1-chloro-4-hydroxy-isoquinoline-3-carbonyl)-amino]-propionic acid;
(S)-2-[(1-Chloro-4-hydroxy-isoquinoline-3-carbonyl)-amino]-propionic acid;
(R)-2-[(1-Chloro-4-hydroxy-isoquinoline-3-carbonyl)-amino]-propionic acid;
(S)-2-[(6-Isopropoxy-1-chloro-4-hydroxy-isoquinoline-3-carbonyl)-amino]-propionic acid;
(R)-2-[6-Isopropoxy-1-chloro-4-hydroxy-isoquinoline-3-carbonyl)-amino]-propionic acid;
(S)-2-[(7-Isopropoxy-1-chloro-4-hydroxy-isoquinoline-3-carbonyl)-amino-propionic acid;
(R)-2-[(7-Isopropoxy-1-chloro-4-hydroxy-isoquinoline-3-carbonyl)-amino]propionic acid;
1-Chloro-4-hydroxy-6-isopropoxy-isoquinoline-3-carboxylic acid (2-hydroxy-1-hydroxymethyl-ethyl)-amide;
1-Chloro-4-hydroxy-7-isopropoxy-isoquinoline-3-carboxylic acid (2-hydroxy-1-hydroxymethyl-ethyl)-amide;
1-Chloro-4-hydroxy-isoquinoline-3-carboxylic acid (2-hydroxy-1-hydroxymethyl-ethyl)-amide;
{[7-(3,5-Difluoro-phenoxy)-4-hydroxy-isoquinoline-3-carbonyl]-amino}-acetic acid;
{[6-(3,5-Difluoro-phenoxy)-4-hydroxy-isoquinoline-3-carbonyl]-amino}-acetic acid;
({ 7-[4-(4-Fluoro-phenoxy)-phenoxy]-4-hydroxy-isoquinoline-3-carbonyl}-amino)-acetic acid;
({ 6-[4-(4-Fluoro-phenoxy)-phenoxy]-4-hydroxy-isoquinoline-3-carbonyl}-amino)-acetic acid;
{[7-(3-Chloro-4-fluoro-phenoxy)-4-hydroxy-isoquinoline-3-carbonyl]-amino}-acetic acid;
{[6-(3-Chloro-4-fluoro-phenoxy)-4-hydroxy-isoquinoline-3-carbonyl]-amino}-acetic acid;
(S)-2-{[7-(3-Fluoro-5-methoxy-phenoxy)-4-hydroxy-isoquinoline-3-carbonyl]-amino}-propionic acid;
2-(S)-[(7-Cyclohexyloxy-4-hydroxy-isoquinoline-3-carbonyl)-amino]-propionic acid;
2-(S)-{[7-(4-Fluoro-phenoxy)-4-hydroxy-1-methyl-isoquinoline-3-carbonyl]-amino}-propionic acid;
2-(S)-{[7-(4-Fluoro-phenoxy)-4-hydroxy-isoquinoline-3-carbonyl]-amino}-propionic acid;
2-(S)-[(4-Hydroxy-1-methyl-7-phenoxy-isoquinoline-3-carbonyl)-amino]-propionic acid;
2-(S)-[(4-Hydroxy-1-methyl-7-phenylsulfanyl-isoquinoline-3-carbonyl)-amino]-propionic acid;
2-(S)-{[4-Hydroxy-7-(4-trifluoromethyl-phenoxy)-isoquinoline-3-carbonyl]-amino}-propionic acid;
{[7-(4-Chloro-phenoxy)-4-hydroxy-1-methyl-isoquinoline-3-carbonyl]-amino}-acetic acid;
{[6-(4-Chloro-phenoxy)-4-hydroxy-1-methyl-isoquinoline-3-carbonyl]-amino}-acetic acid;
{[7-(3,5-Difluoro-phenoxy)-4-hydroxy-1-methyl-isoquinoline-3-carbonyl]-amino}-acetic acid;
{[4-Hydroxy-7-(4-methoxy-phenoxy)-1-methyl-isoquinoline-3-carbonyl]-amino}-acetic acid;
{[4-Hydroxy-6-(4-methoxy-phenoxy)-1-methyl-isoquinoline-3-carbonyl]-amino}-acetic acid;
[(6-Cyclohexyloxy-4-hydroxy-isoquinoline-3-carbonyl)-amino]-acetic acid;
[(7-Cyclohexyloxy-4-hydroxy-isoquinoline-3-carbonyl)-amino]-acetic acid;
[(7-Cyclohexyloxy-4-hydroxy-1-methyl-isoquinoline-3-carbonyl)-amino]-acetic acid;
[(7-Cyclohexylsulfanyl-4-hydroxy-isoquinoline-3-carbonyl)-amino]-acetic acid;
[(7-Cyclohexanesulfonyl-4-hydroxy-isoquinoline-3-carbonyl)-amino]-acetic acid;
[(4-Hydroxy-1-isobutyl-isoquinoline-3-carbonyl)-amino]-acetic acid;
[(4-Hydroxy-1-pyridin-2-yl-isoquinoline-3-carbonyl)-amino]-acetic acid;
[(1-Ethyl-4-hydroxy-7-phenoxy-isoquinoline-3-carbonyl)-amino]-acetic acid;
[(1-Dimethylaminomethyl-4-hydroxy-7-phenylsulfanyl-isoquinoline-3-carbonyl)-amino]-acetic acid;
[(4-Hydroxy-1-methyl-7-phenylsulfanyl-isoquinoline-3-carbonyl)-amino]-acetic acid;
{[4-Hydroxy-1-methyl-7-(4-trifluoromethyl-phenoxy)-isoquinoline-3-carbonyl]-amino}-acetic acid; and pharmaceutically acceptable salts, esters and prodrugs thereof.

In still another embodiment of the invention, a pharmaceutical composition is provided comprising a pharmaceutically acceptable excipient or carrier and a therapeutically effective amount of a compound of formula I or a mixture of such compounds.

Also provided are methods for treating, preventing or pretreating a condition mediated at least in part by HIF and/or EPO is provided. The method comprises administering to a mammalian patient a therapeutically effective amount of a compound having the structure of formula I above with the proviso that the compound is not selected from the group consisting of:

N-((1-chloro-4-hydroxy-7-(2-propyloxy) isoquinolin-3-yl)-carbonyl)-glycine,
N-((1-chloro-4-hydroxy-6-(2-propyloxy) isoquinolin-3-yl)-carbonyl)-glycine,
N-((1-chloro-4-hydroxy-isoquinoline-3-carbonyl)-amino) acetic acid,
N-((1-chloro-4-hydroxy-7-methoxyisoquinolin-3-yl)-carbonyl)-glycine,
N-((1-chloro-4-hydroxy-6-methoxyisoquinolin-3-yl)-carbonyl)-glycine,
N-((7-butyloxy-1-chloro-4-hydroxyisoquinolin-3-yl)-carbonyl)-glycine,
N-((6-benzyloxy-1-chloro-4-hydroxy-isoquinoline-3-carbonyl)-amino)-acetic acid,
N-((7-benzyloxy-1-chloro-4-hydroxy-isoquinoline-3-carbonyl)-amino)-acetic acid,
N-((8-chloro-4-hydroxyisoquinolin-3-yl)-carbonyl)-glycine,
N-((7-butoxy-4-hydroxy-isoquinoline-3-carbonyl)-amino) acetic acid, and
((7-benzyloxy-1-chloro-4-hydroxy-isoquinoline-3-carbonyl)amino)acetic acid methyl ester.

A further embodiment of this invention provides a method of inhibiting the activity hydroxylase enzyme which modifies the alpha subunit of hypoxia inducible factor.

This invention also contemplates a composition comprising the compound of formula 1 or a mixture of compounds of formula 1 in combination with at least one additional therapeutic agent. Preferably, the additional therapeutic agent is erythropoietin.

DETAILED DESCRIPTION OF THE INVENTION

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. (See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, $2^{nd}$ edition, Vols. I-III, Cold Spring Harbor Laboratory Press; Ausubel, F. M. et al., eds. (1999) Short Protocols in Molecular Biology, $4^{th}$ edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag)).

The term "anemia" as used herein refers to any abnormality in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

Anemia can arise due to conditions such as acute or chronic kidney disease, infections, inflammation, cancer, irradiation, toxins, diabetes, and surgery. Infections may be due to, e.g., virus, bacteria, and/or parasites, etc. Inflammation may be due to infection, autoimmune disorders, such as rheumatoid arthritis, etc. Anemia can also be associated with blood loss due to, e.g., stomach ulcer, duodenal ulcer, hemorrhoids, cancer of the stomach or large intestine, trauma, injury, surgical procedures, etc. Anemia is further associated with radiation therapy, chemotherapy, and kidney dialysis. Anemia is also associated with HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure that result in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively and refer to any condition deviating from normal.

The terms "anemic conditions" and "anemic disorders" refer to any condition, disease, or disorder associated with anemia. Such disorders include, but are not limited to, those disorders listed above. Anemic disorders further include, but are not limited to, aplastic anemia, autoimmune hemolytic anemia, bone marrow transplantation, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, sideroblastic anemia, refractory anemia with excess of blasts, rheumatoid arthritis, Shwachman syndrome, sickle cell disease, thalassemia major, thalassemia minor, thrombocytopenic purpura, etc.

The term "erythropoietin-associated conditions" is used inclusively and refers to any condition associated with below normal, abnormal, or inappropriate modulation of erythropoietin. Erythropoietin-associated conditions include any condition wherein an increase in EPO level would provide therapeutic benefit. Levels of erythropoietin associated with such conditions can be determined by any measure accepted and utilized by those of skill in the art.

Erythropoietin-associated conditions include anemic conditions such as those described above.

Erythropoietin-associated conditions further include neurological disorders and/or injuries, including cases of stroke, trauma, epilepsy, neurodegenerative disease and the like, wherein erythropoietin may provide a neuroprotective effect. Neurodegenerative diseases contemplated by the invention include Alzheimer's disease, Parkinson's disease, Huntington's disease, and the like.

The term "erythropoietin" refers to any recombinant or naturally occurring erythropoietin including, e.g., human erythropoietin (GenBank Accession No. AAA52400; Lin et al. (1985) Proc Nat'l Acad. Sci USA 82:7580-7584), EPO-ETIN human recombinant erythropoietin (Amgen, Inc., Thousand Oaks Calif.), ARANESP human recombinant erythropoietin (Amgen), PROCRIT human recombinant erythropoietin (Ortho Biotech Products, L.P., Raritan N.J.), etc.

The term "HIFα" refers to the alpha subunit of hypoxia inducible factor protein. HIFα may be any human or other mammalian protein, or fragment thereof, including human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130 and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675). HIFα may also be any non-mammalian protein or fragment thereof, including Xenopus laevis HIF-1α (Genbank Accession No. CAB96628), Drosophila melanogaster HIF-1α (Genbank Accession No. JC4851), and chicken HIF-1α (Genbank Accession No. BAA34234). HIFα gene sequences may also be obtained by routine cloning techniques, for example by using all or part of a HIFα gene sequence described above as a probe to recover and determine the sequence of a HIFα gene in another species.

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) J Biol. Chem 272:19253-19260), amino acid 556 to 575 (Tanimoto et al., supra), amino acid 557 to 571 (Srinivas et al. (1999) Biochem Biophys Res. Commun 260:557-561), and amino acid 556 to 575 (Ivan and Kaelin (2001) Science 292:464-468). Further, HIFα fragments include any fragment containing at least one occurrence of the motif LXXLAP, (SEQ ID NO:1) e.g., as occurs in the human HIF-1α native sequence at L397TLLAP (SEQ ID NO:2) and L559EMLAP (SEQ ID NO:3).

The terms "amino acid sequence" or "polypeptide" as used herein, e.g., to refer to HIFα and fragments thereof, contemplate an oligopeptide, peptide, or protein sequence, or to a fragment of any of these, and to naturally occurring or synthetic molecules. "Fragments" can refer to any portion of a sequence that retains at least one structural or functional characteristic of the protein. Immunogenic fragments or antigenic fragments are fragments of polypeptides, preferably, fragments of about five to fifteen amino acids in length, that retain at least one biological or immunological activity. Where "amino acid sequence" is used to refer to the polypeptide sequence of a naturally occurring protein molecule, "amino acid sequence" and like terms are not meant to limit the amino acid sequence to the complete native sequence associated with the recited protein molecule.

The term "related proteins" as used herein, for example, to refer to proteins related to HIFα prolyl hydroxylase, encompasses other 2-oxoglutarate dioxygenase enzymes, especially those family members that similarly require $Fe^{2+}$, 2-oxoglutarate, and oxygen to maintain hydroxylase activity. Such enzymes include, but are not limited to, e.g., procollagen lysyl hydroxylase, procollagen prolyl 4-hydroxylase, and Factor Inhibiting HIF (FIH), an asparaginyl hydroxylase responsible for regulating transactivation of HIFα. (GenBank Accession No. AAL27308; Mahon et al. (2001) Genes Dev 15:2675-2686; Lando et al. (2002) Science 295:858-861; and Lando et al. (2002) Genes Dev 16:1466-1471. See also Elkins et al. (2002) J Biol Chem C200644200, etc.)

The terms "HIF prolyl hydroxylase" and "HIF PH" refer to any enzyme capable of hydroxylating a proline residue in the HIF protein. Preferably, the proline residue hydroxylated by HIF PH includes the proline found within the motif LXXLAP, (SEQ ID NO:1) e.g., as occurs in the human HIF-1α native sequence at $L_{397}$TLLAP (SEQ ID NO:2) and $L_{559}$EMLAP (SEQ ID NO:3). HIF PH includes members of the Egl-Nine (EGLN) gene family described by Taylor (2001, Gene 275:125-132), and characterized by Aravind and Koonin (2001, Genome Biol 2: RESEARCH 0007), Epstein et al. (2001, Cell 107:43-54), and Bruick and McKnight (2001, Science 294:1337-1340). Examples of HIF PH enzymes include human SM-20 (EGLN1) (GenBank Accession No. AAG33965; Dupuy et al. (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF PH may include Caenorhabditis elegans EGL-9 (GenBank Accession No. AAD56365) and Drosophila melanogaster CG1114 gene product (GenBank Accession No. AAF52050). HIF PH also includes any fragment of the foregoing full-length proteins that retain at least one structural or functional characteristic.

The term "agonist" refers to a molecule that increases or prolongs the duration of the effect of a particular molecule. Agonists may include proteins, nucleic acids, carbohydrates, or any other molecules that increase the effect(s) of the target molecule.

The term "antagonist" refers to a molecule that decreases the extent or duration of the effect of the biological or immunological activity of a particular molecule. Antagonists may include proteins, nucleic acids, carbohydrates, antibodies, or any other molecules that decrease the effect(s) of the target molecule.

The term "microarray" refers to any arrangement of nucleic acids, amino acids, antibodies, etc., on a substrate. The substrate can be any suitable support, e.g., beads, glass, paper, nitrocellulose, nylon, or any appropriate membrane, etc. A substrate can be any rigid or semi-rigid support including, but not limited to, membranes, filters, wafers, chips, slides, fibers, beads, including magnetic or nonmagnetic beads, gels, tubing, plates, polymers, microparticles, capillaries, etc. The substrate can provide a surface for coating and/or can have a variety of surface forms, such as wells, pins, trenches, channels, and pores, to which the nucleic acids, amino acids, etc., may be bound.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The term "loading dose" as used herein refers to a single or multiple dose administered initially to rapidly achieve the desired pharmacological level. For example, a loading dose in reference to the methods of the invention refers to an initial dosing regimen that rapidly increases, e.g., the plasma concentration of a compound of the invention to a pharmaceutically active level.

The term "induction dose" as used herein refers to a repeated dose strength administered initially to rapidly achieve the desired physiological response. For example, an induction dose in reference to the methods of the invention refers to an initial dosing regimen that rapidly increases the hematocrit or hemoglobin level to within a target range, which may be at or below normal hematocrit/hemoglobin levels.

The term "maintenance dose" as used herein refers to the dose level administered after a loading or induction dose in order to maintain a desired physiological response. For example, a maintenance dose in reference to the methods of the invention refers to a dosing regimen that maintains hematocrit and/or hemoglobin within a desired target range, which may be at or below normal hematocrit/hemoglobin levels.

The term "sample" is used herein in its broadest sense. Samples may be derived from any source, for example, from bodily fluids, secretions, tissues, cells, or cells in culture including, but not limited to, saliva, blood, urine, serum, plasma, vitreous, synovial fluid, cerebral spinal fluid, amniotic fluid, and organ tissue (e.g., biopsied tissue); from chromosomes, organelles, or other membranes isolated from a cell; from genomic DNA, cDNA, RNA, mRNA, etc.; and from cleared cells or tissues, or blots or imprints from such cells or tissues. Samples may be derived from any source, such as, for example, a human subject, or a non-human mammalian subject, etc. Also contemplated are samples derived from any animal model of disease. A sample can be in solution or can be, for example, fixed or bound to a substrate. A sample can refer to any material suitable for testing for the presence of erythropoietin or HIFα or to fragments thereof, or suitable for screening for molecules that increase endogenous levels of erythropoietin or HIFα or to fragments thereof. Methods for obtaining such samples are within the level of skill in the art.

The term "subject" is used herein in its broadest sense. Subjects may include isolated cells, either prokaryotic or eukaryotic, or tissues grown in culture. In certain embodiments, a subject is an animal, particularly an animal selected from a mammalian species including rat, rabbit, bovine, ovine, porcine, canine, feline, murine, equine, and primate, particularly human.

As used herein, "alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, t-butyl, n-pentyl and the like.

"Substituted alkyl" refers to an alkyl group, of from 1 to 10 carbon atoms, preferably, 1 to 5 carbon atoms, having from 1 to 5 substituents, preferably 1 to 3 substituents, independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thiol, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{40}$R$^{40}$ where each R$^{40}$ is hydrogen or alkyl, —NR$^{40}$S(O)$_2$-alkyl, —NR$^{40}$S(O)$_2$-substituted alkyl, —NR$^{40}$S(O)$_2$-aryl, —NR$^{40}$S(O)$_2$-substituted aryl, —NR$^{40}$S(O)$_2$-heteroaryl, —NR$^{40}$S(O)$_2$-substituted heteroaryl, —NR$^{40}$S(O)$_2$-heterocyclic, —NR$^{40}$S(O)$_2$-substituted heterocyclic, —NR$^{40}$S(O)$_2$—NR$^{40}$-alkyl, —NR$_{40}$S(O)$_2$—NR$^{40}$-aryl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic where each R$^{40}$ is hydrogen or alkyl.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to a —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "aminoacyl" or as a prefix "carbamoyl" or "carboxamide" or "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl group preferably having from 2 to 6 carbon atoms and more preferably 2 to 4 carbon atoms and having at least 1 and preferably from 1 to 2 sites of alkenyl unsaturation.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkynyl" refers to alkynyl group preferably having from 2 to 6 carbon atoms and more preferably 2 to 3 carbon atoms and having at least 1 and preferably from 1-2 sites of alkynyl unsaturation.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Amino" refers to the group —NH$_2$.

"Substituted amino" refers to the group —NR$^{41}$R$^{41}$, where each R$^{41}$ group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R$^{41}$ groups are not hydrogen; or the R$^{41}$ groups can be joined together with the nitrogen atom to form a heterocyclic or substituted heterocyclic ring.

"Acylamino" refers to the groups —NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are defined herein.

"Carbonyloxyamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" or as a prefix "carbamoyloxy" or "substituted carbamoyloxy" refers to the groups —OC(O)NR$^{47}$R$^{47}$ where each R$^{47}$ is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each R$^{47}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{49}$C(O)NR$^{49}$— where R$^{49}$ is selected from the group consisting of hydrogen and alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is the aryl group. Preferred aryls include phenyl and naphthyl.

"Substituted aryl" refers to aryl groups, as defined herein, which are substituted with from 1 to 4, preferably 1-3, substituents selected from the group consisting of hydroxy, acyl, acylamino, carbonylaminothio, acyloxy, alkyl, substituted alkyl, alkoxy, substituted alkoxy, alkenyl, substituted alkenyl, alkynyl, substituted alkynyl, amidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino, halo, nitro, heteroaryl, substituted heteroaryl, heterocyclic, substituted heterocyclic, oxycarbonylamino, oxythiocarbonylamino, —S(O)$_2$- alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{51}$R$^{51}$ where each R$^{51}$ is hydrogen or alkyl, —NR$^{51}$S(O)$_2$-alkyl, —NR$^{51}$S(O)$_2$-substituted alkyl, —NR$^{51}$S(O)$_2$-aryl, —NR$^{51}$S(O)$_2$-substituted aryl, —NR$^{51}$S(O)$_2$-heteroaryl, —NR$^{51}$S(O)$_2$-substituted heteroaryl, —NR$^{51}$S(O)$_2$-heterocyclic, —NR$^{51}$S(O)$_2$-substituted heterocyclic, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^{51}$-heterocyclic, —NR$^{51}$S(O)$_2$—NR$^{51}$-substituted heterocyclic where each R$^{51}$ is hydrogen or alkyl, wherein each of the terms is as defined herein.

"Aryloxy" refers to the group aryl-O— that includes, by way of example, phenoxy, naphthoxy, and the like.

"Substituted aryloxy" refers to substituted aryl-O— groups.

"Aryloxyaryl" refers to the group -aryl-O-aryl.

"Substituted aryloxyaryl" refers to aryloxyaryl groups substituted with from 1 to 3 substituents on either or both aryl rings as defined above for substituted aryl.

"Carboxyl" refers to —COOH or salts thereof.

"Carboxyl esters" refers to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Substituted cycloalkyl" refers to a cycloalkyl group, having from 1 to 5 substituents selected from the group consisting of oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to an aromatic group of from 1 to 15 carbon atoms, preferably from 1 to 10 carbon atoms, and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl). Preferred heteroaryls include pyridinyl, pyrrolyl, indolyl, thiophenyl, and furyl.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl provided that the point of attachment is at the heterocycle.

"Substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Thiol" or "mercapto" refers to the group —SH.

"Alkylsulfanyl" and "alkylthio" refer to the groups —S-alkyl where alkyl is as defined above.

"Substituted alkylthio" and "substituted alkylsulfanyl" refer to the group —S-substituted alkyl is as defined above.

"Cycloalkylthio" or "cycloalkylsulfanyl" refers to the groups —S-cycloalkyl where cycloalkyl is as defined above.

"Substituted cycloalkylthio" refers to the group —S-substituted cycloalkyl where substituted cycloalkyl is as defined above.

"Arylthio" refers to the group —S-aryl and "substituted arylthio" refers to the group —S-substituted aryl where aryl and substituted aryl are as defined above.

"Heteroarylthio" refers to the group —S-heteroaryl and "substituted heteroarylthio" refers to the group —S-substituted heteroaryl where heteroaryl and substituted heteroaryl are as defined above.

"Heterocyclicthio" refers to the group —S-heterocyclic and "substituted heterocyclicthio" refers to the group —S-substituted heterocyclic where heterocyclic and substituted heterocyclic are as defined above.

The term "amino acid" refers to any of the naturally occurring amino acids, as well as synthetic analogs (e.g., D-stereoisomers of the naturally occurring amino acids, such as D-threonine) and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (ed.), Synthesis of Optically Active .alpha.-Amino Acids, Pergamon Press (1989); Evans et al., J. Amer. Chem. Soc., 112:4011-4030 (1990); Pu et al., J. Amer. Chem. Soc., 56:1280-1283 (1991); Williams et al., J. Amer. Chem. Soc., 113:9276-9286 (1991); and all references cited therein. The present invention includes the side chains of unnatural amino acids as well.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "prodrug" refers to compounds of this invention which have been modified to include a physiologically and biocompatible removable group which group is removed in vivo to provide for the active drug, a pharmaceutically acceptable salt thereof or a biologically active metabolite thereof. Suitable removable groups are well known in the art and particularly preferred removable groups include esters of the carboxylic acid moiety on the glycine substituent. Preferably such esters include those derived from alkyl alcohols, substituted alkyl alcohols, hydroxy substituted aryls and heteroaryls and the like. Another preferred removable group are the amides formed from the carboxylic acid moiety on the glycine substituent. Suitable amides are derived from amines of the formula $HNR^{20}R^{21}$ where $R^{20}$ and $R^{21}$ are independently hydrogen, alkyl, substituted alkyl, aryl, substituted aryl, and the like.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to—substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

The Methods of the Invention

The present invention provides methods of modulating HIF and/or EPO by inhibiting HIFα hydroxylation, thereby stabilizing HIF and activating HIF-regulated gene expression. The methods can be applied to the prevention, pretreatment, or treatment of conditions associated with HIF and or EPO including anemic, ischemic and hypoxic conditions.

Treatment of HIF-Associated Conditions

Ischemia and Hypoxia are two conditions associated with HIF and include, but are not limited to, myocardial infarction, liver ischemia, renal ischemia, and stroke; peripheral vascular disorders, ulcers, burns, and chronic wounds; pulmonary embolism; and ischemic-reperfusion injury, including, for example, ischemic-reperfusion injury associated with surgery and organ transplantation. In one embodiment, the present invention provides methods of stabilizing HIFα before, during, or immediately after ischemia or hypoxia, particularly in association with myocardial infarction, stroke, or renal ischemic-reperfusion injury.

In one aspect, the invention provides methods for treating various ischemic and hypoxic conditions, in particular, using the compounds described herein. In one embodiment, the methods of the invention produce therapeutic benefit when administered following ischemia or hypoxia. For example, the methods of the invention produce a dramatic decrease in morbidity and mortality following myocardial infarction, and a significant improvement in heart architecture and performance. Further, the methods of the invention improve liver function when administered following hepatic toxic-ischemic injury. Hypoxia is a significant component of liver disease, especially in chronic liver disease associated with hepatotoxic compounds such as ethanol. Additionally, expression of genes known to be induced by HIFα, e.g., nitric oxide synthase and glucose transporter-1, is increased in alcoholic liver disease. (See, e.g., Areel et al. (1997) Hepatology 25:920-926; Strubelt (1984) Fundam. Appl. Toxicol. 4:144-151; Sato (1983) Pharmacol Biochem Behav 18 (Suppl. 1):443-447; Nanji et al. (1995) Am. J. Pathol. 146:329-334; and Morio et al. (2001) Toxicol. Appl. Pharmacol. 172:44-51.)

Therefore, the present invention provides methods of treating conditions associated with ischemia or hypoxia, the method comprising administering a therapeutically effective amount of a compound or a pharmaceutically acceptable salt thereof, alone or in combination with a pharmaceutically acceptable excipient, to a subject. In one embodiment, the compound is administered immediately following a condition producing acute ischemia, e.g., myocardial infarction, pulmonary embolism, intestinal infarction, ischemic stroke, and renal ischemic-reperfusion injury. In another embodiment, the compound is administered to a patient diagnosed with a condition associated with the development of chronic ischemia, e.g., cardiac cirrhosis, macular degeneration, pulmonary embolism, acute respiratory failure, neonatal respiratory distress syndrome, and congestive heart failure. In yet another embodiment, the compound is administered immediately after a trauma or injury.

In another aspect, the invention provides methods for treating a patient at risk of developing an ischemic or hypoxic condition, e.g., individuals at high risk for atherosclerosis, etc., using the compounds described herein. Risk factors for atherosclerosis include, e.g., hyperlipidemia, cigarette smoking, hypertension, diabetes mellitus, hyperinsulinemia, and abdominal obesity. Therefore, the present invention provides methods of preventing ischemic tissue injury, the method comprising administering a therapeutically effective amount of a compound or a pharmaceutically acceptable salt thereof, alone or in combination with a pharmaceutically acceptable excipient, to a patient in need. In one embodiment, the compound can be administered based on predisposing conditions, e.g., hypertension, diabetes, occlusive arterial disease, chronic venous insufficiency, Raynaud's disease, chronic skin ulcers, cirrhosis, congestive heart failure, and systemic sclerosis.

In one specific embodiment, the methods are used to increase vascularization and/or granulation tissue formation in damaged tissue, wounds, and ulcers. For example, compounds of the invention have been shown to be effective in stimulating granulation tissue formation in wound healing. Granulation tissue contains newly formed, leaky blood vessels and a provisional stroma of plasma proteins, such as fibrinogen and plasma fibronectin. Release of growth factors from inflammatory cells, platelets, and activated endothelium, stimulates fibroblast and endothelial cell migration and proliferation within the granulation tissue. Ulceration can occur if vascularization or neuronal stimulation is impaired. The methods of the invention are effective at promoting granulation tissue formation. Thus, the invention provides methods for treating a patient having tissue damage due to, e.g., an infarct, having wounds induced by, e.g., trauma or injury, or having chronic wounds or ulcers produced as a consequence of a disorder, e.g., diabetes. The method comprises administering a therapeutically effective amount of a compound or a pharmaceutically acceptable salt thereof, alone or in combination with a pharmaceutically acceptable excipient, to a patient in need.

In another aspect, the invention provides methods of using the compounds to pretreat a subject to decrease or prevent the development of tissue damage associated with ischemia or hypoxia. The methods of the invention produce therapeutic benefit when administered immediately before a condition involving ischemia or hypoxia. For example, application of the methods of the invention prior to induction of myocardial infarction shows statistically significant improvement in heart architecture and performance. Further, the methods of the invention produce therapeutic benefit when administered immediately before and during ischemic-reperfusion injury, significantly reducing diagnostic parameters associated with renal failure.

Therefore, the invention provides methods of pretreating a subject to decrease or prevent the tissue damage associated with ischemia or hypoxia, the method comprising administering a therapeutically effective amount of a compound or a pharmaceutically acceptable salt thereof, alone or in combination with a pharmaceutically acceptable excipient, to a patient with a history of ischemic disorders, e.g., myocardial infarctions, or having symptoms of impending ischemia, e.g., angina pectoris. In another embodiment, the compound can be administered based on physical parameters implicating possible ischemia, e.g., individuals placed under general anesthesia or temporarily working at high altitudes. In yet another embodiment, the compounds may be used in organ transplants to pretreat organ donors and to maintain organs removed from the body prior to implantation in the recipient.

Previous studies have shown that certain compounds used in the methods of the present invention are effective inhibitors of procollagen prolyl 4-hydroxylase. While it is recognized that recovery from an initial infarct or wound requires connective tissue deposition within the necrotic region, the present invention demonstrates no adverse affects of treatment with respect to scar formation. Thus, based on the benefits provided by certain compounds of the invention on treatment and prevention of hypoxic tissue damage and fibrosis, the present invention contemplates a "dual-therapy" approach to treatment or prevention of conditions involving ischemia or hypoxia, including ischemia or hypoxia associated with subsequent reactive fibrosis, e.g., myocardial infarction and resultant congestive heart failure. The method may use one compound that inhibits more than one 2-oxoglutarate dioxygenase enzyme, e.g., HIF prolyl hydroxylase and procollagen prolyl 4-hydroxylase, with either the same specificity or with different specificities. Alternatively, the method may use a combination of compounds wherein each compound specifically inhibits only one 2-oxoglutarate dioxygenase enzyme, e.g., one compound specifically inhibits HIF prolyl hydroxylase and a second compound specifically inhibits procollagen prolyl 4-hydroxylase.

In one aspect, a compound of the invention inhibits one or more 2-oxoglutarate dioxygenase enzymes. In one embodiment, the compound inhibits at least two 2-oxoglutarate dioxygenase family members, e.g., HIF prolyl hydroxylase and HIF asparagine-hydroxylase (FIH-1), with either the same specificity or with differential specificity. In another embodiment, the compound is specific for one 2-oxoglutarate dioxygenase, e.g., HIF prolyl hydroxylase, and shows little to no specificity for other family members.

The compounds can be administered in combination with various other therapeutic approaches. In one embodiment, the compound is administered with another 2-oxoglutarate dioxygenase inhibitor, wherein the two compounds have differential specificity for individual 2-oxoglutarate dioxygenase family members. The two compounds may be administered at the same time as a ratio of one relative to the other. Determination of a ratio appropriate to a given course of treatment or a particular subject is within the level of skill in the art. Alternatively, the two compounds may be administered consecutively during a treatment time course, e.g., following myocardial infarction. In a particular embodiment, one compound specifically inhibits HIF prolyl hydroxylase enzyme activity, and a second compound specifically inhibits procollagen prolyl 4-hydroxylase enzyme activity. In another specific embodiment, one compound specifically inhibits HIF prolyl hydroxylase enzyme activity, and a second compound specifically inhibits HIF asparaginyl-hydroxylase enzyme activity. In another embodiment, the compound is administered with another therapeutic agent having a different mode of action, e.g., an ACE inhibitor (ACEI), angiotensin-II receptor blocker (ARB), statin, diuretic, digoxin, carnitine, etc.

Treatment EPO-Associated Conditions

The present invention provides methods of increasing endogenous erythropoietin (EPO). These methods can be applied in vivo, e.g., in blood plasma, or in vitro, e.g., in cell culture conditioned media. The invention further provides methods of increasing endogenous EPO levels to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The present methods can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Methods of increasing endogenous EPO can also be used to prevent, pretreat, or treat EPO-associated conditions associated with nerve damage or neural tissue degeneration including, but not limited to, stroke, trauma, epilepsy, spinal cord injury, and neurodegenerative disorders.

Additionally, the methods can be used to increase endogenous EPO levels in an anemic or non-anemic patient scheduled to undergo surgery to reduce the need for allogenic blood transfusions or to facilitate banking of blood prior to surgery. The small decreases in hematocrit that typically occur after presurgical autologous blood donation do not stimulate an increase in endogenous EPO or in compensatory erythropoiesis. However, preoperative stimulation of endogenous EPO would effectively increase erythrocyte mass and autologous donation volumes while maintaining higher hematocrit levels, and such methods are specifically contemplated herein. In some surgical populations, particularly those individuals who experience surgical blood losses in excess of 2 liters, the methods of the invention could be applied to reduce allogeneic blood exposure. Crosby (2002) Amer. J. Therap. 9:371-376.

The methods of the invention can also be used to enhance athletic performance, improve exercise capacity, and facilitate or enhance aerobic conditioning. Such methods can be used, e.g., by athletes to facilitate training and by soldiers to improve, e.g., stamina and endurance.

The methods of the invention have been shown to increase endogenous erythropoietin levels in media from cultured cells treated in vitro and in blood plasma from animals treated in vivo. Although the kidney is the major source of erythropoietin in the body, other organs, including brain, liver, and bone marrow, can and do synthesize erythropoietin upon appropriate stimulation. Using the methods of the invention, endogenous erythropoietin expression can be increased in various organs of the body, including brain, kidney, and liver. Indeed, methods of the invention even increase endogenous erythropoietin levels in animals that have undergone bilateral nephrectomy.

The methods of the invention demonstrate that erythropoietin levels can be increased even when kidney function is compromised. Although the invention is not to be limited by the mechanism by which erythropoietin is produced, the decrease in erythropoietin secretion typically seen during kidney failure may be due to hyperoxia in renal tissue due to increased flowthrough/reperfusion. Priyadarshi et al. (2002) Kidney Int. 61:542-546.

Further, the methods of the invention increase the hematocrit and blood hemoglobin level in animals treated in vivo. The increases in plasma EPO, hematocrit, and blood hemoglobin in response to the compounds used in the methods of the invention are dose-sensitive; however, dosing regimes can be established which produce a constant, controlled level of response to the compounds of the invention. Further, treatment with compounds of the invention can correct anemia, for example, induced by a toxic compound such as the chemotherapeutic agent cisplatin, or due to blood loss, e.g., trauma, injury, parasites, or surgery.

The increase in hematocrit and blood hemoglobin in animals treated with compounds of the invention is preceded by an increase in the percentage of circulating immature red blood cells (reticulocytes) within the blood. As such, the invention contemplates the use of the compounds of the invention in methods to increase reticulocyte levels in the blood of animals for production of cell-free reticulocyte lysates as described by, e.g., Pelham and Jackson. Eur. J. Biochem. 67:247-256 (1976). Circulating reticulocyte levels are increased in animals, e.g., rabbits, etc., by treatment with compounds of the invention, alone or in combination with another compound such as, e.g., acetylphenylhydrazine, etc. The blood is collected, and reticulocytes are pelleted by centrifugation and lysed with distilled water. Extracts can be further processed using any appropriate methodology known to those skilled in the art. See, e.g., Jackson and Hunt (1983) Methods Enzymol. 96:50-74.

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Second Edition, Wiley, New York, 1991, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The compounds of this invention are preferably prepared by a convergent synthetic protocol combining the amino entity and the substituted isoquinoline acetic acid derivative under conventional coupling conditions as illustrated in Scheme 1 below:

Scheme 1

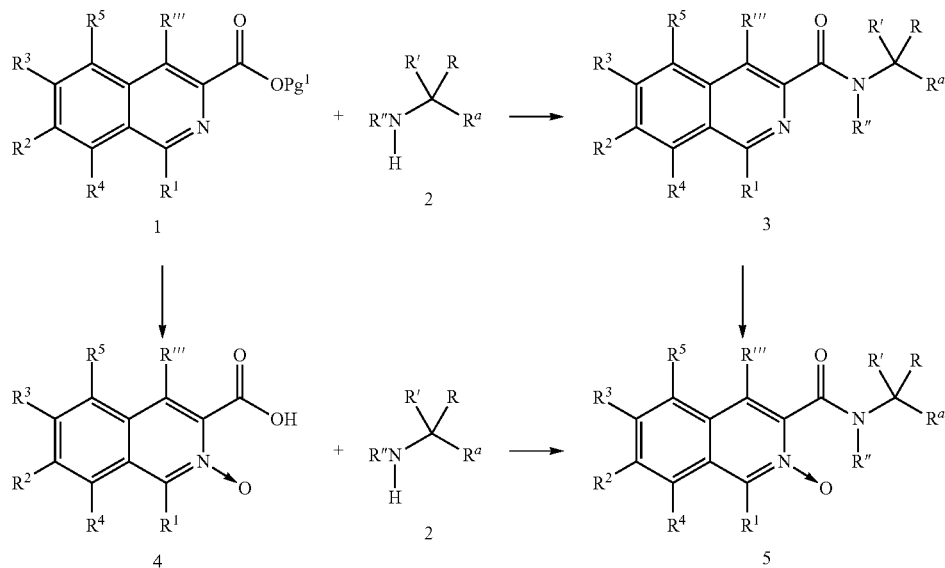

R, R', R'', R''', R¹, R², R³, R⁴, R⁵, and R$^a$ are as defined herein.
Pg¹ refers to a suitable protecting group such as t-butyl esters or orthoesters.

Specifically, in Scheme 1, an appropriately substituted 3-protected carboxyl isoquinoline, compound 1, is combined with at least a stoichiometric amount and preferably an excess of the substituted amine or the N-alkyl derivative thereof, compound 2. The reaction is conducted under conventional coupling conditions well known in the art. In one embodiment, the reaction is conducted in the presence of sodium methoxide in methanol under elevated reaction temperatures and preferably at reflux. The reaction is continued until it is substantially complete which typically occurs within about 1 to 48 hours. Upon reaction completion, compound 3, can be recovered by conventional techniques such as neutralization, extraction, precipitation, chromatography, filtration and the like; or, alternatively, used in the next step without purification and/or isolation.

Alternatively, coupling of the substituted 3-protected carboxyl isoquinoline, compound 1, is combined with the substituted amine or the N-alkyl derivative thereof, compound 2, can proceed via conventional peptide coupling procedures well known in the art. This coupling reaction is typically conducted using well-known coupling reagents such as carbodiimides, BOP reagent (benzotriazol-1-yloxy-tris(dimethylamino)phosphonium hexafluorophosphonate) and the like. Suitable carbodiimides include, by way of example, dicyclohexylcarbodiimide (DCC), 1-(3-dimethyl-amino-propyl)-3-ethylcarbodiimide (DECI) and the like. If desired, polymer supported forms of carbodiimide coupling reagents may also be used including, for example, those described in Tetrahedron Letters, 34(48), 7685 (1993). Additionally, well-known coupling promoters, such as N-hydroxysuccinimide, 1-hydroxybenzotriazole and the like, may be used to facilitate the coupling reaction.

This coupling reaction is typically conducted by contacting compound 1 (typically as the free acid) with about 1 to about 2 equivalents of the coupling reagent and at least one equivalent, preferably about 1 to about 1.2 equivalents, of compound 2, in an inert diluent, such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, compound 3 is recovered by conventional methods including neutralization, extraction, precipitation, chromatography, filtration, and the like.

Alternatively, the substituted 3-protected carboxyl isoquinoline, compound 1, can be converted into an acid halide and the acid halide coupled with compound 2 to provide for compound 3. The acid halide of compound 1 can be prepared by contacting compound 1 with an inorganic acid halide, such as thionyl chloride, phosphorous trichloride, phosphorous tribromide or phosphorous penta-chloride, or preferably, with oxalyl chloride under conventional conditions. Generally, this reaction is conducted using about 1 to 5 molar equivalents of the inorganic acid halide or oxalyl chloride, either neat or in an inert solvent, such as dichloromethane or carbon tetrachloride, at temperature in the range of about 0° C. to about 80° C. for about 1 to about 48 hours. A catalyst, such as DMF, may also be used in this reaction.

The acid halide (not shown) is then contacted with at least one equivalent, preferably about 1.1 to about 1.5 equivalents, of compound 2, in an inert diluent, such as dichloromethane, at a temperature ranging from about –70° C. to about 40° C. for about 1 to about 24 hours.

Preferably, this reaction is conducted in the presence of a suitable base to scavenge the acid generated during the reaction. Suitable bases include, by way of example, tertiary amines, such as triethylamine, diisopropylethylamine, N-methyl-morpholine and the like. Alternatively, the reaction can be conducted under Schotten-Baumann-type conditions using aqueous alkali, such as sodium hydroxide and the like. Upon completion of the reaction, compound 3 is recovered by conventional methods including neutralization, extraction, precipitation, chromatography, filtration, and the like.

In one embodiment, the nitrogen atom of the isoquinoline ring system can be oxidized via conventional techniques to provide for the corresponding N-oxide compound, compounds 4 and 5. Oxidation can proceed by use of conventional oxidizing agents such as m-chloroperbenzoic acid or hydrogen peroxide under conventional conditions. As depicted in Scheme 1, N-oxide formation can occur either with the substituted 3-protected carboxyl isoquinoline, compound 1, or with compound 3.

The starting materials for use in the reactions found in Scheme 1 are either commercially available or can be prepared by methods well known in the art. For example, glycine and N-alkylglycines such as sarcosine, N-ethylglycine, and the like are commercially available from Aldrich Chemical Company, Milwaukee, Wis., USA. ("Aldrich").

The synthesis of substituted isoquinoline acetic acids are also well known in the art and are described in detail by, for example, Weidmann, et al., U.S. Pat. No. 6,093,730 which is incorporated herein by reference in its entirety. One particular method for preparation of such derivatives are set forth in Scheme 2 below:

solid phase by first forming a homogeneous mixture of the reagents and then heating the mixture to an elevated temperature to form a molten mass. Preferably, the reaction is heated to over 200° C. and more preferably from about 210° to about 220° C. The reaction is continued until it is substantially complete which typically occurs within about 48 to 96 hours. Upon reaction completion, the resulting phthalimide, compound 8, can be recovered by conventional techniques such as neutralization, extraction, precipitation, chromatography, filtration and the like; or, alternatively, used in the next step without purification and/or isolation.

Conventional esterification of compound 8 leads to compound 9 where $R^8$ is alkyl. This compound is then subject to ring expansion under basic conditions. Specifically, compound 9 is contacted with an stoichiometric excess, preferably 2 equivalents, of sodium or potassium alkoxide, such as sodium butoxide, in a suitable solvent such as n-butanol and maintained at an elevated temperature of from about 70° C. to about 120° C. and preferably from about 95° C. to about 100° C. The reaction is continued until it is substantially complete which typically occurs within about 0.5 to 6 hours.

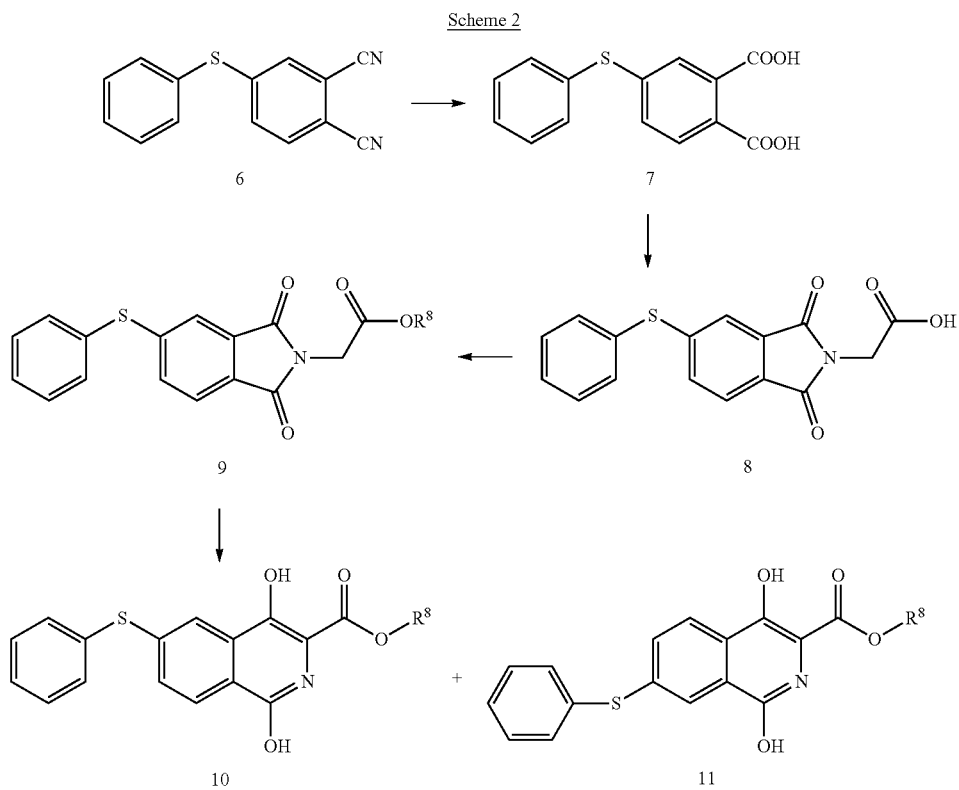

Specifically, in Scheme 2, commercially available 4-phenyl sulfanyl-phthalonitrile, compound 6, is hydrolyzed to the corresponding diacid, compound 7, under conventional conditions such as treatment with a 1:1 mixture of 50% aqueous KOH/methanol. The reaction is continued until it is substantially complete which typically occurs within about 48 to 96 hours. Upon reaction completion, the resulting diacid, compound 7, can be recovered by conventional techniques such as neutralization, extraction, precipitation, chromatography, filtration and the like; or, alternatively, used in the next step without purification and/or isolation.

Compound 7 is cyclized in the presence of a stoichiometric equivalent of glycine. The reaction is conducted in the Upon reaction completion, the resulting isoquinoline isomers, compounds 9 and 10 can be recovered by conventional techniques such as neutralization, extraction, precipitation, chromatography, filtration and the like; or, alternatively, used in the next step without purification and/or isolation.

The reaction conditions set forth above can lead to transesterification of the ester functionality (if $R^8$ is not n-butyl). In any event, the alkyl moiety of the ester group serves as a suitable protecting group for the carboxyl functionality on compound 9 and is depicted as $Pg^1$ in compound 1 of Scheme 1.

As is apparent, the hydroxy functionality at the 1 position is subject to numerous derivation schemes that are well known in the art. Suitable derivations include formation of alkoxy, substituted alkoxy, aryloxy, substituted aryloxy, heteroaryloxy, substituted heteroaryloxy, heterocycyloxy, substituted heterocycloxy, halogenation, dehalogenation (to provide for hydrogen at this position), alkyl, substituted alkyl, aryl, substituted aryl, heteroaryl, substituted heteroaryl products. Still further, the hydroxyl group can be modified using art recognized procedures to provide for —N($R^7$)$R^6$ derivatives which can be achieved by reacting the halo substituent with a suitable amine. Similarly, sulfanyl and oxidized sulfanyl derivatives can be prepared by conventional methods such as reacting the hydroxyl group with phosphorous pentasulfide, Lawesson's reagent, or the like, optionally followed by reaction of the resulting sulfhydryl group with an alkylating agents, such as ethyl iodide or the like, to give an alkylsulfanyl derivative. Sulfanyl derivatives may further be oxidized with standard peroxy acid reagents, such as m-chloroperbenzoic acid.

Still further, substitution on the phenyl ring of the isoquinoline compounds is achieved by appropriate choice of starting materials. Many of these starting materials are commercially available such as 4-phenoxy-phthalonitrile (Aldrich), and the like. Alternatively, compounds such as 4-(2,6-dimethylphenoxy)-phthalonitrile can be prepared by art-recognized techniques.

Alternatively, commercially available substituted phthalic anhydride or phthalic acid can be used in place of compound 7 in Scheme 1. Such anhydrides include, for example, 3-fluorophthalic anhydride (Aldrich), 3-nitrophthalic anhydride (Aldrich), 3-chlorophthalic anhydride (TCI America, Portland Oreg. 97203 "TCI") and the like. Such acids include, for example, 4-trifluoromethyl-phthalic acid (TCI) and the like.

Testing and Administration

Biological Testing

The biological activity of the compounds of the invention may be assessed using any conventionally known methods. Suitable assay methods are well known in the art. The following assays are presented only as examples and are not intended to be limiting. The compounds of the invention are active in at least one of the following assays.

Cell-Based HIFα Stabilization Assay

Human cells derived from various tissues were separately seeded into 35 mm culture dishes and grown at 37° C., 20% $O_2$, 5% $CO_2$ in standard culture medium, e.g., DMEM, 10% FBS. When cell layers reached confluence, the media was replaced with OPTI-MEM media (Invitrogen Life Technologies, Carlsbad Calif.) and cell layers were incubated for approximately 24 hours in 20% $O_2$, 5% $CO_2$ at 37° C. Compound or 0.013% DMSO was then added to existing medium, and incubation was continued overnight.

Following incubation, the media was removed, centrifuged, and stored for analysis (see VEGF and EPO assays below). The cells were washed two times in cold phosphate buffered saline (PBS) and then lysed in 1 ml of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates were centrifuged at 3,000×g for 5 minutes at 4° C., and the cytosolic fractions (supernatant) were collected. The nuclei (pellet) were resuspended and lysed in 100 µl of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) were collected.

Nuclear fractions were analyzed for HIF-1α using a QUANTIKINE immunoassay (R&D Systems, Inc., Minneapolis Minn.) according to the manufacturer's instructions.

Cell-Based VEGF and EPO ELISA Assays

Conditioned media collected from cell cultures as described above was analyzed for vascular endothelial growth factor (VEGF) and/or erythropoietin (EPO) expression using an appropriate QUANTIKINE immunoassay (R&D Systems) according to the manufacturer's instructions.

Oxygen Consumption Assay

Oxygen Sensor cell culture plates (BD Biosciences) contain a ruthenium complex which is more fluorescent in the absence of oxygen. Therefore, the fluorescent read-out is increased by the presence of oxygen-consuming cells in the plate, which change the equilibrium to lower oxygen saturation and higher fluorescence. A compound that stabilizes HIF by inhibiting hydroxylation is expected to decrease oxygen consumption by decreasing oxygen consumed by the hydroxylation event itself and/or by shifting cellular metabolism from aerobic to anaerobic energy production.

Human cells derived from adenovirus-transformed fetal kidney epithelium (293A) or cervical epithelial adenocarcinoma (HeLa) (American Type Culture Collection, Manassas Va.) were grown to confluence in media (high glucose DMEM (Mediatech, Inc., Herndon Va.), 1% penicillin/streptomycin mixture (Mediatech), 1% fetal bovine serum) at 37° C., 10% $CO_2$. Cells were collected and resuspended in media at a density of 500,000 cells/ml. The cell suspension was distributed at 0.2 ml/well into each well of an Oxygen Biosensor 96-well cell culture plate (BD Biosciences, Bedford Mass.). The following treatments were added in 10 µl volumes to triplicate sets of wells: (1) 0.5% DMSO; (2) 200 µM sodium dodecyl sulfate; or (3) 1, 10, or 50 µM compound.

Cultures were incubated at 37° C., 10% $CO_2$ for 72 hours and plates were then read in an FL600 flourimeter (Biotek Instruments, Inc., Winooski Vt.) at an excitation wavelength of 485 nm and emission wavelength of 590 nm. Data was plotted as a function of fold change relative to DMSO control ($O_2$ consumption) or absorbance at a wavelength of 450 nm (WST-1) and descriptive statistical analysis was performed using EXCEL software (Microsoft Corporation, Bellevue Wash.).

HIF-PH2 (PHD2) Assay

Material

HIF-PH2 (EGLN1) was expressed from Hi5 cells and partially purified through a SP ion exchange chromatography column. Ketoglutaric acid-[1-14C]-sodium salt was obtained from Perkin-Elmer. Alphaketoglutaric acid sodium salt was purchased from SIGMA. HPLC purified DLD19 Peptide (Acetyl-DLDLEMLAPYIPMDDDFQL-CONH2) (SEQ ID NO:4) was made by Synpep.

HIF-PH2 (EGLN1) was expressed from insect Hi5 cells and partially purified through a SP ion exchange chromatography column. Enzyme activity was determined by capturing $^{14}CO_2$ using an assay described by Kivirikko and Myllyla (1982, Methods Enzymol 82:245-304). Assay reactions contained 50 mM HEPES (pH 7.4), 100 μM α-ketoglutaric acid sodium salt, 0.30 μCi/ml ketoglutaric acid μ-[1$^{24}$C]-sodium salt; Perkin Elmer, Wellesley Mass.), 40 μM FeSO$_4$, 1 mM ascorbate, 1541.8 units/ml Catalase, with or without 50 μM peptide substrate (Acetyl-DLDLEM-LAPYIPMDDDFQL-CONH$_2$) (SEQ ID NO:4) and various concentrations of compound of the invention. Reactions were initiated by addition of HIF-PH2 enzyme.

The peptide-dependent percent turnover was calculated by subtracting percent turnover in the absence of peptide from percent turnover in the presence of substrate peptide. Percent inhibition and IC$_{50}$ were calculated using peptide-dependent percent turnover at given inhibitor concentrations. Calculation of IC$_{50}$ values for each inhibitor was conducted using GraFit software (Erithacus Software Ltd., Surrey UK).

Pharmaceutical Formulations and Routes of Administration

The compositions of the present invention can be delivered directly or in pharmaceutical compositions along with suitable carriers or excipients, as is well known in the art. Present methods of treatment can comprise administration of an effective amount of a compound of the invention to a subject having or at risk for anemia due to, e.g., chronic renal failure, diabetes, cancer, AIDS, radiation therapy, chemotherapy, kidney dialysis, or surgery. In a preferred embodiment, the subject is a mammalian subject, and in a most preferred embodiment, the subject is a human subject.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for protein stabilization may be employed.

For any composition used in the present methods of treatment, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels of the active moiety that are sufficient to modulate endogenous erythropoietin plasma levels as desired, i.e. minimal effective concentration (MEC). The MEC will vary for each compound but can be estimated from, for example, in vitro data. Dosages necessary to achieve the MEC will depend on individual characteristics and route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration. Alternatively, stimulation of endogenous erythropoietin may be achieved by 1) administering a loading dose followed by a maintenance dose, 2) administering an induction dose to rapidly achieve erythropoietin levels within a target range, followed by a lower maintenance dose to maintain hematocrit within a desired target range, or 3) repeated intermittent dosing.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of conditions, disorders, or diseases in which anemia is a major indication.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

μ=microliter
amu=atomic mass unit
atm=atmosphere
bs=broad singlet
ClCO$_2$iBu=isobutylchloro formate
ClCONMe$_2$=dimethylcarbamic chloride
conc.=concentrated
d=doublet
DABCO=diazobicyclo[2.2.2]octane
dd=doublet of doublets
DMF=dimethyl formamide
DMSO=dimethyl sulfoxide
Et$_2$SO$_4$=ethyl sulfate
EtI=ethyl iodide
EtOAc=ethyl acetate
EtOH=ethanol
EtOH=ethanol
g=gram
h=hour
HATU=N-dimethylamino-1H-1,2,3-triazolo[4,5-b] pyridin-1-ylmethylene-N-methylmethanaminium hexafluorophosphate N-oxide
HBTU=1-H-Benzotriazolium
Hz=Hertz
M=molar
m=multiplet
Me$_2$SO$_4$=methyl sulfate
Me$_3$OBF$_4$=trimethylboroxine
MeI=methyl iodide
MeOCH$_2$I=iodomethoxy methane
MeOH=methanol
MeONa=sodium methoxide
mg=milligram
MHz=mega Hertz
min=minute
ml=milliliter
mmol=millimolar
N=normal
NaOMe=sodium methoxide
n-BuLi=n-butyl lithium
n-BuOH=n-butanol
NEt$_3$=triethyl amine
PhCH$_2$Br=bromomethyl benzene
q=quartet
quint=quintuplet
r.t.=room temperature
R$_f$=retention factor
s=second
t=triplet
TFA=trifluoro acetic acid
THF=tetrahydrofuran
TLC=thin layer chromatography
wt %=weight percent Example A-1

(S)-2-[6-Benzyloxy-1-chloro-4-hydroxy-isoquinoline-3-carbonyl)-amino]-propionic acid a. (S)-2-[6-Benzyloxy-1-chloro-4-hydroxy-isoquinoline-3-carbonyl)-amino]-propionic acid methyl ester 6-Benzyloxy-1-chloro-4-hydroxy-isoquinoline-3-carboxylic-acid (can be obtained according to U.S. Pat. No. 6,093,730, October 1998, Weidmann et al.), 0.33 g, 0.5 ml of triethylamine, 0.38 g of HATU, and 0.151 g of commercial L-Alanine methyl ester hydrochloride were stirred in 15 ml CH$_2$Cl$_2$ at room temperature for 18 h to give, after silica gel chromatography (eluant=4:1 hexane-EtOAc). 0.220 g of (S)-2-[(6-benzyloxy-1-chloro-4-hydroxy-isoquinoline-3-carbonyl)-amino]-propionic acid methyl ester as a white solid, MS–(+)-ion, M+1=415.8 amu.

b. (S)-2-[(6-Benzyloxy-1-chloro-4-hydroxy-isoquinoline-3-carbonyl)-amino]-propionic acid 0.200 g of the (S) methyl ester described in Example A-1 a) and 15 ml of a 1.5 M solution of NaOH in methanol was stirred at room temperature for 3 h and concentrated. The residue was dissolved in water and extracted with EtOAc. The aqueous layer was acidified to pH ~1 with hydrochloric acid and the resulting precipitate was collected by filtration, washed with water, dried in a vacuum oven (70° C.) to give 0.174 g of (S)–2-[(6-Benzyloxy-1-chloro-4-hydroxy-isoquinoline-3-carbonyl)-amino]-propionic acid as an off-white solid, MS-(+)-ion, M+1=401.0 amu.

Example A-2

(R)-2-[(1-Chloro-4-hydroxy-isoquinoline-3-carbonyl)-amino]-3-hydroxy-propionic acid a. (1,3-Dioxo-1,3-dihydro-isoindol-2-yl)-acetic acid butyl ester A mixture of 160 ml of butanol, 20.0 g of (1,3-dioxo-1,3-dihydro-isoindol-2-yl)-acetic acid (94.6 mmol) and 2.0 ml of concentrated sulfuric acid was refluxed with stirring for 24 h. Then 5 g of sodium bicarbonate were added in portions, stirring continued at r.t. for 5 min and the solvent evaporated in vacuo. The residue was partitioned between 100 ml of water and 100 ml of ethyl acetate. The organic phase was washed with 100 ml of brine, dried over sodium sulfate and was evaporated in vacuo to give a yellowish oil that later solidified. 24.02 g of the title compound were obtained; MS-(+)-ion: M+1=261.9 amu.

b. 1,4-Dihydroxy-isoquinoline-3-carboxylic acid butyl ester 4.41 g of sodium (190 mmol) were dissolved in 250 ml of n-butanol with stirring. After the sodium was completely dissolved the solution was allowed to cool to ambient temperature and a solution of 24.0 g (91.9 mmol) of (1,3-dioxo-1,3-dihydro-isoindol-2-yl)-acetic acid butyl ester in 150 ml of butanol was added with stirring. The solution was heated to 100° C. within 30 min and stirred at this temperature for 1 h. Then the mixture was allowed to cool to ambient temperature and was stored at ambient temperature for 18 h. Then the pH of the mixture was adjusted to 2 to 3 by the addition of aqueous 2N hydrochloric acid with stirring. Stirring was continued for 30 min before the solid component was filtered by suction. The filter cake was washed thoroughly with water, and dried in vacuo at 50° C. to give a white solid. 17.75 g of the title compound were obtained; MS-(+)-ion: M+1=262.1 amu.

c. 1-Chloro-4-hydroxy-isoquinoline-3-carboxylic acid butyl ester

A mixture of 17.3 g (66.2 mmol) of 1,4-dihydroxy-isoquinoline-3-carboxylic acid butyl ester and 100 ml of phosphorous oxychloride was stirred at ambient temperature for 1 h, and then heated slowly with stirring in the course of 2 h to reflux temperature. The mixture was refluxed gently with stirring for 30 min. After cooling to room temperature the excess phosphorous oxychloride was evaporated in vacuo, and the residue was dissolved in 100 ml of ethyl acetate. The solution was poured into 300 ml of a saturated aqueous sodium bicarbonate solution with stirring. The precipitate formed was removed by vacuum filtration. The organic phase was separated, and the aqueous phase was extracted with 3×100 ml of ethyl acetate. The combined aqueous phases were dried over sodium sulfate, filtered through a pad of silica gel and evaporated in vacuo to give a brown oil that solidified later. 11.37 g of the title compound were obtained; $^1$H NMR (CDCl$_3$): δ=11.91 (s, 1H), 8.41 (m, 1H), 8.29 (m, 1H), 7.83 (m, 2H), 4.49 (t, 2H), 1.84 (m, 2H), 1.48 (m, 2H), 0.99 (t, 3H).

d. 1-Chloro-4-hydroxy-isoquinoline-3-carboxylic acid

A mixture of 9.23 g of 1-chloro-4-hydroxy-isoquinoline-3-carboxylic acid butyl ester (33 mmol), 90 ml of 2.5N aqueous sodium hydroxide solution, water (20 ml) and ethanol (110 ml) was refluxed with stirring for 2 h. Then the pH of the mixture was adjusted to 2 by the addition of concentrated aqueous hydrochloric acid. During the addition, the temperature of the mixture was kept at 20° C. by cooling with an ice bath. Stirring was then continued for 1 h before the solid component was separated by vacuum filtration. The filter cake was washed with water and dried in vacuo at 85° C. to give a white powder. 6.64 g of the title compound were obtained; MS-(+)-ion: M+1=224.1 amu.

e. (R)-3-tert-Butoxy-2-[(1-chloro-4-hydroxy-isoquinoline-3-carbonyl)-amino]-propionic acid tert-butyl ester To a mixture of 45 mg (0.2 mmol) of 1-chloro-4-hydroxy-isoquinoline-3-carboxylic acid, 76 mg (0.2 mmol) of benzotriazol-1-yl-(bis-dimethylamino-methylene)-oxonium hexafluoro phosphate (HBTU), 50.8 mg (R)-2-amino-3-tert-butoxy-propionic acid tert-butyl ester hydrochloride (0.2 mmol), and 1 ml of dichloromethane was added 122.5 µl (0.7 mmol) of ethyl-diisopropyl-amine with stirring. Stirring was continued at ambient temperature for 40 h. The product was isolated from the reaction mixture by flash column chromatography on silica gel using hexanes: ethyl acetate (9:1) as the eluent to give a colorless oil. 27 mg of the title compound was obtained; MS-(+)-ion: M+1=422.8 amu.

f. (R)-2-[(1-Chloro-4-hydroxy-isoquinoline-3-carbonyl)-amino]-3-hydroxy-propionic acid A mixture of 27 mg (0.06 mmol) of (R)-3-tert-Butoxy-2-[(1-chloro-4-hydroxy-isoquinoline-3-carbonyl)-amino]-propionic acid tert-butyl ester and 2 ml of trifluoroacetic acid was stirred for 2 h at ambient temperature. Then the excess trifluoroacetic acid was evaporated in vacuo, the residue dissolved in 2 ml of absolute ethanol and the solution was concentrated in vacuo to give a tan solid. 27 mg of the title compound was obtained; MS-(+)-ion: M+1=310.9 amu.

Example A-3

(S)-2-[(1-Chloro-4-hydroxy-isoquinoline-3-carbonyl)-amino]-3-hydroxy-propionic acid Prepared in analogy to Example A-2 e) and f) from 1-chloro-4-hydroxy-isoquinoline-3-carboxylic acid from Example A-2 d) and (S)-2-amino-3-tert-butoxy-propionic acid tert-butyl ester hydrochloride; MS-(+)-ion: M+1=310.9 amu.

Example A-4

(R)-2-[(1-Chloro-4-hydroxy-6-isopropoxy-isoquinoline-3-carbonyl)-amino]-3-hydroxy-propionic acid Prepared in analogy to Example A-2 e) and f) from 1-chloro-4-hydroxy-6-isopropoxy-isoquinoline-3-carboxylic acid (can be obtained according to U.S. Pat. No. 6,093,730, October 1998, Weidmann et al.) and (R)-2-amino-3-tert-butoxy-propionic acid tert-butyl ester hydrochloride; MS-(+)-ion: M+1=369.0 amu.

Example A-5

(S)-2-[(1-Chloro-4-hydroxy-6-isopropoxy-isoquinoline-3-carbonyl)-amino]-3-hydroxy-propionic acid Prepared in analogy to Example A-2 e) and f) from 1-chloro-4-hydroxy-6-isopropoxy-isoquinoline-3-carboxylic acid (can be obtained according to U.S. Pat. No. 6,093,730, October 1998, Weidmann et al.) and (S)-2-amino-3-tert-butoxy-propionic acid tert-butyl ester hydrochloride; MS-(+)-ion: M+1=369.0 amu.

Example A-6

(R)-2-[(1-Chloro-4-hydroxy-7-isopropoxy-isoquinoline-3-carbonyl)-amino]-3-hydroxy-propionic acid Prepared in analogy to Example A-2 e) and f) from 1-chloro-4-hydroxy-7-isopropoxy-isoquinoline-3-carboxylic acid (can be obtained according to U.S. Pat. No. 6,093,730, October 1998, Weidmann et al.) and (R)-2-amino-3-tert-butoxy-propionic acid tert-butyl ester hydrochloride; MS-(+)-ion: M+1=369.0 amu.

Example A-7

(S)-2-[(1-Chloro-4-hydroxy-7-isopropoxy-isoquinoline-3-carbonyl)-amino]-3-hydroxy-propionic acid Prepared in analogy to Example A-2 e) and f) from 1-chloro-4-hydroxy-7-isopropoxy-isoquinoline-3-carboxylic acid (can be obtained according to U.S. Pat. No. 6,093,730, October 1998, Weidmann et al.) and (S)-2-amino-3-tert-butoxy-propionic acid tert-butyl ester hydrochloride; MS-(+)-ion: M+1=369.0 amu.

Example A-8

2-[(1-Chloro-4-hydroxy-isoquinoline-3-carbonyl)-amino]-2-methyl-propionic acid

Prepared in analogy to Example A-1 a) and b) from 1-chloro-4-hydroxy-isoquinoline-3-carboxylic acid from Example A-2 d) and 2-amino-2-methyl-propionic acid methyl ester hydrochloride; MS-(+)-ion: M+1=308.9 amu.

Example A-9

2-[(1-Chloro-4-hydroxy-6-isopropoxy-isoquinoline-3-carbonyl)-amino]-2-methyl-propionic acid Prepared in analogy to Example A-1 a) and b) from 1-chloro-4-hydroxy-6-isopropoxy-isoquinoline-3-carboxylic acid (can be obtained according to U.S. Pat. No. 6,093,730, October 1998, Weidmann et al.) and 2-amino-2-methyl-propionic acid methyl ester hydrochloride; MS-(+)-ion: M+1=367.0 amu.

Example A-10

(R)-2-[(1-Chloro-4-hydroxy-isoquinoline-3-carbonyl)-amino]-3-(1H-imidazol-4-yl)-propionic acid; trifluoro-acetic acid salt Prepared in analogy to Example A-2 e) from 1-chloro-4-hydroxy-isoquinoline-3-carboxylic acid from Example A-2 d) and (R)-2-amino-3-(1-trityl-1H-imidazol-4-yl)-propionic acid methyl ester hydrochloride followed by deprotection in analogy to Example A-1 b) and then in analogy to 2 f); MS-(−)-ion: M−1=359.1 amu.

Example A-11

(S)-2-[(1-Chloro-4-hydroxy-isoquinoline-3-carbonyl)-amino]-3-(1H-imidazol-4-yl)-propionic acid; trifluoro-acetic acid salt Prepared in analogy to Example A-2 e) from 1-chloro-4-hydroxy-isoquinoline-3-carboxylic acid from Example A-2 d) and (S)-2-amino-3-(1-trityl-1H-imidazol-4-yl)-propionic acid methyl ester hydrochloride followed by deprotection in analogy to Example A-1 b) and then in analogy to 2 f); MS-(−)-ion: M−1=359.1 amu.

Example A-12

(R)-2-[(1-Chloro-4-hydroxy-isoquinoline-3-carbonyl)-amino]-3-methyl-butyric acid Prepared in analogy to Example A-1 a) and b); MS-(−)-ion: M−1=321.1 amu.

Example A-13

(S)-2-[(1-Chloro-4-hydroxy-isoquinoline-3-carbonyl)-amino]-3-methyl-butyric acid Prepared in analogy to Example A-2 e) and f); MS-(+)-ion: M+1=323.0 amu.

Example A-14

(R)-2-[(1-Chloro-4-hydroxy-6-isopropoxy-isoquinoline-3-carbonyl)-amino]-3-methyl-butyric acid Prepared in analogy to Example A-2 e) and f); MS-(+)-ion: M+1=381.1 amu.

Example A-15

(S)-2-[(1-Chloro-4-hydroxy-6-isopropoxy-isoquinoline-3-carbonyl)-amino]-3-methyl-butyric acid Prepared in analogy to Example A-2 e) and f); MS-(+)-ion: M+1=381.0 amu.

Example A-16

(R)-2-[(1-Chloro-4-hydroxy-7-isopropoxy-isoquinoline-3-carbonyl)-amino]-3-methyl-butyric acid Prepared in analogy to Example A-2 e) and f); MS-(+)-ion: M+1=381.0 amu.

Example A-17

(S)-2-[(1-Chloro-4-hydroxy-7-isopropoxy-isoquinoline-3-carbonyl)-amino]-3-methyl-butyric acid Prepared in analogy to Example A-2 e) and f); MS-(+)-ion: M+1=381.0 amu.

Example A-18

(S)-2-[(6-Benzyloxy-1-chloro-4-hydroxy-isoquinoline-3-carbonyl)-amino]-3-methyl-butyric acid Prepared in analogy to Example A-1 a) and b); MS-(−)-ion: M−1=429.0 amu.

Example A-19

(R)-2-[(1-Chloro-4-hydroxy-isoquinoline-3-carbonyl)-amino]-3-phenyl-propionic acid Prepared in analogy to Example A-2 e) and f); MS-(+)-ion: M+1=371.0 amu.

Example A-20

(S)-2-[(1-Chloro-4-hydroxy-isoquinoline-3-carbonyl)-amino]-3-phenyl-propionic acid Prepared in analogy to Example A-2 e) and f); MS-(+)-ion: M+1=371.0 amu.

Example A-21

(R)-2-[(1-Chloro-4-hydroxy-6-isopropoxy-isoquinoline-3-carbonyl)-amino]-3-phenyl-propionic acid Prepared in analogy to Example A-2 e) and f); MS-(+)-ion: M+1=429.0 amu.

Example A-22

(S)-2-[(1-Chloro-4-hydroxy-6-isopropoxy-isoquinoline-3-carbonyl)-amino]-3-phenyl-propionic acid Prepared in analogy to Example A-2 e) and f); MS-(+)-ion: M+1=429.0 amu.

Example A-23

(R)-2-[(1-Chloro-4-hydroxy-7-isopropoxy-isoquinoline-3-carbonyl)-amino]-3-phenyl-propionic acid Prepared in analogy to Example A-2 e) and f); MS-(+)-ion: M+1=429.0 amu.

Example A-24

(S)-2-[(1-Chloro-4-hydroxy-7-isopropoxy-isoquinoline-3-carbonyl)-amino]-3-phenyl-propionic acid Prepared in analogy to Example A-2 e) and f); MS-(+)-ion: M+1=429.0 amu.

Example A-25

(R)-2-[(1-Chloro-4-hydroxy-isoquinoline-3-carbonyl)-amino]-3-(4-hydroxy-phenyl)-propionic acid Prepared in analogy to Example A-2 e) and f); MS-(−)-ion: M−1=385.0 amu.

Example A-26

(S)-2-[(1-Chloro-4-hydroxy-isoquinoline-3-carbonyl)-amino]-3-(4-hydroxy-phenyl)-propionic acid Prepared in analogy to Example A-2 e) and f); MS-(+)-ion: M+1=387.1 amu.

Example A-27

(R)-2-[(1-Chloro-4-hydroxy-6-isopropoxy-isoquinoline-3-carbonyl)-amino]-3-(4-hydroxy-phenyl)-propionic acid Prepared in analogy to Example A-2 e) and f); MS-(−)-ion: M−1=443.0 amu.

Example A-28

(S)-2-[(1-Chloro-4-hydroxy-isoquinoline-3-carbonyl)-amino]-3-(4-hydroxy-phenyl)-propionic acid Prepared in analogy to Example A-2 e) and f); MS-(−)-ion: M−1=443.0 amu.

Example A-29

(R)-2-[(1-Chloro-4-hydroxy-7-isopropoxy-isoquinoline-3-carbonyl)-amino]-3-(4-hydroxy-phenyl)-propionic acid Prepared in analogy to Example A-2 e) and f); MS-(+)-ion: M+1=445.1 amu.

Example A-30

(S)-2-[(1-Chloro-4-hydroxy-7-isopropoxy-isoquinoline-3-carbonyl)-amino]-3-(4-hydroxy-phenyl)-propionic acid Prepared in analogy to Example A-2 e) and f); MS-(+)-ion: M+1=445.1 amu.

Example A-31

(R)-2-[(1-Chloro-4-hydroxy-6-isopropoxy-isoquinoline-3-carbonyl)-amino]-pentanoic acid Prepared in analogy to Example A-1 a) and b); MS-(+)-ion: M+1=381.0 amu.

Example A-32

(S)-2-[(1-Chloro-4-hydroxy-6-isopropoxy-isoquinoline-3-carbonyl)-amino]-pentanoic acid Prepared in analogy to Example A-1 a) and b); MS-(−)-ion: M−1=379.0 amu.

Example A-33

(R)-1-(1-Chloro-4-hydroxy-isoquinoline-3-carbonyl)-pyrrolidine-2-carboxylic acid Prepared in analogy to Example A-2 e) and f); MS-(+)-ion: M+1=321.0 amu.

Example A-34

(S)-1-(1-Chloro-4-hydroxy-isoquinoline-3-carbonyl)-pyrrolidine-2-carboxylic acid Prepared in analogy to Example A-2 e) and f); MS-(+)-ion: M+1=321.0 amu.

Example A-35

(R)-1-(1-Chloro-4-hydroxy-6-isopropoxy-isoquinoline-3-carbonyl)-pyrrolidine-2-carboxylic acid Prepared in analogy to Example A-2 e) and f); MS-(+)-ion: M+1=379.1 amu.

Example A-36

(S)-1-(1-Chloro-4-hydroxy-6-isopropoxy-isoquinoline-3-carbonyl)-pyrrolidine-2-carboxylic acid Prepared in analogy to Example A-2 e) and f); MS-(+)-ion: M+1=379.1 amu.

Example A-37

(R)-6-Amino-2-[(1-chloro-4-hydroxy-isoquinoline-3-carbonyl)-amino]-hexanoic acid; trifluoroacetic acid salt Prepared in analogy to Example A-2 e) and f); MS-(+)-ion: M+1=352.2 amu.

Example A-38

(S)-6-Amino-2-[(1-chloro-4-hydroxy-isoquinoline-3-carbonyl)-amino]-hexanoic acid; trifluoroacetic acid salt Prepared in analogy to Example A-2 e) and f); MS-(+)-ion: M+1=352.1 amu.

Example A-39

(R)-6-Amino-2-[(1-chloro-4-hydroxy-6-isopropoxy-isoquinoline-3-carbonyl)-amino]-hexanoic acid; trifluoroacetic acid salt Prepared in analogy to Example A-2 e) and f); MS-(+)-ion: M+1=410.1 amu.

Example A-40

(S)-6-Amino-2-[(1-chloro-4-hydroxy-6-isopropoxy-isoquinoline-3-carbonyl)-amino]-hexanoic acid; trifluoroacetic acid salt Prepared in analogy to Example A-2 e) and f); MS-(+)-ion: M+1=410.1 amu.

Example A-41

(R)-6-Amino-2-[(1-chloro-4-hydroxy-7-isopropoxy-isoquinoline-3-carbonyl)-amino]-hexanoic acid; trifluoroacetic acid salt Prepared in analogy to Example A-2 e) and f); MS-(+)-ion: M+1=410.1 amu.

Example A-42

(S)-6-Amino-2-[(1-chloro-4-hydroxy-7-isopropoxy-isoquinoline-3-carbonyl)-amino]-hexanoic acid; trifluoroacetic acid salt Prepared in analogy to Example A-2 e) and f); MS-(+)-ion: M+1=410.1 amu.

Example A-43

(R)-2-[(1-Chloro-4-hydroxy-isoquinoline-3-carbonyl)-amino]-succinic acid

Prepared in analogy to Example A-1 a) and b); MS-(+)-ion: M+1=338.9 amu.

Example A-44

(S)-2-[(1-Chloro-4-hydroxy-isoquinoline-3-carbonyl)-amino]-succinic acid

Prepared in analogy to Example A-2 e) and f); MS-(−)-ion: M−1=337.0 amu.

Example A-45

(R)-2-[(1-Chloro-4-hydroxy-6-isopropoxy-isoquinoline-3-carbonyl)-amino]-succinic acid Prepared in analogy to Example A-1 a) and b); MS-(+)-ion: M+1=397.0 amu.

Example A-46

(S)-2-[(1-Chloro-4-hydroxy-6-isopropoxy-isoquinoline-3-carbonyl)-amino]-succinic acid Prepared in analogy to Example A-2 e) and f); MS-(+)-ion: M+1=397.1 amu.

Example A-47

(R)-2-[(1-Chloro-4-hydroxy-7-isopropoxy-isoquinoline-3-carbonyl)-amino]-succinic acid Prepared in analogy to Example A-1 a) and b); MS-(+)-ion: M+1=397.0 amu.

Example A-48

1-[(1-Chloro-4-hydroxy-isoquinoline-3-carbonyl)-amino]-cyclopropanecarboxylic acid Prepared in analogy to Example A-1 a) and b); MS-(−)-ion: M−1=305.0 amu.

Example A-49

1-[(1-Chloro-4-hydroxy-6-isopropoxy-isoquinoline-3-carbonyl)-amino]-cyclopropanecarboxylic acid Prepared in analogy to Example A-1 a) and b); MS-(+)-ion: M+1=365.0 amu.

Example A-50

Dideutero-[(1-chloro-4-hydroxy-isoquinoline-3-carbonyl)-amino]-acetic acid

A mixture of 70 mg (0.25 mmol) of 1-chloro-4-hydroxy-isoquinoline-3-carboxylic acid butyl ester from Example A-2c), 193 mg (2.5 mmol) of glycine-2,2-$d_2$, and 5 ml of a 0.5N sodium methoxide solution in methanol was refluxed with stirring for 15 h. Then the solvent was evaporated in vacuo, the residue dissolved in 8 ml of water, and the solution was washed with 2×20 ml of ethyl acetate. The pH of the solution was adjusted to 3 by addition of aqueous 1N hydrochloric acid and the mixture was extracted with 3×20 ml of ethyl acetate. The combined extracts were dried over magnesium sulfate and concentrated in vacuo to give a white solid. 61 mg of the title compound were obtained; MS-(−)-ion: M−1=280.9 amu.

Example A-51

(R)-2-[(6-Benzyloxy-1-chloro-4-hydroxy-isoquinoline-3-carbonyl)-amino]-propionic acid a. (R)-2-[(6-Benzyloxy-1-chloro-4-hydroxy-isoqunoline-3-carbonyl-amino]-propionic acid methyl ester 6-Benzyloxy-1-chloro-4-hydroxy-isoquinoline-3-carboxylic acid, 0.33 g, was coupled with D-Alanine methyl ester hydrochloride, 0.150 g, analogously to Example A-1a). 0.205 g of off-white, solid product were obtained, MS-(+)-ion, M+1=415.0 amu.

b. (R)-2-[(6-Benzyloxy-1-chloro-4-hydroxy-isoquinoline-3-carbonyl)-amino]-propionic acid 0.164 g of white solid, prepared analogously to Example A-1 b): MS-(=)-ion, M+1=401.1 amu.

Example A-52

(S)-2-[(7-Benzyloxy-1-chloro-4-hydroxy-isoquinoline-3-carbonyl)-amino]-propionic acid a. (S)-2-[(7-Benzyloxy-1-chloro-4-hydroxy-isoquinoline-3-carbonyl)-amino]-propionic acid methyl ester 7-Benzyloxy-1-chloro-4-hydroxy-isoquinoline-3-carboxylic acid, 0.33 g, was coupled with L-Alanine methyl ester hydrochloride, 0.150 g, analogously to Example A-1 a). 0.264 G of white solid were obtained: MS-(+)-ion, M+1=415. amu.

b. (S)-2-[(7-Benzyloxy-1-chloro-4-hydroxy-isoquinoline-3-carbonyl)-amino]-propionic acid 0.216 g of white solid, prepared analogously to Example A-1 b): MS-(+)-ion, M+1=401.9 amu.

Example A-53

(R)-2-[(7-Benzyloxy-1-chloro-4-hydroxy-isoquinoline-3-carbonyl)-amino]-propionic acid a. (R)-2-[(7-Benzyloxy-1-chloro-4-hydroxy-isoquinoline-3-carbonyl)-amino]-propionic acid methyl ester 7-Benzyloxy-1-chloro-4-hydroxy-isoquinoline-3-carboxylic acid, 0.33 g, was coupled with D-Alanine methyl ester analogously to Example A-1 a). 0.246 g of off-white solid were obtained: MS-(+)-ion, M+1=415.0 amu.

b. (R)-2-[(7-Benzyloxy-1-chloro-4-hydroxy-isoquinoline-3-carbonyl)-amino]-propionic acid 0.211 g of an off-white solid, prepared analogously to Example A-1 b): MS-(+)-ion, M+1=401.0 amu.

Example A-54

(S)-2-[(1-Chloro-4-hydroxy-isoquinoline-3-carbonyl)-amino]-propionic acid a) (S)-2-[(1-Chloro-4-hydroxy-isoquinoline-3-carbonyl)-amino]-propionic acid methyl ester 1-Chloro-4-hydroxy-isoquinoline-3-carboxylic acid, 0.55 g, 1.5 ml of triethylamine, 0.55 g of DECI, and 0.56 g of (L)-Alanine methyl ester hydrochloride were stirred in 15 ml of methylene chloride at room temperature for 72 h. The reaction mixture was partitioned between ethyl acetate and water, the organic layer was separated and successively washed with 1M aqueous HCl, satd. aqueous NaHCO$_3$, and satd. aqueous NaCl. The organic layer was dried with sodium sulfate, filtered, and concentrated under vacuum to afford 0.133 g of off-white solid product: MS-(+)-ion, M+1=308.9 Daltons.

b) (S)-2-[(1-Chloro-4-hydroxy-isoquinoline-3-carbonyl)-amino]-propionic acid 0.116 g of (S) methyl ester, described in Example A-54 a), were saponified/acidified analogously to Example A-1 b) to give 0.087 g of a white solid product: MS–(+)-ion, M+1=294.9 amu.

Example A-55

(R)-2-[(1-Chloro-4-hydroxy-isoquinoline-3-carbonyl)-amino]-propionic acid a. (R)-2-[(1-Chloro-4-hydroxy-isoquinoline-3-carbonyl)-amino]-propionic acid methyl ester 1-Chloro-4-hydroxy-isoquinoline-3-carboxylic acid, 0.55 g, was coupled with 0.40 g of D-Alanine methyl ester analogously to Example A-54 a) and 0.200 g of off-white, solid product were obtained: MS-(+)-icon, M+1=308.8 amu.

b. (R)-2-[(1-Chloro-4-hydroxy-isoquinoline-3-carbonyl)-amino]-propionic acid 0.127 g of white solid, prepared analogously to Example A-1 b): MS-(+)-ion, M+1=294.9 amu.

Example A-56

(S)-2-[(6-Isopropoxy-1-chloro-4-hydroxy-isoquinoline-3-carbonyl)-amino]-propionic acid 0.030 g of 6-isopropoxy-1-chloro-4-hydroxy-isoquinoline-3-carboxylic acid and 0.046 g of HATU were allowed to react with 0.017 g of L-Alanine methyl ester under analogous conditions to Example A-1 a). Treatment of the crude product ester with 0.014 g of NaOH in 0.1 ml of 1:1 methanol-water at room temperature for 2 days, followed by acidification to pH=~2 with 1M hydrochloric acid, gave a solid product. The product was collected by filtration, washed with water, and dried to give 0.023 g of an off-white solid: MS-(−)-ion, M−1=353.0 amu.

Example A-57

(R)-2-[6-Isopropoxy-1-chloro-4-hydroxy-isoquinoline-3-carbonyl)-amino]-propionic acid Analogously to Example A-56, 0.030 g of 6-isopropoxy-1-chloro-4-hydroxy-isoquinoline-3-carboxylic acid was coupled with D-Alanine methyl ester hydrochloride and the product was hydrolyzed to give 0.022 g of an off-white solid: MS-(−)ion, M−1=353.0 amu.

Example A-58

(S)-2-[(7-Isopropoxy-1-chloro-4-hydroxy-isoquinoline-3-carbonyl)-amino-propionic acid Analogously to Example A-56, 0.040 g of 7-isopropoxy-1-chloro-4-hydroxy-isoquinoline-3-carboxylic acid were allowed to react with 0.020 g of L-Alanine methyl ester hydrochloride to give, after hydrolysis of the intermediate ester, 0.047 g of a white solid: MS-(−)-ion, M−1=353.1 amu.

Example A-59

(R)-2-[(7-Isopropoxy-1-chloro-4-hydroxy-isoquinoline-3-carbonyl)-amino]propionic acid Analogously to Example A-56, 0.040 g of 7-isopropoxy-1-chloro-4-hydroxy-isoquinoline-3-carboxylic acid were allowed to react with D-Alanine methyl ester hydrochloride. The intermediate ester product was hydrolyzed as in Example A-56 to give 0.042 g of a white solid: MS-(−)-ion, M−1=353.0 amu.

Example A-60

2-(S)-{[7-(4-Chloro-phenoxy)-4-hydroxy-isoquinoline-3-carbonyl]-amino}-propionic acid a) 4-(4-Chloro-phenoxy)-phthalonitrile

A mixture of 4-nitrophthalonitrile (5.0 g), 4-chlorophenol (3.13 ml) and potassium carbonate (7.99 g) in acetone (87 ml) was refluxed for 3 h. After filtration and concentration, the residue was dissolved in ethyl acetate (100 ml). The solution was washed with NaOH (1N, 50 ml×3) and brine. The organic layer was dried, filtered, concentrated and diluted with dichloromethane. Filtration and rinse through a pad of silica gel gave 5.7 g of the title compound. $^1$NMR (200 MHz, DMSO) δ8.09 (d, J=9 Hz, 1H), 7.83 (d, J=2.6, 1H), 7.53 (d, J=8.6 Hz, 2H), 7.42 (dd, J=2.8, 8.6 Hz, 1H), 7.24 (d, J=8.6, 2H).

b) 4-(4-Chloro-phenoxy)-phthalic acid

A mixture of 1.31 g of 4-(4-Chloro-phenoxy)-phthalonitrile, 45% potassium hydroxide (3.5 ml), and methanol (3.5 ml) was refluxed 18 h. 6N HCl was added to adjust pH to 4. The precipitate was filtered, washed with water, and dried to give 1.45 g of the title compound. MS-(−)-ion: M−1=291.0.

c) [5-(4-Chloro-phenoxy)-1,3-dioxo-1,3-dihydro-isoindol-2-yl]-acetic acid butyl ester A mixture of 500 mg 4-(4-Chloro-phenoxy)-phthalic acid and glycine n-butyl ester (286 mg) was heated at 250° C. for 5 min. The reaction mixture was purified by chromatography with dichloromethane as eluent to give 436 mg the title compound. $^1$H NMR (200 MHz, DMSO) δ7.48 (d, J=8.6 Hz, 1H), 7.59 (d, J=9.0 Hz, 2H), 7.46 (m, 2H), 7.29 (d, J=9.0 Hz, 2H), 4.46 (s, 2H), 4.16 (t, J=6.2 Hz, 2H), 1.61 (m, 2H), 1.38 (m, 2H), 0.92 (t, J=7.0 Hz, 3H).

d) 6- and 7-(4-Chloro-phenoxy)-1,4-dihydroxy-isoquinoline-3-carboxylic acid butyl ester Prepared in analogy to Example A-2 b). Mixture of two isomers. MS-(−)-ion: M−1=386.1.

e) 1-Chloro-6- and 7-(4-chloro-phenoxy)-4-hydroxy-isoquinoline-3-carboxylic acid butyl ester Prepared in analogy to Example A-2 c). Mixture of two isomers. MS-(−)-ion: M−1=404.2.

f) 6- and 7-(4-Chloro-phenoxy)-4-hydroxy-isoquinoline-3-carboxylic acid butyl ester A mixture of 1-Chloro-6- and 7-(4-chloro-phenoxy)-4-hydroxy-isoquinoline-3-carboxylic acid butyl ester (280 mg), 0.27 ml of 57 wt % HI, glacial acetic acid (3 ml), and red phosphorous (43 mg) was refluxed for 25 min. Then the mixture was diluted with water, basified by solid NaHCO$_3$ to pH 8, extracted with ethyl acetate (2×). The ethyl acetate layer was washed with sodium metabisulfite solution, saturated sodium bicarbonate, dried and concentrated. Purification by chromatography with hexanes/ethyl acetate gave 7-(4-Chloro-phenoxy)-4-hydroxy-isoquinoline-3-carboxylic acid butyl ester (103 mg, Compound of Example A-60 a): MS-(−)-ion: M−1=370.3 and 6-(4-Chloro-phenoxy)-4-hydroxy-isoquinoline-3-carboxylic acid butyl ester (71 mg, Compound of Example 60 b): MS-(−)-ion: M−1=370.3.

g) 2-(S)-{[7-(4-Chloro-phenoxy)-4-hydroxy-isoquinoline-3-carbonyl]-amino}-propionic acid Prepared in analogy to Example A-50 by reacting 7-(4-Chloro-phenoxy)-4-hydroxy-isoquinoline-3-carboxylic acid butyl ester (compound of example A-60 a) with L-alanine in a microwave reactor for 20 min at 130 C. MS-(−)-ion: M−1=385.1.

Example A-61

2-(S)-{[6-(4-Chloro-phenoxy)-4-hydroxy-isoquinoline-3-carbonyl]-amino}-propionic acid Prepared in analogy to Example A-50 by reacting 6-(4-Chloro-phenoxy)-4-hydroxy-isoquinoline-3-carboxylic acid butyl ester (compound of Example A-60 b) with L-alanine in a microwave reactor for 25 min at 130° C. MS-(−)-ion: M−1=385.1

Example A-62

2-{[7-(3,4-Difluoro-phenoxy)-4-hydroxy-isoquinoline-3-carbonyl]-amino}-propionic acid a) 5-(3,4-Difluoro-phenoxy)-isoindole-1,3-dione 3,4-Difluorophenol (650 mg) was azeotroped with benzene and dissolved in sodium methoxide solution in methanol (0.5 M, 10 ml). The methanol was then removed under reduced pressure under nitrogen. Then an anhydrous DMF (10 ml) solution of 4-nitrophthalimide (769 mg) was added to the previous mixture. The resulting mixture was refluxed under nitrogen for 23 h. The reaction was cooled down and added 80 ml water. The resulting precipitate was filtered, washed with water (4×) and dried to give the title compound 685 mg. MS-(−)-ion: M−1=274.3.

b) [5-(3,4-Difluoro-phenoxy)-1,3-dioxo-1,3-dihydro-isoindol-2-yl]-acetic acid methyl ester To a pressure tube was added 5-(3,4-difluoro-phenoxy)-isoindole-1,3-dione (680 mg), potassium carbonate (1 g), 3-pentanone (20 ml), and methyl bromoacetate (295 µL). The resulting mixture was heated to 105° C. for 17 h. The reaction was diluted with 20 ml water and extracted with ethyl acetate (2×). The organic layer was dried and concentrated. The mixture was purified through silica gel chromatography with 4:1 hexanes/ethyl acetate and 3:1 hexanes/ethyl acetate to give 657 mg title compound. $^1$H NMR (200 MHz, DMSO) δ7.95 (d, J=9.0 Hz, 1H), 7.64-7.41 (m, 4H), 7.15-7.08 (m, 1H), 4.44 (s, 2H), 3.70 (s, 3H).

c) 6- and 7-(3,4-Difluoro-phenoxy)-1,4-dihydroxy-isoquinoline-3-carboxylic acid butyl ester Prepared in analogy to example A-2 b). Mixture of two isomers. MS-(−)-ion: M−1=388.1.

d) 1-Chloro-6- and 7-(3,4-difluoro-phenoxy)-4-hydroxy-isoquinoline-3-carboxylic acid butyl ester Prepared in analogy to Example A-2 c). Mixture of two isomers was directly carried on to next step.

e) 6- and 7-(3,4-Difluoro-phenoxy)-4-hydroxy-isoquinoline-3-carboxylic acid butyl ester To a solution of 1-Chloro-6- and 7-(3,4-difluoro-phenoxy)-4-hydroxy-isoquinoline-3-carboxylic acid butyl ester (220 mg) in ethyl acetate (4 ml) was added 10% Pd/C (50% wet, 88 mg) and then ammonium formate (340 mg). Resulting mixture was heated to reflux for 0.5 h. After cooling, the reaction mixture was diluted with ethyl acetate and filtered through a pad of Celite. Filtrate was concentrated and separated by chromatography to give 131 mg 7-(3,4-Difluoro-phenoxy)-4-hydroxy-isoquinoline-3-carboxylic acid butyl ester (Compound of Example A-62 a) and 55 mg 6-(3,4-Difluoro-phenoxy)-4-hydroxy-isoquinoline-3-carboxylic acid butyl ester (Compound of Example A-62 b).

f) 2-{[7-(3,4-Difluoro-phenoxy)-4-hydroxy-isoquinoline-3-carbonyl]-amino}-propionic acid Prepared in analogy to Example A-50 by reacting 7-(3,4-Difluoro-phenoxy)-4-hydroxy-isoquinoline-3-carboxylic acid butyl ester (compound of Example A-62 a) with L-alanine in a pressure tube for 3 days at 85° C. MS-(+)-ion: M−1=389.2.

Example A-63

2-(S)-[(4-Hydroxy-7-phenylsulfanyl-isoquinoline-3-carbonyl)-amino]-propionic acid a) 4-Phenylsulfanyl-phthalic acid A mixture of 5.06 g of 4-phenylsulfanyl-phthalonitrile (21.4 mmol), 10 ml of 50% aqueous KOH, and 10 ml of methanol was refluxed with stirring for 3.5 days. Then the mixture was diluted with 100 ml of water and acidified with concentrated hydrochloric acid. The precipitated product was filtered by suction, washed thoroughly with water, and dried in vacuo at 60° C. 5.75 g of the title compound were obtained; MS-(−)-ion: M−1=273.0.

b) (1,3-Dioxo-5-phenylsulfanyl-1,3-dihydro-isoindol-2-yl)-acetic acid 5.62 g of 4-phenylsulfanyl-phthalic acid (20.5 mmol) and 1.55 g of glycine (20.5 mmol) were ground thoroughly together in a mortar. Then the mixture was heated to 210° C. to 220° C. in an oil bath. The molten mass was stirred with a spatula at this temperature for 15 min before it was allowed to cool to ambient temperature in vacuo. 6.30 g of the title compound were obtained; MS-(−)-ion: M−1=311.8; $^1$H NMR (DMSO-d6): δ=7.82 (d, 1H), 7.46 to 7.62 (m, 7H), 4.26 (s, 2H).

c) (1,3-Dioxo-5-phenylsulfanyl-1,3-dihydro-isoindol-2-yl)-acetic acid methyl ester A mixture of 20 ml of methanol, 6.27 g of (1,3-dioxo-5-phenylsulfanyl-1,3-dihydro-isoindol-2-yl)-acetic acid (20 mmol) and 0.3 ml of concentrated sulfuric acid was refluxed with stirring for 18 h. Then 100 ml of concentrated aqueous sodium bicarbonate solution were added and the mixture was extracted with 100 ml of ethyl acetate. The organic phase was dried over MgSO$_4$ and evaporated in vacuo. 6.30 g of the title compound were obtained; MS-(+)-ion: M+1=328.0; $^1$H NMR (CDCl$_3$): δ=7.69 (d, 1H), 7.41 to 7.55 (m, 7H), 4.40 (s, 2H), 3.75 (s, 3H).

d) 1,4-Dihydroxy-7-phenylsulfanyl-isoquinoline-3-carboxylic acid butyl ester (A) and 1,4-Dihydroxy-6-phenylsulfanyl-isoquinoline-3-carboxylic acid butyl ester (B)

0.92 g of sodium (40 mmol) were dissolved in 100 ml of n-butanol with stirring. Then the temperature was raised to 95° C. to 100° C., a hot solution of 6.5 g of (1,3-dioxo-5-phenylsulfanyl-1,3-dihydro-isoindol-2-yl)-acetic acid methyl ester (19.85 mmol) in 20 ml of n-butanol was added and stirring was continued at 95° C. to 100° C. for 1 h. Subsequently, the solvent was evaporated in vacuo, 25 ml of aqueous 2N HCl and 100 ml of ethyl acetate were added and the mixture was stirred vigorously for 1 h before it was filtered by suction. The filter cake was washed thoroughly with water, and dried in vacuo at 60° C. to give 4.43 g of a yellow solid. 4.4 g of this mixture of A and B were separated by flash column chromatography on silica gel eluting with dichloromethane:ethyl acetate (98:2). Evaporation of the first fraction yielded 1.99 g of A; $^1$H NMR (CDCl$_3$): δ=10.48 (bs, 1H), 8.39 (bs, 1H), 8.24 (d, 1H), 8.01 (d, 1H), 7.35 to 7.55 (m, 6H), 4.39 (t, 2H), 1.77 (m, 2H), 1.46 (m, 2H), 0.99 (t, 3H). Evaporation of the second fraction yielded 2.26 g of B; $^1$H NMR (CDCl$_3$): δ=10.38 (bs, 1H), 8.32 (bs, 1H), 8.24 (d, 1H), 7.86 (d, 1H), 7.37 to 7.56 (m, 6H), 4.39 (t, 2H), 1.77 (m, 2H), 1.46 (m, 2H), 0.99 (t, 3H).

e) 1-Bromo-4-hydroxy-7-phenylsulfanyl-isoquinoline-3-carboxylic acid butyl ester To a solution of 4.59 g of phosphorous oxybromide (16 mmol) in 25 ml of anhydrous acetonitrile were added 1.11 g of 1,4-dihydroxy-7-phenylsulfanyl-isoquinoline-3-carboxylic acid butyl ester (3 mmol) and the mixture was refluxed gently with stirring for 1 h. Then 5.04 g of sodium bicarbonate (60 mmol) were added, followed by the dropwise addition of 8 ml of water. After stirring at ambient temperature for 90 min the mixture was concentrated in vacuo to about one third of its volume, 40 ml of water were added and the mixture was extracted with 30 ml of ethyl acetate. The mixture was filtered by suction. The organic phase was separated, dried over $MgSO_4$, and filtered through a pad of silica gel. Evaporation in vacuo gave 0.885 g of the title compound; $^1$H NMR ($CDCl_3$): δ=11.84 (s, 1H), 8.21 (d, 1H), 7.91 (d, 1H), 7.40 to 7.55 (m, 6H), 4.46 (t, 2H), 1.84 (m, 2H), 1.48 (m, 2H), 0.98 (t, 3H).

f) 4-Hydroxy-7-phenylsulfanyl-isoquinoline-3-carboxylic acid butyl ester

A mixture of 432 mg of 1-bromo-4-hydroxy-7-phenylsulfanyl-isoquinoline-3-carboxylic acid butyl ester (1 mmol), 63 mg of red phosphorous (2 mmol), 0.4 ml of aqueous 57 wt % HI (3 mmol), and 1 ml of glacial acetic acid was refluxed with stirring for 30 min. Then the reaction mixture was diluted with 25 ml of ethyl acetate, filtered by suction through a pad of celite, washed with a solution of 0.2 g of $NaHSO_3$ in 5 ml of water, and washed two times with 5 ml of concentrated aqueous sodium bicarbonate solution. The organic phase was dried over $MgSO_4$ and evaporated in vacuo. The residue was purified by flash column chromatography on silica gel eluting with hexanes:ethyl acetate (85:15). 123 mg of the title compound were obtained; $^1$H NMR ($CDCl_3$): δ=11.85 (s, 1H), 8.60 (s, 1H), 8.23 (d, 1H), 7.38 to 7.63 (m, 7H), 4.49 (t, 2H), 1.87 (m, 2H), 1.47 (m, 2H), 0.98 (t, 3H).

g) 2-(S)-[(4-Hydroxy-7-phenylsulfanyl-isoquinoline-3-carbonyl)-amino]-propionic acid A mixture of 4-hydroxy-7-phenylsulfanyl-isoquinoline-3-carboxylic acid butyl ester (0.20 g) and L-alanine (0.75 g) in 0.5 M NaOMe/MeOH (11.3 ml) was heated to reflux for 36 h. After cooling, reaction mixture was concentrated. The residue was suspended in water (50 ml) and extracted with ethyl acetate (50 ml) which was discarded. The aqueous layer was acidified by 2 N HCl aqueous solution. Extracted with ethyl acetate (2×50 ml). Combined organic layers were dried over magnesium sulfate, filtered, and concentrated to give the title compound (0.15 g). MS-(−)-ion: M−1=367.1.

Example A-64

2-(R)-[(4-Hydroxy-7-phenylsulfanyl-isoquinoline-3-carbonyl)-amino]-propionic acid Prepared in analogy to Example A-63 g) by reacting 4-hydroxy-7-phenylsulfanyl-isoquinoline-3-carboxylic acid butyl ester with D-alanine. MS-(−)-ion: M−1=367.1.

Example A-65

2-(R)-[(4-Hydroxy-7-phenoxy-isoquinoline-3-carbonyl)-amino]-propionic acid a) 4-Phenoxy-phthalic acid Synthesized from 4-phenoxy-phthalonitrile in analogy to Example A-63 a); MS-(−)-ion: M−1=256.9; $^1$H NMR (DMSO-$d_6$): δ=7.93 (d, 1H), 7.07 to 7.52 (m, 7H).

b) (1,3-Dioxo-5-phenoxy-1,3-dihydro-isoindol-2-yl)-acetic acid

Synthesized from 4-phenoxy-phthalic acid in analogy to Example A-63 b). MS-(+)-ion: M+1=297.9; $^1$H NMR (DMSO-$d_6$): δ=7.87 (d, 1H), 7.17 to 7.52 (m, 7H), 4.26 (s, 2H).

c) (1,3-Dioxo-5-phenoxy-1,3-dihydro-isoindol-2-yl)-acetic acid methyl ester

Synthesized from (1,3-dioxo-5-phenoxy-1,3-dihydro-isoindol-2-yl)-acetic acid in analogy to Example A-63 c); $^1$H NMR ($CDCl_3$): δ=7.83 (d, 1H), 7.05 to 7.46 (m, 7H), 4.41 (s, 2H), 3.76 (s, 3H).

d) 1,4-Dihydroxy-7-phenoxy-isoquinoline-3-carboxylic acid butyl ester (A) and 1,4-Dihydroxy-6-phenoxy-isoquinoline-3-carboxylic acid butyl ester (B)

Synthesized from (1,3-dioxo-5-phenoxy-1,3-dihydro-isoindol-2-yl)-acetic acid methyl ester in analogy to Example A-63 d); Compound A: $^1$H NMR ($CDCl_3$): δ=10.58 (bs, 1H), 8.37 (bs, 1H), 8.14 (d, 1H), 7.87 (d, 1H), 7.05 to 7.49 (m, 6H), 4.39 (t, 2H), 1.77 (m, 2H), 1.46 (m, 2H), 0.99 (t, 3H); Compound B: $^1$H NMR ($CDCl_3$): δ=10.38 (bs, 1H), 8.38 (d, 1H), 8.28 (bs, 1H), 7.56 (d, 1H), 7.06 to 7.47 (m, 6H), 4.40 (t, 2H), 1.77 (m, 2H), 1.46 (m, 2H), 0.99 (t, 3H).

e) 1-Bromo-4-hydroxy-7-phenoxy-isoquinoline-3-carboxylic acid butyl ester

Synthesized from 1,4-dihydroxy-7-phenoxy-isoquinoline-3-carboxylic acid butyl ester in analogy to Example A-63 e); $^1$H NMR ($CDCl_3$): δ=11.89 (s, 1H), 8.35 (d, 1H), 7.63 (d, 1H), 7.08 to 7.52 (m, 6H), 4.47 (t, 2H), 1.84 (m, 2H), 1.48 (m, 2H), 0.99 (t, 3H).

f) 4-Hydroxy-7-phenoxy-isoquinoline-3-carboxylic acid butyl ester

A mixture of 208 mg of 1-Bromo-4-hydroxy-7-phenoxy-isoquinoline-3-carboxylic acid butyl ester (0.5 mmol), 49 mg of sodium acetate (0.6 mmol), 50 mg of 10 wt % palladium on charcoal, 10 ml of methanol, and 5 ml of ethyl acetate was stirred under hydrogen at 1 atm for 15 h. Then the mixture was filtered by suction through a pad of celite and was concentrated in vacuo. The residue was partitioned between 2 ml of half concentrated aqueous bicarbonate solution and 8 ml of ethyl acetate. The organic phase was dried over $MgSO_4$. Evaporation in vacuo gave 130 mg of the title compound; $^1$H NMR ($CDCl_3$): δ=11.89 (bs, 1H), 8.61 (s, 1H), 8.36 (d, 1H), 7.10 to 7.53 (m, 7H), 4.49 (t, 2H), 1.87 (m, 2H), 1.47 (m, 2H), 0.98 (t, 3H).

g) 2-(R)-[(4-Hydroxy-7-phenoxy-isoquinoline-3-carbonyl)-amino]-propionic acid

Prepared in analogy to Example A-63 g) by reacting 4-hydroxy-7-phenoxy-isoquinoline-3-carboxylic acid butyl ester with D-alanine at the reflux condition for 5 days. MS-(−)-ion: M−1=351.1.

Example A-66

2-(S)-{[4-Hydroxy-7-(4-methoxy-phenoxy)-isoquinoline-3-carbonyl]-amino}-propionic acid a) 4-(4-Methoxy-phenoxy)-phthalonitrile A mixture of 4-nitro-phthalonitrile (4.00 g), 4-methoxy-phenol (3.46 g) and potassium carbonate (6.39 g) in acetone (64 ml) was heated to reflux for 2 h. Reaction mixture was cooled and filtered. Filtrate was concentrated and the residue was dissolved in ethyl acetate (100 ml). The solution was washed with NaOH (1 N, 50 ml), water, and then brine. The organic layer was dried over magnesium sulfate, filtered, and concentrated to give the product (6.14 g). $^1$H NMR (200 MHz, CDCl$_3$) δ6.70 (d, J=7.8 Hz, 1H), 7.21 (m, 2H), 6.96 (m, 4H), 3.84 (s, 3H).

b) 4-(4-Methoxy-phenoxy)-phthalic acid

Prepared in analogy to Example A-63 a). MS-(−)-ion: M−1=286.9.

c) [5-(4-Methoxy-phenoxy)-1,3-dioxo-1,3-dihydro-isoindol-2-yl]-acetic acid methyl ester Prepared in analogy to examples A-63 b and c). $^1$H NMR (200 MHz, CDCl$_3$) δ7.74 (d, J=8.6 Hz, 1H), 7.25 (m, 2H), 6.98 (m, 4H), 4.40 (s, 2H), 3.83 (s, 3H), 3.75 (s, 3H).

d) 6- and 7-(4-Methoxy-phenoxy)-1,4-dihydroxy-isoquinoline-3-carboxylic acid butyl ester Prepared in analogy to Example A-63 d). MS-(+)-ion: M+1=384.10.

e) 6- and 7-(4-methoxy-phenoxy)-1-bromo-4-hydroxy-isoquinoline-3-carboxylic acid butyl ester Prepared in analogy to Example A-63 e). MS-(+)-ion: M+1=448.05, 446.05.

g) 7-(4-Methoxy-phenoxy)-4-hydroxy-isoquinoline-3-carboxylic acid butyl ester (A) and 6-(4-Methoxy-phenoxy)-4-hydroxy-isoquinoline-3-carboxylic acid butyl ester (B)

To a solution of the above compound (2.78 g) in ethyl acetate (50 ml) was added 10 wt % palladium on charcoal (wet) (1.2 g) and then ammonium formate (5.9 g). Resulting mixture was refluxed for 4 h. After cooling, it was filtered and rinsed with ethyl acetate (100 ml). Filtrate was concentrated and the residue was purified by silica gel chromatography (33%-50% ethyl acetate in hexanes) to give 7-(4-methoxy-phenoxy)-4-hydroxy-isoquinoline-3-carboxylic acid butyl ester (A) (0.74 g) (MS-(+)-ion: M+1=368.16) and 6-(4-methoxy-phenoxy)-4-hydroxy-isoquinoline-3-carboxylic acid butyl ester (B) (1.11 g) (MS-(+)-ion: M+1=368.17).

h) 2-(S)-{[4-Hydroxy-7-(4-methoxy-phenoxy)-isoquinoline-3-carbonyl]-amino}-propionic acid Prepared in analogy to Example A-63 g) from 7-(4-methoxy-phenoxy)-4-hydroxy-isoquinoline-3-carboxylic acid butyl ester (of Example of A-66 a) and L-alanine. MS-(−)-ion: M−1=381.13.

Example A-67

2-(S)-[(7-Benzenesulfonyl-4-hydroxy-isoquinoline-3-carbonyl)-amino]-propionic acid a) 7-benzenesulfonyl-4-hydroxy-isoquinoline-3-carboxylic acid butyl ester A mixture of 7-benzenesulfonyl-4-hydroxy-isoquinoline-3-carboxylic acid butyl ester (Compound 363 f) (165 mg) and m-chloroperoxy benzoic acid (77%) (377 mg) in methylene chloride (5 ml) was stirred at room temperature overnight. Reaction mixture was filtered. Filtrate was diluted with methylene chloride (20 ml) and washed sequentially with saturated sodium bicarbonate aqueous solution (2×20 ml), water and brine. Organic layer was dried over magnesium sulfate, filtered, and concentrated. The crude product was purified by silica gel chromatography (eluting with 0%-20% ethyl acetate in methylene chloride) to give the title compound 120 mg. MS-(+)-ion: M+1=386.11.

b) 2-(S)-[(7-Benzenesulfonyl-4-hydroxy-isoquinoline-3-carbonyl)-amino]-propionic acid Prepared in analogy to Example A-63 g) from 7-benzenesulfonyl-4-hydroxy-isoquinoline-3-carboxylic acid butyl ester and L-alanine. MS-(−)-ion: M−1=399.1.

Example A-68

(R)-2-[(4-Hydroxy-1-methoxymethyl-7-phenoxy-isoquinoline-3-carbonyl)-amino]-propionic acid a) 1-Bromo-4-hydroxy-7-phenoxy-isoquinoline-3-carboxylic acid A mixture of 1-Bromo-4-hydroxy-7-phenoxy-isoquinoline-3-carboxylic acid butyl ester (3.52 g, 8.45 mmol; Example A-65 e) aqueous 2N NaOH (50 ml, 100 mmol) and EtOH (50 ml) was refluxed with stirring for 2 h. Then the solution was concentrated in vacuo to ½ of its volume, diluted with water (180 ml), and was acidified by addition of aqueous 6N HCl (20 ml). After stirring at ambient temperature for 30 min the resulting suspension was submitted to vacuum filtration. The filter cake was washed thoroughly with water and dried in vacuo at 70° C. to give the title compound as a white solid (3.05 g); $^1$H NMR (DMSO-d6): δ=8.33 (d, 1H), 7.20 to 7.61 (m, 7H).

b) 4-Benzyloxy-1-methoxymethyl-7-phenoxy-isoquinoline-3-carboxylic acid benzyl ester To a solution of 1-Bromo-4-hydroxy-7-phenoxy-isoquinoline-3-carboxylic acid (721 mg, 2 mmol) in anhydrous THF (100 ml) was added slowly a 2.5 M solution of n-BuLi in hexanes (3.2 ml, 8 mmol) at −78° C. with stirring. After stirring for another 5 min MeOCH$_2$I (357 μl, 4 mmol) was added. Stirring was continued for additional 15 min at −78° C. before water (50 ml) and aqueous 6N HCl (1.5 ml) were added. The mixture was allowed to warm up to ambient temperature with stirring, and was then concentrated in vacuo to ca. 1/3 of its volume. Traces of iodine were removed by addition of sodium-meta-bisulfite before the mixture was extracted with EtOAc (100 ml). The organic phase was dried over MgSO$_4$ and concentrated in vacuo to give a tan solid (576 mg). A mixture of 570 mg of the aforementioned yellowish solid, benzyl bromide (0.97 ml, 8 mmol), K₂CO₃ (2.76 g, 20 mmol) and acetone (40 ml) was refluxed with stirring for 3.5 d. Then the mixture was concentrated in vacuo. To the residue was added water (15 ml) and the mixture was extracted with EtOAc (60 ml). The organic phase was dried over MgSO₄ and concentrated in vacuo to give a yellowish oil. Purification by flash column chromatography on silica gel using hexanes:EtOAc=75:25 as the eluent gave the title compound as yellow oil (490 mg); MS-(+)-ion: M+1=506.2.

c) 4-Benzyloxy-1-methoxymethyl-7-phenoxy-isoquinoline-3-carboxylic acid

A mixture of 4-Benzyloxy-1-methoxymethyl-7-phenoxy-isoquinoline-3-carboxylic acid benzyl ester (480 mg, 0.95 mmol), KOH (325 mg, 5 mmol) and EtOH (10 ml) was stirred at ambient temperature for 48 h before the solvent was evaporated in vacuo. To the residue was added water (10 ml), the mixture was acidified by the addition of aqueous 6N HCl and extracted with EtOAc (2×25 ml). The combined organic phases were dried over MgSO₄ and concentrated in vacuo to give the title compound as a tan solid (355 mg); MS-(−)-ion: M−1=414.1.

d) (R)-2-[(4-Benzyloxy-1-methoxymethyl-7-phenoxy-isoquinoline-3-carbonyl)-amino]-propionic acid tert-butyl ester To a mixture of 4-Benzyloxy-1-methoxymethyl-7-phenoxy-isoquinoline-3-carboxylic acid (79 mg, 0.19 mmol), NEt₃ (56 µl, 0.4 mmol), and CH₂Cl₂ (5 ml) cooled with an ice bath was added ClCO₂iBu (26.5 µl, 0.2 mmol) with stirring. After stirring for 15 min (R)-alanine tert-butyl ester hydrochloride (36 mg, 0.2 mmol) was added and the mixture was allowed to warm up to ambient temperature overnight with stirring. Subsequently; the mixture was concentrated in vacuo. To the residue was added water (10 ml) and a few drops of aqueous 6N HCl. The mixture was extracted with EtOAc (2×15 ml). The organic phase was dried over MgSO₄ and concentrated in vacuo. Purification by flash column chromatography on silica gel using EtOAc as the eluent gave the title compound as a tan oil (88 mg); MS-(+)-ion: M+23=565.2.

e) (R)-[(4-Hydroxy-1-methoxymethyl-7-phenoxy-isoquinoline-3-carbonyl)-amino]-acetic acid tert-butyl ester A mixture of (R)-2-[(4-Benzyloxy-1-methoxymethyl-7-phenoxy-isoquinoline-3-carbonyl)-amino]-propionic acid tert-butyl ester (81 mg, 0.15 mmol), Pd/C (50 mg, 10 wt % Pd), EtOAc (15 ml) was stirred under a H₂-atmosphere at ambient pressure and temperature for 18 h. Then the mixture was filtered through a pad of celite. Celite and filter cake were washed thoroughly with EtOAc and the combined organic phases were concentrated in vacuo to give the title compound as a tan oil (63 mg); MS-(−)-ion: M−1=451.2.

f) (R)-2-[(4-Hydroxy-1-methoxymethyl-7-phenoxy-isoquinoline-3-carbonyl)-amino]-propionic acid A mixture of (R)-[(4-Hydroxy-1-methoxymethyl-7-phenoxy-isoquinoline-3-carbonyl)-amino]-acetic acid tert-butyl ester (59 mg, 0.13 mmol) and trifluoroacetic acid (4 ml) was stirred at ambient temperature for 4 h. Then the mixture was concentrated in vacuo and the residue dissolved in EtOH. The solvent was evaporated in vacuo to give the title compound as a tan solid (52 mg); MS-(+)-ion: M+1=397.1.

Example A-69

(S)-2-[(4-Hydroxy-1-methoxymethyl-7-phenoxy-isoquinoline-3-carbonyl)-amino]-propionic acid a) (S)-2-[(4-Benzyloxy-1-methoxymethyl-7-phenoxy-isoquinoline-3-carbonyl)-amino]-propionic acid tert-butyl ester Synthesized from (S)-alanin tert-butyl ester and 4-Benzyloxy-1-methoxymethyl-7-phenoxy-isoquinoline-3-carboxylic acid (Example A-68 c) in analogy to Example A-68 d); MS-(+)-ion: M+23=565.2.

b) (S)-2-[(4-Hydroxy-1-methoxymethyl-7-phenoxy-isoquinoline-3-carbonyl)-amino]-propionic acid tert-butyl ester Synthesized from (S)-2-[(4-Benzyloxy-1-methoxymethyl-7-phenoxy-isoquinoline-3-carbonyl)-amino]-propionic acid tert-butyl ester in analogy to Example A-68 e); MS-(−)-ion: M−1=451.2.

c) (S)-2-[(4-Hydroxy-1-methoxymethyl-7-phenoxy-isoquinoline-3-carbonyl)-amino]-propionic acid Synthesized from (S)-2-[(4-Hydroxy-1-methoxymethyl-7-phenoxy-isoquinoline-3-carbonyl)-amino]-propionic acid tert-butyl ester in analogy to Example A-68 f); MS-(+)-ion: M+1=397.1.

Example A-70

(S)-2-[(4-Mercapto-7-phenoxy-isoquinoline-3-carbonyl)-amino]-propionic acid a) 4-Dimethylthiocarbamoyloxy-7-phenoxy-isoquinoline-3-carboxylic acid butyl ester To a solution of 1.5 g of 4-Hydroxy-7-phenoxy-isoquinoline-3-carboxylic acid butyl ester, Example A-65.f, in 6.3 ml of anhydrous DMF was added 578 mg of dimethylthiocarbamoylchloride and 1.5 g of 1,4-diazabicyclo[2.2.2]octane. The mixture was stirred overnight at room temperature. The mixture was poured into 30 ml of 1 N HCl and extracted three times with 30 ml portions of ethyl acetate. The organic fractions were washed with water and brine, dried over anhydrous sodium sulfate, and concentrated to 1.9 g of product; MS (+) m/z 425.27 (M+1)

b) 4-Dimethylcarbamoylsulfanyl-7-phenoxy-isoquinoline-3-carboxylic acid butyl ester A solution of 1.9 g of 4-Dimethylthiocarbamoyloxy-7-phenoxy-isoquinoline-3-carboxylic acid butyl ester in 22 ml of phenyl ether was heated to 190° C. for 2 hours. The solution was concentrated under vacuum to give a crude residue, which was purified by column chromatography on silica gel, eluting the product with a gradient of 30-80% ethyl acetate in hexanes to give 1.73 g; MS (+) m/z 425.07 (M+1)

c) 4-Mercapto-7-phenoxy-isoquinoline-3-carboxylic acid methyl ester

To a solution of 6.5 ml of 0.5 N sodium methoxide in methanol was added 460 mg of 4-Dimethylcarbamoylsulfanyl-7-phenoxy-isoquinoline-3-carboxylic acid butyl ester. The resultant solution was heated to 50-60° C. for 8 hours, cooled to room temperature, and diluted with 10 ml water and 7.0 ml 1 N HCl. The resulting yellow precipitate was collected by filtering the solution through a (medium) porous buchner filter funnel to give 307 mg of product; MS (+) m/z 312.08 (M+1)

d) (S)-2-[(4-Mercapto-7-phenoxy-isoquinoline-3-carbonyl)-amino]-propionic acid

To a solution of 6.0 ml of 0.5 M sodium methoxide in methanol was added 100 mg of 4-Mercapto-7-phenoxy-isoquinoline-3-carboxylic acid methyl ester and 286 mg of L-alanine. The mixture was heated to 150° C. for 15 minutes using a CEM Discover microwave reactor. The resultant solution was acidified to pH 3 with 1 N HCl, diluted with 10 ml water, and extracted with 20 ml of ethyl acetate. The organic fraction was washed with brine, dried over anhydrous sodium sulfate, and concentrated to 114 mg of product; MS (−): m/z 369.07 (M−1).

Example A-71

(S)-2-{[1-(4-Chloro-phenylsulfanyl)-4-hydroxy-isoquinoline-3-carbonyl]-amino}-propionic acid a) 1-bromo-4-hydroxy-isoquinoline-3-carboxylic acid butyl ester The title compound was prepared from (1,3-Dioxo-1,3-dihydro-isoindol-2-yl)-acetic acid methyl ester in analogy to examples A-65 c)-e); $^1$H NMR (200 MHz, CD$_3$OD) δ11.89 (s, 1H), 8.41 (m, 1H), 8.25 (m, 1H), 7.84 (m, 2H), 4.49 (t, J=7.0 Hz, 2H), 1.87 (m, 2H), 1.47 (m, 2H), 1.00 (t, J=7.2 Hz, 3H).

b) (S)-2-{[1-bromo-4-hydroxy-isoquinoline-3-carbonyl]-amino}-propionic acid 400 mg of 1-bromo-4-hydroxy-isoquinoline-3-carboxylic acid butyl ester and 890 mg of (L)-Alanine was suspended in a 20 ml solution of 0.5 M of sodium methoxide in methanol. The mixture was heated to 160° C. for 12 min using a CEM Discover microwave reactor. The resultant solution was concentrated to ca. 10 ml, and 0.5 N HCl was added until a pH 3 was reached. The solution was extracted three times with ethyl acetate, and the organic fractions dried over sodium sulfate and concentrated to a tan solid; MS (−): m/z 337.14 (M−1)

c) (S)-2-{[1-(4-Chloro-phenylsulfanyl)-4-hydroxy-isoquinoline-3-carbonyl]-amino}-propionic acid To a solution of 250 mg of (S)-2-{[1-bromo-4-hydroxy-isoquinoline-3-carbonyl]-amino}-propionic acid in 0.7 ml of 1-methyl-2-pyrrolidinone was added 433 mg of 4-chloro-benzenethiol. The solution was heated at 210° C. for 30 min. using a CEM Discover microwave reactor. The solution was concentrated under vacuum. The resultant residue was crystallized from methanol to yield 18 mg of a tan solid; MS (−): m/z 401.10 (M−1)

Example A-72

(R)-2-{[1-(4-Chloro-phenylsulfanyl)-4-hydroxy-isoquinoline-3-carbonyl]-amino}-propionic acid The title compound was prepared from 1-bromo-4-hydroxy-isoquinoline-3-carboxylic acid butyl ester, Example A-71 a), and (D)-alanine under conditions analogous to Example A-71.b-c; MS (−): m/z 401.08 (M−1).

Example A-73

(S)-2-{[7-(3-Fluoro-5-methoxy-phenoxy)-4-hydroxy-isoquinoline-3-carbonyl]-amino}-propionic acid a) 4-(3,4-Difluoro-phenoxy)-phthalonitrile Prepared in analogy to Example A-60 a). $^1$H NMR (200 MHz, DMSO) δ8.14 (d, J=9 Hz, 1H), 7.95 (d, J=2.6, 1H), 7.56 (dd, J=2.6, 8.6 Hz, 1H), 7.19 (dt, J=2.4, 9.2 Hz, 1H), 7.04 (m, 2H).

b) 4-(3-Fluoro-5-methoxy-phenoxy)-phthalic acid

Prepared in analogy to Example A-60 b). One of the fluoro group is substituted by a methoxy group during the hydrolysis. MS-(−)-ion M−1=305.0.

c) [5-(3-Fluoro-5-methoxy-phenoxy)-1,3-dioxo-1,3-dihydro-isoindol-2-yl]-acetic acid butyl ester Prepared in analogy to Example A-60 c). $^1$H NMR (200 MHz, DMSO) δ7.93 (d, J=8.6 Hz, 1H), 7.43 (m, 2H), 6.79-6.63 (m, 3H), 4.41 (s, 2H), 4.10 (t, J=6.2, 2H), 1.54 (m, 2H), 1.30 (m, 2H), 0.86 (t, J=7.0, 3H).

d) 6- and 7-(3-Fluoro-5-methoxy-phenoxy)-1,4-dihydroxy-isoquinoline-3-carboxylic acid butyl ester Prepared in analogy to Example A-2 b). Mixture of two isomers. MS-(−)-ion M−1=400.1.

e) 1-Chloro-6- and 7-(3-fluoro-5-methoxy-phenoxy)-4-hydroxy-isoquinoline-3-carboxylic acid butyl ester Prepared in analogy to Example A-2 c). Mixture of two isomers. MS-(−)-ion M−1=418.3.

f) 6- and 7-(3-Fluoro-5-methoxy-phenoxy)-4-hydroxy-isoquinoline-3-carboxylic acid butyl ester Prepared in analogy to example A-62 e). The mixture of isomers were separated to give 7-(3-fluoro-5-methoxy-phenoxy)-4-hydroxy-isoquinoline-3-carboxylic acid butyl ester (Compound of example A-73 a) and 6-(3-fluoro-5-methoxy-phenoxy)-4-hydroxy-isoquinoline-3-carboxylic acid butyl ester (Compound of example A-73 b). $^1$H NMR (200 MHz, CD$_3$OD) δ8.73 (s, 1H), 8.15 (d, J=9.0 Hz, 1H), 7.71 (s, 1H), 7.59 (m, 1H), 6.65-6.47 (m, 3H), 4.49 (t, J=6.6 Hz, 2H), 3.81 (s, 3H), 1.87 (m, 2H), 1.56 (m, 2H), 1.03 (t, J=7.4. 3H).

g) (S)-2-{[7-(3-Fluoro-5-methoxy-phenoxy)-4-hydroxy-isoquinoline-3-carbonyl]-amino}-propionic acid Prepared in analogy to Example A-50 by reacting 7-(3-fluoro-5-methoxy-phenoxy)-4-hydroxy-isoquinoline-3-carboxylic acid butyl ester (compound of example A-73 a) with L-alanine in a pressure tube for 3 days at 90 C. MS-(−)-ion M−1=399.1.

Example A-74

2-(S)-[(7-Cyclohexyloxy-4-hydroxy-isoquinoline-3-carbonyl)-amino]-propionic acid a. (5-Hydroxy-1,3-dioxo-1,3-dihydro-isoindol-2-yl)-acetic acid ethyl ester

Prepared in analogy to example D-100 c) from 4-hydroxy-phthalic acid and glycine ethyl ester HCl salt. $^1$H NMR (200 MHz, DMSO-$d_6$) δ11.0 (br s, 1H), 7.74 (d, J=7.8 Hz, 1H), 7.17 (m, 2H), 4.35 (s, 2H), 4.13 (q, J=7.0 Hz, 2H), 1.20 (t, J=7.0 Hz, 3H).

b. (5-Cyclohexyloxy-1,3-dioxo-1,3-dihydro-isoindol-2-yl)-acetic acid ethyl ester To a mixture of (5-hydroxy-1,3-dioxo-1,3-dihydro-isoindol-2-yl)-acetic acid ethyl ester (8.0 g) in anhydrous tetrahydrofuran (160 ml) was added cyclohexanol (3.2 g), diethylazadicarboxylate (6,9 g) and then triphenyl phosphine (12.6 g). Resulting mixture was stirred at room temperature overnight and concentrated. Residue was partitioned between water and ethyl acetate. Aqueous layer was extracted with ethyl acetate. Combined organic layers were washed with brine, dried over magnesium sulfate and filtered. Filtrate was concentrated and purified by silica gel chromatography (eluting with 5% ethyl acetate in methylene chloride) to give the title compound (6.2 g). $^1$H NMR (200 MHz, CDCl$_3$) δ7.73 (dd, J=8.2, 0.8 Hz, 1H), 7.30 (br s, 1H), 7.12 (m, 1H), 4.38 (m, 3H), 4.21 (q, J=7.1 Hz, 2H), 2.02 (m, 2H), 1.82-1.25 (m, 13H).

c. 6- and 7-Cyclohexyloxy-1,4-dihydroxy-isoquinoline-3-carboxylic acid butyl ester Prepared in analogy to Example A-63 d) to give 7-cyclohexyloxy-1,4-dihydroxy-isoquinoline-3-carboxylic acid butyl ester (Compound A-74 c1) (MS-(+)-ion M+1=360.16) and 6-cyclohexyloxy-1,4-dihydroxy-isoquinoline-3-carboxylic acid butyl ester (Compound A-74 c2) (MS-(+)-ion M+1=360.18).

d. 1-Bromo-7-cyclohexyloxy-4-hydroxy-isoquinoline-3-carboxylic acid butyl ester A mixture of 7-cyclohexyloxy-1,4-dihydroxy-isoquinoline-3-carboxylic acid butyl ester (Compound A-74 c1) (1.3 g) and phosphorus oxybromide (1.35 g) in anhydrous toluene (25 ml) was heated in a microwave reactor (sealed tube) at 130° C. for 15 min. After cooling, reaction mixture was concentrated. The residue was treated with saturated sodium bicarbonate aqueous solution (100 ml) and stirred at room temperature for 20 min. Extracted with ethyl acetate. Organic layer was washed with water, brine, dried over magnesium sulfate, filtered, and concentrated to give the title compound (1.2 g). MS-(+)-ion M+1=422.12, 424.12.

e. 7-Cyclohexyloxy-4-hydroxy-isoquinoline-3-carboxylic acid butyl ester

To a mixture of 1-bromo-7-cyclohexyloxy-4-hydroxy-isoquinoline-3-carboxylic acid butyl ester (936 mg) in ethyl acetate (25 ml) was added 10% Pd/C (50% wet) (430 mg) and then ammonium formate (1.4 g). Resulting mixture was refluxed for 4 h. After cooling, reaction mixture was filtered and concentrated. The residue was purified by silica gel chromatography (3%-10% ethyl acetate in methylene chloride) to give the title compound (550 mg). MS-(+)-ion M+1=344.22.

f. 2-(S)-[(7-Cyclohexyloxy-4-hydroxy-isoquinoline-3-carbonyl)-amino]-propionic acid A mixture of 7-cyclohexyloxyl-4-hydroxy-isoquinoline-3-carboxylic acid butyl ester (80 mg) and L-alanine (207 mg) in 0.5 M sodium methoxide in methanol (3.7 ml) was heated in a microwave reactor (sealed tube) at 120° C. for 40 min. Reaction mixture was concentrated, dissolved in water (30 ml), and acidified by 2 N HCl to pH=4. It was extracted with ethyl acetate. Organic layer was washed with water, brine, dried over magnesium sulfate, and filtered. Filtrate was concentrated and purified by silica gel chromatography to give the title compound (52 mg). MS-(+)-ion M+1=359.18.

Example A-75

2-(S)-{[7-(4-Fluoro-phenoxy)-4-hydroxy-1-methyl-isoquinoline-3-carbonyl]-amino}-propionic acid a. 5-(4-Fluoro-phenoxy)-isoindole-1,3-dione

A mixture of 5-Nitro-isoindole-1,3-dione (177 g, 0.904 mol), 4-fluoro-phenol (128 g, 1.13 mol), K$_2$CO$_3$ (419 g, 3 mol) and DMF (2 l) was refluxed with stirring for 3 h before the mixture was poured into water (12 l) with stirring. The precipitate formed was isolated by vacuum filtration, washed with water (8 l) and dried in vacuo at 70° C. to give the title compound as a tan powder (43.2 g); $^1$H NMR (CDCl$_3$) δ=7.79 (d, 1H), 7.57 (br s, 1H), 7.01 to 7.29 (m, 6H).

b. [5-(4-Fluoro-phenoxy)-1,3-dioxo-1,3-dihydro-isoindol-2-yl]-acetic acid methyl ester A mixture of 5-(4-fluoro-phenoxy)-isoindole-1,3-dione (42.9 g, 167 mmol), Bromo-acetic acid methyl ester (21.1 ml, 223 mmol), K$_2$CO$_3$ (62.3 g, 446 mmol) and Et$_2$CO (700 ml) was refluxed with stirring for 16 h before the mixture was concentrated in vacuo. To the residue was added water (150 ml) and the resulting slurry was extracted with EtOAc (1×750 ml, 1×250 ml). The combined organic phases were dried over MgSO$_4$ and concentrated in vacuo to give the title compound as a tan solid (49.7 g); $^1$H NMR (CDCl$_3$) δ=7.80 (d, 1H), 7.01 to 7.30 (m, 6H), 4.41 (s, 2H), 3.76 (s, 3H).

c. 7-(4-Fluoro-phenoxy)-1,4-dihydroxy-isoquinoline-3-carboxylic acid butyl ester Sodium (7.2 g, 310 mmol) was dissolved in n-butanol (300 ml) with stirring at 70° C. Afterwards, the temperature was raised to 95-100° C. and a solution of [5-(4-Fluoro-phenoxy)-1,3-dioxo-1,3-dihydro-isoindol-2-yl]-acetic acid methyl ester (49.4 g, 150 mmol) in hot n-butanol (300 ml) was added with vigorous stirring. The mixture was stirred for another 90 min at 95-100° C. and was then allowed to cool to 60° C. with stirring before 2 N HCl (160 ml) was added. The mixture was stirred vigorously for 30 min and was then allowed to cool to ambient temperature. Subsequently, the mixture was submitted to vacuum filtration. The filter cake was washed thoroughly with water and dried in vacuo at 70° C. to give a pale yellow solid. Purification by flash column chromatography on silica gel using CH$_2$Cl$_2$ EtOAc=98 2 as the eluent gave the title compound (14.4 g, first fraction); $^1$H NMR (CDCl$_3$) δ=8.40 (br s, 1H), 8.14 (d, 1H), 7.80 (d, 1H), 7.42 to 7.48 (m, 1H), 7.04 to 7.14 (m, 4H), 4.39 (t, 2H), 1.70 to 1.85 (m, 2H), 1.37 to 1.55 (m, 2H), 0.99 (t, 3H).

d. 1-Bromo-7-(4-fluoro-phenoxy)-4-hydroxy-isoquinoline-3-carboxylic acid butyl ester A mixture of 7-(4-Fluoro-phenoxy)-1,4-dihydroxy-isoquinoline-3-carboxylic acid butyl ester (14.33 g, 38.6 mmol), POBr$_3$ (44.7 g, 154.4 mmol) and anhydrous methyl cyanide (290 ml) was refluxed gently with stirring for 75 min before NaHCO$_3$ (100.8 g, 1.2 mol) was added in small portions with stirring. Subsequently, water (200 ml) was added slowly with stirring and the mixture was stirred vigorously for 1 h at ambient temperature before it was concentrated in vacuo to ca. ½ of its volume. Then water (200 ml) was added and the mixture was extracted with EtOAc (1×400 ml, 1×200 ml). The combined organic phases were dried over MgSO$_4$ and evaporated in vacuo to give a tan solid. The tan solid was dissolved in CH$_2$Cl$_2$ and purified by filtration through a plug of silica gel. In vacuo concentration of the resulting CH$_2$Cl$_2$ solution yielded the title compound (11.4 g); $^1$H NMR (CDCl$_3$) δ=11.89 (s, 1H), 8.36 (d, 1H), 7.57 (d, 1H), 7.44 to 7.50 (m, 1H), 7.08 to 7.16 (m, 4H), 4.47 (t, 2H), 1.78 to 1.93 (m, 2H), 1.38 to 1.58 (m, 2H), 0.99 (t, 3H).

e. 7-(4-Fluoro-phenoxy)-4-hydroxy-1-methyl-isoquinoline-3-carboxylic acid butyl ester A mixture of 1-Bromo-7-(4-fluoro-phenoxy)-4-hydroxy-isoquinoline-3-carboxylic acid butyl ester (434 mg, 1 mmol), Pd(PPh$_3$)$_4$ (116 mg, 0.1 mmol), trimethylboroxine (140° C. mmol), K$_2$CO$_3$ (414 mg, 3 mmol), and 1,4-dioxane (8 ml) was refluxed with stirring for 2 h. Subsequently, the mixture was concentrated in vacuo. To the residue was added water (10 ml). The mixture was acidified by the addition of aqueous 6N HCl and then extracted with EtOAc (40 ml). The organic phase was dried over MgSO$_4$ and evaporated in vacuo. Purification of the residue by flash column chromatography on silica gel using hexanes:EtOAc=94:6 as the eluent gave the title compound as white solid (229 mg); MS-(+)-ion M+1=370.1.

f) 2-(S)-{[7-(4-Fluoro-phenoxy)-4-hydroxy-1-methyl-isoquinoline-3-carbonyl]-amino}-propionic acid A mixture of 7-(4-Fluoro-phenoxy)-4-hydroxy-1-methyl-isoquinoline-3-carboxylic acid butyl ester (92 mg, 0.25 mmol), (S)-alanine (225 mg, 2.5 mmol) and a 0.5 N solution of MeONa in MeOH (5 ml, 2.5 mmol) was heated in a microwave oven with stirring for 20 min at 140° C. before the mixture was concentrated in vacuo. To the residue was added water (10 ml) and the mixture was washed with EtOAc (2×25 ml). The so purified aq. solution was acidified by the addition of 6 N HCl and extracted with EtOAc (1×25 ml). The organic phase was dried over MgSO$_4$ and concentrated in vacuo to give the title compound as a tan solid (69 mg); MS-(+)-ion M+1=385.1.

Example A-76

2-(S)-{[7-(4-Fluoro-phenoxy)-4-hydroxy-isoquinoline-3-carbonyl]-amino}-propionic acid a. 7-(4-Fluoro-phenoxy)-4-hydroxy-isoquinoline-3-carboxylic acid butyl ester A mixture of 1-Bromo-7-(4-fluoro-phenoxy)-4-hydroxy-isoquinoline-3-carboxylic acid butyl ester (4.34 g, 10 mmol, see example A-75d), sodium acetate (984 mg, 12 mmol), Pd/C (2.0 g, 10 wt % Pd, 50 wt % water), EtOAc (400 ml) and MeOH (200 ml) was stirred under an H$_2$-atmosphere at ambient pressure and temperature for 2.5 h before the mixture was filtered through a plug of celite. The celite was washed with EtOAc (500 ml). The combined organic phases were concentrated in vacuo. To the residue was added a half concentrated NaHCO$_3$ solution (50 ml) and the mixture was extracted with CH$_2$Cl$_2$ (1×200 ml). The organic phase was dried over MgSO$_4$ and concentrated in vacuo to yield the title compound as a tan oil (3.45 g); MS-(+)-ion M+1=356.1.

b. 2-(S)-{[7-(4-Fluoro-phenoxy)-4-hydroxy-isoquinoline-3-carbonyl]-amino}-propionic acid A mixture of 7-(4-fluoro-phenoxy)-4-hydroxy-isoquinoline-3-carboxylic acid butyl ester (154 mg, 0.43 mmol), (S)-alanine (225 mg, 2.5 mmol) and a 0.5 N solution of MeONa in MeOH (5 ml, 2.5 mmol) was heated in a microwave oven with stirring for 20 min at 130° C. before the mixture was concentrated in vacuo. To the residue was added water (15 ml) and the mixture was washed with Et$_2$O (3×30 ml). The purified aq. solution was acidified by the addition of 6 N HCl and extracted with EtOAc (1×30 ml). The organic phase was dried over MgSO$_4$ and concentrated in vacuo to give the title compound as a tan solid (79 mg); MS-(−)-ion M−1=369.1.

Example A-77

2-(S)-[(4-Hydroxy-1-methyl-7-phenoxy-isoquinoline-3-carbonyl)-amino]-propionic acid a. 1-Chloro-4-hydroxy-6-phenoxy-isoquinoline-3-carboxylic acid butyl ester and 1-Chloro-4-hydroxy-7-phenoxy-isoquinoline-3-carboxylic acid butyl ester (regioisomeric mixture)

To POCl$_3$ (300 ml) was added a regioisomeric mixture of 1,4-dihydroxy-6-phenoxy-isoquinoline-3-carboxylic acid butyl ester and 1,4-dihydroxy-7-phenoxy-isoquinoline-3-carboxylic acid butyl ester (40.63 g, 115 mmol, see example A-65d). The mixture was refluxed gently with stirring for 30 min before it was concentrated in vacuo. The residue was dissolved in EtOAc (800 ml) and water (400 ml) was added. To the vigorously stirred mixture was then added NaHCO$_3$ (ca. 100 g) in small portions. Subsequently, the mixture was stirred for 1 h at ambient temperature before it was filtered through a pad of celite. The organic phase was separated, dried over MgSO$_4$ and evaporated in vacuo to give a tan solid. The tan solid was dissolved in CH$_2$Cl$_2$ and purified by filtration through a plug of silica gel. In vacuo concentration of the resulting CH$_2$Cl$_2$ solution yielded the title compounds (15.51 g) as a tan solid; MS-(−)-ion M−1=370.2.

b. 4-Hydroxy-1-methyl-7-phenoxy-isoquinoline-3-carboxylic acid butyl ester

To a mixture of anhydrous 1,4-dioxane (200 ml), Pd(PPh$_3$)$_4$ (3.47 g, 3 mmol), trimethylboroxine (4.22 ml, 30 mmol), and K₂CO₃ (12.44 g, 90 mmol) was added a regioisomeric mixture of 1-chloro-4-hydroxy-6-phenoxy-isoquinoline-3-carboxylic acid butyl ester and 1-Chloro-4-hydroxy-7-phenoxy-isoquinoline-3-carboxylic acid butyl ester (11.15 g, 30 mmol). The mixture was refluxed under N₂-protection with stirring for 3 h and was then stirred at ambient temperature for 48 h. Subsequently, the mixture was concentrated in vacuo. To the residue was added water (100 ml) and the mixture was extracted with EtOAc (300 ml). The organic phase was dried over MgSO₄ and evaporated in vacuo. Purification of the residue by flash column chromatography on silica gel using hexanes:EtOAc=9:1 as the eluent gave the title compound as a yellowish solid (4.40 g, first fraction); MS-(+)-ion M+1=352.1.

c. 2-(S)-[(4-Hydroxy-1-methyl-7-phenoxy-isoquinoline-3-carbonyl)-amino]-propionic acid A mixture of 4-Hydroxy-1-methyl-7-phenoxy-isoquinoline-3-carboxylic acid butyl ester (176 mg, 0.5 mmol), (S)-alanine (225 mg, 2.5 mmol) and a 0.5 N solution of MeONa in MeOH (5 ml, 2.5 mmol) was heated in a microwave oven with stirring for 20 min at 120° C. before the mixture was concentrated in vacuo. To the residue was added water (15 ml) and the mixture was washed with Et₂O (3×30 ml). The so purified aq. solution was acidified by the addition of 6 N HCl and extracted with EtOAc (1×30 ml). The organic phase was dried over MgSO₄ and concentrated in vacuo to give the title compound as a tan solid (108 mg); MS-(−)-ion M−1=365.1.

Example A-78

2-(S)-[(4-Hydroxy-1-methyl-7-phenylsulfanyl-isoquinoline-3-carbonyl)-amino]-propionic acid a) 1-Bromo-4-hydroxy-7-phenylsulfanyl-isoquinoline-3-carboxylic acid 1,4-Dihydroxy-7-phenylsulfanyl-isoquinoline-3-carboxylic acid butyl ester (Example A-63 d) Compound A) (29.0 g) and phosphorous oxybromide (67.5 g) in 600 ml anhydrous acetonitrile was stirred at reflux for 4 hours. After cooling the reaction mixture was concentrated and saturated sodium bicarbonate solution and ethyl acetate were added to the residue and stirred overnight. Precipitate that formed between layers was collected and washed with water to give the title compound (10.2 g). MS-(+)-ion M+1=376.0, 378.1.

b) 1-Bromo-4-hydroxy-7-phenylsulfanyl-isoquinoline-3-carboxylic acid methyl ester 1-Bromo-4-hydroxy-7-phenylsulfanyl-isoquinoline-3-carboxylic acid (10.0 g), potassium carbonate (3.7 g) and methyl sulfate (3.4 g) were suspended in 500 ml acetone and stirred at reflux overnight. Reaction mixture was concentrated and residue partitioned between 1 N hydrochloric acid and ethyl acetate. Organic layer was dried over magnesium sulfate and filtered. Filtrate concentrated to give title compound (9.6 g). MS-(+)-ion M+1=389.9, 391.9.

c) 4-Hydroxy-1-methyl-7-phenylsulfanyl-isoquinoline-3-carboxylic acid methyl ester 1-Bromo-4-hydroxy-7-phenylsulfanyl-isoquinoline-3-carboxylic acid methyl ester (0.2 g), tetrakis(triphenylphosphine)palladium (60 mg), methyl boroxine (65 mg), and potassium carbonate in 1,4-dioxane (4 ml) were heated in a microwave reactor (sealed tube) for 10 min at 140° C. After cooling reaction mixture was concentrated and partitioned between 1 N hydrochloric acid and ethyl acetate. Organic layer dried over magnesium sulfate and filtered. Filtrate concentrated and separated by silica gel chromatography (eluting with 2% ethyl acetate in methylene chloride) to give the title compound (47 mg). MS-(+)-ion M+1=326.1.

d) 2-(S)-[(4-Hydroxy-1-methyl-7-phenylsulfanyl-isoquinoline-3-carbonyl)-amino]-propionic acid Prepared in analogy to Example A-74 f). ¹H NMR (200 MHz, DMSO-d6) δ13.26 (br s, 1H), 9.07 (s, 1H), 8.61 (s, 1H), 8.33 (d, J=8.2 Hz 1H), 7.97 (d, J=8.6 Hz, 1H), 7.81 (br s, 2H), 7.52 (br s, 3H), 4.52 (br s, 1H), 2.91 (s, 3H), 1.49 (d, J=7.0 Hz, 3H).

Example A-79

2-(S)-{[4-Hydroxy-7-(4-trifluoromethyl-phenoxy)-isoquinoline-3-carbonyl]amino}-propionic acid a) 4-(4-Trifluoromethyl-phenoxy)-phthalonitrile Prepared in analogy to Example A-66 a). ¹H NMR (200 MHz, CDCl₃) δ7.74 (m, 2H), 7.47 (d, J=8.6 Hz, 1H), 7.25 (m, 3H), 6.87 (d, J=8.9 Hz, 1H).

b) 4-(4-Trifluoromethyl-phenoxy)-phthalic acid

Prepared in analogy to Example A-66 b). ¹H NMR (200 MHz, DMSO-d6) δ8.24 (d, J=9.0 Hz, 1H), 7.75 (m, 3H), 7.19 (m, 3H).

c) [1,3-Dioxo-5-(4-trifluoromethyl-phenoxy)-1,3-dihydro-isoindol-2-yl]-acetic acid methyl ester Prepared in analogy to Example A-66 c). ¹H NMR (200 MHz, CDCl₃) δ7.86 (d, J=8.5 Hz, 1H), 7.67 (d, J=8.2 Hz, 2H), 7.40-7.13 (m, 4H), 4.43 (s, 2H), 3.76 9s, 3H).

d) 7-(4-trifluoromethyl-phenoxy)-1,4-dihydroxy-isoquinoline-3-carboxylic acid butyl ester Prepared in analogy to Example A-66 d). Two isomers were separated by chromatography to give the title compound. MS-(+)-ion M+1=422.0 e) 1-Chloro-4-hydroxy-7-(4-trifluoromethyl-phenoxy)-isoquinoline-3-carboxylic acid butyl ester Prepared in analogy to Example A-2 c). MS-(−)-ion M−1=438.3.

f) 4-Hydroxy-7-(4-trifluoromethyl-phenoxy)-isoquinoline-3-carboxylic acid butyl ester Prepared in analogy to Example A-74 e). MS-(+)-ion M+1=406.1.

g) 2-(S)-{[4-Hydroxy-7-(4-trifluoromethyl-phenoxy)-isoquinoline-3-carbonyl]-amino}-propionic acid Prepared in analogy to Example A-74 f). MS-(+)-ion M+1=421.2.

Example B-1

1-Chloro-4-hydroxy-isoquinoline-3-carboxylic acid (2-amino-ethyl)-amide; trifluoro-acetic acid salt a. (1,3-Dioxo-1,3-dihydro-isoindol-2-yl)-acetic acid butyl ester

A mixture of 160 ml of butanol, 20.0 g of (1,3-dioxo-1,3-dihydro-isoindol-2-yl)-acetic acid (94.6 mmol) and 2.0 ml of concentrated sulfuric acid was refluxed with stirring for 24 h. Then 5 g of sodium bicarbonate were added in portions, stirring continued at r.t. for 5 min and the solvent evaporated in vacuo. The residue was partitioned between 100 ml of water and 100 ml of ethyl acetate. The organic phase was washed with 100 ml of brine, dried over sodium sulfate and was evaporated in vacuo to give a yellowish oil that later solidified. 24.02 g of the title compound were obtained; MS-(+)-ion: M+1=261.9.

b. 1,4-Dihydroxy-isoquinoline-3-carboxylic acid butyl ester 4.41 g of sodium (190 mmol) were dissolved in 250 ml of n-butanol with stirring. After the sodium was completely dissolved the solution was allowed to cool to ambient temperature and a solution of 24.0 g (91.9 mmol) of (1,3-dioxo-1,3-dihydro-isoindol-2-yl)-acetic acid butyl ester in 150 ml of butanol was added with stirring. The solution was heated to 100° C. within 30 min and stirred at this temperature for 1 h. Then the mixture was allowed to cool to ambient temperature and was stored at ambient temperature for 18 h. Then the pH of the mixture was adjusted to 2 to 3 by the addition of aqueous 2N hydrochloric acid with stirring. Stirring was continued for 30 min before the solid component was filtered by suction. The filter cake was washed thoroughly with water, and dried in vacuo at 50° C. to give a white solid. 17.75 g of the title compound were obtained; MS-(+)-ion: M+1=262.1.

c. 1-Chloro-4-hydroxy-isoquinoline-3-carboxylic acid butyl ester

A mixture of 17.3 g (66.2 mmol) of 1,4-dihydroxy-isoquinoline-3-carboxylic acid butyl ester and 100 ml of phosphorous oxychloride was stirred at ambient temperature for 1 h, and then heated slowly with stirring in the course of 2 h to reflux temperature. The mixture was refluxed gently with stirring for 30 min. After cooling to room temperature the excess phosphorous oxychloride was evaporated in vacuo, and the residue was dissolved in 100 ml of ethyl acetate The solution was poured into 300 ml of a saturated aqueous sodium bicarbonate solution with stirring. The precipitate formed was removed by vacuum filtration. The organic phase was separated, and the aqueous phase was extracted with 3×100 ml of ethyl acetate. The combined aqueous phases were dried over sodium sulfate, filtered through a pad of silica gel and evaporated in vacuo to give a brown oil that solidified later. 11.37 g of the title compound were obtained; $^1$H NMR (CDCl$_3$): δ=11.91 (s, 1H), 8.41 (m, 1H), 8.29 (m, 1H), 7.83 (m, 2H), 4.49 (t, 2H), 1.84 (m, 2H), 1.48 (m, 2H), 0.99 (t, 3H).

d. 1-Chloro-4-hydroxy-isoquinoline-3-carboxylic acid

A mixture of 9.23 g of 1-chloro-4-hydroxy-isoquinoline-3-carboxylic acid butyl ester (33 mmol), 90 ml of 2.5 N aqueous sodium hydroxide solution, water (20 ml) and ethanol (110 ml) was refluxed with stirring for 2 h. Then the pH of the mixture was adjusted to 2 by the addition of concentrated aqueous hydrochloric acid. During the addition the temperature of the mixture was kept at 20° C. by cooling with an ice bath. Stirring was then continued for 1 h before the solid component was separated by vacuum filtration. The filter cake was washed with water and dried in vacuo at 85° C. to give a white powder. 6.64 g of the title compound were obtained; MS-(+)-ion: M+1=224.1.

e. {2-[(1-Chloro-4-hydroxy-isoquinoline-3-carbonyl)-amino]-ethyl}-carbamic acid tert-butyl ester To a mixture of 45 mg (0.2 mmol) of 1-chloro-4-hydroxy-isoquinoline-3-carboxylic acid, 76 mg (0.2 mmol) of benzotriazol-1-yl-(bis-dimethylamino-methylene)-oxonium hexafluoro phosphate (HBTU), 32 µl (2-amino-ethyl)-carbamic acid tert-butyl ester (0.2 mmol), and 1 ml of dichloromethane was added 96 µl (0.55 mmol) of ethyl-diisopropyl-amine with stirring. Stirring was continued at ambient temperature for 5 days. The product was isolated from the reaction mixture by flash column chromatography on silica gel using hexanes:ethyl acetate (8:2) as the eluent to give a tan gum. 8 mg of the title compound were obtained; MS-(−)-ion: M−1=364.0.

f. 1-Chloro-4-hydroxy-isoquinoline-3-carboxylic acid (2-amino-ethyl)-amide; trifluoro-acetic acid salt A mixture of 8 mg (0.022 mmol) of {2-[(1-chloro-4-hydroxy-isoquinoline-3-carbonyl)-amino]-ethyl}-carbamic acid tert-butyl ester and 2 ml of trifluoroacetic acid was stirred for 2 h at ambient temperature. Then the excess trifluoroacetic acid was evaporated in vacuo, the residue dissolved in absolute ethanol and the solution concentrated in vacuo to give a tan solid. 8.5 mg of the title compound were obtained; MS-(+)-ion: M+1=266.0.

Example B-2

1-Chloro-4-hydroxy-isoquinoline-3-carboxylic acid (2-methoxy-ethyl)-amide

To a mixture of 45 mg (0.2 mmol) of 1-chloro-4-hydroxy-isoquinoline-3-carboxylic acid (from example A-1 d), 76 mg (0.2 mmol) of benzotriazol-1-yl-(bis-dimethylamino-methylene)-oxonium hexafluoro phosphate (HBTU), 18 µl 2-methoxy-ethylamine (0.2 mmol), and 1 ml of dichloromethane were added 96 µl (0.55 mmol) of ethyl-diisopropyl-amine with stirring. Stirring was continued at ambient temperature for 12 days. The product was isolated from the reaction mixture by flash column chromatography on silica gel using hexanes:ethyl acetate (9:1) as the eluent to give a white solid. 8.8 mg of the title compound were obtained; MS-(+)-ion: M+1=281.0.

Example B-3

1-Chloro-4-hydroxy-isoquinoline-3-carboxylic acid (2-hydroxy-ethyl)-amide

Synthesized from 1-chloro-4-hydroxy-isoquinoline-3-carboxylic acid from example A-1 d) and 2-amino-ethanol in analogy to example 2; MS-(−)-ion: M−1=265.2.

Example B-4

1-Chloro-4-hydroxy-isoquinoline-3-carboxylic acid (2-dimethylamino-ethyl)-amide

A mixture of 28 mg (0.1 mmol) of 1-chloro-4-hydroxy-isoquinoline-3-carboxylic acid butyl ester from example A-1 c), 116 µl (1 mmol) of N,N-dimethyl-ethane-1,2-diamine and 0.5 ml of absolute ethanol was stirred at ambient temperature for 18 h. Then the solvent was evaporated in vacuo, the residue suspended in 5 ml of water, and mixture was extracted with 2×35 ml of ethyl acetate. The combined organic phases were dried over sodium sulfate and evaporated in vacuo to give a yellowish solid. 29 mg of the title compound were obtained; MS-(+)-ion: M+1=294.1.

Example B-5

1-Chloro-4-hydroxy-isoquinoline-3-carboxylic acid (2-acetylamino-ethyl)-amide

A mixture of 56 mg (0.2 mmol) of 1-chloro-4-hydroxy-isoquinoline-3-carboxylic acid butyl ester from example B-1 c), 227 mg (2 mmol) of N-(2-amino-ethyl)-acetamide and 0.8 ml of absolute ethanol was stirred at ambient temperature for 3 days. Then the solvent was evaporated in vacuo, the residue suspended in 3 ml of water, and the pH of the mixture was adjusted 2 to 3 by the addition of aqueous 1N HCl. The mixture was extracted with 2×25 ml of ethyl acetate. The combined organic phases were dried over sodium sulfate and evaporated in vacuo to give a yellowish solid. 64 mg of the title compound were obtained; MS-(+)-ion: M+1=308.1.

Example B-6

1-Chloro-4-hydroxy-6-isopropoxy-isoquinoline-3-carboxylic acid (2-hydroxy-ethyl)-amide Synthesized from 1-chloro-4-hydroxy-6-isopropoxy-isoquinoline-3-carboxylic acid butyl ester (can be obtained according to U.S. Pat. No. 6,093,730, October 1998, Weidmann et al.) and 2-amino-ethanol in analogy to example B-5; MS-(+)-ion: M+1=325.1.

Example B-7

1-Chloro-4-hydroxy-6-isopropoxy-isoquinoline-3-carboxylic acid (2-methoxy-ethyl)-amide Synthesized from 1-chloro-4-hydroxy-6-isopropoxy-isoquinoline-3-carboxylic acid butyl ester (can be obtained according to U.S. Pat. No. 6,093,730, October 1998, Weidmann et al.) and 2-methoxy-ethylamine in analogy to example B-5; MS-(+)-ion: M+1=339.0.

Example B-8

1-Chloro-4-hydroxy-6-isopropoxy-isoquinoline-3-carboxylic acid (2-amino-ethyl)-amide; trifluoroacetic acid salt Synthesized from 1-chloro-4-hydroxy-6-isopropoxy-isoquinoline-3-carboxylic acid butyl ester (can be obtained according to U.S. Pat. No. 6,093,730, October 1998, Weidmann et al.) and (2-amino-ethyl)-carbamic acid tert-butyl ester in analogy to example B-5, followed by deprotection in analogy to example B-1 f); MS-(+)-ion: M+1=324.1.

Example B-9

1-Chloro-4-hydroxy-6-isopropoxy-isoquinoline-3-carboxylic acid (2-dimethylamino-ethyl)-amide Synthesized from 1-chloro-4-hydroxy-6-isopropoxy-isoquinoline-3-carboxylic acid butyl ester (can be obtained according to U.S. Pat. No. 6,093,730, October 1998, Weidmann et al.) and N,N-dimethyl-ethane-1,2-diamine in analogy to example B-4, followed by deprotection in analogy to example B-1 f); MS-(+)-ion: M+1=352.1.

Example B-10

1-Chloro-4-hydroxy-7-isopropoxy-isoquinoline-3-carboxylic acid (2-amino-ethyl)-amide; trifluoroacetic acid salt Synthesized from 1-chloro-4-hydroxy-7-isopropoxy-isoquinoline-3-carboxylic acid butyl ester (can be obtained according to U.S. Pat. No. 6,093,730, October 1998, Weidmann et al.) and (2-amino-ethyl)-carbamic acid tert-butyl ester in analogy to example B-5, followed by deprotection in analogy to example B-1 f); MS-(+)-ion: M+1=324.0.

Example B-11

1-Chloro-4-hydroxy-7-isopropoxy-isoquinoline-3-carboxylic acid (2-methoxy-ethyl)-amide Synthesized from 1-chloro-4-hydroxy-7-isopropoxy-isoquinoline-3-carboxylic acid butyl ester (can be obtained according to U.S. Pat. No. 6,093,730, October 1998, Weidmann et al.) and 2-methoxy-ethylamine in analogy to example B-5; MS-(−)-ion: M−1=337.1.

Example B-12

1-Chloro-4-hydroxy-7-isopropoxy-isoquinoline-3-carboxylic acid (2-dimethylamino-ethyl)-amide Synthesized from 1-chloro-4-hydroxy-7-isopropoxy-isoquinoline-3-carboxylic acid butyl ester (can be obtained according to U.S. Pat. No. 6,093,730, October 1998, Weidmann et al.) and N,N-dimethyl-ethane-1,2-diamine in analogy to example B-4, followed by deprotection in analogy to example B-1 f); MS-(+)-ion: M+1=352.1.

Example B-13

1-Chloro-4-hydroxy-7-isopropoxy-isoquinoline-3-carboxylic acid (2-hydroxy-ethyl)-amide Synthesized from 1-chloro-4-hydroxy-7-isopropoxy-isoquinoline-3-carboxylic acid butyl ester (can be obtained according to U.S. Pat. No. 6,093,730, October 1998, Weidmann et al.) and 2-amino-ethanol in analogy to example B-5; MS-(−)-ion: M−1=323.2.

Example C-1

1-Chloro-4-hydroxy-6-isopropoxy-isoquinoline-3-carboxylic acid (2-hydroxy-1-hydroxymethyl-ethyl)-amide 0.035 gm of 1-chloro-4-hydroxy-6-isopropoxy-isoquinoline-3-carboxylic acid butyl ester and 0.088 g of 2-amino-propane-1,3-diol were dissolved in 1 ml of ethanol and the mixture was refluxed for 24 h. The reaction mixture was concentrated and the residue was dissolved in 10 ml of ethyl acetate. The ethyl acetate solution was extracted with 5 ml of aqueous 1 M HCl and water, dried (sodium sulfate) and concentrated to give 0.042 g of a white solid: MS-(+)-ion: 355.1.

Example C-2

1-Chloro-4-hydroxy-7-isopropoxy-isoquinoline-3-carboxylic acid (2-hydroxy-1-hydroxymethyl-ethyl)-amide Prepared from 1-chloro-4-hydroxy-7-isopropoxy-isoquinoline-3-carboxylic acid butyl ester and 2-amino-propane-1,3-diol analogously to Example C-1: MS-(−)-ion: 353.2.

Example C-3

1-Chloro-4-hydroxy-isoquinoline-3-carboxylic acid (2-hydroxy-1-hydroxymethyl-ethyl)-amide Prepared from 1-chloro-4-hydroxy-isoquinoline-3-carboxylic acid butyl ester and 2-amino-propane-1,3-diol analogously to Example C-1: MS-(−)-ion: 295.2.

Example D-1

[(4-Hydroxy-7-phenylsulfanyl-isoquinoline-3-carbonyl)-amino]-acetic acid a) 4-Phenylsulfanyl-phthalic acid A mixture of 5.06 g of 4-phenylsulfanyl-phthalonitrile (21.4 mmol), 10 ml of 50% aqueous KOH, and 10 ml of methanol was refluxed with stirring for 3.5 days. Then the mixture was diluted with 100 ml of water and acidified with concentrated hydrochloric acid. The precipitated product was filtered by suction, washed thoroughly with water, and dried in vacuo at 60° C. 5.75 g of the title compound were obtained; MS-(−)-ion: M−1=273.0.

b) (1,3-Dioxo-5-phenylsulfanyl-1,3-dihydro-isoindol-2-yl)-acetic acid 5.62 g of 4-phenylsulfanyl-phthalic acid (20.5 mmol) and 1.55 g of glycine (20.5 mmol) were ground thoroughly together in a mortar. Then the mixture was heated to 210° C. to 220° C. in an oil bath. The molten mass was stirred with a spatula at this temperature for 15 min before it was allowed to cool to ambient temperature in vacuo. 6.30 g of the title compound were obtained; MS-(−)-ion: M−1=311.8.

c) (1,3-Dioxo-5-phenylsulfanyl-1,3-dihydro-isoindol-2-yl)-acetic acid methyl ester A mixture of 20 ml of methanol, 6.27 g of (1,3-dioxo-5-phenylsulfanyl-1,3-dihydro-isoindol-2-yl)-acetic acid (20 mmol) and 0.3 ml of concentrated sulfuric acid was refluxed with stirring for 18 h. Then 100 ml of concentrated aqueous sodium bicarbonate solution were added and the mixture was extracted with 100 ml of ethyl acetate. The organic phase was dried over $MgSO_4$ and evaporated in vacuo. 6.54 g of the title compound were obtained; MS-(+)-ion: M+1=328.0.

d) 1,4-Dihydroxy-7-phenylsulfanyl-isoquinoline-3-carboxylic acid butyl ester (A) and 1,4-Dihydroxy-6-phenylsulfanyl-isoquinoline-3-carboxylic acid butyl ester (B)

0.92 g of sodium (40 mmol) were dissolved in 100 ml of n-butanol with stirring. Then the temperature was raised to 95° C. to 100° C., a hot solution of 6.5 g of (1,3-dioxo-5-phenylsulfanyl-1,3-dihydro-isoindol-2-yl)-acetic acid methyl ester (19.85 mmol) in 20 ml of n-butanol was added and stirring was continued at 95° C. to 100° C. for 1 h. Subsequently, the solvent was evaporated in vacuo, 25 ml of aqueous 2N HCl and 100 ml of ethyl acetate were added and the mixture was stirred vigorously for 1 h before it was filtered by suction. The filter cake was washed thoroughly with water, and dried in vacuo at 60° C. to give 4.43 g of a yellow solid. 4.4 g of this mixture of A and B were separated by flash column chromatography on silica gel eluting with dichloromethane:ethyl acetate (98:2). Evaporation of the first fraction yielded 1.99 g of A; $^1$H NMR ($CDCl_3$): δ=10.48 (bs, 1H), 8.39 (bs, 1H), 8.24 (d, 1H), 8.01 (d, 1H), 7.35 to 7.55 (m, 6H), 4.39 (t, 2H), 1.77 (m, 2H), 1.46 (m, 2H), 0.99 (t, 3H). Evaporation of the second fraction yielded 2.26 g of B; $^1$H NMR ($CDCl_3$): δ=10.38 (bs, 1H), 8.32 (bs, 1H), 8.24 (d, 1H), 7.86 (d, 1H), 7.37 to 7.56 (m, 6H), 4.39 (t, 2H), 1.77 (m, 2H), 1.46 (m, 2H), 0.99 (t, 3H).

e) 1-Bromo-4-hydroxy-7-phenylsulfanyl-isoquinoline-3-carboxylic acid butyl ester To a solution of 4.59 g of phosphorous oxybromide (16 mmol) in 25 ml of anhydrous acetonitrile were added 1.108 g of 1,4-dihydroxy-7-phenylsulfanyl-isoquinoline-3-carboxylic acid butyl ester (3 mmol) and the mixture was refluxed gently with stirring for 1 h. Then 5.04 g of sodium bicarbonate (60 mmol) were added, followed by the dropwise addition of 8 ml of water. After stirring at ambient temperature for 90 min the mixture was concentrated in vacuo to about one third of its volume, 40 ml of water were added and the mixture was extracted with 30 ml of ethyl acetate. The mixture was filtered by suction. The organic phase was separated, dried over $MgSO_4$, and filtered through a pad of silica gel. Evaporation in vacuo gave 0.885 g of the title compound; $^1$H NMR ($CDCl_3$): δ=11.84 (s, 1H), 8.21 (d, 1H), 7.91 (d, 1H), 7.40 to 7.55 (m, 6H), 4.46 (t, 2H), 1.84 (m, 2H), 1.48 (m, 2H), 0.98 (t, 3H).

f) 4-Hydroxy-7-phenylsulfanyl-isoquinoline-3-carboxylic acid butyl ester

A mixture of 432 mg of 1-bromo-4-hydroxy-7-phenylsulfanyl-isoquinoline-3-carboxylic acid butyl ester (1 mmol), 63 mg of red phosphorous (2 mmol), 0.4 ml of aqueous 57 wt % HI (3 mmol), and 1 ml of glacial acetic acid was refluxed with stirring for 30 min. Then the reaction mixture was diluted with 25 ml of ethyl acetate, filtered by suction through a pad of celite, washed with a solution of 0.2 g of $NaHSO_3$ in 5 ml of water, and washed twice with 5 ml of concentrated aqueous sodium bicarbonate solution. The organic phase was dried over MgSO₄ and evaporated in vacuo. The residue was purified by flash column chromatography on silica gel eluting with hexanes:ethyl acetate (85:15). 123 mg of the title compound were obtained; $^1$H NMR (CDCl₃): δ=11.85 (s, 1H), 8.60 (s, 1H), 8.23 (d, 1H), 7.38 to 7.63 (m, 7H), 4.49 (t, 2H), 1.87 (m, 2H), 1.47 (m, 2H), 0.98 (t, 3H).

g) [(4-Hydroxy-7-phenylsulfanyl-isoquinoline-3-carbonyl)-amino]-acetic acid

A mixture of 113 mg of 4-hydroxy-7-phenylsulfanyl-isoquinoline-3-carboxylic acid butyl ester (0.32 mmol), 244 mg of glycine (3.2 mmol), and 6.4 ml of a 0.5 N solution of sodium methoxide in methanol (3.2 mmol) was refluxed for 24 h with stirring. Then the solvent was evaporated in vacuo, the residue dissolved in 25 ml of water and the resulting solution was washed twice with 50 ml of ethyl acetate. The pH of the solution was subsequently adjusted to about 3 by addition of concentrated hydrochloric acid and the resulting slurry was extracted twice with 25 ml of ethyl acetate. The combined extracts were dried over MgSO₄ and evaporated in vacuo. 103 mg of the title compound were obtained; $^1$H NMR (DMSO-d₆): δ=9.32 (t, 1H), 8.74 (s, 1H), 8.19 (d, 1H), 7.94 (d, 1H), 7.45 to 7.65 (m, 6H), 4.02 (d, 2H).

Example D-2

[(4-Hydroxy-6-phenylsulfanyl-isoquinoline-3-carbonyl)-amino]-acetic acid a) 1-Bromo-4-hydroxy-6-phenylsulfanyl-isoquinoline-3-carboxylic acid butyl ester 1.447 g of compound B (4 mmol) from Example D-1d) were reacted with phosphorous oxybromide analogously to Example D-1 e). The crude product was purified by flash column chromatography on silica gel eluting with dichloromethane. 0.985 g of the title compound were obtained by evaporation of the first fraction; $^1$H NMR (CDCl₃): δ=11.77 (s, 1H), 8.08 (d, 1H), 8.05 (s, 1H), 7.41 to 7.56 (m, 6H), 4.46 (t, 2H), 1.85 (m, 2H), 1.48 (m, 2H), 0.98 (t, 3H).

b) 4-Hydroxy-6-phenylsulfanyl-isoquinoline-3-carboxylic acid butyl ester 540 mg of 1-bromo-4-hydroxy-6-phenylsulfanyl-isoquinoline-3-carboxylic acid butyl ester (1.25 mmol) were reacted with red phosphorous and HI analogously to Example D-1 f). The crude product was purified by flash column chromatography on silica gel eluting with hexanes: ethyl acetate (85:15). 150 mg of the title compound were obtained; $^1$H NMR (CDCl₃): δ=11.78 (s, 1H), 8.71 (d, 1H), 8.11 (t, 1H), 7.79 (d, 1H), 7.39 to 7.54 (m, 6H), 4.49 (t, 2H), 1.87 (m, 2H), 1.47 (m, 2H), 0.98 (t, 3H).

c) [(4-Hydroxy-6-phenylsulfanyl-isoquinoline-3-carbonyl)-amino]-acetic acid 127 mg of 4-hydroxy-6-phenylsulfanyl-isoquinoline-3-carboxylic acid butyl ester (0.36 mmol) were reacted with glycine and sodium methylate analogously to Example D-1 g). 118 mg of the title compound were obtained; $^1$H NMR (DMSO-d₆): δ=9.33 (t, 1H), 8.80 (s, 1H), 8.11 (d, 1H), 7.79 (s, 1H), 7.49 to 7.65 (m, 6H), 4.01 (d, 2H).

Example D-3

[(1-Chloro-4-hydroxy-7-phenylsulfanyl-isoquinoline-3-carbonyl)-amino]-acetic acid a. 1-Chloro-4-hydroxy-7-phenylsulfanyl-isoquinoline-3-carboxylic acid butyl ester A mixture of 554 mg of compound A (1.5 mmol) from Example D-1d) and 5 ml of phosphorous oxychloride was refluxed gently with stirring for 30 min. Then the excess phosphorous oxychloride was evaporated in vacuo, and the residue was dissolved in 15 ml of acetonitrile. 2.94 g of sodium bicarbonate (35 mmol) was added, followed by the dropwise addition of 4 ml of water. After stirring for 1 h the mixture was concentrated in vacuo to about one third of its volume, 20 ml of water were added and the mixture was extracted twice with 20 ml of ethyl acetate. The combined organic phases were dried over MgSO₄ and filtered through a pad of silica gel by suction. Evaporation in vacuo gave 426 mg of the title compound; $^1$H NMR (CDCl₃): δ=11.85 (s, 1H), 8.23 (d, 1H), 7.95 (d, 1H), 7.50 to 7.57 (m, 6H), 4.47 (t, 2H), 1.84 (m, 2H), 1.48 (m, 2H), 0.98 (t, 3H).

b) [(1-Chloro-4-hydroxy-7-phenylsulfanyl-isoquinoline-3-carbonyl)-amino]-acetic acid 194 mg of 1-chloro-4-hydroxy-7-phenylsulfanyl-isoquinoline-3-carboxylic acid butyl ester (0.5 mmol) were reacted with glycine and sodium methylate analogously to Example D-1 g). 168 mg of the title compound were obtained; $^1$H NMR (DMSO-d₆): δ=9.17 (t, 1H), 8.24 (d, 1H), 7.51 to 7.79 (m, 7H), 4.00 (d, 2H).

Example D-4

[(1-Chloro-4-hydroxy-6-phenylsulfanyl-isoquinoline-3-carbonyl)-amino]-acetic acid a) 1-Chloro-4-hydroxy-6-phenylsulfanyl-isoquinoline-3-carboxylic acid butyl ester 554 mg of compound B (1.5 mmol) from Example D-1d) were reacted with phosphorous oxychloride analogously to Example D-3a). The crude product was purified by flash column chromatography on silica gel eluting with dichloromethane. 205 mg of the title compound were obtained by evaporation of the first fraction; $^1$H NMR (CDCl₃): δ=11.78 (s, 1H), 8.08 (d, 1H), 8.06 (s, 1H), 7.41 to 7.56 (m, 6H), 4.46 (t, 2H), 1.85 (m, 2H), 1.48 (m, 2H), 0.98 (t, 3H).

b) [(1-Chloro-4-hydroxy-6-phenylsulfanyl-isoquinoline-3-carbonyl)-amino]-acetic acid 194 mg of 1-chloro-4-hydroxy-6-phenylsulfanyl-isoquinoline-3-carboxylic acid butyl ester (0.5 mmol) were reacted with glycine and sodium methylate analogously to Example D-1 g). 155 mg of the title compound were obtained; $^1$H NMR (DMSO-d₆): δ=9.19 (t, 1H), 8.18 (d, 1H), 7.52 to 7.79 (m, 7H), 4.00 (d, 2H).

Example D-5

[(1-Bromo-4-hydroxy-7-phenylsulfanyl-isoquinoline-3-carbonyl)-amino]-acetic acid 216 mg of 1-bromo-4-hydroxy-7-phenylsulfanyl-isoquinoline-3-carboxylic acid butyl ester (0.5 mmol) from Example D-1 e) were reacted with glycine and sodium methylate analogously to Example D-1 g). 192 mg of the title compound were obtained; $^1$H NMR (DMSO-d$_6$): δ=9.15 (t, 1H), 8.22 (d, 1H), 7.52 to 7.74 (m, 7H), 4.01 (d, 2H).

Example D-6

[(1-Bromo-4-hydroxy-6-phenylsulfanyl-isoquinoline-3-carbonyl)-amino]-acetic acid 216 mg of 1-bromo-4-hydroxy-6-phenylsulfanyl-isoquinoline-3-carboxylic acid butyl ester (0.5 mmol) from Example D-2a) were reacted with glycine and sodium methylate analogously to Example D-1 g). 194 mg of the title compound were obtained; $^1$H NMR (DMSO-d$_6$): δ=9.17 (t, 1H), 8.12 (d, 1H), 7.51 to 7.78 (m, 7H), 4.00 (d, 2H).

Example D-7

[(4-Hydroxy-7-phenoxy-isoquinoline-3-carbonyl)-amino]-acetic acid a) 4-Phenoxy-phthalic acid Synthesized from 4-phenoxy-phthalonitrile in analogy to Example D-1 a); MS-(−)-ion: M−1=256.9.

b) (1,3-Dioxo-5-phenoxy-1,3-dihydro-isoindol-2-yl)-acetic acid

Synthesized from 4-phenoxy-phthalic acid in analogy to Example D-1 b); MS-(+)-ion: M+1=297.9.

c) (1,3-Dioxo-5-phenoxy-1,3-dihydro-isoindol-2-yl)-acetic acid methyl ester

Synthesized from (1,3-dioxo-5-phenoxy-1,3-dihydro-isoindol-2-yl)-acetic acid in analogy to Example D-1c) (purification of the crude product by flash column chromatography on silica gel eluting with hexanes:ethyl acetate (1:1)); $^1$H NMR (CDCl$_3$): δ=7.83 (d, 1H), 7.05 to 7.46 (m, 7H), 4.41 (s, 2H), 3.76 (s, 3H).

d) 1,4-Dihydroxy-7-phenoxy-isoquinoline-3-carboxylic acid butyl ester (A) and 1,4-Dihydroxy-6-phenoxy-isoquinoline-3-carboxylic acid butyl ester (B)

Synthesized from (1,3-dioxo-5-phenoxy-1,3-dihydro-isoindol-2-yl)-acetic acid methyl ester in analogy to Example D-1 d); A: $^1$H NMR (CDCl$_3$): δ=10.58 (bs, 1H), 8.37 (bs, 1H), 8.14 (d, 1H), 7.87 (d, 1H), 7.05 to 7.49 (m, 6H), 4.39 (t, 2H), 1.77 (m, 2H), 1.46 (m, 2H), 0.99 (t, 3H); B: $^1$H NMR (CDCl$_3$): δ=10.38 (bs, 1H), 8.38 (d, 1H), 8.28 (bs, 1H), 7.56 (d, 1H), 7.06 to 7.47 (m, 6H), 4.40 (t, 2H), 1.77 (m, 2H), 1.46 (m, 2H), 0.99 (t, 3H).

e) 1-Bromo-4-hydroxy-7-phenoxy-isoquinoline-3-carboxylic acid butyl ester

Synthesized from 1,4-dihydroxy-7-phenoxy-isoquinoline-3-carboxylic acid butyl ester in analogy to Example D-1e); $^1$H NMR (CDCl$_3$): δ=11.89 (s, 1H), 8.35 (d, 1H), 7.63 (d, 1H), 7.08 to 7.52 (m, 6H), 4.47 (t, 2H), 1.84 (m, 2H), 1.48 (m, 2H), 0.99 (t, 3H).

f) 4-Hydroxy-7-phenoxy-isoquinoline-3-carboxylic acid butyl ester

A mixture of 208 mg of 1-Bromo-4-hydroxy-7-phenoxy-isoquinoline-3-carboxylic acid butyl ester (0.5 mmol), 49 mg of sodium acetate (0.6 mmol), 50 mg of 10 wt % palladium on charcoal, 10 ml of methanol, and 5 ml of ethyl acetate was stirred under hydrogen at 1 atm for 15 h. Then the mixture was filtered by suction through a pad of celite and was concentrated in vacuo. The residue was partitioned between 2 ml of half concentrated aqueous bicarbonate solution and 8 ml of ethyl acetate. The organic phase was dried over MgSO$_4$. Evaporation in vacuo gave 130 mg of the title compound; $^1$H NMR (CDCl$_3$): δ=11.89 (bs, 1H), 8.61 (s, 1H), 8.36 (d, 1H), 7.10 to 7.53 (m, 7H), 4.49 (t, 2H), 1.87 (m, 2H), 1.47 (m, 2H), 0.98 (t, 3H).

g) [(4-Hydroxy-7-phenoxy-isoquinoline-3-carbonyl)-amino]acetic acid

Synthesized from 4-hydroxy-7-phenoxy-isoquinoline-3-carboxylic acid butyl ester in analogy to Example D-1 g); $^1$H NMR (DMSO-d$_6$): δ=9.29 (t, 1H), 8.75 (s, 1H), 8.28 (d, 1H), 7.18 to 7.63 (m, 6H), 4.01 (d, 2H).

Alternatively, the title compound is prepared as follows:

a') 4-Bromo-2-methyl-benzoic acid ethyl ester 25.3 g of 4-bromo-2-methyl benzoic acid and 5 mL of concentrated sulfuric acid were added to 425 mL of ethanol. The mixture was heated at reflux temperature for 3 days. The solution was cooled to room temperature, adjusted to neutral pH with the addition of sodium bicarbonate, and concentrated to ca. 100 mL volume under reduced pressure. The reduced mixture was partitioned between ethyl acetate and water, and the organic phase was successively washed with saturated bicarbonate and brine solutions. The organic fraction was dried over anhydrous sodium sulfate, and concentrated to 28.2 g of a clear liquid product; $^1$H NMR (200 MHz, CDCl$_3$) δ7.78-7.73 (d, J=8.2 Hz, 1H), 7.38-7.32 (m, 2H), 4.40-4.28 (q, J=7 Hz, 2H), 2.57 (s, 3H), 1.42-1.35 (t, J=7 Hz, 3H).

b') 2-Methyl-4-phenoxy-benzoic acid ethyl ester 27.5 g of 4-bromo-2-methyl-benzoic acid ethyl ester was dissolved in 120 mL of anhydrous toluene. To the solution was added 21.3 g of phenol, 73.6 g of Cs$_2$CO$_3$, 551 μL of ethyl acetate, 22 g of activated 4 A molecular sieves, and 5.68 g of 90% copper(I) trifluoromethanesulfonate benzene complex. The reaction was placed under a nitrogen atmosphere and heated at reflux temperature for 48 h. The resultant mixture was partitioned between water and ethyl acetate, and the mixture filtered through a fine sintered glass filter to remove insoluble material. The organic fraction was washed three times with 1.0 N NaOH, once with brine, dried over anhydrous sodium sulfate, and concentrated to 18.2 g of a pale tan liquid: $^1$H NMR (200 MHz, CDCl$_3$) δ7.93-7.88 (dd, J=1.3, 7.8 Hz, 1H) 7.39-7.30 (m, 2H), 7.19-7.10 (tt, J=1.2, 7.4 Hz, 1H), 7.06-7.7.0 (m, 2H), 6.80-6.75 (m, 2H), 4.37-4.26 (q, J=7.0 Hz, 2H), 2.56 (s, 3H), 1.40-1.33 (t, J=7.0 Hz, 3H).

c') 2-{[(2,4-Dimethoxy-benzyl)-ethoxycarbonylmethyl-amino]-methyl}-4-phenoxy-benzoic acid ethyl ester Ethyl N-(2,4-dimethoxybenzyl)glycinate was prepared following literature procedures. (Ananthan S, et al., J. Med. Chem. (1993), 36(4), pp 479-490.) 13.0 g of 2-Methyl-4- phenoxy-benzoic acid ethyl ester was dissolved in 102 mL of carbon tetrachloride. To the solution was added 9.05 g of N-bromosuccinamide and 492 mg of benzoyl peroxide. The mixture was heated at reflux temperature for 18 h under a nitrogen atmosphere, cooled to room temperature, and filtered through a pad of silica gel to remove all insoluble material. The resultant solution was concentrated to 16.5 g of a crude oil.

2.0 g of the above crude oil was dissolved in 10 mL of anhydrous DMF. To the solution was added 1.0 g of Ethyl N-(2,4-dimethoxybenzyl)glicinate and 552 mg of potassium carbonate. The reaction mixture was stirred for 16 h. under a nitrogen atmosphere. The resultant mixture was poured into 80 mL of water, and extracted three times with 50 mL portions of ethyl acetate. The combined organic fractions were washed successively with half-saturated bicarbonate solution and brine. The organic fractions were concentrated to an oily residue under reduced pressure, and re-suspended in 50 mL of ether and 10 mL hexanes. The solution was cooled to 0 deg C., and filtered to remove trace insoluble material. A solution of 4 M HCl in dioxane was added slowly to the cold solution to precipitate out solid material. The solid salt was collected by filtration, and washed twice with cold ether. The solid was then dissolved by partitioning between 150 mL of ethyl acetate and 100 mL of aqueous sodium bicarbonate solution. The organic fraction was separated, washed with brine, dried over anhydrous sodium sulfate, and concentrated to provide 1.8 g of a tan oil; MS (+) m/z 508.13 (m+1).

d') 2-(2,4-Dimethoxy-benzyl)-4-hydroxy-7-phenoxy-1,2-dihydro-isoquinoline-3-carboxylic acid ethyl ester 460 mg of 2-{[(2,4-Dimethoxy-benzyl)-ethoxycarbonylmethyl-amino]-methyl}-4-phenoxy-benzoic acid ethyl ester was dissolved in 16 mL of anhydrous THF and the resultant solution cooled to ~78 deg C. under a nitrogen atmosphere. To the solution was added 1.95 mL of 1.0 M lithium bis(trimethylsilyl) amide in THF. The reaction was stirred at −78 deg C. for 1.5 h, and at room temperature for 4.5 hours. The resultant solution was poured into a solution of saturated aqueous ammonium chloride and extracted three times with ethyl acetate. The organic fractions were washed with brine, dried over anhydrous sodium sulfate and concentrated to yellow oil. The oil was flash columned on silica gel, eluting with a gradient of 20-75% ethyl acetate in hexanes. The eluted fractions were concentrated under reduced pressure to 373 mg of a yellow oil, which was determined to be a mixture of the enol and keto tautomers of the desired product; MS (+) m/z 484.20 (m+23).

e') 4-Hydroxy-7-phenoxy-isoquinoline-3-carboxylic acid ethyl ester 365 mg of 2-(2,4-dimethoxy-benzyl)-4-hydroxy-7-phenoxy-1,2-dihydro-isoquinoline-3-carboxylic acid ethyl ester was dissolved in 7.9 ml of dichloromethane. To the solution was added 92 μL of thionyl chloride. The reaction was stirred at room temperature for 6.5 h, and then 500 μL of ethanol was added and the reaction stirred for an additional 10 min. The mixture was partitioned between ethyl acetate and sodium bicarbonate. The organic fraction was successively washed with 0.5 M HCl, water, brine; dried over anhydrous sodium sulfate, and concentrated to 468 mg of a yellow oil. The oil was purified by flash chromatography on silica gel, eluting with a gradient of 15-50% ethyl acetate in hexanes, to produce 232 mg of crude product, which was crystallized from ether and hexanes to give 193 mg of off-white solid; MS (+) m/z 310.08 (m+1).

f) [(4-Hydroxy-7-phenoxy-isoquinoline-3-carbonyl)-amino]acetic acid

The title compound is prepared from 4-Hydroxy-7-phenoxy-isoquinoline-3-carboxylic acid ethyl ester under conditions analogous to example D1-g.

Another alternative synthetic route is for 4-hydroxy-7-phenoxy-isoquinoline-3-carboxylic acid ethyl ester provided below.

a") 2-Dibromomethyl-4-phenoxy-benzoic acid ethyl ester

To a flask with 2-methyl-4-phenoxy-benzoic acid ethyl ester (example D-7 b'), 3.05 g), N-bromosuccinamide (4.65 g), and benzylperoxide (115 mg) was added carbon tetrachloride 40 mL. The resulting mixture was refluxed for 16 h under nitrogen. The insoluble was filtered off and concentrated. The oil was diluted with 10% ethyl acetate in hexanes (50 mL) and filtered through a pad of silica gel, further rinse with the same solvent mix was continued twice. The filtrate solution was concentrated to give 5 g of 2-dibromomethyl-4-phenoxy-benzoic acid ethyl ester as an oil. $^1$H NMR (200 MHz, CDCl$_3$) δ8.07 (s, 1H), 7.86 (d, J=9 Hz, 1H), 7.74 (d, J=2.4 Hz, 1H), 7.41 (d, J=7.6, 2H), 7.21 (m, 1H), 7.08 (m, 2H), 6.86 (dd, J=2.5, 8.7, 1H), 4.37 (q, J=7.0 Hz, 2H), 1.40 (t, J=7.0 Hz, 3H).

b") 2-Formyl-4-phenoxy-benzoic acid ethyl ester

2-Dibromomethyl-4-phenoxy-benzoic acid ethyl ester (2.07 g) was dissolved in tetrahydrofuran (40 mL) and water (15 mL). Silver nitrate (2.56 g) was added. The resulting mixture was heated to reflux for 5 h. The precipitate was filtered off and the reaction was diluted with ethyl acetate. The organic layer was separated and the aqueous layer was extracted again with ethyl acetate. The combined ethyl acetate layer was washed with saturated sodium bicarbonate solution, brine, and dried with magnesium sulfate. After concentration, the crude oil was diluted with 20% ethyl acetate in hexanes (100 mL) and filtered through a pad of silica gel. Further rinse was continued twice. The filtrate solution was concentrated to give the title compound 1.13 g as an oil. $^1$H NMR (200 MHz, CDCl$_3$) δ10.62 (s, 1H), 7.98 (d, J=8.6 Hz, 1H), 7.42-7.35 (m, 3H), 7.20-7.14 (m, 2H), 7.04 (d, J=8.2, 2H), 4.41 (q, J=7.0 Hz, 2H), 1.41 (t, J=7.0 Hz, 3H).

c") 2-(Ethoxycarbonylmethylimino-methyl)-4-phenoxy-benzoic acid ethyl ester

To a dried flask with glycine ethyl ester hydrochloride salt (62 mg) was added anhydrous dichloromethane (2 mL), followed by triethylamine (124 μL). Then magnesium sulfate (pre-dried on high vacuum by heat gun, 100 mg) was added, followed by addition of a dichloromethane (1 mL) solution of 2-formyl-4-phenoxy-benzoic acid ethyl ester (120 mg). The flask of 2-formyl-4-phenoxy-benzoic acid ethyl ester was further rinsed with 0.5 mL of dichloromethane. The resulting mixture was stirred at room temperature under nitrogen for 15 h. The mixture was filtered and rinsed with dichloromethane. After removal of solvent, the reaction was diluted with ether (15 mL) and washed with brine twice and dried. Filtration and removal of solvent gave the title compound 160 mg as an oil with good purity. $^1$H NMR (200 MHz, CDCl$_3$) δ9.02 (d, J=1.2, 1H), 7.94 (d, J=8.6 Hz, 1H), 7.63 (d, J=2.4, 1H), 7.40-7.32 (m, 2H), 7.20-7.11 (m, 1H), 7.06-6.97 (m, 3H), 4.41 (s, 2H), 4.35 (q, J=7.0 Hz, 2H), 4.21 (q, J=7.4 Hz, 2H), 1.39 (t, J=7.0 Hz, 3H), 1.28 (t, J=7.0 Hz, 3H).

d″) 4-Hydroxy-7-phenoxy-isoquinoline-3-carboxylic acid ethyl ester

Potassium tert-butoxide (47 mg) was dried on high-vacuum pump around 90 degree for more than one hour. Under nitrogen, anhydrous tetrahydrofuran (1.4 mL) was added to it followed by a tetrahydrofuran solution (1.6 mL) of 2 (ethoxycarbonylmethylimino-methyl)-4-phenoxy-benzoic acid ethyl ester (60 mg) and a further 0.5 mL of tetrahydrofuran. The mixture turned orange-red. After stirring at room temperature for 2.5 h, the mixture was refluxed for another 2.5 h and then quenched with water (5 mL). Ethyl acetate (30 mL) was added. The organic phase was separated and washed with brine and dried. Removal of solvent gave 26 mg of the title compound as an oil with good purity. 1H NMR (200 MHz, CDCl$_3$): identical to that of example D-7 e').

Example D-8

[(4-Hydroxy-6-phenoxy-isoquinoline-3-carbonyl)-amino]-acetic acid a) 1-Bromo-4-hydroxy-6-phenoxy-isoquinoline-3-carboxylic acid butyl ester Synthesized from dihydroxy-6-phenoxy-isoquinoline-3-carboxylic acid butyl ester from Example D-7 d) in analogy to Example D-1e); $^1$H NMR (CDCl$_3$): δ=11.76 (s, 1H), 8.22 (d, 1H), 7.68 (d, 1H), 7.10 to 7.55 (m, 6H), 4.46 (t, 2H), 1.85 (m, 2H), 1.48 (m, 2H), 0.99 (t, 3H).

b) 4-Hydroxy-6-phenoxy-isoquinoline-3-carboxylic acid butyl ester

Synthesized from 1-bromo-4-hydroxy-6-phenoxy-isoquinoline-3-carboxylic acid butyl ester in analogy to Example D-7 f); $^1$H NMR (CDCl$_3$): δ=11.76 (s, 1H), 8.74 (s, 1H), 7.93 (d, 1H), 7.69 (d, 1H), 7.10 to 7.52 (m, 6H), 4.49 (t, 2H), 1.87 (m, 2H), 1.47 (m, 2H), 0.98 (t, 3H).

c) [(4-Hydroxy-6-phenoxy-isoquinoline-3-carbonyl)-amino]-acetic acid

Synthesized from 4-hydroxy-6-phenoxy-isoquinoline-3-carboxylic acid butyl ester in analogy to Example D-1 g); $^1$H NMR (DMSO-d$_6$): δ=9.33 (t, 1H), 8.82 (s, 1H), 8.23 (d, 1H), 7.20 to 7.63 (m, 7H), 4.01 (d, 2H).

Example D-9

[(1-Chloro-4-hydroxy-7-phenoxy-isoquinoline-3-carbonyl)-amino]-acetic acid a) 1-Chloro-4-hydroxy-7-phenoxy-isoquinoline-3-carboxylic acid butyl ester Synthesized from 1,4-dihydroxy-7-phenoxy-isoquinoline-3-carboxylic acid butyl ester from Example D-7d) in analogy to Example D-3a); $^1$H NMR (CDCl$_3$): δ=11.90 (s, 1H), 8.37 (d, 1H), 7.10 to 7.64 (m, 7H), 4.47 (t, 2H), 1.84 (m, 2H), 1.48 (m, 2H), 0.99 (t, 3H).

b) [(1-Chloro-4-hydroxy-7-phenoxy-isoquinoline-3-carbonyl)-amino]-acetic acid

Synthesized from 1-chloro-4-hydroxy-7-phenoxy-isoquinoline-3-carboxylic acid butyl ester in analogy to Example D-1 g); $^1$H NMR (DMSO-d$_6$): δ=9.16 (t, 1H), 8.36 (d, 1H), 7.23 to 7.72 (m, 7H), 4.01 (d, 2H).

Example D-10

[(1-Chloro-4-hydroxy-6-phenoxy-isoquinoline-3-carbonyl)-amino]-acetic acid a) 1-Chloro-4-hydroxy-6-phenoxy-isoquinoline-3-carboxylic acid butyl ester Synthesized from 1,4-dihydroxy-6-phenoxy-isoquinoline-3-carboxylic acid butyl ester from Example D-7d) in analogy to Example D-3a); $^1$H NMR (CDCl$_3$): δ=11.77 (s, 1H), 8.25 (d, 1H), 7.69 (d, 1H), 7.10 to 7.55 (m, 6H), 4.47 (t, 2H), 1.85 (m, 2H), 1.48 (m, 2H), 0.98 (t, 3H).

b) [(1-Chloro-4-hydroxy-6-phenoxy-isoquinoline-3-carbonyl)-amino]-acetic acid

Synthesized from 1-chloro-4-hydroxy-6-phenoxy-isoquinoline-3-carboxylic acid butyl ester in analogy to Example D-1 g); $^1$H NMR (DMSO-d$_6$): δ=9.19 (t, 1H), 8.31 (d, 1H), 7.23 to 7.74 (m, 7H), 4.00 (d, 2H).

Example D-11

[(1-Bromo-4-hydroxy-7-phenoxy-isoquinoline-3-carbonyl)-amino]-acetic acid

Synthesized from 1-Bromo-4-hydroxy-7-phenoxy-isoquinoline-3-carboxylic acid butyl ester from Example D-7 e) in analogy to Example D-1 g); MS-(+)-ion: M+1=417.0

Example D-12

[(1-Bromo-4-hydroxy-6-phenoxy-isoquinoline-3-carbonyl)-amino]-acetic acid

Synthesized from 1-bromo-4-hydroxy-6-phenoxy-isoquinoline-3-carboxylic acid butyl ester from Example D-8 a) in analogy to Example D-1g); MS-(−)-ion: M−1=414.9.

Example D-13

{[7-(2,6-Dimethyl-phenoxy)-4-hydroxy-isoquinoline-3-carbonyl]-amino}-acetic acid a) 4-(2,6-Dimethyl-phenoxy)-phthalic acid Synthesized from 4-(2,6-dimethyl-phenoxy)-phthalonitrile in analogy to Example D-1 a); $^1$H NMR (CDCl$_3$): δ=7.89 (d, 1H), 7.19 (d, 1H), 7.08 (bs, 3H), 6.79 (m, 1H), 2.10 (s, 6H).

b) [5-(2,6-Dimethyl-phenoxy)-1,3-dioxo-1,3-dihydro-isoindol-2-yl]-acetic acid methyl ester 4-(2,6-dimethyl-phenoxy)-phthalic acid was reacted with glycine in analogy to Example D-1 b). The crude product was then reacted with methanol in analogy to Example D-1 c); $^1$H NMR (CDCl$_3$): δ=7.80 (d, 1H), 7.09 to 7.17 (m, 5H), 4.40 (s, 2H), 3.76 (s, 3H), 2.11 (s, 6H).

c) 7-(2,6-Dimethyl-phenoxy)-1,4-dihydroxy-isoquinoline-3-carboxylic acid butyl ester 0.79 g of sodium (34 mmol) were dissolved in 100 ml of n-butanol with stirring. Then the temperature was raised to 95° C. to 100° C., 5.70 g of [5-(2,6-dimethyl-phenoxy)-1,3-dioxo-1,3-dihydro-isoindol-2-yl]-acetic acid methyl ester (16.8 mmol) were added in one portion and stirring was continued at 95° C. to 100° C. for 3 h. Subsequently, the solvent was evaporated in vacuo, 25 ml of aqueous 2N HCl and 100 ml of ethyl acetate were added and the mixture was stirred vigorously for 30 min before it was filtered by suction. The organic phase was separated from the filtrate, dried over MgSO$_4$ and was evaporated in vacuo to give a brown gum that was triturated with methanol. The resulting precipitate was filtered by suction and dried in vacuo to give 870 mg of a yellowish solid (A). The filtrate was evaporated in vacuo, dissolved in a small amount of methanol and stored overnight in a refrigerator. The resulting precipitate was filtered by suction and dried in vacuo to give 246 mg of a yellowish solid (B). A and B were pooled and purified by flash column chromatography on silica gel eluting with dichloromethane:ethyl acetate (98:2). Evaporation of the first fraction yielded 762 mg of the title compound; $^1$H NMR (CDCl$_3$): δ=8.31 (bs, 1H), 8.12 (d, 1H), 7.60 (d, 1H), 7.35 (m, 1H), 7.09 (bs, 3H), 4.39 (t, 2H), 2.11 (s, 6H), 1.77 (m, 2H), 1.44 (m, 2H), 0.99 (t, 3H).

d) 1-Bromo-7-(2,6-dimethyl-phenoxy)-4-hydroxy-isoquinoline-3-carboxylic acid butyl ester Synthesized from 7-(2,6-dimethyl-phenoxy)-1,4-dihydroxy-isoquinoline-3-carboxylic acid butyl ester in analogy to Example D-1 e); $^1$H NMR (CDCl$_3$): δ=11.88 (s, 1H), 8.33 (m, 1H), 7.35 to 7.40 (m, 2H), 7.13 to 7.16 (m, 3H), 4.46 (t, 2H), 2.14 (s, 6H), 1.83 (m, 2H), 1.48 (m, 2H), 0.98 (t, 3H).

e) 7-(2,6-Dimethyl-phenoxy)-4-hydroxy-isoquinoline-3-carboxylic acid butyl ester Synthesized from 1-bromo-7-(2,6-dimethyl-phenoxy)-4-hydroxy-isoquinoline-3-carboxylic acid butyl ester in analogy to Example D-7 f); $^1$H NMR (CDCl$_3$): δ=11.87 (s, 1H), 8.35 (s, 1H), 8.36 (d, 1H), 7.47 (dd, 1H), 7.14 (m, 2H), 6.87 (d, 1H), 4.48 (t, 2H), 2.14 (s, 6H), 1.87 (m, 2H), 1.47 (m, 2H), 0.98 (t, 3H).

f) {[7-(2,6-Dimethyl-phenoxy)-4-hydroxy-isoquinoline-3-carbonyl]-amino}-acetic acid Synthesized from 7-(2,6-Dimethyl-phenoxy)-4-hydroxy-isoquinoline-3-carboxylic acid butyl ester in analogy to Example D-1 g); MS-(+)-ion: M+1=367.1.

Example D-14

{[1-Chloro-7-(2,6-dimethyl-phenoxy)-4-hydroxy-isoquinoline-3-carbonyl]-amino}-acetic acid a) 1-Chloro-7-(2,6-dimethyl-phenoxy)-4-hydroxy-isoquinoline-3-carboxylic acid butyl ester Synthesized from 7-(2,6-dimethyl-phenoxy)-1,4-dihydroxy-isoquinoline-3-carboxylic acid butyl ester from Example D-13 c) in analogy to Example D-3 a); $^1$H NMR (CDCl$_3$): δ=11.89 (s, 1H), 8.35 (d, 1H), 7.34 to 7.43 (m, 2H), 7.13 to 7.14 (m, 3H), 4.47 (t, 2H), 2.14 (s, 6H), 1.85 (m, 2H), 1.48 (m, 2H), 0.99 (t, 3H).

b) {[1-Chloro-7-(2,6-dimethyl-phenoxy)-4-hydroxy-isoquinoline-3-carbonyl]-amino}-acetic acid Synthesized from 1-chloro-7-(2,6-dimethyl-phenoxy)-4-hydroxy-isoquinoline-3-carboxylic acid butyl ester in analogy to Example D-1 g); MS-(−)-ion: M−1=398.9.

Example D-15

{[1-Bromo-7-(2,6-dimethyl-phenoxy)-4-hydroxy-isoquinoline-3-carbonyl]-amino}-acetic acid Synthesized from 1-bromo-7-(2,6-dimethyl-phenoxy)-4-hydroxy-isoquinoline-3-carboxylic acid butyl ester from Example D-13 d) in analogy to Example D-1 g); MS-(−)-ion: M−1=442.9.

Example D-16

[(1-Bromo-7-chloro-4-hydroxy-isoquinoline-3-carbonyl)-amino]-acetic acid a) (5-Chloro-1,3-dioxo-1,3-dihydro-isoindol-2-yl)-acetic acid Synthesized in analogy to Example D-1 b) (5-chloro-isobenzofuran-1,3-dione was used as starting material instead of the corresponding phthalic acid); $^1$H NMR (DMSO-d$_6$/D$_2$O): δ=8.01 (s, 1H), 7.93 (s, 2H), 4.32 (s, 2H).

b) (5-Chloro-1,3-dioxo-1,3-dihydro-isoindol-2-yl)-acetic acid methyl ester

Synthesized from (5-chloro-1,3-dioxo-1,3-dihydro-isoindol-2-yl)-acetic acid in analogy to Example D-1 c); $^1$H NMR (CDCl$_3$): δ=7.67 to 7.86 (m, 3H), 4.43 (s, 2H), 3.76 (s, 3H).

c) 7-Chloro-1,4-dihydroxy-isoquinoline-3-carboxylic acid butyl ester (A) and 6-Chloro-1,4-dihydroxy-isoquinoline-3-carboxylic acid butyl ester (B)

Synthesized from (5-chloro-1,3-dioxo-1,3-dihydro-isoindol-2-yl)-acetic acid methyl ester in analogy to Example D-1 d) (pure B was obtained by recrystallization from chloroform after chromatography); A: $^1$H NMR (CDCl$_3$): δ=8.46 (bs, 1H), 8.41 (d, 1H), 8.10 (d, 1H), 7.73 (dd, 1H), 4.41 (t, 2H), 1.77 (m, 2H), 1.46 (m, 2H), 1.00 (t, 3H); B: $^1$H NMR (CDCl$_3$): δ=8.34 to 8.38 (m, 2H), 8.12 (d, 1H), 7.64 (dd, 1H), 4.42 (t, 2H), 1.77 (m, 2H), 1.46 (m, 2H), 1.00 (t, 3H).

d) 1-Bromo-7-chloro-4-hydroxy-isoquinoline-3-carboxylic acid butyl ester

Synthesized from 7-Chloro-1,4-dihydroxy-isoquinoline-3-carboxylic acid butyl ester in analogy to Example D-1 e); $^1$H NMR (CDCl$_3$): δ=11.92 (s, 1H), 8.34 (d, 1H), 8.25 (d, 1H), 7.75 (dd, 1H),4.49 (t, 2H), 1.86 (m, 2H), 1.48 (m, 2H), 1.00 (t, 3H).

e) [(1-Bromo-7-chloro-4-hydroxy-isoquinoline-3-carbonyl)-amino]-acetic acid

Synthesized from 1-bromo-7-chloro-4-hydroxy-isoquinoline-3-carboxylic acid butyl ester in analogy to Example D-1 g); MS-(−)-ion: M−1=356.8.

Example D-17

[(1-Bromo-6-chloro-4-hydroxy-isoquinoline-3-carbonyl)-amino]-acetic acid a) 1-Bromo-6-chloro-4-hydroxy-isoquinoline-3-carboxylic acid butyl ester Synthesized from 6-chloro-1,4-dihydroxy-isoquinoline-3-carboxylic acid butyl ester from Example D-16 c) in analogy to Example D-1 e); $^1$H NMR (CDCl$_3$): δ=11.88 (s, 1H), 8.37 (d, 1H), 8.19 (d, 1H), 7.75 (dd, 1H), 4.49 (t, 2H), 1.86 (m, 2H), 1.48 (m, 2H), 0.99 (t, 3H).

b) [(1-Bromo-6-chloro-4-hydroxy-isoquinoline-3-carbonyl)-amino]-acetic acid

Synthesized from 1-bromo-6-chloro-4-hydroxy-isoquinoline-3-carboxylic acid butyl ester in analogy to Example D-1 g); MS-(−)-ion: M−1=356.9.

Example D-18

[(1-Bromo-4-hydroxy-7-trifluoromethyl-isoquinoline-3-carbonyl)-amino]-acetic acid a) (1,3-Dioxo-5-trifluoromethyl-1,3-dihydro-isoindol-2-yl)-acetic acid methyl ester 4-trifluoromethyl-phthalic acid was reacted with glycine in analogy to Example D-1 b). The crude product was then reacted with methanol in analogy to Example D-1 c); $^1$H NMR (CDCl$_3$): δ=8.14 (s, 1H), 8.02 (m, 2H), 4.48 (s, 2H), 3.78 (s, 3H).

b) 1,4-Dihydroxy-7-trifluoromethyl-isoquinoline-3-carboxylic acid butyl ester (A) and 1,4-Dihydroxy-6-trifluoromethyl-isoquinoline-3-carboxylic acid butyl ester (B)

Synthesized from (1,3-dioxo-5-trifluoromethyl-1,3-dihydro-isoindol-2-yl)-acetic acid methyl ester in analogy to Example D-1 d); A: $^1$H NMR (CDCl$_3$): δ=10.47 (bs, 1H), 8.76 (bs, 1H), 8.72 (d, 1H), 8.29 (m, 1H), 7.99 (m, 1H), 4.45 (t, 2H), 1.77 (m, 2H), 1.46 (m, 2H), 1.00 (t, 3H); B: $^1$H NMR (CDCl$_3$): δ=10.48 (bs, 1H), 8.44 to 8.57 (m, 3H), 7.91 (d, 1H), 4.44 (t, 2H), 1.77 (m, 2H), 1.46 (m, 2H), 1.01 (t, 3H).

c) 1-Bromo-4-hydroxy-7-trifluoromethyl-isoquinoline-3-carboxylic acid butyl ester Synthesized from 1,4-dihydroxy-7-trifluoromethyl-isoquinoline-3-carboxylic acid butyl ester in analogy to Example D-1 e); $^1$H NMR (CDCl$_3$): δ=11.96 (s, 1H), 8.52 to 8.56 (m, 2H), 7.99 (dd, 1H), 4.51 (t, 2H), 1.86 (m, 2H), 1.48 (m, 2H), 1.00 (t, 3H).

d) [(1-Bromo-4-hydroxy-7-trifluoromethyl-isoquinoline-3-carbonyl)-amino]-acetic acid Synthesized from 1-bromo-4-hydroxy-7-trifluoromethyl-isoquinoline-3-carboxylic acid butyl ester in analogy to Example D-1 g); MS-(−)-ion: M−1=391.0.

Example D-19

[(1-Bromo-4-hydroxy-6-trifluoromethyl-isoquinoline-3-carbonyl)-amino]-acetic acid a) 1-Bromo-4-hydroxy-6-trifluoromethyl-isoquinoline-3-carboxylic acid butyl ester Synthesized from 1,4-dihydroxy-6-trifluoromethyl-isoquinoline-3-carboxylic acid butyl ester from Example D-18 b) in analogy to Example D-1 e); MS-(−)-ion: M−1=390.3.

b) [(1-Bromo-4-hydroxy-6-trifluoromethyl-isoquinoline-3-carbonyl)-amino]-acetic acid Synthesized from 1-bromo-4-hydroxy-6-trifluoromethyl-isoquinoline-3-carboxylic acid butyl ester in analogy to Example D-1 g); MS-(−)-ion: M−1=390.9.

Example D-20

[(4-Hydroxy-1-phenoxy-isoquinoline-3-carbonyl)-amino]-acetic acid a) (1,3-Dioxo-1,3-dihydro-isoindol-2-yl)-acetic acid methyl ester Synthesized from (1,3-dioxo-1,3-dihydro-isoindol-2-yl)-acetic acid in analogy to Example D-1 c); $^1$H NMR (CDCl$_3$): δ=7.84 to 7.91 (m, 2H), 7.71 to 7.77 (m, 2H), 4.45 (s, 2H), 3.77 (s, 3H).

b) 1,4-Dihydroxy-isoquinoline-3-carboxylic acid butyl ester

Synthesized from (1,3-Dioxo-1,3-dihydro-isoindol-2-yl)-acetic acid methyl ester in analogy to Example D-1 d) (the solvent was not evaporated before adding hydrochloric acid, no ethyl acetate was added); $^1$H NMR (DMSO-d$_6$): δ=10.66 (bs, 1H), 10.55 (bs, 1H), 8.27 (d, 1H), 8.08 (d, 1H), 7.72 to 7.92 (m, 2H), 4.33 (t, 2H), 1.74 (m, 2H), 1.44 (m, 2H), 0.93 (t, 3H).

c) 1-Chloro-4-hydroxy-isoquinoline-3-carboxylic acid butyl ester

Synthesized from 1,4-Dihydroxy-isoquinoline-3-carboxylic acid butyl ester in analogy to Example D-3 a); $^1$H NMR (CDCl$_3$): δ=11.91 (s, 1H), 8.41 (m, 1H), 8.29 (m, 1H), 7.83 (m, 2H), 4.49 (t, 2H), 1.84 (m, 2H), 1.48 (m, 2H), 0.99 (t, 3H).

d) 4-Hydroxy-1-phenoxy-isoquinoline-3-carboxylic acid butyl ester

A mixture of 1.399 g of 1-Chloro-4-hydroxy-isoquinoline-3-carboxylic acid butyl ester (5 mmol) and 2.86 g of phenol was heated at 145° C. to 150° C. for 24 h. After cooling to ambient temperature the mixture was suspended in 50 ml of aqueous 2N NaOH and the mixture was extracted with 4×25 ml of ethyl acetate. The combined organic phases were washed with 3×25 ml of aqueous 2N NaOH, 50 ml of brine, dried over MgSO$_4$, and evaporated in vacuo. The residue was purified by flash column chromatography on silica gel eluting with hexanes:ethyl acetate (9:1) and (95:5). 0.650 g of the title compound were obtained; $^1$H NMR (CDCl$_3$): δ=11.52 (s, 1H), 8.32 to 8.39 (m, 2H), 7.72 to 7.86 (m, 2H), 7.13 to 7.42 (m, 5H), 4.31 (t, 2H), 1.69 (m, 2H), 1.37 (m, 2H), 0.93 (t, 3H).

e) [(4-Hydroxy-1-phenoxy-isoquinoline-3-carbonyl)-amino]-acetic acid

Synthesized from 4-Hydroxy-1-phenoxy-isoquinoline-3-carboxylic acid butyl ester in analogy to Example D-1 g); MS-(+)-ion: M+1=339.1.

Example D-21

[(1,7-dibromo-4-hydroxy-isoquinoline-3-carbonyl)-amino]-acetic acid a) (5-Bromo-1,3-dioxo-1,3-dihydro-isoindol-2-yl)-acetic acid ethyl ester Bromophthalimide (35 g, 155 mmol) and bromoethylacetate (31 g, 186 mmol) were dissolved in 700 ml of acetone. Potassium carbonate (64.2 g, 465 mmol) was added and resulting suspension was stirred at reflux for 18 h. After cooling, the mixture was filtered. Filtrate was evaporated to give 48.12 g (154 mmol) of solid product. $^1$H NMR (200 MHz, CDCl$_3$) δ8.00 (s, 1H), 7.89 (d, J=7.8 Hz, 1H), 7.73 (d, J=7.8 Hz, 1H), 4.41 (s, 2H), 4.21 (q, J=7.0 Hz, 2H), 1.28 (t, J=7.0 Hz, 3H).

b) 6- and 7-Bromo-1,4-dihydroxy-isoquinoline-3-carboxylic acid butyl ester

Sodium (10.45 g) was dissolved in 460 ml of n-butanol with heating (45-50° C.). The above ester (68 g, 218 mmol) was dissolved in 460 ml of n-butanol (heated to homogeneous), and then added to the sodium solution. Combined mixture was stirred mechanically at 75° C. for 1 h. Mixture was removed from heat and stirred at room temperature overnight. Solution was acidified using 2 N HCl to pH ~3. Precipitate was collected by vacuum filtration and washed with water and then methanol to give 59.4 g (175 mmol) of product as a mixture of two isomers.

c) 7-Bromo-1,4-dihydroxy-isoquinoline-3-carboxylic acid butyl ester 10 g of the above isomeric mixtures was subjected to silica gel flash chromatography eluting with 10% ethyl acetate in methylene chloride to give 3 g of product as white solid. MS-(+)-ion: M+1=342.02, 340.02 d) 1,7-dibromo-4-hydroxy-isoquinoline-3-carboxylic acid butyl ester

The above ester (2.4 g, 7.1 mmol) was dissolved in 150 ml of anhydrous acetonitrile. Phosphorous oxybromide (14.1 g, 49.4 mmol) was added. Mixture was stirred at reflux for 3 h. After cooling, the reaction mixture was concentrated and the residue was taken into ethyl acetate. Ethyl acetate mixture was poured into saturated sodium bicarbonate solution with efficient stirring. Two phases were separated. Organic layer was dried over magnesium sulfate, filtered and concentrated to give 2 g (5.0 mmol) of product. MS-(+)-ion: M+1=403.90 e) [(1,7-dibromo-4-hydroxy-isoquinoline-3-carbonyl)-amino]-acetic acid

The above ester (0.2 g, 0.5 mmol) was dissolved in 5 ml of ethanol. Glycine (0.24 g, 9.9 mmol) and sodium ethoxide (0.34 g, 5 mmol) were added to the solution. Mixture was stirred at reflux for 3 days. Mixture was evaporated. Residue was dissolved in water and washed with ethyl acetate. Aqueous layer was acidified using 1N HCl aqueous solution to pH=3-4, then extracted with ethyl acetate. Organic layer was dried over magnesium sulfate, filtered and concentrated to give 0.17 g of product as white solid. $^1$H NMR (200 MHz, DMSO-d6) δ9.26 (t, J=6.2 Hz, 1H), 8.32 (d, J=1.6 Hz, 1H), 8.23 (d, J=9.0 Hz, 1H), 8.11 (dd, J=9.0, 1.6 Hz, 1H), 4.02 (d, J=6.2 Hz, 2H).

Example D-22

[(7-Bromo-1-chloro-4-hydroxy-isoquinoline-3-carbonyl)-amino]-acetic acid a) 7-Bromo-1-chloro-4-hydroxy-isoquinoline-3-carboxylic acid butyl ester 170 mg (0.5 mmol) of 7-bromo-1,4-dihydroxy-isoquinoline-3-carboxylic acid butyl ester (from Example D-21c) was dissolved in 2 ml of anhydrous acetonitrile. Phosphorous oxychloride (536 mg, 3.5 mmol) was added and the resulting mixture was stirred at reflux for 4 h. After cooling, the mixture was concentrated and the residue was taken into ethyl acetate. Ethyl acetate mixture was poured into saturated sodium bicarbonate solution with efficient stirring for 1 h. Two phases were separated. Aqueous layer was extracted with ethyl acetate. Combined organic layer was dried over magnesium sulfate, filtered and concentrated. Crude product was purified by silica gel chromatography eluing with methylene chloride to give 78 mg of product as white solid. MS-(+)-ion: M+1=359.96, 357.98 b) [(7-Bromo-1-chloro-4-hydroxy-isoquinoline-3-carbonyl)-amino]-acetic acid 75 mg (0.21 mmol) of the above ester was reacted with glycine (314 mg, 4.18 mmol) and sodium ethoxide (143 mg, 2.09 mmol) analogously to Example D-21e). 58 mg of product was obtained. $^1$H NMR (200 MHz, CD3OD) δ8.44 (d, J=1.6 Hz, 1H), 8.28 (d, J=9.0 Hz, 1H), 8.00 (dd, J=9.0, 1.6 Hz, 1H), 4.17 (s, 2H).

Example D-23

[(6-Bromo-4-hydroxy-isoquinoline-3-carbonyl)-amino]-acetic acid a) 6-Bromo-4-hydroxy-isoquinoline-3-carboxylic acid butyl ester 2.58 g (6.40 mmol) of 6- and 7-Bromo-1,4-dihydroxy-isoquinoline-3-carboxylic acid butyl ester mixtures (from Example D-21b) was dissolved in 30 ml of glacial acetic acid. A palladium (10% in activated carbon) slurry in 10 ml of glacial acetic acid was added. The mixture was stirred under hydrogen atmosphere (balloon pressure) for 2 h. Catalyst was filtered off through a pad of celite and rinsed with methylene chloride. Filtrated was concentrated and residue was triturated in methylene chloride. Insoluble solid was collected by filtration and subjected to silica gel chromatography eluting with (3/1) hexanes/ethyl acetate to give 192 mg of product. MS-(−)-ion: M−1=324.11, 322.13 b) [(6-Bromo-4-hydroxy-isoquinoline-3-carbonyl)-amino]-acetic acid 178 mg (0.55 mmol) of the above ester was reacted with glycine (1.23 g, 16.43 mmol) and sodium ethoxide (746 mg, 10.96 mmol) analogously to Example D-21e. The product obtained was further triturated with 30 ml of methanol to give 58 mg of product. $^1$H NMR (200 MHz, CD$_3$OD) δ8.72 (s, 1H), 8.46 (s, 1H), 7.98 (d, J=8.8 Hz), 7.86 (d, J=8.8 Hz, 1H), 4.14 (s, 2H).

Example D-24

[(1-Bromo-7-fluoro-4-hydroxy-isoquinoline-3-carbonyl)-amino]-acetic acid a) (5-Fluoro-1,3-dioxo-1,3-dihydro-isoindol-2-yl)-acetic acid methyl ester A solid mixture of 5-fluoro-isobenzofuran-1,3-dione (3.68 g, 22.15 mmol) and glycine (1.66 g, 22.15 mmol) was stirred at 200-220° C. for 5 min. After cooling, it was dissolved in 25 ml of acetone. Methyl sulfate (4.19 g, 33.23 mmol) and potassium carbonate (4.59 g, 33.23 mmol) was added. The mixture was stirred at reflux for 2 h. After cooling, it was diluted with 100 ml of ethyl acetate. Insoluble was filtered off and filtrate was concentrated. Residue was taken into 200 ml of ethyl acetate and washed with water and brine. Ethyl acetate layer was dried over sodium sulfate, filtered, and concentrated to give 5.1 g of product. $^1$H NMR (200 MHz, CDCl$_3$) δ7.88 (dd, J=8.2, 4.3 Hz, 1H), 7.54 (dd, J=6.8, 2.2 Hz, 1H), 7.40 (m, 1H), 4.44 (s, 2H), 3.77 (s, 3H).

b) 7-Fluoro-1,4-dihydroxy-isoquinoline-3-carboxylic acid butyl ester (A) and 6-Fluoro-1,4-dihydroxy-isoquinoline-3-carboxylic acid butyl ester (B)

3.0 g (12.66 mmol) of the above ester was rearranged analogously to Example D-21b at 95-100° C. for 2 h to give 2.5 g of product as a mixture of isomers. The isomeric mixtures were purified by silica gel chromatography eluting with 5-20% ethyl acetate in methylene chloride. The first fraction was concentrated and recrystallized from 60 ml of ethanol to give 268 mg of solid product (A). The second fraction was concentrated to give 313 mg of solid product (B). For product A: MS-(−)-ion: M−1=278.02; For product B: MS-(−)-ion: M−1=278.03.

Differentiation of the isomers A and B can be measured on the silica gel TLC plate with 10% ethyl acetate in methylene chloride: A: R$_f$ about 0.79; B: R$_f$ about 0.53)

c) 1-Bromo-7-fluoro-4-hydroxy-isoquinoline-3-carboxylic acid butyl ester 250 mg (0.90 mmol) of the above ester (A) was brominated analogously to Example D-21 d (10% methanol in methylene chloride was used instead of ethyl acetate) to give 156 mg of solid product. MS-(+)-ion: M+1=344.00, 341.99 d) [(1-Bromo-7-fluoro-4-hydroxy-isoquinoline-3-carbonyl)-amino]-acetic acid 60 mg (0.18 mmol) of the above ester was reacted with glycine analogously to Example D-21e. (Reaction time was 48 h). 10% Methanol in methylene chloride was used to extracted the product. The organic layer was dried over magnesium sulfate, filtered, and concentrated to give 50 mg of the product. MS-(−)-ion: M−1=343.02, 340.92; $^1$H NMR (200 MHz, acetone-d6) δ13.56 (s, 1H), 8.81 (br s, 1H), 8.43 (dd, J=9.0, 5.4 Hz, 1H), 7.79 (m, 2H), 4.29 (d, J=6.2 Hz, 2H).

Example D-25

[(7-Fluoro-4-hydroxy-isoquinoline-3-carbonyl)-amino]-acetic acid 42 mg (0.12 mmol) of the above carboxylic acid was dissolved in 5 ml of (4/1) methanol/water. Sodium carbonate (13 mg, 0.12 mmol) and palladium (wet, 10% dry basis on activated carbon) (40 mg) were added. The mixture was stirred under hydrogen atmosphere (balloon pressure) for 2 h. Catalyst was filtered off through a pad of celite, rinsed with 10 ml of (4/1) methanol/water and then 2 ml of water. Filtrate was concentrated to remove most methanol and acidified by 1 N HCl to pH=3-4. Precipitate was collected by filtration and dried under high vacuum to give 14 mg of product. MS-(−)-ion: M−1=262.99; $^1$H NMR (200 MHz, CD$_3$OD) δ8.69 (s, 1H), 8.38 (dd, J=9.0, 5.5 Hz, 1H), 7.24 (dd, J=9.3, 2.4 Hz, 1H), 7.60 (m, 1H), 4.14 (s, 2H).

Example D-26

[(1-Chloro-7-fluoro-4-hydroxy-isoquinoline-3-carbonyl)-amino]-acetic acid a. 1-Chloro-7-fluoro-4-hydroxy-isoquinoline-3-carboxylic acid butyl ester 135 mg (0.48 mmol) of 7-fluoro-1,4-dihydroxy-isoquinoline-3-carboxylic acid butyl ester (product A from Example D-24b) was dissolved in 3 ml of anhydrous acetonitrile. Phosphorous oxychloride (1.24 g, 8.07 mmol) was added. The mixture was stirred at reflux for 6 h. After cooling, it was concentrated and suspended in 10 ml of saturated sodium bicarbonate aqueous solution. Stirred for 1 h and extracted with 5% methanol in methylene chloride. Organic layer was washed with brine, dried over magnesium sulfate, filtered, and concentrated. Crude residue was purified by silica gel chromatography eluting with methylene chloride to give 58 mg of product. MS-(−)-ion: M−1=296.12 b. [(1-Chloro-7-fluoro-4-hydroxy-isoquinoline-3-carbonyl)-amino]-acetic acid 55 mg (0.19 mmol) of the above ester was reacted with glycine analogously to Example D-21e. After acidification, it was extracted with 10% methanol in methylene chloride. Organic layer was washed with brine, dried over magnesium sulfate, filtered, and concentrated. The residue was purified by preparative TLC on 10% methanol in methylene chloride to give 6 mg of product. $^1$H NMR (200 MHz, acetone-d6)

δ13.59 (s, 1H), 8.90 (br s, 1H), 8.47 (dd, J=9.0, 5.1 Hz, 1H), 7.94 (dd, J=9.7, 2.4 Hz, 1H), 7.81 (m, 1H), 4.28 (d, J=6.2 Hz, 2H).

Example D-27

[(Chloro-4-hydroxy-benzo[g]isoquinoline-3-carbonyl)-amino]-acetic acid a) (1,3-Dioxo-1,3-dihydro-benzo[f]isoindol-2-yl)-acetic acid ethyl ester 2 g (10.1 mmol) Benzo[f]isoindole-1,3-dione was reacted with bromoacetic acid ethyl ester analogously to Example D-21a. The crude product obtained was partitioned between ethyl acetate and water. Organic layer was washed with brine, dried over magnesium sulfate, filtered, and evaporated to give 2.68 g (9.5 mmol) of product. $^1$H NMR (200 MHz, CDCl$_3$) δ8.36 (s, 2H), 8.05 (m, 2H), 7.68 (m, 2H), 4.49 (s, 2H), 4.22 (q, J=7.0 Hz, 2H), 1.29 (t, 7.0 Hz, 3H).

b) 1,4-Dihydroxy-benzo[g]isoquinoline-3-carboxylic acid butyl ester 2.6 g (9.2 mmol) of the above isoindol ester was rearranged analogously to Example D-21b to give 1.23 g (3.9 mmol) of product. $^1$H NMR (200 MHz, CDCl$_3$) δ10.73 (br s, 1H), 9.00 (s, 1H), 8.68 (s, 1H), 8.24 (br s, 1H), 8.06 (m, 2H), 7.68 (m, 2H), 4.24 (t, J=6.6 Hz, 2H), 1.80 (m, 2H), 1.47 (m, 2H), 1.00 (t, J=7.4 Hz, 3H).

c) 1-Chloro-4-hydroxy-benzo[g]isoquinoline-3-carboxylic acid butyl ester 1 g (3.2 mmol) of the above ester was reacted with 5 ml of phosphorous oxychloride analogously to Example D-22a without using acetonitrile as a co-solvent to give 0.88 g (2.7 mmol) of product. $^1$H NMR (200 MHz, CDCl$_3$) δ12.24 (s, 1H), 8.97 (s, 1H), 8.85 (s, 1H), 8.12 (m, 2H), 7.70 (m, 2H), 4.51 (t, J=7.0 Hz, 2H), 1.89 (m, 2H), 1.56 (m, 2H), 1.00 (t, J=7.2 Hz, 3H).

d) [(Chloro-4-hydroxy-benzo[g]isoquinoline-3-carbonyl)-amino]-acetic acid 0.88 g (2.7 mmol) of the above ester was reacted with glycine analogously to Example D-21e. The resulting precipitate after acidification was collected by filtration and dried in high vacuum to give 0.30 g (0.9 mmol) of product. $^1$H NMR (200 MHz, DMSO-d6) δ9.34 (br s, 1H), 9.00 (s, 1H), 8.92 (s, 1H), 8.34 (m, 2H), 7.74 (m, 2H), 3.94 (d, J=5.4 Hz, 2H).

Example D-28

[(1-Bromo-4-hydroxy-isoquinoline-3-carbonyl)-amino]-acetic acid a) 1-Bromo-4-hydroxy-isoquinoline-3-carboxylic acid butyl ester 2 g (7.7 mmol) of 1,4-Dihydroxy-isoquinoline-3-carboxylic acid butyl ester (from Example D-20b) dissolved in 100 ml of acetonitrile. 15.4 g (53.6 mmol) of phosphorous oxybromide added to solution and mixture stirred at 80° C. for 64 h. 100 ml of water was added to mixture, and mixture was removed from heat. Mixture was partitioned between ethyl acetate and water. Two phases were separated and the aqueous layer was extracted with ethyl acetate. Organic layers were combined, washed with brine, dried over magnesium sulfate, filtered, and evaporated. Residue was purified by silica gel flash chromatography to give 0.1 g (0.3 mmol) of product. $^1$H NMR (200 MHz, CDCl$_3$) δ11.89 (s, 1H), 8.41 (m, 1H), 8.25 (m, 1H), 7.84 (m, 2H), 4.49 (t, J=7.0 Hz, 2H), 1.87 (m, 2H), 1.47 (m, 2H), 1.00 (t, J=7.2 Hz, 3H).

b) [(1-Bromo-4-hydroxy-isoquinoline-3-carbonyl)-amino]-acetic acid g (0.3 mmol) of the above isoquinoline ester was reacted with glycine analogously to Example D-21e to give 0.08 g (0.2 mmol) of product. $^1$H NMR (200 MHz, CD$_3$OD) δ8.94 (br s, 1H), 8.34 (m, 1H), 8.24 (m, 1H), 7.86 (m, 2H), 4.18 (d, J=6.2 Hz, 2H).

Example D-29

[(4-Hydroxy-6-phenyl-isoquinoline-3-carbonyl)-amino]-acetic acid

The title compound was prepared from [(1-Chloro-4-hydroxy-6-phenyl-isoquinoline-3-carbonyl)-amino]-acetic acid, Example D-33, following a procedure analogous to that described in detail in Example D-37. The final product was purified by chromatography on silica gel using a gradient of 0 to 15% methanol in dichloromethane with 0.5% acetic acid to elute the desired product; MS (−): m/z 321.00 (M−1)

Example D-30

[(4-Hydroxy-7-phenyl-isoquinoline-3-carbonyl)-amino]-acetic acid

The title compound was prepared from [(1-Chloro-4-hydroxy-7-phenyl-isoquinoline-3-carbonyl)-amino]-acetic acid, Example D-34, following a procedure analogous to that described in detail in Example D-37. The final product was purified by chromatography on silica gel using a gradient of 0 to 15% methanol in dichloromethane with 0.5% acetic acid to elute the desired product; MS (−): m/z 321.02 (M−1)

Example D-31

[(1-Chloro-4-hydroxy-6-phenyl-isoquinoline-3-carbonyl)-amino]-acetic acid a) (5-Bromo-1,3-dioxo-1,3-dihydro-isoindol-2-yl)-acetic acid methyl ester 50.3 g of 4-bromophthalimide, 92.0 g of potassium carbonate, and 24.5 ml of methyl bromoacetate were added to 888 ml of acetone. The resultant mixture was heated to reflux temperature for 24 h, and then cooled to room temperature. The mixture was filtered through a fine glass frit to remove all solid material, and the solution was then concentrated under vacuum to provide 66 g of the desired product, a white solid; $^1$H NMR (CDCl$_3$): δ=3.76 (s, 3H), 4.43 (s, 2H), 7.71-7.75 (m, 1H), 7.85-7.90 (dd, 1H), 8.00 (m, 1H).

b) (1,3-Dioxo-5-phenyl-1,3-dihydro-isoindol-2-yl)-acetic acid methyl ester 6.0 g of the above bromo-phthalimide product was dissolved in 70 ml of ethylene glycol dimethyl ether. To the solution was added 3.7 g of phenyl boronic acid, 13 g cesium carbonate, and 2 g tetakis(triphenylphosphine)palladium (O). The mixture was stirred under a nitrogen atmosphere at 65° C. for 48 h. The resultant mixture was poured into 250 ml of half saturated aqueous sodium bicarbonate solution, and then extracted with 200 ml portions of ethyl acetate three times. The combined organic fractions were successively washed with 200 ml of water, saturated sodium bicarbonate, and brine solutions, and then dried over sodium sulfate. The solution was concentrated to a residue (11 g), which was purified by chromatography on silica gel using a gradient of 0 to 25% ethyl acetate in hexanes to elute the desired product. 1.1 g of purified product was obtained; MS (+): m/z 296.02 (M+1)

c) 1,4-Dihydroxy-7-phenyl-isoquinoline-3-carboxylic acid butyl ester (A) and 1,4-Dihydroxy-6-phenyl-isoquinoline-3-carboxylic acid butyl ester (B)

1.4 g of the above product was added to 18.8 ml solution of 0.5 N sodium n-butoxide in n-butanol. The resultant mixture was heated to 100° C. for 2 h, and then cooled to room temperature. The mixture was poured into a 100 ml solution of 0.5 N aqueous hydrochloric acid solution, and extracted with 100 ml portions of ethyl acetate three times. The combined organic extracts were filtered to remove any insoluble material and then washed successively with water and brine. The solution was dried over sodium sulfate and concentrated under vacuum to a residue (1.1 g), which was purified by chromatography on silica gel using a gradient of 0 to 20% ethyl acetate in dichloromethane to elute two major products ($R_f$ isomer A=0.64, $R_f$ B=0.48; 15% Ethyl acetate: 85% Dichloromethane)

Isomer A: 397 mg; MS (+) m/z 388.11 (M+1)
Isomer B: 195 mg; MS (+) m/z 388.10 (M+1)

d) 1-Chloro-4-hydroxy-6-phenyl-isoquinoline-3-carboxylic acid butyl ester

The title compound was prepared using the above isomer B, 1,4-Dihydroxy-6-phenyl-isoquinoline-3-carboxylic acid butyl ester, under conditions analogous to those described in detail in Example D-39.d; MS (+): m/z 356.06 (M+1)

e) [(1-Chloro-4-hydroxy-6-phenyl-isoquinoline-3-carbonyl)-amino]-acetic acid The title compound was obtained as follows: 95 mg of the above ester and 300 mg of glycine were suspended in a solution of 5.4 ml of 0.5 sodium methoxide in methanol. The mixture was heated to reflux temperature for 42 h, and then cooled to room temperature. The mixture was diluted with 30 ml of aqueous bicarbonate and washed with 30 ml ethyl acetate. The aqueous solution was acidified to pH 3 with 6 N aqueous hydrochloric acid, and then extracted with 35 ml ethyl acetate three times. The combined organic extracts were dried over sodium sulfate and concentrated under vacuum to provide 73 mg of the desired product, a white solid; MS (−): m/z 354.99 (M−1)

Example D-32

[(1-Chloro-4-hydroxy-7-phenyl-isoquinoline-3-carbonyl)-amino]-acetic acid

The title compound was prepared from 1,4-Dihydroxy-7-phenyl-isoquinoline-3-carboxylic acid butyl ester, Example D-33c isomer A, following procedures analogous to those described in detail in examples D-39d and D-39e;

1-Chloro-4-hydroxy-7-phenyl-isoquinoline-3-carboxylic acid butyl ester; MS (+): m/z 356.09 (M+1)

[(1-Chloro-4-hydroxy-7-phenyl-isoquinoline-3-carbonyl)-amino]-acetic acid; MS (−): m/z 355.01 (M−1)

Example D-33

[(1-Bromo-4-hydroxy-6-phenyl-isoquinoline-3-carbonyl)-amino]-acetic acid 161 mg of 1,4-Dihydroxy-6-phenyl-isoquinoline-3-carboxylic acid butyl ester, Example D-33c isomer B, was suspended in 3 ml of anhydrous acetonitrile. 896 mg of phosphorous oxybromide was added, and the mixture was heated to reflux temperature for 5 h. The mixture was cooled to room temperature, concentrated to a residue under reduced pressure, and suspended in a mixture of 40 ml ethyl acetate and 40 ml of half-saturated aqueous sodium bicarbonate. The biphasic mixture was rapidly stirred for 10 min., and then was extracted with 40 ml portions of ethyl acetate three times. The combined organic extracts were concentrated under vacuum and purified by chromatography on silica gel using a gradient of 0-5% ethyl acetate in dichloromethane to elute one major fraction. 26 mg of material was recovered and used directly in the next reaction.

The residue and 58 mg of glycine were suspended in a solution of 1.4 ml of 0.5 sodium methoxide in methanol. The mixture was heated to reflux for 18 h, then cooled to room temperature, and concentrated to ca. 0.5 ml under reduced pressure. The mixture was diluted with 30 ml of water and acidified to pH 3 with 6 N aqueous hydrochloric acid. The resulting precipitate was collected and washed with cold water two times. The solid product was dried under vacuum to yield 16 mg of the desired product; MS (−): m/z 398.90, 400.92 (M−1, M+1; Br isotopes)

Example D-34

[(1-Bromo-4-hydroxy-7-phenyl-isoquinoline-3-carbonyl)-amino]-acetic acid

The title compound was prepared from 1,4-Dihydroxy-7-phenyl-isoquinoline-3-carboxylic acid butyl ester, Example D-33c isomer A, using conditions analogous to those described in detail in Example D-35. The final product was purified by chromatography on silica gel using a gradient of 0 to 10% methanol in dichloromethane with 0.5% acetic acid to elute the desired product; MS (−): m/z 398.91, 400.95 (M−1, M+1; Br isotopes)

Example D-35

[(4-Hydroxy-5-phenyl-isoquinoline-3-carbonyl)-amino]-acetic acid 200 mg of [(1-Chloro-4-hydroxy-5-phenyl-isoquinoline-3-carbonyl)-amino]-acetic acid, from Example D-39.e, was suspended in a solution of 12 ml MeOH and 4 ml water. 45 mg of sodium carbonate and 100 mg of palladium 10 wt. % on activated carbon were added, and the mixture was stirred for 18 h under a hydrogen atmosphere provided by a hydrogen filled balloon. The resultant mixture was diluted with methanol and aqueous sodium bicarbonate and then filtered through a celite pad. The solution was concentrated under reduced pressure to ca. 6 ml, then diluted to 30 ml with half saturated bicarbonate solution, and then acidified to pH 3 with concentrated aqueous hydrochloric acid. The aqueous solution was extracted with 30 ml portions of ethyl acetate three times. The combined organic extracts were dried over sodium sulfate and concentrated under reduced pressure to provide 107 mg of the desired product as a white solid; MS (+): m/z 323.08 (M+1)

Example D-36

[(4-Hydroxy-8-phenyl-isoquinoline-3-carbonyl)-amino]-acetic acid

The title compound was prepared from [(1-Chloro-4-hydroxy-8-phenyl-isoquinoline-3-carbonyl)-amino]-acetic acid, Example D-40, using conditions analogous to those described in detail in Example D-37; MS (+): m/z 323.06 (M+1)

Example D-37

[(1-Chloro-4-hydroxy-5-phenyl-isoquinoline-3-carbonyl)-amino]-acetic acid a) Biphenyl-2,3-dicarboxylic acid 15 g of 2-methyl-3-biphenylmethanol and 75 mg cetyltrimethylammonium bromide were added to 150 ml of water, and the resultant mixture was cooled to 0° C. in an ice bath. 48 g of potassium permanganate was added to the cold mixture and reaction was stirred at 0° C. for 10 min., at room temperature for 16 h, then at 70° C. for 48 h. The clear solution containing black solid was filtered through a pad of celite, and washed with 100 ml of dichloromethane. The aqueous solution was then acidified to pH 3 with 6 N aqueous hydrochloric acid and extracted four times with 150 ml portions of ethyl acetate. The combined organic fractions were dried over anhydrous sodium sulfate, and concentrated to 12.9 g of product; $^1$H NMR (d6-DMSO): δ=7.28-7.46 (m, 5H), 7.51-7.61 (m, 2H), 7.84-7.89 (dd, 1H), 13.0 (s, 2H).

b) (1,3-Dioxo-4-phenyl-1,3-dihydro-isoindol-2-yl)-acetic acid methyl ester 10.5 g of the above di-acid and 3.25 g of glycine were mixed with a mortar and pestle and then heated in an oil bath kept between 210 to 230° C. for 15 min. The mixture was cooled and the resultant solid was used directly in the next reaction.

To a solution of the crude phthalimide product, from the above reaction, in 125 ml of acetone was added 7.4 g of potassium carbonate and 5.7 ml of methyl sulfate. The mixture was heated to reflux for 24 h, and then cooled to room temperature. The mixture was diluted with 500 ml of water and extracted with 500 ml of ethyl acetate three times. The combined organic fractions were washed with brine and dried over sodium sulfate. The solution was concentrated and resultant solid was crystallized from ethyl acetate to yield 5.0 g of a pale yellow solid; $^1$H NMR (CDCl$_3$): δ=3.74 (s, 3H), 4.40 (s, 2H), 7.91-7.43 (m, 8H)

c) 1,4-Dihydroxy-8-phenyl-isoquinoline-3-carboxylic acid butyl ester (A) and 1,4-Dihydroxy-5-phenyl-isoquinoline-3-carboxylic acid butyl ester (B)

5.07 g of the above product was added to 68.8 ml of 0.5 N sodium n-butoxide in n-butanol. The resultant mixture was heated to 95° C. for 4 h, and then cooled to room temperature. 2.1 ml of acetic acid was added and the mixture was concentrated under reduced pressure to ca. 15 ml volume. The crude products were diluted with half-saturated sodium bicarbonate solution and extracted with ethyl acetate three times. The combined organic fractions were washed with water, then brine, and were dried over sodium sulfate. The solution was concentrated and the residue (5.3 g) was purified by chromatography on silica gel using a gradient of 0 to 25% ethyl acetate in dichloromethane to elute two major fractions (R$_f$ isomer A=0.68, R$_f$ B=0.52, 15% ethyl acetate: 85% dichloromethane):

Isomer A, 2.19 g; MS (+) m/z 338.15 (M+1)

Isomer B, 1.22 g; MS (+) m/z 388.04 (M+1)

d) 1-Chloro-4-hydroxy-5-phenyl-isoquinoline-3-carboxylic acid butyl ester 500 mg of isomer B from the above reaction was suspended in 5 ml of phosphorous oxychloride and heated to 100° C. for 1 h. The reaction mixture was cooled, concentrated to a residue under reduced pressure, and then diluted with 30 ml of water and 30 ml of ethyl acetate while rapidly stirring. The pH of the aqueous phase was monitored and adjusted to ca. pH 7 with the addition of sodium bicarbonate. The biphasic mixture was stirred for 30 min. and then extracted with 30 ml of ethyl acetate 3 times. The combined organic fractions were washed with saturated sodium bicarbonate solution and brine, and then dried over sodium sulfate. The solution was concentrated under reduced pressure, and the residue (494 mg) was purified was purified by chromatography on silica gel using a gradient of 5 to 20% ethyl acetate in dichloromethane to elute one major fraction. 442 mg of product was obtained; MS: (+) m/z 355.99 (M+1)

e) [(1-Chloro-4-hydroxy-5-phenyl-isoquinoline-3-carbonyl)-amino]-acetic acid 435 mg of the above ester and 1.0 g of glycine were suspended in a solution of 24.4 ml of 0.5 N sodium methoxide in methanol. The mixture was heated to reflux for 18 h, then cooled to room temperature, and concentrated to ca. 5 ml under reduced pressure. The mixture was diluted with 50 ml of water and acidified to pH 3 with 1 N aqueous hydrochloric acid. The resulting precipitate was collected and washed with cold water two times. The solid product was dried under vacuum to yield 414 mg of product; MS (+) m/z 356.99 (M+1)

Example D-38

[(1-Chloro-4-hydroxy-8-phenyl-isoquinoline-3-carbonyl)-amino]-acetic acid

The title compound was prepared from 1,4-Dihydroxy-8-phenyl-isoquinoline-3-carboxylic acid butyl ester, Example D-39c isomer A, using conditions analogous to those described in detail in examples D-39d and D-39e.

1-Chloro-4-hydroxy-8-phenyl-isoquinoline-3-carboxylic acid butyl ester; MS (+): m/z 356.05 (M+1)

[(1-Chloro-4-hydroxy-8-phenyl-isoquinoline-3-carbonyl)-amino]-acetic acid; MS (+): m/z 356.99 (M+1)

Example D-39

[(1-Bromo-4-hydroxy-5-phenyl-isoquinoline-3-carbonyl)-amino]-acetic acid a) 1-Bromo-4-hydroxy-5-phenyl-isoquinoline-3-carboxylic acid butyl ester 411 mg of 1,4-Dihydroxy-5-phenyl-isoquinoline-3-carboxylic acid butyl ester, from Example D-39c isomer B, was suspended in 15 ml of anhydrous acetonitrile. 2.0 g of phosphorous oxybromide was added and the reaction mixture was heated to reflux for 3.5 h. The reaction mixture was cooled and poured into 75 ml of 0° C. saturated aqueous sodium bicarbonate solution. The mixture was stirred for 5 min and then extracted with 75 ml portions of ethyl acetate three times. The combined organic fractions were washed with brine, dried over sodium sulfate, and concentrated under reduced pressure. The residue (434 mg) was purified by chromatography on silica gel using a gradient of 0 to 25% ethyl acetate in hexanes to elute the product as one major fraction. 480 mg of the desired product was obtained; MS (+): m/z 422.02 (M+23)

b) [(1-Bromo-4-hydroxy-5-phenyl-isoquinoline-3-carbonyl)-amino]-acetic acid The title compound was obtained as follows: 200 mg of the above ester and 412 mg of glycine were suspended in a solution of 10 ml of 0.5 N sodium methoxide in methanol. The mixture was heated to reflux for 24 h, then cooled to room temperature, and concentrated to ca. 3 ml under reduced pressure. The mixture was diluted with 50 ml of water and acidified to pH 3 with 1 N aqueous hydrochloric acid. The resulting precipitate was collected and washed with cold water two times. The solid product was dried under vacuum to yield 188 mg of product; MS (−): m/z 398.96, 400.95 (M−1, M+1; Br isotopes)

Example D-40

[(1-Bromo-4-hydroxy-8-phenyl-isoquinoline-3-carbonyl)-amino]-acetic acid

The title compound was prepared from 1,4-Dihydroxy-8-phenyl-isoquinoline-3-carboxylic acid butyl ester, Example D-39c isomer A, using conditions analogous to those described in detail in Example D-41;
1-Bromo-4-hydroxy-8-phenyl-isoquinoline-3-carboxylic acid butyl ester; MS (+): m/z 400.00, 402.03 (M+1, M+3; Br isotopes)
[(1-Bromo-4-hydroxy-8-phenyl-isoquinoline-3-carbonyl)-amino]-acetic acid; MS (−): m/z 398.95, 400.98 (M−1, M+1; Br isotopes)

Example D-41

[(1-Ethylsulfanyl-4-hydroxy-isoquinoline-3-carbonyl)-amino]-acetic acid a) 1-Ethylsulfanyl-4-hydroxy-isoquinoline-3-carboxylic acid butyl ester 52 mg of 1-Chloro-4-hydroxy-isoquinoline-3-carboxylic acid butyl ester, Example D-20c, was dissolved in 2 ml of ethanethiol and heated in a sealed tube at 70° C. for 24 h, and 100° C. for 48 h. The resultant solution was concentrated under vacuum and the residue (54 mg) was purified by chromatography on silica gel using a gradient of 0 to 20 percent ethyl acetate in hexanes to elute the product. 25 mg of product was obtained; MS (+): m/z 306.06 (M+1)

b) [(1-Ethylsulfanyl-4-hydroxy-isoquinoline-3-carbonyl)-amino]-acetic acid

The title compound was obtained using the ester above, under conditions analogous to those described in detail in Example D-39e; MS (−) m/z 304.98 (M−1)

Example D-42

{[4-Hydroxy-1-(4-methoxy-phenylsulfanyl)-isoquinoline-3-carbonyl]-amino}-acetic acid To a solution of 100 mg of [(1-Chloro-4-hydroxy-isoquinoline-3-carbonyl)-amino]-acetic acid, (U.S. Pat. No. 6,093,730, disclosed as N-((1-Chloro-4-hydroxyisoquinoline-3-yl)carbonyl)glycine), in 1 ml N,N-dimethylformamide was added 1 ml of 4-methoxybenzenethiol. The solution was heated at 120 to 130° C. in a sealed tube for 72 h. The solution was then concentrated under vacuum. The resultant residue (76 mg) was purified by chromatography on silica gel using a gradient of 0 to 15% methanol in dichloromethane with 0.5% acetic acid to elute the product. 6 mg of product was obtained; MS (+) m/z 385.05 (M+1)

Example D-43

[(1-Chloro-4-hydroxy-7-iodo-isoquinoline-3-carbonyl)-amino]-acetic acid a) (5-Iodo-1,3-dioxo-1,3-dihydro-isoindol-2-yl)-acetic acid

4-Iodo-phthalic acid, 10 g, was mixed intimately with 2.63 g of glycine and the mixture was heated to 200° C. for 10 min. After cooling, the solid reaction mixture was extracted with ethyl acetate to give, after concentration, 6.40 g of tan solid: MS-(−)-ion, Proton NMR (200 MHz, methanol-d-4): δ8.26-8.18 (m, 2H), 7.68-7.61 (m, 1H), 4.39 (s, 1H).

b) (5-Iodo-1,3-dioxo-1,3-dihydro-isoindol-2-yl)-acetic acid methyl ester 6.4 g of the carboxylic acid product of Example D-55 a) were esterified for 3 h with 2.7 g of dimethyl sulfate and 3.0 g of potassium carbonate in 25 ml of refluxing acetone. The reaction mixture was diluted with ethyl acetate, filtered, and concentrated. The residue was dissolved in fresh ethyl acetate and the organic layer was washed (water, brine), and dried over sodium sulfate. Concentration of the dry filtered ethyl acetate solution gave 5.8 g of a light yellow solid: Proton NMR (200 MHz, chloroform-d): δ8.24-8.20 (m, 1H), 8.14-8.06 (m, 1H), 7.62-7.56 (d, 1H), 4.40 (s, 2H), 3.75 (s, 3H).

c) 4-Hydroxy-7-iodo-1-oxo-1,2-dihydroisoquinoline-3-carboxylic acid butyl ester and 4-hydroxy-6-iodo-1-oxo-1,2-dihydro-isoquinoline-3-carboxylic acid butyl ester Freshly cut sodium metal, 0.40 g, was dissolved in 22 ml of n-butanol at 65° C. under a nitrogen atmosphere. A mixture of 3.0 g of (5-iodo-1,3-dioxo-1,3-dihydro-isoindol-2-yl)-acetic acid methyl ester in 22 ml of n-butanol was added to the sodium butoxide solution and the reaction mixture was heated to 80° C. for 2 h. The cooled reaction mixture was acidified with 100 ml of 1 M hydrochloric acid to give a solid precipitate. The solid was collected by filtration and separated by silica gel chromatography (eluant; 19:1 dichloromethane:ethyl acetate) to give 0.219 g of 4-hydroxy-7-iodo-1-oxo-1,2-dihydro-isoquinoline-3-carboxylic acid butyl ester: MS-(–)-ion, M−1=386.0 amu, and 0.150 g of 4-hydroxy-6-iodo-1-oxo-1,2-dihydro-isoquinoline-3-carboxylic acid butyl ester: MS-(–) ion, M−1=386.0 amu.

d) 1-Chloro-4-hydroxy-7-iodo-isoquinoline-3-carboxylic acid butyl ester 0.215 g of 4-hydroxy-7-iodo-1-oxo-1,2-dihydro-isoquinoline-3-carboxylic acid butyl ester were added to 5 ml of $POCl_3$ at room temperature. The mixture was refluxed for 3 h and $POCl_3$ was removed under vacuum. The residue was dissolved in ethyl acetate and the solution was washed with satd. aqueous sodium bicarbonate, dried ($MgSO_4$), filtered, and concentrated to give 0.205 g of a while solid: Proton NMR (200 MHz, chloroform-d) δ11.91 (s, 1H), 8.67 (m, 1H), 8.10 (m, 2H), 4.49 (t, J=7 Hz, 2H), 1.95-1.75 (m, 2H), 1.60-1.39 (m, 2H), 1.00 (t, J=7 Hz, 3H).

e) [(1-Chloro-4-hydroxy-7-iodo-isoquinoline-3-carbonyl)-amino]-acetic acid 0.095 g of 1-chloro-4-hydroxy-7-iodo-isoquinoline-3-carboxyline acid butyl ester were added to a mixture of 0.263 g of glycine in 4.7 ml of 0.5M sodium methoxide and the reaction mixture was refluxed for 18 h. The mixture was concentrated, the residue was dissolved in water, and the solution was acidified with 1M hydrochloric acid. The precipitate was extracted with ethyl acetate and the organic layer was washed with water, dried ($MgSO_4$), filtered, and concentrated to give 0.079 g of a pale yellow product MS-(–)-ion, M−1=406.9 amu.

Example D-44

[(1-Chloro-4-hydroxy-6-iodo-isoquinoline-3-carbonyl)-amino]-acetic acid a) 1-Chloro-4-hydroxy-6-iodo-isoquinoline-3-carboxylic acid butyl ester

Analogously to Example D-43 d), 0.150 g of 4-hydroxy-6-iodo-1-oxo-1,2-dihydro-isoquinoline-3-carboxylic acid butyl ester was allowed to react with 5 ml of $POCl_3$ to afford 0.057 g of a pale white solid: Proton NMR (200 MHz, chloroform-d): δ11.9 (s, 1H), 8.89 (m, 1H), 8.1 (m, 1H), 7.97 (m, 1H), 4.5 (t, J=7 Hz, 2H), 2.0-1.8 (m, 2H), 1.65-1.4 (m, 2H), 1.00 (t, J=7 Hz, 3H).

b) [(1-Chloro-4-hydroxy-6-iodo-isoquinoline-3-carbonyl)-amino]-acetic acid 0.053 of the butyl ester from Example D-44 a) were allowed to react with a mixture of 0.147 g of glycine in 2.6 ml of a 0.5M solution of sodium methoxide in methanol under conditions analogous to Example D-55 e) to give 0.047 g of product as an off-white solid: MS-(–)-ion, M−1=406.9 amu.

Example D-45

[(4-Hydroxy-7-iodo-isoquinoline-3-carbonyl)-amino]acetic acid a) 4-Hydroxy-7-iodo-isoquinoline-3-carboxylic acid butyl ester 0.100 G of the product from Example D-43 d) were dissolved in 1.5 ml of glacial acetic acid containing 0.015 g of red phosphorous and 56 microliters of hydroiodic acid (d=1.701 g/ml). The reaction mixture was refluxed for 1 h, diluted with ethyl acetate, and filtered through a Celite plug. The filtrate was washed with satd. aqueous sodium thiosulfate and satd. aqueous sodium bicarbonate, dried ($MgSO_4$), filtered, and concentrated to give a crude product. Silica gel chromatography of the crude product (eluant, 99:1 $CH_2Cl_2$-ethyl acetate) gave 0.073 g of a white solid: Proton NMR (200 MHz, chloroform-d): δ11.9 (s, 1H), 8.70 (s, 1H), 8.40-8.30 (m, 1H), 8.12-8.05 (m, 1H), 8.05-7.96 (m, 1H), 4.48 (t, J=7 Hz, 2H), 1.95-1.80 (m, 2H), 1.60-1.40 (m, 2H), 0.99 (t, J=7 Hz, 3H).

b) [(4-Hydroxy-7-iodo-isoquinoline-3-carbonyl)-amino]-acetic acid 0.042 g was obtained by allowing the butyl ester from Example D-45 a) to react with a mixture of 0.142 g of glycine in 2.5 ml of 0.5M methanolic sodium methoxide analogously to Example D-55 e): MS-(–)-ion, M−1=3.73.0 amu.

Example D-46

[(1-Bromo-4-hydroxy-7-methyl-isoquinoline-3-carbonyl)-amino]-acetic acid a) 4-Hydroxy-7-methyl-1-oxo-1,2-dihydro-isoquinoline-3-carboxylic acid butyl ester 5.0 g of 4-methyl-phthalic acid gave, after a sequence of reaction analogous to Examples D-43 a)-D-43 c), 0.213 g of 4-hydroxy-7-methyl-1-oxo-1,2-dihydro-isoquinoline-3-carboxylic acid butyl ester: MS-(–)-ion, M−1=274.1 amu.

b) 1-Bromo-4-hydroxy-7-methyl-isoquinoline-3-carboxylic acid butyl ester 0.210 g of the ester product from Example D-46 a) was added to 3.5 ml of acetonitrile. Phosphorus oxybromide, 1.52 g, was added and the mixture was refluxed for 6 h, cooled, and dissolved in ethyl acetate. The ethyl acetate solution was washed with satd. aqueous $NaHCO_3$, dried ($MgSO_4$), filtered, and concentrated to give 0.266 g of a crude product. Silica gel chromatography of the crude material (eluant: methylene chloride) gave 0.094 g of a white solid: Proton NMR (200 MHz, chloroform-d): δ11.85 (s, 1H), 8.30-8.20 (d, 1H), 8.00 (br s, 1H), 7.70-7.60 (m, 1H), 4.47 (t, J=7 Hz, 2H), 2.62 (s, 3H), 1.95-1.75 (m, 2H), 1.60-1.35 (m, 2H), 1.00 (t, J=7 Hz, 3H).

c) [(1-Bromo-4-hydroxy-7-methyl-isoquinoline-3-carbonyl)-amino]-acetic acid 0.094 g of butyl ester from Example D-46 b) were allowed to react with a mixture of 0.312 g of glycine in 5.5 ml of 0.5M methanolic sodium methoxide analogously to Example D-55 e) to give 0.083 g of an off-white solid: MS-(−)-ion, M−1=339.0 amu.

Example D-47

[(1-Bromo-7-butoxy-4-hydroxy-isoquinoline-3-carbonyl)-amino]-acetic acid a) 1-Bromo-7-butoxy-4-hydroxy-isoquinoline-3-carboxylic acid butyl ester 0.150 g of 7-butoxy-4-hydroxy-1-oxo-1,2-dihydro-isoquinoline-3-carboxylic acid butyl ester, were allowed to react with phosphorous oxybromide analogously to Example D-46 b) to give 0.105 g of an off-white solid: Proton NMR (200 MHz, chloroform-d): δ11.82 (s, 1H), 8.68 (s, 1H), 8.26 (d, 1H), 7.35 (dd, 1H), 7.19 (d, 1H), 4.49 (t, J=7 Hz, 2H), 4.12 (t, J=7 Hz, 2H), 1.95-1.75 (m, 4H), 1.70-1.40 (m, 4H), 1.05-0.95 (m, 6H).

b) [(1-Bromo-7-butoxy-4-hydroxy-isoquinoline-3-carbonyl)-amino]-acetic acid 0.100 g of butyl ester from Example D-47 a) were allowed to react with a mixture of glycine in methanolic sodium methoxide analogously to Example D-11 e) to give 0.094 g of a white solid: MS-(−)-ion, M−1=397.0 amu.

Example D-48

[(1-Bromo-6-butoxy-4-hydroxy-isoquinoline-3-carbonyl)-amino]-acetic acid a) 1-Bromo-6-butoxy-4-hydroxy-isoquinoline-3-carboxylic acid butyl ester 0.175 g of 6-butoxy-4-hydroxy-isoquinoline-3-carboxylic acid butyl ester, [1] were allowed to react with phosphorous oxybromide analogously to Example D-46 b) to give 0.073 g of a white solid: Proton NMR (200 MHZ, chloroform-d): δ11.84 (s, 1H), 8.13 (d, 1H), 7.60 (m, 1H), 7.42-7.35 (m, 1H), 4.48 (t, J=7 Hz, 2H), 4.15 (t, J=7 Hz, 2H), 1.95-1.75 (m, 4H), 1.65-1.40 (m, 4H), 1.05-0.95 (m, 6H).

b) [(1-Bromo-6-butoxy-4-hydroxy-isoquinoline-3-carbonyl)-amino]-acetic acid 0.068 g of butyl ester from Example D-48 a) were allowed to react with glycine in methanolic sodium methoxide analogously to Example D-43 e) to give 0.063 g of an off-white solid: MS-(−)-ion, M−1=397.0 amu.

Example D-49

[(6-Benzyloxy-1-chloro-4-hydroxy-isoquinoline-3-carbonyl)-methyl-amino]-acetic acid 6-Benzyloxy-1-chloro-4-hydroxy-isoquinoline-3-carboxylic acid, 0.33 g, 0.5 ml of triethylamine, 0.400 g of HATU, and 0.165 g of ethyl N-methyl-amino-acetate hydrochloride were combined in 15 ml of dichloromethane and the reaction mixture was stirred at room temperature for 18 h to give, after silica gel chromatography, 0.232 g of an off-white solid, MS-(+)-ion: 429.0 amu. 0.208 g of this intermediate product were dissolved in 10 ml of methanolic NaOH (1.5 M) and the mixture was stirred at room temperature for 3 h. The solvent was removed with a rotary evaporator, the residue was dissolved in water, and the aqueous layer was extracted with 50 ml of ethyl acetate. The aqueous layer was acidified to pH=1 with aqueous HCl to give a solid precipitate. The solid was collected by suction filtration, washed with water, and dried in a vacuum oven (80° C.) to give 0.180 g of white solid: MS-(+)-ion: 401.0 amu.

Example D-50

[(1-Chloro-4-hydroxy-isoquinoline-3-carbonyl)-methyl-amino]-acetic acid

Prepared from 1-chloro-4-hydroxy-isoquinoline-3-carboxylic acid analogously to Example D-49: MS-(+)-ion: 294.9 amu.

Example D-51

[(1-Chloro-4-hydroxy-6-isopropoxy-isoquinoline-3-carbonyl)-methyl-amino]-acetic acid Prepared from 1-chloro-4-hydroxy-6-isopropoxy-isoquinoline-3-carboxylic acid analogously to Example D-49: MS-(+)-ion: 353.0 amu.

Example D-52

[(1-Chloro-4-hydroxy-7-isopropoxy-isoquinoline-3-carbonyl)-methyl-amino]-acetic acid Prepared from 1-chloro-4-hydroxy-7-isopropoxy-isoquinoline-3-carboxylic acid analogously to Example D-49: MS-(+)-ion: 353.0 amu.

Example D-53

[Carboxymethyl-(1-chloro-4-hydroxy-isoquinoline-3-carbonyl)-amino]-acetic acid

Prepared from 1-chloro-4-hydroxy-isoquinoline-3-carboxylic acid and (ethoxycarbonylmethyl-amino)-acetic acid ethyl ester analogously to Example D-49: MS-(+)-ion: 339.0 amu.

Example D-54

[Carboxymethyl-(1-chloro-4-hydroxy-6-isopropoxy-isoquinoline-3-carbonyl)-amino]-acetic acid Prepared from 1-chloro-4-hydroxy-6-isopropoxy-isoquinoline-3-carboxylic acid and (ethoxycarbonylmethyl-amino)-acetic acid ethyl ester analogously to Example D-49 MS-(+)-ion: 397.0 amu.

Example D-55

{[4-Hydroxy-1-(naphthalen-2-yloxy)-isoquinoline-3-carbonyl]-amino}-acetic acid a) 4-Hydroxy-1-(naphthalen-2-yloxy)-isoquinoline-3-carboxylic acid butyl ester Synthesized from 1-chloro-4-hydroxy-isoquinoline-3-carboxylic acid butyl ester and Naphthalen-2-ol in analogy to Example D-20 d); MS-(+)-ion: M+1=388.1.

b) {[4-Hydroxy-1-(naphthalen-2-yloxy)-isoquinoline-3-carbonyl]-amino}-acetic acid Synthesized from 4-hydroxy-1-(naphthalen-2-yloxy)-isoquinoline-3-carboxylic acid butyl ester in analogy to Example D-1 g); MS-(+)-ion: M+1=389.1.

Example D-56

{[4-Hydroxy-1-(pyridin-3-yloxy)-isoquinoline-3-carbonyl]-amino}-acetic acid a) 4-Hydroxy-1-(pyridin-3-yloxy)-isoquinoline-3-carboxylic acid butyl ester Synthesized from 1-chloro-4-hydroxy-isoquinoline-3-carboxylic acid butyl ester and pyridin-3-ol in analogy to Example D-20 d); MS-(+)-ion: M+1=339.1.

b) {[4-Hydroxy-1-(pyridin-3-yloxy)-isoquinoline-3-carbonyl]-amino}-acetic acid

Synthesized from 4-hydroxy-1-(pyridin-3-yloxy)-isoquinoline-3-carboxylic acid butyl ester in analogy to Example D-1 g); MS-(+)-ion: M+1=340.1.

Example D-57

{[4-Hydroxy-1-(4-methoxy-phenoxy)-isoquinoline-3-carbonyl]-amino}-acetic acid a) 4-Hydroxy-1-(4-methoxy-phenoxy)-isoquinoline-3-carboxylic acid butyl ester Synthesized from 1-chloro-4-hydroxy-isoquinoline-3-carboxylic acid butyl ester and 4-methoxy-phenol in analogy to Example D-20 d); MS-(+)-ion: M+1=368.1.

b) {[4-Hydroxy-1-(4-methoxy-phenoxy)-isoquinoline-3-carbonyl]-amino}-acetic acid Synthesized from 4-hydroxy-1-(4-methoxy-phenoxy)-isoquinoline-3-carboxylic acid butyl ester in analogy to Example D-1 g); MS-(+)-ion: M+1=369.1.

Example D-58

{[4-hydroxy-1-(3-methoxy-phenoxy)-isoquinoline-3-carbonyl]-amino}-acetic acid a) 4-hydroxy-1-(3-methoxy-phenoxy)-isoquinoline-3-carboxylic acid butyl ester Synthesized from 1-chloro-4-hydroxy-isoquinoline-3-carboxylic acid butyl ester and 3-methoxy phenol in analogy to Example D-20 d); MS-(+)-ion: M+1=368.1.

b) {[4-hydroxy-1-(3-methoxy-phenoxy)-isoquinoline-3-carbonyl]-amino}-acetic acid Synthesized from 4-hydroxy-1-(3-methoxy-phenoxy)-isoquinoline-3-carboxylic acid butyl ester in analogy to Example D-1 g); MS-(−)-ion: M−1=367.0.

Example D-59

{[1-(3-Fluoro-phenoxy)-4-hydroxy-isoquinoline-3-carbonyl]-amino}-acetic acid a) 1-(3-fluoro-phenoxy)-4-hydroxy-isoquinoline-3-carboxylic acid butyl ester Synthesized from 1-chloro-4-hydroxy-isoquinoline-3-carboxylic acid butyl ester and 3-Fluoro phenol in analogy to Example D-20 d); MS-(+)-ion: M+1=356.1.

b) {[1-(3-Fluoro-phenoxy)-4-hydroxy-isoquinoline-3-carbonyl]-amino}-acetic acid

Synthesized from 1-(3-fluoro-phenoxy)-4-hydroxy-isoquinoline-3-carboxylic acid butyl ester in analogy to Example D-1 g); MS-(+)-ion: M+1=357.09.

Example D-60

{[1-(4-fluoro-phenoxy)-4-hydroxy-isoquinoline-3-carbonyl]-amino}-acetic acid a) 1-(4-fluoro-phenoxy)-4-hydroxy-isoquinoline-3-carboxylic acid butyl ester Synthesized from 1-chloro-4-hydroxy-isoquinoline-3-carboxylic acid butyl ester and 4-fluoro phenol in analogy to Example D-20 d); MS-(+)-ion: M+1=356.1.

b) {[1-(4-fluoro-phenoxy)-4-hydroxy-isoquinoline-3-carbonyl]-amino}-acetic acid

Synthesized from 1-(4-fluoro-phenoxy)-4-hydroxy-isoquinoline-3-carboxylic acid butyl ester in analogy to Example D-1 g); MS-(+)-ion: M+1=357.0.

Example D-61

{[1-(2-Fluoro-phenoxy)-4-hydroxy-isoquinoline-3-carbonyl]-amino}-acetic acid a) 1-(2-Fluoro-phenoxy)-4-hydroxy-isoquinoline-3-carboxylic acid butyl ester Synthesized from 1-Chloro-4-hydroxy-isoquinoline-3-carboxylic acid butyl ester and 2-fluorophenol in analogy to Example D-20 d); MS-(+)-ion: M+1=356.1.

b) {[1-(2-Fluoro-phenoxy)-4-hydroxy-isoquinoline-3-carbonyl]-amino}-acetic acid

Synthesized from 1-(2-fluoro-phenoxy)-4-hydroxy-isoquinoline-3-carboxylic acid butyl ester in analogy to Example D-1 g); MS-(+)-ion: M+1=357.11.

Example D-62

{[4-Hydroxy-1-(2-methoxy-phenoxy)-isoquinoline-3-carbonyl]-amino}-acetic acid a) 4-Hydroxy-1-(2-methoxy-phenoxy)-isoquinoline-3-carboxylic acid butyl ester Synthesized from 1-chloro-4-hydroxy-isoquinoline-3-carboxylic acid butyl ester and 2-methoxy phenol in analogy to Example D-20 d); MS-(+)-ion: M+1=368.13.

b) {[4-Hydroxy-1-(2-methoxy-phenoxy)-isoquino-line-3-carbonyl]-amino}-acetic acid Synthesized from 4-hydroxy-1-(2-methoxy-phenoxy)-isoquinoline-3-carboxylic acid butyl ester in analogy to Example D-1 g); MS-(+)-ion: M+1=369.09.

Example D-63

{[1-(4-Acetylamino-phenoxy)-4-hydroxy-isoquino-line-3-carbonyl]-amino}-acetic acid a) 4-Acetoxy-1-(4-acetylamino-phenoxy)-isoquino-line-3-carboxylic acid butyl ester 4-hydroxy-1-phenoxy-isoquinoline-3-carboxylic acid butyl ester (261 mg, 0.77 mmol; see Example D-20 d) was dissolved in conc. $H_2SO_4$ (4 ml) at ambient temperature. The solution was cooled to 0° C. and $KNO_3$ (79 mg, 0.77 mmol) was added slowly with stirring. The mixture was stirred at 0° C. for 2 h before it was poured into ice water (100 ml) with stirring. The mixture was extracted with EtOAc (3×30 ml). The combined organic phases were washed with aqueous $NaHCO_3$ solution and brine, dried, and concentrated in vacuo. The residue was dissolved in a mixture of EtOAc (20 ml) and MeOH (10 ml). Sodium acetate (70 mg, 0.85 mmol) and Pd/C (75 mg, 10 wt. % Pd) were added and the mixture was stirred under a $H_2$-atmosphere (1 atm) at ambient temperature for 24 h. The mixture was then filtered through a pad of celite. Celite and filter cake were washed with hot MeOH (3×4 ml) and the combined organic phases were concentrated in vacuo. 150 mg of the resulting residue (total: 380 mg) were dissolved in EtOAc (8 ml). Triethylamine (325 µl, 2.3 mmol) was added and the solution was cooled to 0° C. Then acetic anhydride (110 µl, 1.15 mmol) was added slowly with vigorous stirring. The mixture was allowed to warm up to ambient temperature over night and was then stirred for another 20 h at ambient temperature. Subsequently, EtOAc (50 ml) was added. The mixture was washed with aqueous $NaHCO_3$ solution and brine, dried, and concentrated in vacuo. The residue was purified by flash column chromatography on silica gel using $CH_2Cl_2$: MeOH=100:1 to 100:3 as the eluent to give 150 mg of 4-Acetoxy-1-(4-acetylamino-phenoxy)-isoquinoline-3-carboxylic acid butyl ester; MS-(+)-ion: M+1=437.11.

b) {[1-(4-Acetylamino-phenoxy)-4-hydroxy-isoqui-noline-3-carbonyl]-amino}-acetic acid A mixture of 4-Acetoxy-1-(4-acetylamino-phenoxy)-iso-quinoline-3-carboxylic acid butyl ester (150 mg, 0.34 mmol), glycine (290 mg, 3.4 mmol), and 7.8 ml of a 0.5 N solution of sodium methoxide in methanol (3.9 mmol) was refluxed over the weekend with stirring. Then the solvent was evaporated in vacuo and the residue dissolved in 25 ml of water. The pH of the solution was subsequently adjusted to about 2 and the resulting slurry was extracted with ethyl acetate (3×30 ml). The combined extracts were dried over $MgSO_4$ and evaporated in vacuo. Recrystallization of the residue from methanol/$CH_2Cl_2$ gave 86 mg of the title compound; MS-(+)-ion: M+1=396.15.

Example D-64

{[4-Hydroxy-1-(4-methanesulfonylamino-phenoxy)-isoquinoline-3-carbonyl]-amino}-acetic acid 4-Hydroxy-1-phenoxy-isoquinoline-3-carboxylic acid butyl ester (261 mg, 0.77 mmol; see Example D-20 d) was dissolved in conc. $H_2SO_4$ (4 ml) at ambient temperature. The solution was cooled to 0° C. and $KNO_3$ (79 mg, 0.77 mmol) was added slowly with stirring. The mixture was stirred at 0° C. for 2 h before it was poured into ice water (100 ml) with stirring. The mixture was extracted with EtOAc (3×30 ml). The combined organic phases were washed with aqueous $NaHCO_3$ solution and brine, dried, and concentrated in vacuo. The residue was dissolved in a mixture of EtOAc (20 ml) and MeOH (10 ml). Sodium acetate (70 mg, 0.85 mmol) and Pd/C (75 mg, 10 wt. % Pd) were added and the mixture was stirred under a $H_2$-atmosphere (1 atm) at ambient temperature for 24 h. The mixture was then filtered through a pad of celite. Celite and filter cake were washed with hot MeOH (3×4 ml) and the combined organic phases were concentrated in vacuo. 150 mg of the resulting residue (total: 380 mg) were dissolved in $CH_2Cl_2$ (8 ml). Triethylamine (165 µl) was added and the solution was cooled to −20° C. Then $MeSO_2Cl$ (36 µl) was added slowly with vigorous stirring. The mixture was allowed to warm up to ambient temperature over night and was then stirred for another 20 h at ambient temperature. Subsequently, EtOAc (50 ml) was added. The mixture was washed with aqueous $NaHCO_3$ solution and brine, dried, and concentrated in vacuo. The residue was purified by flash column chromatography on silica gel using $CH_2Cl_2$: MeOH=100:0 to 100:3 as the eluent. To the purified product (168 mg) was added glycine (293 mg, 3.4 mmol), and 7.8 ml of a 0.5 N solution of sodium methoxide in methanol (3.9 mmol) and the mixture was refluxed over the weekend with stirring. Then the solvent was evaporated in vacuo and the residue dissolved in 30 ml of water. The pH of the solution was subsequently adjusted to about 2 and the resulting mixture was extracted with ethyl acetate (3×30 ml). The combined extracts were dried over $MgSO_4$ and evaporated in vacuo. Recrystallization of the residue from methanol/$CH_2Cl_2$ gave 89 mg of the title compound; MS-(+)-ion: M+1=432.12.

Example D-65

[(4-Hydroxy-1-phenylamino-isoquinoline-3-carbo-nyl)-amino]-acetic acid a) 4-Hydroxy-1-phenylamino-isoquinoline-3-carboxylic acid butyl ester A mixture of 1-bromo-4-hydroxy-isoquinoline-3-carbox-ylic acid butyl ester (810 mg, 2.5 mmol, Example D-28 a) and aniline (3 ml) was stirred in a pressure tube in a microwave oven at 150° C. for 20 min. The reaction was repeated on the same scale. Both reaction mixtures were combined, EtOAc (100 ml) was added and the mixture was washed with $H_2O$ (5×30 ml, pH=1-2). The organic phase was dried and concentrated in vacuo. The residue was purified by flash column chromatography on silica gel using hexanes/EtOAc as the eluent to give 770 mg of 4-hydroxy-1-phenylamino-isoquinoline-3-carboxylic acid butyl ester; MS-(+)-ion: M+1=337.21.

b) [(4-Hydroxy-1-phenylamino-isoquinoline-3-car-bonyl)-amino]-acetic acid

Synthesized from hydroxy-1-phenylamino-isoquinoline-3-carboxylic acid butyl ester in analogy to Example D-1 g); MS-(+)-ion: M+1=338.14.

Example D-66

{[4-Hydroxy-6-(pyridin-3-yloxy)-isoquinoline-3-carbonyl]-amino}-acetic acid a) 4-(Pyridin-3-yloxy)-phthalonitrile A mixture of 4-nitro-phthalonitrile (3.46 g, 20 mmol), pyridin-3-ol (1.90 g, 20 mmol), $K_2CO_3$ (8.29 g, 60 mmol), and DMF (50 ml) was stirred at ambient temperature overnight. The reaction mixture was then combined with another batch of the same reaction performed on the same scale. Subsequently, the solid components were removed by filtration and the filtrate was concentrated in vacuo. To the residue was added water and the mixture was extracted with EtOAc. The organic phase was then washed with brine, dried, and evaporated in vacuo. The residue was recrystallized from EtOAc/MeOH to give 8.3 g of the title compound; $^1H$ NMR ($CDCl_3$): δ=8.56 to 8.59 (m, 1H), 8.45 to 8.47 (m, 1H), 7.76 (d, 1H), 7.42 to 7.44 (m, 2H), 7.22 to 7.32 (m, 2H).

b) 4-(Pyridin-3-yloxy)-phthalic acid

Synthesized from 4-(pyridin-3-yloxy)-phthalonitrile in analogy to Example D-1 a); MS-(+)-ion: M+1=260.2.

c) [1,3-Dioxo-5-(pyridin-3-yloxy)-1,3-dihydro-isoindol-2-yl]-acetic acid

Synthesized from 4-(pyridin-3-yloxy)-phthalic acid in analogy to Example D-1 b); MS-(+)-ion: M+1=299.25.

d) [1,3-Dioxo-5-(pyridin-3-yloxy)-1,3-dihydro-isoindol-2-yl]-acetic acid methyl ester Synthesized from [1,3-dioxo-5-(pyridin-3-yloxy)-1,3-dihydro-isoindol-2-yl]-acetic acid in analogy to Example D-1 c); MS-(+)-ion: M+1=313.21.

e) 1,4-Dihydroxy-6-(pyridin-3-yloxy)-isoquinoline-3-carboxylic acid butyl ester and 1,4-Dihydroxy-7-(pyridin-3-yloxy)-isoquinoline-3-carboxylic acid butyl ester Synthesized from [1,3-dioxo-5-(pyridin-3-yloxy)-1,3-dihydro-isoindol-2-yl]-acetic acid methyl ester in analogy to Example D-1 d). However, after addition of 2N HCl (pH was adjusted to 8-9) the mixture was extracted three times with EtOAc. The combined org. phases were dried and concentrated in vacuo. The residue was treated with MeOH and stored overnight in a refrigerator. The precipitate formed was filtered, washed with a small amount of cold MeOH and dried in vacuo to give a regioisomeric mixture of the title compounds as a white solid. 1,4-dihydroxy-6-(pyridin-3-yloxy)-isoquinoline-3-carboxylic acid butyl ester and 1,4-Dihydroxy-7-(pyridin-3-yloxy)-isoquinoline-3-carboxylic acid butyl ester were not separated; MS-(+)-ion: M+1=355.09.

f) 1-Chloro-4-hydroxy-6-(pyridin-3-yloxy)-isoquinoline-3-carboxylic acid butyl ester and 1-Chloro-4-hydroxy-7-(pyridin-3-yloxy)-isoquinoline-3-carboxylic acid butyl ester Synthesized from [1,4-dihydroxy-6-(pyridin-3-yloxy)-isoquinoline-3-carboxylic acid butyl ester and 1,4-dihydroxy-7-(pyridin-3-yloxy)-isoquinoline-3-carboxylic acid butyl ester regioisomeric mixture in analogy to Example D-43 d). The regioisomers were not separated; MS-(+)-ion: M+1=373.01.

g) 4-Hydroxy-6-(pyridin-3-yloxy)-isoquinoline-3-carboxylic acid butyl ester (A) and 4-Hydroxy-7-(pyridin-3-yloxy)-isoquinoline-3-carboxylic acid butyl ester (B)

Synthesized from 1-chloro-4-hydroxy-6-(pyridin-3-yloxy)-isoquinoline-3-carboxylic acid butyl ester and 1-Chloro-4-hydroxy-7-(pyridin-3-yloxy)-isoquinoline-3-carboxylic acid butyl ester regioisomeric mixture in analogy to Example D-7 f). The regioisomers were separated by flash column chromatography on silica gel eluting with $CH_2Cl_2$:EtOAc (90:10 to 80:20). Evaporation of the first fraction yielded B; MS-(+)-ion: M+1=339.09. Evaporation of the second fraction yielded A; MS-(+)-ion: M+1=339.10.

h) {[4-Hydroxy-6-(pyridin-3-yloxy)-isoquinoline-3-carbonyl]-amino}-acetic acid

Synthesized from 4-hydroxy-6-(pyridin-3-yloxy)-isoquinoline-3-carboxylic acid butyl ester in analogy to Example D-1 g); MS-(+)-ion: M+1=340.06.

Example D-67

{[4-Hydroxy-7-(pyridin-3-yloxy)-isoquinoline-3-carbonyl]-amino}-acetic acid

Synthesized from 4-hydroxy-7-(pyridin-3-yloxy)-isoquinoline-3-carboxylic acid butyl ester (Example D-66 g) in analogy to Example D-1 g); MS-(+)-ion: M+1=340.06.

Example D-68

[(1-Chloro-4-methoxy-isoquinoline-3-carbonyl)-amino]-acetic acid a) [(1-Chloro-4-methoxy-isoquinoline-3-carbonyl)-amino]-acetic acid methyl ester A mixture of [(1-chloro-4-hydroxy-isoquinoline-3-carbonyl)-amino]-acetic acid (56 mg, 0.2 mmol; can be obtained according to U.S. Pat. No. 6,093,730, October 1998, Weidmann et al.), $Me_2SO_4$ (57 µl, 0.6 mmol), $KHCO_3$ (306 mg, 3 mmol) and acetone (4 ml) was refluxed with stirring for 48 h. The solvent was evaporated after that time and water (4 ml) was added to the residue. The mixture was extracted with EtOAc (3×20 ml). The combined organic phases were dried over $MgSO_4$ and evaporated in vacuo to give a brown oil. Purification by flash column chromatography on silica gel using hexanes:EtOAc=7:3 as the eluent gave the title compound as a pale yellow oil (21 mg); MS-(+)-ion: M+1=308.9.

b) [(1-Chloro-4-methoxy-isoquinoline-3-carbonyl)-amino]-acetic acid

A mixture of [(1-chloro-4-methoxy-isoquinoline-3-carbonyl)-amino]-acetic acid methyl ester (21 mg, 0.07 mmol), KOH (23 mg, 0.35 mmol) and EtOH (1 ml) was stirred at ambient temperature for 3 h. Then the solvent was evaporated in vacuo. The residue was dissolved in water (2 ml) and the pH of the solution was adjusted to 2-3 by the addition of aqueous 1N HCl. The mixture was extracted with EtOAc (4×10 ml). The combined org. phases were dried over MgSO$_4$ and evaporated in vacuo to give the title compound as a slightly yellowish solid (18 mg); MS-(+)-ion: M+1=295.0.

Example D-69

[(1-Chloro-4-ethoxy-isoquinoline-3-carbonyl)-amino]-acetic acid a) [(1-Chloro-4-ethoxy-isoquinoline-3-carbonyl)-amino]-acetic acid ethyl ester A mixture of [(1-chloro-4-hydroxy-isoquinoline-3-carbonyl)-amino]-acetic acid (56 mg, 0.2 mmol; can be obtained according to U.S. Pat. No. 6,093,730, October 1998, Weidmann et al.), Et$_2$SO$_4$ (59 µl, 0.44 mmol), KHCO$_3$ (306 mg, 3 mmol) and Et$_2$CO (3 ml) was refluxed with stirring for 18 h. Then the solvent was evaporated and water (4 ml) was added to the residue. The mixture was stirred vigorously for 5 min before it was filtered. The filter cake was dissolved in EtOAc and the solution was dried over MgSO$_4$. The solution was concentrated in vacuo. The resulting brown solid was dissolved in EtOAc (0.5 ml) and hexanes was added. The mixture was stored for 14 h at ambient temperature before the solvent was decanted from precipitate formed. The precipitate was dried in vacuo to give the title compound as white crystals (8 mg); MS-(+)-ion: M+1=337.0.

b) [(1-Chloro-4-ethoxy-isoquinoline-3-carbonyl)-amino]-acetic acid

Synthesized from [(1-chloro-4-ethoxy-isoquinoline-3-carbonyl)-amino]-acetic acid ethyl ester in analogy to Example D-68 b); MS-(+)-ion: M+1=309.0.

Example D-70

[(4-Hydroxy-1-methoxy-isoquinoline-3-carbonyl)-amino]-acetic acid a)
4-Benzyloxy-1-hydroxy-isoquinoline-3-carboxylic acid butyl ester A mixture of 1,4-dihydroxy-isoquinoline-3-carboxylic acid butyl ester (26.13 g, 100 mmol; Example D-20 b), PhCH$_2$Br (18.2 ml, 150 mmol), MeONa (0.5 M in MeOH, 200 ml, 100 mmol) was stirred at ambient temperature for 48 h. Then the solvent was evaporated and EtOAc (100 ml) was added to the residue. The mixture was stirred vigorously for 10 min before it was filtered. The filtrate was washed with aqueous 2.5N NaOH (2×100 ml) and aqueous 2N HCl (1×100 ml). The organic phase was dried over MgSO$_4$ and evaporated in vacuo. The residue was recrystallized from MeOH (500 ml)/water (300 ml). The resulting yellow solid was further purified by flash column chromatography on silica gel using hexanes:EtOAc:NEt$_3$=65:30:5 as the eluent to give 10.8 g of a yellow solid. 2 g of this material were further purified by flash column chromatography on silica gel using hexanes:EtOAc:NEt$_3$=75:20:5 as the eluent to give 1.57 g of the title compound as a slightly yellowish solid; $^1$H NMR (CDCl$_3$): δ=8.88 (bs, 1H), 8.46 (d, 1H), 8.42 (d, 1H), 7.26 to 7.96 (m, 7H), 5.06 (s, 2H), 4.38 (t, 2H), 1.69 (m, 2H), 1.37 (m, 2H), 0.91 (t, 3H).

b)
4-Benzyloxy-1-methoxy-isoquinoline-3-carboxylic acid butyl ester

A mixture of 4-benzyloxy-1-hydroxy-isoquinoline-3-carboxylic acid butyl ester (1 eq.), Me$_3$OBF$_4$ (6 eq), KHCO$_3$ (14 eq) and CH$_2$Cl$_2$ (10 ml/mmol 4-benzyloxy-1-hydroxy-isoquinoline-3-carboxylic acid butyl ester) was stirred at ambient temperature for 24 h. Then water (10 ml/mmol) was added and the mixture was extracted with CH$_2$Cl$_2$ (40 ml/mmol). The organic phase was separated, dried over MgSO$_4$ and evaporated in vacuo to give a yellowish solid. The crude product was purified by flash column chromatography on silica gel using hexanes:EtOAc=85:15 as the eluent. Evaporation of the first fraction gave the title compound as a colorless oil in 20% yield; $^1$H NMR (CDCl$_3$): δ=8.21 to 8.25 (m, 1H), 8.05 to 8.09 (m, 1H), 7.33 to 7.73 (m, 7H), 5.13 (s, 2H), 4.38 (t, 2H), 4.16 (s, 3H), 1.69 (m, 2H), 1.37 (m, 2H), 0.94 (t, 3H).

c) 4-Hydroxy-1-methoxy-isoquinoline-3-carboxylic acid butyl ester

A mixture of 4-benzyloxy-1-methoxy-isoquinoline-3-carboxylic acid butyl ester (164 mg, 0.45 mmol), Pd/C (50 mg, 10 wt % Pd) and EtOAc (15 ml) was stirred under a H$_2$-atmosphere at ambient pressure and temperature for 16 h. Then the mixture was filtered through a pad of celite. Celite and filter cake were washed thoroughly with EtOAc and the combined organic phases were concentrated in vacuo to give the title compound as a white solid (115 mg); $^1$H NMR (CDCl$_3$): δ=11.48 (s, 1H), 8.27 to 8.32 (m, 1H), 8.17 to 8.21 (m, 1H), 7.65 to 7.78 (m, 2H), 4.43 (t, 2H), 4.10 (s, 3H), 1.87 (m, 2H), 1.54 (m, 2H), 1.02 (t, 3H).

d) [(4-Hydroxy-1-methoxy-isoquinoline-3-carbonyl)-amino]-acetic acid

Synthesized from 4-hydroxy-1-methoxy-isoquinoline-3-carboxylic acid butyl ester in analogy to Example D-1 g); MS-(−)-ion: M−1=275.0.

Example D-71

[(1-Ethoxy-4-hydroxy-isoquinoline-3-carbonyl)-amino]-acetic acid a) 1-Ethoxy-4-hydroxy-isoquinoline-3-carboxylic acid butyl ester A mixture of 4-benzyloxy-1-hydroxy-isoquinoline-3-carboxylic acid butyl ester (422 mg, 1.2 mmol, Example D-70 a), KHCO$_3$ (2.22 g, 22 mmol), and 1M Et$_3$OBF$_4$ in CH$_2$Cl$_2$ (10 ml, 10 mmol) was stirred for 16 h at ambient temperature and then was refluxed with stirring for another 3 days. According to TLC 4-Benzyloxy-1-hydroxy-isoquinoline-3-carboxylic acid butyl ester did not react under these conditions. Therefore, additional KHCO$_3$ (2.22 g, 22 mmol) and 1M Et$_3$OBF$_4$ in CH$_2$Cl$_2$ (10 ml, 10 mmol) were added and the mixture was concentrated in vacuo. Subsequently, 1,2-dichloroethane (10 ml) was added and the mixture was refluxed with stirring for 16 h. Then the solvent was evaporated in vacuo. To the residue was added water (25 ml) and the mixture was extracted with EtOAc (2×50 ml). The combined organic phases were dried over MgSO$_4$ and evaporated in vacuo to give a yellowish solid (374 mg). Purification by flash column chromatography on silica gel using hexanes:EtOAc=85:15 as the eluent gave a yellowish oil (104 mg). The chromatographical purification was repeated using hexanes:EtOAc=99:2, and, subsequently 99:1 as the eluent to give the title compound as a colorless oil (60 mg); $^1$H NMR (CDCl$_3$): δ=11.45 (s, 1H), 8.20 to 8.32 (m, 2H), 7.64 to 7.78 (m, 2H), 4.38 to 4.59 (m, 4H), 1.84 (m, 2H), 1.54 (m, 5H), 1.01 (t, 3H).

b) [(1-Ethoxy-4-hydroxy-isoquinoline-3-carbonyl)-amino]-acetic acid

Synthesized from 1-Ethoxy-4-hydroxy-isoquinoline-3-carboxylic acid butyl ester in analogy to Example D-1 g); MS-(+)-ion: M+1=291.0.

Example D-72

[(4-Acetoxy-1-phenyl-isoquinoline-3-carbonyl)-amino]-acetic acid a) [(1-Oxo-3-phenyl-1H-indene-2-carbonyl)-amino]-acetic acid methyl ester A mixture of 1-oxo-3-phenyl-1H-indene-2-carboxylic acid (2.13 g, 8.5 mmol; can be obtained according to M. R. Barvian et al. in Bioorg. Med. Chem. Lett. 1997, 7, 2903-2908) and SOCl$_2$ (17 ml) was refluxed with stirring for 15 min. Excess SOCl$_2$ was then evaporated in vacuo. The residue was dissolved in anhydrous CH$_2$Cl$_2$ (20 ml), and subsequently the solution was concentrated in vacuo again to remove last traces of SOCl$_2$. The residue was dissolved in anhydrous CH$_2$Cl$_2$ (20 ml). The solution was cooled with an ice bath before glycine methyl ester hydrochloride (1.27 g, 10 mmol) and subsequently NEt$_3$ (3.52 ml, 25 mmol, dropwise addition) were added with stirring. The ice bath was then removed and stirring was continued at ambient temperature for 45 min before the mixture was concentrated in vacuo. To the residue was added water (10 ml) and aqueous 2N HCl (15 ml) and the mixture was extracted with ethyl acetate (1×70 ml). The organic phase was dried over MgSO$_4$ and evaporated in vacuo to give an orange solid (2.77 g). Purification by flash column chromatography on silica gel using hexanes:EtOAc=2:1 as the eluent gave the title compound as an orange solid (2.11 g); MS-(+)-ion: M+1=322.0.

b) [(4-acetoxy-1-phenyl-isoquinoline-3-carbonyl)-amino]acetic acid methyl ester

[(1-Oxo-3-phenyl-1H-indene-2-carbonyl)-amino]-acetic acid methyl ester (1.864 g, 5.8 mmol) was dissolved in a mixture of concentrated H$_2$SO$_4$ (16 ml) and glacial acetic acid (16 ml) at 50 to 60° C. Then NaN$_3$ (985 mg, 15 mmol) was added in portions with stirring so that the temperature did not exceed 60° C. Stirring was then continued at 50 to 60° C. for additional 30 min before the mixture was poured onto ice (200 g). The resulting mixture was basified by addition of concentrated aqueous NH$_3$ (55 ml, D=0.89 g/ml) and extracted with CH$_2$Cl$_2$ (2×100 ml). The combined organic phases were dried over MgSO$_4$ and then filtered through silica gel. The filtrate was discarded. The silica gel was washed with EtOAc (ca. 400 ml). The resulting solution was concentrated in vacuo to give a dark oil (250 mg). Further purification by flash column chromatography on silica gel using EtOAc and then EtOAc:hexanes=7:3 as the eluent gave the title compound as a tan solid (19 mg); $^1$H NMR (CDCl$_3$): δ=7.11 to 7.98 (m), 3.75 (d, 2H), 3.68 (s, 1H), 2.19 (s, 3H).

c) [(4-Acetoxy-1-phenyl-isoquinoline-3-carbonyl)-amino]acetic acid

A mixture of [(4-Acetoxy-1-phenyl-isoquinoline-3-carbonyl)-amino]-acetic acid methyl ester (3.8 mg, 0.01 mmol) and aqueous 6N HCl (1 ml) was stirred at ambient temperature for 16 h before the pH of the solution was adjusted to ca. 8 by addition of concentrated aqueous NaHCO$_3$ solution. The solution was washed with EtOAc (2×10 ml) before it was acidified by addition of aqueous 2N HCl. Subsequently, the mixture was extracted with EtOAc (2×10 ml). The combined organic phases were dried over MgSO$_4$ and evaporated in vacuo to give the title compound as a yellow oil (1.9 mg); MS-(+)-ion: M+1=364.9.

Example D-73

[(4-Hydroxy-1-phenyl-isoquinoline-3-carbonyl)-amino]-acetic acid a) 4-Hydroxy-1-phenyl-isoquinoline-3-carboxylic acid ethyl ester A mixture of 4-acetoxy-1-phenyl-isoquinoline-3-carboxylic acid ethyl ester (671 mg, 2 mmol; can be obtained according to D. A. Walsh et al. in J. Med. Chem. 1978, 21, 582-585), n-BuOH (60 ml) and concentrated H$_2$SO$_4$ (1.7 ml) was refluxed with stirring for 4 h before the reaction mixture was added to concentrated aqueous NaHCO$_3$ solution (60 ml) with stirring. Then EtOAc (120 ml) was added and the mixture was stirred vigorously for 15 min. Subsequently, the organic phase was separated, dried over MgSO$_4$ and concentrated in vacuo. Purification of the residue by flash column chromatography on silica gel using hexanes:EtOAc=95:5 as the eluent gave the title compound as a solid (126 mg); $^1$H NMR (CDCl$_3$): δ=11.96 (s, 1H), 8.44 to 8.49 (m, 1H), 8.01 to 8.05 (m, 1H), 7.43 to 7.80 (m, 7H), 4.56 (q, 2H), 1.49 (t, 3H).

b) [(4-Hydroxy-1-phenyl-isoquinoline-3-carbonyl)-amino]-acetic acid

Synthesized from 4-Hydroxy-1-phenyl-isoquinoline-3-carboxylic acid ethyl ester in analogy to Example D-1 g); MS-(+)-ion: M+1=323.1.

Example D-74

[(1-Ethoxy-4-phenyl-isoquinoline-3-carbonyl)-amino]-acetic acid a) 1-Chloro-4-phenyl-isoquinoline-3-carboxylic acid ethyl ester A mixture of 1-hydroxy-4-phenyl-isoquinoline-3-carboxylic acid ethyl ester (1.17 g, 4 mmol; can be obtained according to A. Marsili et al., Ann. Chim. (Rome), 1962, 52, 112-120), and concentrated POCl$_3$ (10 ml) was refluxed with stirring for 1 h. Then the mixture was concentrated in vacuo. The residue was dissolved in EtOAc (50 ml), concentrated aqueous NaHCO$_3$ solution (40 ml) was added and the mixture was stirred vigorously for 1 h. Subsequently, the organic phase was separated, dried over MgSO$_4$ and concentrated in vacuo to give the title compound as a yellowish solid (1.20 g); MS-(+)-ion: M+1=312.0.

b) [(1-Chloro-4-phenyl-isoquinoline-3-carbonyl)-amino]-acetic acid methyl ester A mixture of 1-chloro-4-phenyl-isoquinoline-3-carboxylic acid ethyl ester (1.184 g, 3.8 mmol) aqueous 2N NaOH (15 ml, 30 mmol) and EtOH (15 ml) was refluxed with stirring for 2.5 h. Then the mixture was concentrated to ½ of its volume. Subsequently, the solution was acidified by addition of concentrated HCl and the resulting suspension was extracted with EtOAc (2×50 ml). The combined organic phases were dried over $MgSO_4$ and evaporated in vacuo to give a yellowish solid (1.018 g). To 996 mg of this yellowish solid was added $SOCl_2$ (7 ml) and the mixture was refluxed with stirring for 1 h. Excess $SOCl_2$ was then evaporated in vacuo. The residue was dissolved in anhydrous $CH_2Cl_2$ (10 ml), and subsequently the solution was concentrated in vacuo again to remove last traces of $SOCl_2$. The residue was dissolved in anhydrous $CH_2Cl_2$ (8 ml). The solution was cooled with an ice bath before glycine methyl ester hydrochloride (507 mg, 4 mmol) and subsequently $NEt_3$ (1.55 ml, 11 mmol, dropwise addition) were added with stirring. The ice bath was then removed and stirring was continued at ambient temperature for 1 h before the mixture was concentrated in vacuo. To the residue was added water (15 ml) and the mixture was extracted with ethyl acetate (1×50 ml). The organic phase was dried over $MgSO_4$ and evaporated in vacuo to give a tan solid (1.07 g). Recrystallization from MeOH (30 ml)/water (10 ml) gave the title compound as a slightly yellowish solid (430 mg); MS-(+)-ion: M+1=355.0.

c) [(1-Ethoxy-4-phenyl-isoquinoline-3-carbonyl)-amino]-acetic acid

A mixture of [(1-Chloro-4-phenyl-isoquinoline-3-carbonyl)-amino]-acetic acid methyl ester (177 mg, 0.5 mmol), KOH (325 mg, 5 mmol) and EtOH (10 ml) was stirred at ambient temperature for 90 min before the solvent was evaporated in vacuo. The residue was dissolved in water (10 ml). The solution was acidified by addition of concentrated aqueous HCl and extracted with EtOAc (2×15 ml). The combined organic phases were dried over $MgSO_4$ and concentrated in vacuo to give the title compound as a slightly yellowish solid (169 mg); MS-(+)-ion: M+1=351.0.

Example D-75

[(1-Chloro-4-phenyl-isoquinoline-3-carbonyl)-amino]-acetic acid

A mixture of [(1-chloro-4-phenyl-isoquinoline-3-carbonyl)-amino]-acetic acid methyl ester (50 mg, 0.14 mmol, Example D-74 b), and aqueous 6N HCl was stirred at ambient temperature for 11 days before the solution was neutralized by the addition of concentrated aqueous $NaHCO_3$. The mixture was extracted with EtOAc (50 ml). The organic phase was dried over $MgSO_4$ and concentrated in vacuo to give the title compound as a white solid (35 mg); MS-(+)-ion: M+1=341.0.

Example D-76

[(4-Phenyl-isoquinoline-3-carbonyl)-amino]-acetic acid a) [(4-Phenyl-isoquinoline-3-carbonyl)-amino]-acetic acid methyl ester

A mixture of [(1-chloro-4-phenyl-isoquinoline-3-carbonyl)-amino]-acetic acid methyl ester (177 mg, 0.5 mmol, Example D-74 b), Pd/C (50 mg, 10 wt % Pd), sodium acetate (49 mg, 0.6 mmol), MeOH (10 ml) and EtOAc (5 ml) was stirred under a $H_2$-atmosphere at ambient pressure and temperature for 2 h. Then the mixture was filtered through a pad of celite. Celite and filter cake were washed thoroughly with EtOAc and the combined organic phases were concentrated in vacuo. To the residue was added concentrated aqueous $NaHCO_3$ (10 ml) and the mixture was extracted with EtOAc (2×15 ml). The combined organic phases were dried over $MgSO_4$ and concentrated in vacuo to give the title compound as a colorless gum (154 mg); MS-(+)-ion: M+1=321.0.

b) [(4-Phenyl-isoquinoline-3-carbonyl)-amino]-acetic acid

A mixture of [(4-Phenyl-isoquinoline-3-carbonyl)-amino]-acetic acid methyl ester (144 mg, 0.45 mmol), KOH (325 mg, 5 mmol) and EtOH (10 ml) was stirred at ambient temperature for 18 h before the solvent was evaporated in vacuo. The residue was dissolved in water. The pH of the solution was adjusted to 3-4 by addition of concentrated aqueous HCl. The solution was then extracted with EtOAc (2×25 ml). The combined organic phases were dried over $MgSO_4$ and concentrated in vacuo to give the title compound as a yellowish solid (127 mg); MS-(+)-ion: M+1=307.1.

Example D-77

[(4-Hydroxy-1-methyl-isoquinoline-3-carbonyl)-amino]-acetic acid a) 1-Bromo-4-hydroxy-isoquinoline-3-carboxylic acid

A mixture of 1-bromo-4-hydroxy-isoquinoline-3-carboxylic acid butyl ester (8.18 g, 25 mmol; Example D-28 a) aqueous 2N NaOH (80 ml, 160 mmol) and EtOH (80 ml) was refluxed with stirring for 2 h. Then the solution was concentrated in vacuo to ½ of its volume, diluted with water (200 ml), and was acidified by addition of concentrated aqueous HCl. After stirring at ambient temperature for 1 h the resulting suspension was submitted to vacuum filtration. The filter cake was washed thoroughly with water and dried in vacuo at 75° C. to give the title compound as a white solid (6.10 g); $^1$H NMR (DMSO-d6): δ=8.30 to 8.37 (m, 1H), 8.16 to 8.22 (m, 1H), 7.93 to 8.03 (m, 2H).

b) 4-Hydroxy-1-methyl-isoquinoline-3-carboxylic acid methyl ester

To a solution of 1-bromo-4-hydroxy-isoquinoline-3-carboxylic acid (670 mg, 2.5 mmol) in anhydrous THF (100 ml) was added slowly a 2.5 M solution of n-BuLi in hexanes (4 ml, 10 mmol) at −78° C. with stirring. After stirring for another 5 min MeI (316A 5 mmol) was added. Stirring was continued for additional 10 min at −78° C. before water (50 ml) and aqueous 2N HCl (6 ml) were added. The mixture was allowed to warm up to ambient temperature with stirring and was then concentrated in vacuo to ca. ½ of its volume. The resulting precipitate was sucked off, washed with water, dried in vacuo at 80° C. and was recrystallized from EtOH to give a light tan solid (141 mg). A mixture of 102 mg of the aforementioned light tan solid, $Me_2SO_4$ (48 μl, 0.5 mmol), $KHCO_3$ (1.0 g, 10 mmol) and acetone (10 ml) was refluxed with stirring for 15 h. Then the mixture was concentrated in vacuo. To the residue was added water (20 ml) and the mixture was extracted with EtOAc (3×20 ml). The combined organic phases were dried over MgSO$_4$ and concentrated in vacuo to give the title compound as a tan solid; $^1$H NMR (CDCl$_3$): δ=11.66 (s, 1H), 8.39 to 8.44 (m, 1H), 8.02 to 8.09 (m, 1H), 7.74 to 7.81 (m, 2H), 4.08 (s, 3H), 2.90 (s, 3H).

c) [(4-Hydroxy-1-methyl-isoquinoline-3-carbonyl)-amino]-acetic acid

Synthesized from 4-hydroxy-1-methyl-isoquinoline-3-carboxylic acid methyl ester in analogy to Example D-1 g); MS-(−)-ion: M−1=259.0.

Example D-78

[(4-Hydroxy-1-methoxymethyl-isoquinoline-3-carbonyl)-amino]-acetic acid a) 4-Benzyloxy-1-methoxymethyl-isoquinoline-3-carboxylic acid benzyl ester To a solution of 1-bromo-4-hydroxy-isoquinoline-3-carboxylic acid (670 mg, 2.5 mmol; Example D-77 a) in anhydrous THF (100 ml) was added slowly a 2.5 M solution of n-BuLi in hexanes (4 ml, 10 mmol) at −78° C. with stirring. After stirring for another 5 min MeOCH$_2$I (446 µl, 5 mmol) was added. Stirring was continued for additional 5 min at −78° C. before water (50 ml) and aqueous 6N HCl (2 ml) were added. The mixture was allowed to warm up to ambient temperature with stirring, was then concentrated in vacuo to ca. 1/3 of its volume and extracted with EtOAc (50 ml). The organic phase was washed with a solution of sodium metabisulfite (0.5 g) in water (10 ml), then dried over MgSO$_4$ and concentrated in vacuo to give a yellowish solid (432 mg). A mixture of 429 mg of the aforementioned yellowish solid, benzyl bromide (0.6 ml, 5 mmol), K$_2$CO$_3$ (2.07 g, 15 mmol) and acetone (40 ml) was refluxed with stirring for 2.5 d. Then the mixture was concentrated in vacuo. To the residue was added water (40 ml) and the mixture was extracted with EtOAc (50 ml). The organic phase was dried over MgSO$_4$ and concentrated in vacuo to give a brown oil. Purification by flash column chromatography on silica gel using hexanes:EtOAc=6:4 as the eluent gave the title compound as yellow oil (201 mg); MS-(+)-ion: M+1=414.1.

b) 4-Benzyloxy-1-methoxymethyl-isoquinoline-3-carboxylic acid

A mixture of 4-Benzyloxy-1-methoxymethyl-isoquinoline-3-carboxylic acid benzyl ester (198 mg, 0.48 mmol), KOH (325 mg, 5 mmol) and EtOH (10 ml) was stirred at ambient temperature for 18 h before the solvent was evaporated in vacuo. To the residue was added water (25 ml) and the mixture was washed with Et$_2$O (2×25 ml). Then the solution was acidified by addition of aqueous 6N HCl and extracted with EtOAc (25 ml). The organic phase was dried over MgSO$_4$ and concentrated in vacuo to give the title compound as a yellow oil (140 mg); MS-(+)-ion: M+1=324.1.

c) [(4-Benzyloxy-1-methoxymethyl-isoquinoline-3-carbonyl)-amino]-acetic acid benzyl ester To a mixture of 4-benzyloxy-1-methoxymethyl-isoquinoline-3-carboxylic acid (120 mg, 0.37 mmol), NEt$_3$ (109 µl, 0.78 mmol), and CH$_2$Cl$_2$ (7 ml) cooled with an ice bath was added ClCO$_2$/Bu (52 µl, 0.39 mmol) with stirring. After stirring for 15 min glycine benzyl ester hydrochloride (79 mg, 0.39 mmol) was added and the mixture was stirred for another 15 min before the ice bath was removed. Stirring was then continued at ambient temperature for additional 1.5 h. Subsequently the mixture was concentrated in vacuo. To the residue was added water (10 ml) and a few drops of aqueous 6N HCl. The mixture was extracted with EtOAc (15 ml). The organic phase was dried over MgSO$_4$ and concentrated in vacuo to give a yellowish gum. Purification by flash column chromatography on silica gel using hexanes:EtOAc=7:3 as the eluent gave the title compound as a yellow oil (141 mg); MS-(+)-ion: M+1=471.1.

d) [(4-Hydroxy-1-methoxymethyl-isoquinoline-3-carbonyl)-amino]-acetic acid

A mixture of [(4-benzyloxy-1-methoxymethyl-isoquinoline-3-carbonyl)-amino]-acetic acid benzyl ester (134 mg, 0.285 mmol), Pd/C (100 mg, 10 wt % Pd), EtOAc (10 ml) and MeOH (50 ml) was stirred under a H2-atmosphere at ambient pressure and temperature for 18 h. Then the mixture was filtered through a pad of celite. Celite and filter cake were washed thoroughly with EtOAc and the combined organic phases were concentrated in vacuo to give the title compound as a tan solid (74 mg); MS-(−)-ion: M−1=289.2.

Example D-79

[(1-Dimethylcarbamoyl-4-hydroxy-isoquinoline-3-carbonyl)-amino]-acetic acid a) 4-Benzyloxy-1-dimethylcarbamoyl-isoquinoline-3-carboxylic acid benzyl ester To a solution of 1-bromo-4-hydroxy-isoquinoline-3-carboxylic acid (670 mg, 2.5 mmol; Example D-77 a) in anhydrous THF (100 ml) was added slowly a 2.5 M solution of n-BuLi in hexanes (4 ml, 10 mmol) at −78° C. with stirring. After stirring for another 5 min ClCONMe$_2$ (468 µl, 5 mmol) was added. Stirring was continued for additional 25 min at −78° C. before water (50 ml) and aqueous 6N HCl (2 ml) were added. The mixture was allowed to warm up to ambient temperature with stirring, was then concentrated in vacuo to ca. 1/3 of its volume and extracted with EtOAc (2×50 ml). The combined organic phases were dried over MgSO$_4$ and concentrated in vacuo to give a yellow solid (501 mg). A mixture of 492 mg of the aforementioned yellow solid, benzyl bromide (0.6 ml, 5 mmol), K$_2$CO$_3$ (2.07 g, 15 mmol) and acetone (40 ml) was refluxed with stirring for 2.5 days. Then the mixture was concentrated in vacuo. To the residue was added water (20 ml) and the mixture was extracted with EtOAc (50 ml). The organic phase was dried over MgSO$_4$ and concentrated in vacuo to give a brown oil. Purification by flash column chromatography on silica gel using hexanes:EtOAc=6:4 as the eluent gave the title compound as yellow oil (311 mg); MS-(+)-ion: M+1=441.1.

b) 4-Benzyloxy-1-dimethylcarbamoyl-isoquinoline-3-carboxylic acid

A mixture of 4-benzyloxy-1-dimethylcarbamoyl-isoquinoline-3-carboxylic acid benzyl ester (308 mg, 0.7 mmol), KOH (325 mg, 5 mmol) and EtOH (10 ml) was stirred at ambient temperature for 18 h before the solvent was evaporated in vacuo. To the residue was added water (25 ml) and the mixture was washed with Et$_2$O (2×25 ml). Then the solution was acidified by addition of aqueous 6N HCl and extracted with EtOAc (2×25 ml). The combined organic phases were dried over MgSO$_4$ and concentrated in vacuo to give the title compound as a yellowish gum (220 mg); MS-(+)-ion: M+1=351.0.

c) [(4-Benzyloxy-1-dimethylcarbamoyl-isoquinoline-3-carbonyl)-amino]-acetic acid benzyl ester To a mixture of 4-benzyloxy-1-dimethylcarbamoyl-isoquinoline-3-carboxylic acid (210 mg, 0.6 mmol), NEt$_3$ (175 µl, 1.25 mmol), and CH$_2$Cl$_2$ (12 ml) cooled with an ice bath was added ClCO$_2$iBu (83 µl, 0.63 mmol) with stirring. After stirring for 15 min glycine benzyl ester hydrochloride (127 mg, 0.63 mmol) was added and the mixture was stirred for another 15 min before the ice bath was removed. Stirring was then continued at ambient temperature for additional 1.5 h. Subsequently; the mixture was concentrated in vacuo. To the residue was added water (10 ml) and a few drops of aqueous 6N HCl. The mixture was extracted with EtOAc (15 ml). The organic phase was dried over MgSO$_4$ and concentrated in vacuo to give a yellowish gum. Purification by flash column chromatography on silica gel using hexanes:EtOAc=7:3 as the eluent gave the title compound as a slightly yellowish gum (211 mg); MS-(+)-ion: M+1=498.1.

d) [(1-Dimethylcarbamoyl-4-hydroxy-isoquinoline-3-carbonyl)-amino]-acetic acid

A mixture of [(4-Benzyloxy-1-dimethylcarbamoyl-isoquinoline-3-carbonyl)-amino]-acetic acid benzyl ester (209 mg, 0.42 mmol), Pd/C (100 mg, 10 wt % Pd), EtOAc (10 ml) and MeOH (50 ml) was stirred under a H2-atmosphere at ambient pressure and temperature for 18 h. Then the mixture was filtered through a pad of celite. Celite and filter cake were washed thoroughly with EtOAc and the combined organic phases were concentrated in vacuo to give the title compound as a brown solid (122 mg); MS-(−)-ion: M−1=316.1.

Example D-80

[(4-Hydroxy-1-methyl-6-phenoxy-isoquinoline-3-carbonyl)-amino]-acetic acid a) 1-Bromo-4-hydroxy-6-phenoxy-isoquinoline-3-carboxylic acid Synthesized from 1-bromo-4-hydroxy-6-phenoxy-isoquinoline-3-carboxylic acid butyl ester (Example D-8 a) in analogy to Example D-77 a); $^1$H NMR (DMSO-d6): δ=8.20 (d, 1H), 7.21 to 7.74 (m, 7H).

b) 4-Benzyloxy-1-methyl-6-phenoxy-isoquinoline-3-carboxylic acid benzyl ester

To a solution of 1-Bromo-4-hydroxy-6-phenoxy-isoquinoline-3-carboxylic acid (721 mg, 2 mmol) in anhydrous THF (100 ml) was added slowly a 2.5 M solution of n-BuLi in hexanes (3.2 ml, 8 mmol) at −78° C. with stirring. After stirring for another 10 min MeI (253 µl, 4 mmol) was added dropwise. Stirring was continued for additional 15 min at −78° C. before water (50 ml) and aqueous 2N HCl (5 ml) were added. The mixture was allowed to warm up to ambient temperature with stirring, was then concentrated in vacuo to ca. 1/3 of its volume. The precipitate formed was sucked off, washed with water, and dried in vacuo to give a tan solid (758 mg). A mixture of 738 mg of the aforementioned tan solid, benzyl bromide (1.0 ml, 8 mmol), K$_2$CO$_3$ (2.76 g, 20 mmol) and acetone (50 ml) was refluxed with stirring for 3 days. Then the mixture was concentrated in vacuo. To the residue was added water (30 ml) and the mixture was extracted with EtOAc (50 ml). The organic phase was dried over MgSO$_4$ and concentrated in vacuo to give a yellowish oil. Purification by flash column chromatography on silica gel using hexanes:EtOAc=8:2 as the eluent gave a tan solid. Recrystallization from MeOH gave the title compound as slightly yellowish solid (172 mg); MS-(+)-ion: M+1=476.1.

c) 4-Benzyloxy-1-methyl-6-phenoxy-isoquinoline-3-carboxylic acid

Synthesized from 4-benzyloxy-1-methyl-6-phenoxy-isoquinoline-3-carboxylic acid benzyl ester in analogy to Example D-78 b); MS-(+)-ion: M+1=386.1.

d) [(4-Benzyloxy-1-methyl-6-phenoxy-isoquinoline-3-carbonyl)-amino]-acetic acid benzyl ester Synthesized from 4-benzyloxy-1-methyl-6-phenoxy-isoquinoline-3-carboxylic acid in analogy to Example D-78 c); MS-(+)-ion: M+1=533.0.

e) [(4-Hydroxy-1-methyl-6-phenoxy-isoquinoline-3-carbonyl)-amino]-acetic acid

Synthesized from [(4-benzyloxy-1-methyl-6-phenoxy-isoquinoline-3-carbonyl)-amino]-acetic acid benzyl ester in analogy to Example D-78 d); MS-(+)-ion: M+1=353.1.

Example D-81

[(4-Hydroxy-1-methyl-7-phenoxy-isoquinoline-3-carbonyl)-amino]-acetic acid a) 1-Bromo-4-hydroxy-7-phenoxy-isoquinoline-3-carboxylic acid Synthesized from 1-bromo-4-hydroxy-7-phenoxy-isoquinoline-3-carboxylic acid butyl ester (Example D-7 e) in analogy to Example D-77 a); MS-(+)-ion: M+1=359.9.

b) 4-Benzyloxy-1-methyl-7-phenoxy-isoquinoline-3-carboxylic acid benzyl ester

Synthesized from MeI and 1-Bromo-4-hydroxy-7-phenoxy-isoquinoline-3-carboxylic acid in analogy to Example D-78 a); MS-(+)-ion: M+1=476.1.

c) 4-Benzyloxy-1-methyl-7-phenoxy-isoquinoline-3-carboxylic acid

Synthesized from 4-benzyloxy-1-methyl-7-phenoxy-isoquinoline-3-carboxylic acid benzyl ester in analogy to Example D-78 b); MS-(+)-ion: M+1=386.0.

d) [(4-Benzyloxy-1-methyl-7-phenoxy-isoquinoline-3-carbonyl)-amino]-acetic acid benzyl ester Synthesized from 4-benzyloxy-1-methyl-7-phenoxy-isoquinoline-3-carboxylic acid in analogy to Example D-78 c); MS-(+)-ion: M+1=533.0.

e) [(4-Hydroxy-1-methyl-7-phenoxy-isoquinoline-3-carbonyl)-amino]-acetic acid

Synthesized from [(4-benzyloxy-1-methyl-7-phenoxy-isoquinoline-3-carbonyl)-amino]-acetic acid benzyl ester in analogy to Example D-78 d); MS-(−)-ion: M−1=351.1.

Example D-82

[(4-Benzyloxy-1-methyl-7-phenoxy-isoquinoline-3-carbonyl)-amino]-acetic acid

A mixture of [(4-benzyloxy-1-methyl-7-phenoxy-isoquinoline-3-carbonyl)-amino]-acetic acid benzyl ester (160 mg, 0.3 mmol; Example D-81 d), KOH (325 mg, 5 mmol) and EtOH (10 ml) was stirred at ambient temperature for 18 h before the solvent was evaporated in vacuo. To the residue was added water (5 ml) and the mixture was washed with Et$_2$O (2×20 ml). Then the solution was acidified by addition of aqueous 6N HCl and extracted with EtOAc (2×20 ml). The combined organic phases were dried over MgSO$_4$ and concentrated in vacuo to give the title compound as a tan gum (93 mg); MS-(+)-ion: M+1=443.0.

Example D-83

[(4-Ethoxy-1-methyl-7-phenoxy-isoquinoline-3-carbonyl)-amino]-acetic acid a) 4-Ethoxy-1-methyl-7-phenoxy-isoquinoline-3-carboxylic acid ethyl ester To a solution of 1-bromo-4-hydroxy-7-phenoxy-isoquinoline-3-carboxylic acid (721 mg, 2 mmol, Example D-81 a) in anhydrous THF (100 ml) was added slowly a 2.5 M solution of n-BuLi in hexanes (3.2 ml, 8 mmol) at −78° C. with stirring. After stirring for another 5 min MeI (253 µl, 4 mmol) was added dropwise. Stirring was continued for additional 15 min at −78° C. before water (100 ml) and aqueous 2N HCl (5 ml) were added. The mixture was allowed to warm up to ambient temperature with stirring, was then concentrated in vacuo to ca. 1/2 of its volume and extracted with EtOAc (300 ml). The organic phase was dried over MgSO$_4$ and concentrated in vacuo to give an orange solid (462 mg). A mixture of 440 mg of the aforementioned orange solid, EtI (0.61 ml, 7.5 mmol), K$_2$CO$_3$ (3.0 g, 21.7 mmol) and acetone (45 ml) was refluxed with stirring for 16 h. Then the mixture was concentrated in vacuo. To the residue was added water (30 ml) and the mixture was extracted with EtOAc (2×50 ml). The combined organic phases were dried over MgSO$_4$ and concentrated in vacuo to give a brown oil. Purification by flash column chromatography on silica gel using hexanes:EtOAc=8:2 as the eluent gave the title compound as yellowish oil (34 mg); $^1$H NMR (CDCl$_3$): δ=8.22 (d, 1H), 7.07 to 7.50 (m, 7H), 4.50 (q, 2H), 4.20 (q, 2H), 2.80 (s, 3H), 1.43 to 1.58 (m, 6H).

b) 4-Ethoxy-1-methyl-7-phenoxy-isoquinoline-3-carboxylic acid

Synthesized from 4-ethoxy-1-methyl-7-phenoxy-isoquinoline-3-carboxylic acid ethyl ester in analogy to Example D-78 b); MS-(+)-ion: M+1=324.1.

c) [(4-Ethoxy-1-methyl-7-phenoxy-isoquinoline-3-carbonyl)-amino]-acetic acid tert-butyl ester Synthesized from glycine tert-butyl ester hydrochloride and 4-ethoxy-1-methyl-7-phenoxy-isoquinoline-3-carboxylic acid in analogy to Example D-78 c); MS-(+)-ion: M+1=437.1.

d) [(4-Ethoxy-1-methyl-7-phenoxy-isoquinoline-3-carbonyl)-amino]-acetic acid

A mixture of [(4-ethoxy-1-methyl-7-phenoxy-isoquinoline-3-carbonyl)-amino]-acetic acid tert-butyl ester (14 mg, 0.032 mmol) and trifluoroacetic acid (2 ml) was stirred at ambient temperature for 3 h. Then the mixture was concentrated in vacuo and the residue dissolved in EtOH (5 ml). The mixture was evaporated in vacuo to give the title compound as a yellowish solid (12 mg); MS-(−)-ion: M−1=381.1.

Example D-84

[(1-Dimethylcarbamoyl-4-hydroxy-7-phenoxy-isoquinoline-3-carbonyl)-amino]-acetic acid a) 4-Benzyloxy-1-dimethylcarbamoyl-7-phenoxy-isoquinoline-3-carboxylic acid benzyl ester Synthesized from 1-bromo-4-hydroxy-7-phenoxy-isoquinoline-3-carboxylic acid (Example D-81 a) in analogy to Example D-79 a (6 eq of ClCONMe$_2$ were used, reaction mixture was stirred at −78° C. for 75 min after the addition of ClCONMe$_2$ was finished before adding water and HCl); MS-(+)-ion: M+1=533.2.

b) 4-Benzyloxy-1-dimethylcarbamoyl-7-phenoxy-isoquinoline-3-carboxylic acid

Synthesized from 4-benzyloxy-1-dimethylcarbamoyl-7-phenoxy-isoquinoline-3-carboxylic acid benzyl ester in analogy to Example D-79 b); MS-(−)-ion: M−1=441.1.

c) [(4-Benzyloxy-1-dimethylcarbamoyl-7-phenoxy-isoquinoline-3-carbonyl)-amino]-acetic acid benzyl ester Synthesized from 4-benzyloxy-1-dimethylcarbamoyl-7-phenoxy-isoquinoline-3-carboxylic acid in analogy to Example D-79 c); MS-(+)-ion: M+1=590.0.

d) [(1-Dimethylcarbamoyl-4-hydroxy-7-phenoxy-isoquinoline-3-carbonyl)-amino]-acetic acid Synthesized from [(4-benzyloxy-1-dimethylcarbamoyl-7-phenoxy-isoquinoline-3-carbonyl)-amino]-acetic acid benzyl ester in analogy to Example D-79 d); MS-(+)-ion: M+1=410.0.

Example D-85

[(4-Hydroxy-1-methoxymethyl-7-phenoxy-isoquinoline-3-carbonyl)-amino]-acetic acid a) 4-Benzyloxy-1-methoxymethyl-7-phenoxy-isoquinoline-3-carboxylic acid benzyl ester Synthesized from 1-bromo-4-hydroxy-7-phenoxy-isoquinoline-3-carboxylic acid (Example D-81 a) in analogy to Example D-78 a); MS-(+)-ion: M+1=506.2.

b) 4-Benzyloxy-1-methoxymethyl-7-phenoxy-isoquinoline-3-carboxylic acid

Synthesized from 4-Benzyloxy-1-methoxymethyl-7-phenoxy-isoquinoline-3-carboxylic acid benzyl ester in analogy to Example D-78 b); MS-(−)-ion: M−1=414.1.

c) [(4-Benzyloxy-1-methoxymethyl-7-phenoxy-isoquinoline-3-carbonyl)-amino]-acetic acid benzyl ester Synthesized from 4-benzyloxy-1-methoxymethyl-7-phenoxy-isoquinoline-3-carboxylic acid in analogy to Example D-78 c); MS-(+)-ion: M+1=563.1.

d) [(4-Hydroxy-1-methoxymethyl-7-phenoxy-isoquinoline-3-carbonyl)-amino]-acetic acid Synthesized [(4-benzyloxy-1-methoxymethyl-7-phenoxy-isoquinoline-3-carbonyl)-amino]-acetic acid benzyl ester in analogy to Example D-78 d); MS-(+)-ion: M+1=383.0.

Example D-86

[(4-Hydroxy-1-p-tolyl-isoquinoline-3-carbonyl)-amino]-acetic acid a) 4-Benzyloxy-1-bromo-isoquinoline-3-carboxylic acid butyl ester

A mixture of 1-bromo-4-hydroxy-isoquinoline-3-carboxylic acid butyl ester (6.48 g, 20 mmol; Example D-28 a), benzyl bromide (3.6 ml, 30 mmol), $K_2CO_3$ (12.44 g, 90 mmol) and acetone (300 ml) was refluxed with stirring for 2.5 d. The solvent was then evaporated in vacuo. To the residue was added water (100 ml) and the mixture was extracted with EtOAc (100 ml). The organic phase was dried over $MgSO_4$ and evaporated in vacuo to give the title compound as a yellowish solid; MS-(+)-ion: M+1=414.1.

b) 4-Benzyloxy-1-p-tolyl-isoquinoline-3-carboxylic acid butyl ester

4-Benzyloxy-1-bromo-isoquinoline-3-carboxylic acid butyl ester (207 mg, 0.5 mmol) and $Pd(PPh_3)_4$ (23 mg, 0.02 mmol) were dissolved in THF (3 ml) and the solution was stirred for 10 min before a solution of p-tolylboronic acid (68 mg, 0.5 mmol) in EtOH (0.5 ml) and a solution of $Na_2CO_3$ (106 mg, 1 mmol) in water (0.5 ml) were added. The resulting mixture was refluxed with stirring for 4 h. Subsequently, the mixture was concentrated in vacuo. To the residue was added water (2 ml) and the mixture was extracted with EtOAc (10 ml). The organic phase was dried over $MgSO_4$ and evaporated in vacuo to give a yellowish oil (225 mg). Purification by flash column chromatography on silica gel using hexanes: EtOAc=94:6 as the eluent gave the title compound as a colorless oil; MS-(+)-ion: M+1=426.2.

c) 4-Hydroxy-1-p-tolyl-isoquinoline-3-carboxylic acid butyl ester

Synthesized from (4-benzyloxy-1-p-tolyl-isoquinoline-3-carboxylic acid butyl ester in analogy to Example D-78 d) (EtOAc was used as the solvent); MS-(+)-ion: M+1=336.2.

d) [(4-Hydroxy-1-p-tolyl-isoquinoline-3-carbonyl)-amino]-acetic acid

Synthesized from 4-hydroxy-1-p-tolyl-isoquinoline-3-carboxylic acid butyl ester in analogy to Example D-1 g); MS-(+)-ion: M+1=337.1.

Example D-87

{[7-(4-Fluoro-phenoxy)-4-hydroxy-1-methyl-isoquinoline-3-carbonyl]-amino}-acetic acid a) 1-Bromo-7-(4-fluoro-phenoxy)-4-hydroxy-isoquinoline-3-carboxylic acid butyl ester Synthesized from 7-(4-fluoro-phenoxy)-1,4-dihydroxy-isoquinoline-3-carboxylic acid butyl ester (Example D-96 e) in analogy to Example D-1 e); $^1$H NMR (CDCl$_3$): δ=11.89 (s, 1H), 8.36 (d, 1H), 7.44 to 7.57 (m, 2H), 7.08 to 7.25 (m, 4H), 4.47 (q, 2H), 1.85 (m, 2H), 1.50 (m, 2H), 0.99 (t, 3H).

b) 7-(4-Fluoro-phenoxy)-4-hydroxy-1-methyl-isoquinoline-3-carboxylic acid butyl ester A mixture of 1-bromo-7-(4-fluoro-phenoxy)-4-hydroxy-isoquinoline-3-carboxylic acid butyl ester (434 mg, 1 mmol), $Pd(PPh_3)_4$ (116 mg, 0.1 mmol), trimethylboroxine (140 μl, 1 mmol), $K_2CO_3$ (414 mg, 3 mmol), and 1,4-dioxane (8 ml) was refluxed with stirring for 2 h. Subsequently, the mixture was concentrated in vacuo. To the residue was added water (10 ml). The mixture was acidified by the addition of aqueous 6N HCl and then extracted with EtOAc (40 ml). The organic phase was dried over $MgSO_4$ and evaporated in vacuo. Purification of the residue by flash column chromatography on silica gel using hexanes:EtOAc=94:6 as the eluent gave the title compound as white solid (229 mg); MS-(+)-ion: M+1=370.1.

c) {[7-(4-Fluoro-phenoxy)-4-hydroxy-1-methyl-isoquinoline-3-carbonyl]-amino}-acetic acid Synthesized from 7-(4-fluoro-phenoxy)-4-hydroxy-1-methyl-isoquinoline-3-carboxylic acid butyl ester in analogy to Example D-1 g); MS-(+)-ion: M+1=371.1.

The above method can be used to synthesize other intermediates used herein.

Example D-88

{[1-Chloro-4-hydroxy-7-(4-methoxy-phenoxy)-isoquinoline-3-carbonyl]-amino}-acetic acid a) 4-(4-Methoxy-phenoxy)-phthalonitrile

A mixture of 4-nitro-phthalonitrile (4.00 g), 4-methoxyphenol (3.46 g) and potassium carbonate (6.39 g) in acetone (64 ml) was heated to reflux for 2 h. Reaction mixture was cooled and filtered. Filtrate was concentrated and the residue was dissolved in ethyl acetate (100 ml). The solution was washed with NaOH (1 N, 50 ml), water, and then brine. The organic layer was dried over magnesium sulfate, filtered, and concentrated to give the product (6.14 g). $^1$H NMR (200 MHz, CDCl$_3$) δ6.70 (d, J=7.8 Hz, 1H), 7.21 (m, 2H), 6.96 (m, 4H), 3.84 (s, 3H).

b) 4-(4-Methoxy-phenoxy)-phthalic acid

Prepared in analogy to Example D-1 a). MS-(−)-ion: M−1=286.9.

c) [5-(4-Methoxy-phenoxy)-1,3-dioxo-1,3-dihydro-isoindol-2-yl]-acetic acid methyl ester Prepared in analogy to Example D-37 b). $^1$H NMR (200 MHz, CDCl$_3$) δ7.74 (d, J=8.6 Hz, 1H), 7.25 (m, 2H), 6.98 (m, 4H), 4.40 (s, 2H), 3.83 (s, 3H), 3.75 (s, 3H).

d) 6- and 7-(4-Methoxy-phenoxy)-1,4-dihydroxy-isoquinoline-3-carboxylic acid butyl ester Prepared in analogy to Example D-21 b). MS-(+)-ion: M+1=384.10.

e) 7-(4-Methoxy-phenoxy)-1,4-dihydroxy-isoquinoline-3-carboxylic acid butyl ester Prepared in analogy to Example D-21 c). MS-(+)-ion: M+1=384.11.

f) 1-Chloro-4-hydroxy-7-(4-methoxy-phenoxy)-isoquinoline-3-carboxylic acid butyl ester Prepared in analogy to Example D-43 d). MS-(+)-ion: M+1=402.0.

g) {[1-Chloro-4-hydroxy-7-(4-methoxy-phenoxy)-isoquinoline-3-carbonyl]amino}-acetic acid Prepared in analogy to Example D-1 g). MS-(−)-ion: M−1=400.96.

Example D-89

{[4-Hydroxy-7-(4-methoxy-phenoxy)-isoquinoline-3-carbonyl]-amino}-acetic acid a) {[4-Hydroxy-7-(4-methoxy-phenoxy)-isoquinoline-3-carbonyl]-amino}-acetic acid Synthesized from {[1-chloro-4-hydroxy-7-(4-methoxy-phenoxy)-isoquinoline-3-carbonyl]-amino}-acetic acid in analogy to Example D-25. MS-(−)-ion: M−1=367.0.

Example D-90

{[1-Chloro-4-hydroxy-6-(4-methoxy-phenoxy)-isoquinoline-3-carbonyl]-amino}-acetic acid a) 6-(4-Methoxy-phenoxy)-1,4-dihydroxy-isoquinoline-3-carboxylic acid butyl ester Separate from the mixtures of 6- and 7-(4-methoxy-phenoxy)-1,4-dihydroxy-isoquinoline-3-carboxylic acid butyl ester obtained from Example D-88 e). MS-(+)-ion: M+1=384.1 b) 1-Chloro-4-hydroxy-6-(4-methoxy-phenoxy)-isoquinoline-3-carboxylic acid butyl ester Prepared in analogy to Example D-43 d). MS-(+)-ion: M+1=402.0.

c) {[1-Chloro-4-hydroxy-6-(4-methoxy-phenoxy)-isoquinoline-3-carbonyl]-amino}-acetic acid Prepared in analogy to Example D-1 g). MS-(+)-ion: M+1=403.0.

Example D-91

{[4-Hydroxy-6-(4-methoxy-phenoxy)-isoquinoline-3-carbonyl]-amino}-acetic acid

Prepared in analogy to Example D-2 a) from {[1-chloro-4-hydroxy-6-(4-methoxy-phenoxy)-isoquinoline-3-carbonyl]-amino}-acetic acid. MS-(−)-ion: M−1=367.0.

The compounds of Example D-92-99 below were obtained by process analogous to those described in Examples D88-D91.

Example D-92

{[1-Chloro-4-hydroxy-7-(4-trifluoromethyl-phenoxy)-isoquinoline-3-carbonyl]-amino}-acetic acid a) 4-(4-Trifluoromethyl-phenoxy)-phthalonitrile $^1$H NMR (200 MHz, CDCl$_3$) δ7.74 (m, 2H), 7.47 (d, J=8.6 Hz, 1H), 7.25 (m, 3H), 6.87 (d, J=8.9 Hz, 1H).

b) 4-(4-Trifluoromethyl-phenoxy)-phthalic acid $^1$H NMR (200 MHz, DMSO-d6) δ8.24 (d, J=9.0 Hz, 1H), 7.75 (m, 3H), 7.19 (m, 3H)

c) [1,3-Dioxo-5-(4-trifluoromethyl-phenoxy)-1,3-dihydro-isoindol-2-yl]-acetic acid methyl ester $^1$H NMR (200 MHz, CDCl$_3$) δ7.86 (d, J=8.5 Hz, 1H), 7.67 (d, J=8.2 Hz, 2H), 7.40-7.13 (m, 4H), 4.43 (s, 2H), 3.76 9s, 3H)

d) 6- and 7-(4-trifluoromethyl-phenoxy)-1,4-dihydroxy-isoquinoline-3-carboxylic acid butyl ester Mixture of two isomers.

e) 7-(4-trifluoromethyl-phenoxy)-1,4-dihydroxy-isoquinoline-3-carboxylic acid butyl ester MS-(+)-ion: M+1=422.0 f) 1-Chloro-4-hydroxy-7-(4-trifluoromethyl-phenoxy)-isoquinoline-3-carboxylic acid butyl ester MS-(−)-ion: M−1=438.3 g) {[1-Chloro-4-hydroxy-7-(4-trifluoromethyl-phenoxy)-isoquinoline-3-carbonyl]-amino}-acetic acid MS-(−)-ion: M−1=439.0.

Example D-93

{[4-Hydroxy-7-(4-trifluoromethyl-phenoxy)-isoquinoline-3-carbonyl]-amino}-acetic acid MS-(−)-ion: M−1=405.1

Example D-94

{[1-Chloro-4-hydroxy-6-(4-trifluoromethyl-phenoxy)-isoquinoline-3-carbonyl]-amino}-acetic acid a) 1,4-Dihydroxy-6-(4-trifluoromethyl-phenoxy)-isoquinoline-3-carboxylic acid butyl ester MS-(+)-ion: M+1=422.0 b) 1-Chloro-4-hydroxy-6-(4-trifluoromethyl-phenoxy)-isoquinoline-3-carboxylic acid butyl ester $^1$H NMR (200 MHz, CDCl$_3$) δ11.82 (s, 1H), 8.30 (d, J=9.0 Hz, 1H), 7.81 (d, J=2.3 Hz, 1H), 7.67 (d, J=8.6 Hz, 2H), 7.54 (dd, J=9.0, 2.7 Hz, 1H), 7.18 (d, J=8.2 Hz, 2H), 4.48 (t, J=7.0 Hz, 2H), 1.85 (m, 2H), 1.46 (m, 2H), 0.98 (t, J=7.0 Hz, 3H).

c) {[1-Chloro-4-hydroxy-6-(4-trifluoromethyl-phenoxy)-isoquinoline-3-carbonyl]-amino}-acetic acid MS-(−)-ion: M−1=439.1.

Example D-95

{[4-Hydroxy-6-(4-trifluoromethyl-phenoxy)-isoquinoline-3-carbonyl]-amino}-acetic acid MS-(−)-ion: M−1=405.0.

Example D-96

{[1-Chloro-7-(4-fluoro-phenoxy)-4-hydroxy-isoquinoline-3-carbonyl]-amino}-acetic acid a) 4-(4-Fluoro-phenoxy)-phthalonitrile $^1$H NMR (200 MHz, CDCl$_3$) δ7.71 (d, J=8.6 Hz, 1H), 7.23-7.15 (m, 6H).

b) 4-(4-Fluoro-phenoxy)-phthalic acid $^1$H NMR (200 MHz, CDCl$_3$) δ7.74 (d, J=8.9 Hz, 1H), 7.33-7.15 (m, 6H).

c) [5-(4-Fluoro-phenoxy)-1,3-dioxo-1,3-dihydro-isoindol-2-yl]-acetic acid methyl ester $^1$H NMR (200 MHz, CDCl$_3$) δ7.80 (d, J=7.4 Hz, 1H), 7.28 (m, 2H), 7.08 (m, 4H), 4.41 (s, 2H), 3.76 (s, 3H).

d) 6- and 7-(4-Fluoro-phenoxy)-1,4-dihydroxy-isoquinoline-carboxylic acid butyl ester A mixture of two isomers.

e) 7-(4-Fluoro-phenoxy)-1,4-dihydroxy-isoquinoline-3-carboxylic acid butyl ester MS-(+)-ion: M+1=372.1 f) 1-Chloro-7-(4-fluoro-phenoxy)-4-hydroxy-isoquinoline-3-carboxylic acid butyl ester $^1$H NMR (200 MHz, CDCl$_3$) δ11.90 (s, 1H), 8.36 (d, J=9.0 Hz, 1H), 7.56 (m, 2H), 7.10 (m, 4H), 4.47 (t, J=7.0 Hz, 2H), 1.85 (m, 2H), 1.46 (m, 2H), 0.99 (t, J=7.4 Hz, 3H).

g) {[1-Chloro-7-(4-fluoro-phenoxy)-4-hydroxy-isoquinoline-3-carbonyl]-amino}-acetic acid MS-(−)-ion: M−1=389.0.

Example D-97

{[7-(4-Fluoro-phenoxy)-4-hydroxy-isoquinoline-3-carbonyl]-amino}-acetic acid

MS-(−)-ion: M−1=355.1.

Example D-98

{[1-Chloro-6-(4-fluoro-phenoxy)-4-hydroxy-isoquinoline-3-carbonyl]-amino}-acetic acid a) 6-(4-Fluoro-phenoxy)-1,4-dihydroxy-isoquinoline-3-carboxylic acid butyl ester MS-(+)-ion: M+1=372.1 b) 1-Chloro-6-(4-fluoro-phenoxy)-4-hydroxy-isoquinoline-3-carboxylic acid butyl ester $^1$H NMR (200 MHz, CDCl$_3$) δ11.77 (s, 1H), 8.25 (d, J=9.0 Hz, 1H), 7.62 (d, J=2.3 Hz, 1H), 7.50 (dd, J=9.0, 2.3 Hz, 1H), 7.10 (m, 4H), 4.46 (t, J=7.0 Hz, 2H), 1.85 (m, 2H), 1.45 (m, 2H), 0.98 (t, J=7.4 Hz, 3H).

c) {[1-Chloro-6-(4-fluoro-phenoxy)-4-hydroxy-isoquinoline-3-carbonyl]-amino}-acetic acid MS-(−)-ion: M−1=389.1.

Example D-99

{[6-(4-Fluoro-phenoxy)-4-hydroxy-isoquinoline-3-carbonyl]-amino}-acetic acid

MS-(−)-ion: M−1=355.1.

Example D-100

{[4-Hydroxy-7-(pyridin-4-ylsulfanyl)-isoquinoline-3-carbonyl]-amino}-acetic acid a) 4-(Pyridin-4-ylsulfanyl)-phthalonitrile A mixture of 4-nitro-phthalonitrile (17.28 g), pyridine-4-thiol (10.68 g) and potassium carbonate (25.17 g) in N,N-dimethyl-formamide (160 ml) was heated to 85 C and stirred for 3 h. After cooling, the reaction mixture was filtered through a pad of celite, and rinsed with ethyl acetate. Filtrate was concentrated in vacuo and the residue was purified by silica gel chromatography (eluting with 15-30% of ethyl acetate in methylene chloride) to give the title compound 13.29 g. $^1$H NMR (200 MHz, CDCl$_3$) δ8.59 (d, J=6.2 Hz, 2H), 7.68 (m, 3H), 7.24 (d, J=6.3 Hz, 2H).

b) 4-(Pyridin-4-ylsulfanyl)-phthalic acid

Prepared in analogy to Example D-1 a). MS-(+)-ion: M+1=276.1.

c) [1,3-Dioxo-5-(pyridin-4-ylsulfanyl)-1,3-dihydro-isoindol-2-yl]-acetic acid butyl ester A solid mixture of 4-(pyridin-4-ylsulfanyl)-phthalic acid (11.40 g) and glycine n-butyl ester hydrochloride salt (6.95 g) was heated in a oil bath (250° C.) with efficient stirring for 20 min. until the water bubble evaporation ceased. After cooling, it was partitioned between ethyl acetate (300 ml) and saturated sodium bicarbonate aqueous solution (150 ml). Two layers were separated and the aqueous layer was extracted with ethyl acetate (300 ml). Combined organic layers were washed with brine, dried over magnesium sulfate, filtered and concentrated to give the title compound 10.70 g. MS-(+)-ion: M+1=371.2.

d) 6- and 7-(Pyridin-4-ylsulfanyl)-1,4-dihydroxy-isoquinoline-3-carboxylic acid butyl ester Prepared in analogy to Example D-21 b).

e) 6- and 7-(Pyridin-4-ylsulfanyl)-1-chloro-4-hydroxy-isoquinoline-3-carboxylic acid butyl ester Prepared in analogy to Example D-43 d). MS-(+)-ion: M+1=389.1.

f) 6- and 7-(Pyridin-4-ylsulfanyl)-4-hydroxy-isoquinoline-3-carboxylic acid butyl ester Prepared in analogy to Example D-1 f). Crude product was purified by silica gel chromatography (50%-80% ethyl acetate in methylene chloride) to give 7-(pyridin-4-ylsulfanyl)-1-chloro-4-hydroxy-isoquinoline-3-carboxylic acid butyl ester (Compound D-100A) (MS-(+)-ion: M+1=355.04) and 6-(pyridin-4-ylsulfanyl)-1-chloro-4-hydroxy-isoquinoline-3-carboxylic acid butyl ester (Compound D-100B) (MS-(+)-ion: M+1=355.13).

g) {[4-Hydroxy-7-(pyridin-4-ylsulfanyl)-isoquinoline-3-carbonyl]-amino}-acetic acid Prepared in analogy to Example D-1 g). MS-(+)-ion: M+1=356.1.

Example D-101

{[4-Hydroxy-6-(pyridin-4-ylsulfanyl)-isoquinoline-3-carbonyl]-amino}-acetic acid Prepared in analogy to Example D-1 g) from 6-(pyridin-4-ylsulfanyl)-1-chloro-4-hydroxy-isoquinoline-3-carboxylic acid butyl ester (Compound D-100 B). MS-(+)-ion: M+1=356.1.

Example D-102

[(7-Benzenesulfinyl-4-hydroxy-isoquinoline-3-carbonyl)-amino]-acetic acid a) 7-Benzenesulfinyl-4-hydroxy-isoquinoline-3-carboxylic acid butyl ester

A slurry mixture of 4-hydroxy-7-phenylsulfanyl-isoquinoline-3-carboxylic acid butyl ester (300 mg) and OXONE® Dupont Specialty Chemicals, Wilmington, Del., USA) (366 mg) in (3/2) methanol/water (5 ml) was stirred at room temp for 4 h. Reaction mixture was partitioned between methylene chloride and saturated aqueous sodium bicarbonate solution. Organic layer was washed with saturated aqueous sodium bicarbonate solution and water. Dried over magnesium sulfate and filtered. Filtrate was concentrated and the residue was purified by silica gel chromatograph (0%-50% ethyl acetate in methylene chloride) to give the title compound 7-benzenesulfinyl-4-hydroxy-isoquinoline-3-carboxylic acid butyl ester (Compound D-102 A) (50 mg) (MS-(+)-ion: M+1=370.1) and 7-benzenesulfonyl-4-hydroxy-isoquinoline-3-carboxylic acid butyl ester (Compound D-102B) (90 mg) (MS-(+)-ion: M+1=386.1).

b) [(7-Benzenesulfinyl-4-hydroxy-isoquinoline-3-carbonyl)-amino]-acetic acid Prepared in analogy to Example D-1 g) from 7-benzenesulfinyl-4-hydroxy-isoquinoline-3-carboxylic acid butyl ester (Compound D-102 A). MS-(+)-ion: M+1=371.1.

Example D-103

[(7-Benzenesulfonyl-4-hydroxy-isoquinoline-3-carbonyl)-amino]-acetic acid

Prepared in analogy to Example D-1 g) from 7-benzenesulfonyl-4-hydroxy-isoquinoline-3-carboxylic acid butyl ester (Compound D-102 B). MS-(+)-ion: M+1=387.1.

Example D-104

[(6-Benzenesulfinyl-4-hydroxy-isoquinoline-3-carbonyl)-amino]-acetic acid a) 6-Benzenesulfinyl-4-hydroxy-isoquinoline-3-carboxylic acid butyl ester

Prepared in analogy to Example D-18 a) from 4-hydroxy-6-phenylsulfanyl-isoquinoline-3-carboxylic acid butyl ester. Two compounds were isolated from chromatography: the title compound 6-benzenesulfinyl-4-hydroxy-isoquinoline-3-carboxylic acid butyl ester (Compound D-104 A) (MS-(+)-ion: M+1=370.1) and 6-benzenesulfonyl-4-hydroxy-isoquinoline-3-carboxylic acid butyl ester (Compound D-104 B) (MS-(+)-ion: M+1=386.1).

b) [(6-Benzenesulfinyl-4-hydroxy-isoquinoline-3-carbonyl)-amino]-acetic acid Prepared in analogy to Example D-1 g) from 6-benzenesulfinyl-4-hydroxy-isoquinoline-3-carboxylic acid butyl ester (Compound D-104 A). MS-(−)-ion: M−1=369.0.

Example D-105

[(6-Benzenesulfonyl-4-hydroxy-isoquinoline-3-carbonyl)-amino]-acetic acid

Prepared in analogy to Example D-1 g) from 6-benzenesulfonyl-4-hydroxy-isoquinoline-3-carboxylic acid butyl ester (Compound D-104 B). MS-(−)-ion: M−1=385.1.

Example D-106

[(6-Amino-4-hydroxy-isoquinoline-3-carbonyl)-amino]-acetic acid a) (5-Nitro-1,3-dioxo-1,3-dihydro-isoindol-2-yl)-acetic acid ethyl ester

Potassium carbonate (57.8 g) was added to a solution mixture of 5-nitro-isoindole-1,3-dione (26.2 g) and bromoacetic acid ethyl ester (25.1 g) in acetone (500 ml). The resulting mixture was refluxed overnight (18 h). After cooling, reaction mixture was filtered and rinsed with ethyl acetate. Filtrate was concentrated and the residue was triturated with ether (200 ml). Solid was collected and rinsed with ether. Dried in vacuo to give the title compound 231.9 g. $^1$H NMR (200 MHz, CDCl$_3$) δ8.69 (m, 2H), 8.07 (d, J=8.2 Hz, 1H), 4.48 (s, 2H), 4.24 (q, J=7.0 Hz, 2H), 1.30 (t, J=7.0 Hz, 3H).

b) (5-Amino-1,3-dioxo-1,3-dihydro-isoindol-2-yl)-acetic acid ethyl ester

10% Palladium/C (50% wet) solid (2.0 g) was added to a solution mixture of (5-nitro-1,3-dioxo-1,3-dihydro-isoindol-2-yl)-acetic acid ethyl ester (10.0 g) in glacial acetic acid (150 ml). Stirred vigorously under H2 (balloon pressure) at room temperature overnight (18 h). Catalyst was filtered off through a pad of celite and rinsed with methylene chloride. Filtrate was concentrated to give the title compound (7.0 g). $^1$H NMR (200 MHz, CDCl$_3$) δ7.59 (d, J=8.2 Hz, 1H), 7.02 (d, J=2.0 Hz, 1H), 6.81 (dd, J=8.2, 2.0 Hz, 1H), 4.38 (br S, 2H), 4.36 (s, 2H), 4.20 (q, J=7.0 Hz, 2H), 1.27 (t, J=7.0 Hz, 3H).

c) [5-(Benzhydrylidene-amino)-1,3-dioxo-1,3-dihydro-isoindol-2-yl]-acetic acid ethyl ester Titanium tetrachloride (1.99 g) was slowly added to a mixture of (5-amino-1,3-dioxo-1,3-dihydro-isoindol-2-yl)-acetic acid ethyl ester (3.48 g), benzophenone (2.81 g) and DABCO (4.72 g) in chlorobenzene (112 ml). Resulting mixture was heated to reflux for 2.5 h. After cooling, reaction mixture was filtered through a pad of celite and rinsed with ethyl acetate. Filtrate was concentrated and the residue was purified by silica gel chromatography (25%-40% ethyl acetate in hexanes) to give the title compound (3.03 g). MS-(+)-ion: M+1=413.3.

d) 6- and 7-(Benzhydrylidene-amino)-1,4-dihydroxy-isoquinoline-3-carboxylic acid butyl ester Prepared in analogy to Example D-21 b). MS-(+)-ion: M+1=441.2 e) 6- and 7-Amino-1-chloro-4-hydroxy-isoquinoline-3-carboxylic acid butyl ester Prepared in analogy to Example D-43 d). The crude product was purified by silica gel chromatography (eluting with 50% ethyl acetate in hexanes) to give the title compounds. MS-(+)-ion: M+1=295.1.

f) 6- and 7-Amino-4-hydroxy-isoquinoline-3-carboxylic acid butyl ester

To a solution of 6- and 7-Amino-1-chloro-4-hydroxy-isoquinoline-3-carboxylic acid butyl ester (220 mg) in ethyl acetate (5 ml) was added 10% Pd/C (50% wet) (110 mg) and then ammonium formate (471 mg). Resulting mixture was heated to reflux for 0.5 h. After cooling, the reaction mixture was diluted with ethyl acetate (50 ml) and filtered. Filtrate was concentrated to give the title compounds 182 mg. MS-(+)-ion: M+1=261.2.

g) 6- and 7-Amino-4-(4-methoxy-benzenesulfonyloxy)-isoquinoline-3-carboxylic acid butyl ester A mixture of 6- and 7-amino-4-hydroxy-isoquinoline-3-carboxylic acid butyl ester (180 mg), 4-methoxy-benzenesulfonyl chloride (145 mg) and triethyl amine (85 mg) in methylene chloride (7 ml) was stirred at room temperature for 18 h. It was diluted with water (20 ml) and acidified to pH 4 by 0.1 N HCl aqueous solution. Two phases were separated and the aqueous layer was extracted with methylene chloride. Combined organic layers were washed with brine, dried over magnesium sulfate, filtered and concentrated. Crude product was purified by silica gel chromatography (55%-80% ethyl acetate in hexanes) to two products: 7-amino-4-(4-methoxy-benzenesulfonyloxy)-isoquinoline-3-carboxylic acid butyl ester (Compound D-106 A) (79 mg) (MS-(+)-ion: M+1=431.1) and 6-amino-4-(4-methoxy-benzenesulfonyloxy)-isoquinoline-3-carboxylic acid butyl ester (Compound D-106 B) (70 mg) (MS-(+)-ion: M+1=431.1).

h) [(6-Amino-4-hydroxy-isoquinoline-3-carbonyl)-amino]-acetic acid

Prepared from 6-amino-4-(4-methoxy-benzenesulfonyloxy)-isoquinoline-3-carboxylic acid butyl ester (Compound D-106 B) in analogy to Example D-1 g). MS-(−)-ion: M−1=260.1.

Example D-107

{[4-Hydroxy-7-(4-methoxy-benzenesulfonylamino)-isoquinoline-3-carbonyl]-amino}-acetic acid a) 7-[(N,N-Di-4-methoxy-benzenesulfonyl)amino]-4-(4-methoxy-benzenesulfonyloxy)-isoquinoline-3-carboxylic acid butyl ester A mixture of 7-amino-4-(4-methoxy-benzenesulfonyloxy)-isoquinoline-3-carboxylic acid butyl ester (Compound D-106 A) (75 mg), 4-methoxy-benzenesulfonyl chloride (140 mg) and triethyl amine (76 mg) in methylene chloride (2 ml) in a sealed vessel was heated in a microwave reactor to 120 C for 10 min. After cooling, reaction mixture was concentrated and purified by silica gel chromatography (eluting with 5%-10% ethyl acetate in methylene chloride) to give the title compound (68 mg). MS-(+)-ion: M+1=770.99.

b) {[4-Hydroxy-7-(4-methoxy-benzenesulfonylamino)-isoquinoline-3-carbonyl]-amino}-acetic acid A mixture of the above ester (68 mg) and glycine (86 mg) in 0.5 N sodium methoxide/methanol (2.7 ml) in a sealed vessel was heated in a microwave reactor (150° C., 17 min). After cooling, reaction mixture was concentrated. Residue was dissolved in water (10 ml) and extracted with ethyl acetate (15 ml). Aqueous layer was acidified by 2 N HCl aqueous solution to pH=4 and extracted with ethyl acetate (2×50 ml). Combined organic layers were washed with brine, dried over magnesium sulfate, filtered, and concentrated. The crude product was triturated with methanol and (1/1) ethyl acetate/hexanes to give the title compound. 14 mg. MS-(−)-ion: M−1=430.

Example D-108

{[4-Hydroxy-7-(3-phenyl-ureido)-isoquinoline-3-carbonyl]-amino}-acetic acid a) 6- and 7-(3-Phenyl-ureido)-4-hydroxy-isoquinoline-3-carboxylic acid butyl ester A mixture of 6- and 7-Amino-4-hydroxy-isoquinoline-3-carboxylic acid butyl ester (160 mg) and phenyl isocyanate (73 mg) in methylene chloride (4 ml) was stirred at room temperature overnight (18 h) and concentrated. Residue was triturated with (1/1) ethyl acetate/methylene chloride (8 ml). Insoluble solid was collected by filtration and rinsed with methylene chloride (5 ml). It was dried to give 7-(3-phenyl-ureido)-4-Hydroxy-isoquinoline-3-carboxylic acid butyl ester (Compound D-108 A) (82 mg) (MS-(+)-ion: M+1=380.18). Filtrate was concentrated and the residue was purified by silica gel chromatography and then recrystalized from methanol to give 6-(3-phenyl-ureido)-4-hydroxy-isoquinoline-3-carboxylic acid butyl ester (Compound D-108 B) (82 mg) (MS-(+)-ion: M+1=380.15).

b) {[4-Hydroxy-7-(3-phenyl-ureido)-isoquinoline-3-carbonyl]-amino}-acetic acid

Prepared from 7-(3-phenyl-ureido)-4-hydroxy-isoquinoline-3-carboxylic acid butyl ester (Compound D-108 A) in analogy to Example D-1 g). MS-(−)-ion: M−1=379.07.

Example D-109

{[4-Hydroxy-6-(3-phenyl-ureido)-isoquinoline-3-carbonyl]-amino}-acetic acid a) {[4-Hydroxy-6-(3-phenyl-ureido)-isoquinoline-3-carbonyl]-amino}-acetic acid Prepared from 7-(3-phenyl-ureido)-4-hydroxy-isoquinoline-3-carboxylic acid butyl ester (Compound D-108 B) in analogy to Example D-1 g). MS-(−)-ion: M−1=379.08.

Example D-110

[(4-Hydroxy-1-phenylsulfanyl-isoquinoline-3-carbonyl)-amino]-acetic acid

The title compound was prepared as follows: To a solution of 250 mg of [(1-chloro-4-hydroxy-isoquinoline-3-carbonyl)-amino]-acetic acid, (U.S. Pat. No. 6,093,730, disclosed as N-((1-chloro-4-hydroxyisoquinoline-3-yl)carbonyl)glycine), in 1 ml 1-methyl-2-pryrrolidinone was added 1.2 ml of benzenethiol. The solution was heated at 130 to 150° C. in a sealed tube for 16 h. The solution was concentrated under vacuum. The resultant residue was crystallized from methanol to yield 91 mg of a tan solid; MS (−) m/z 353.07 (M−1)

Example D-111

{[1-(4-Chloro-phenylsulfanyl)-4-hydroxy-isoquinoline-3-carbonyl]-amino}-acetic acid The title compound was prepared from [(1-chloro-4-hydroxy-isoquinoline-3-carbonyl)-amino]-acetic acid (U.S. Pat. No. 6,093,730) and 4-chlorobenzenethiol under conditions analogous to Example D-110; MS (+) m/z 389.06 (M+1)

Example D-112

[(4-Hydroxy-1-p-tolylsulfanyl-isoquinoline-3-carbonyl)-amino]-acetic acid

The title compound was prepared from [(1-chloro-4-hydroxy-isoquinoline-3-carbonyl)-amino]-acetic acid (U.S. Pat. No. 6,093,730) and 4-methylbenzenethiol under conditions analogous to Example D-110; MS (−) m/z 367.09 (M−1)

Example D-113

{[4-Hydroxy-1-(pyridin-2-ylsulfanyl)-isoquinoline-3-carbonyl]-amino}-acetic acid The title compound was prepared from [(1-chloro-4-hydroxy-isoquinoline-3-carbonyl)-amino]-acetic acid (U.S. Pat. No. 6,093,730) and 2-mercaptopyridine under conditions analogous to Example D-110. The final product was purified by column chromatography on silica gel using a gradient of 3-15% methanol in dicloromethane with 0.5% acetic acid to elute the product; MS (−) m/z 354.10 (M−1)

Example D-114

{[4-Hydroxy-1-(3-methoxy-phenylsulfanyl)-isoquinoline-3-carbonyl]-amino}-acetic acid The title compound was prepared from [(1-chloro-4-hydroxy-isoquinoline-3-carbonyl)-amino]-acetic acid (U.S. Pat. No. 6,093,730) and 3-methoxybenzenethiol under conditions analogous to Example D-110. The final product was precipitated from a solution of ethyl acetate using hexanes; MS (−) m/z 385.12 (M−1)

Example D-115

{[4-Hydroxy-1-(2-methoxy-phenylsulfanyl)-isoquinoline-3-carbonyl]-amino}-acetic acid The title compound was prepared from [(1-chloro-4-hydroxy-isoquinoline-3-carbonyl)-amino]-acetic acid (U.S. Pat. No. 6,093,730) and 2-methoxybenzenethiol under conditions analogous to Example D-110. The final product was crystallized from dichloromethane; MS (−) m/z 383.08 (M−1)

Example D-116

{[4-Hydroxy-1-(naphthalen-2-ylsulfanyl)-isoquinoline-3-carbonyl]-amino}-acetic acid The title compound was prepared from [(1-chloro-4-hydroxy-isoquinoline-3-carbonyl)-amino]-acetic acid (U.S.

Pat. No. 6,093,730) and 2-napthalenethiol under conditions analogous to Example D-110. The final product was purified by triturating the crude product twice with methanol and twice with dichloromethane; MS (+) m/z 405.08 (M+1).

Example D-117

[(1-Benzenesulfinyl-4-hydroxy-isoquinoline-3-carbonyl)-amino]-acetic acid

The title compound was prepared as follows: 50 mg of [(4-hydroxy-1-phenylsulfanyl-isoquinoline-3-carbonyl)-amino]-acetic acid, Example D-110, was dissolved in 0.3 ml 1-methyl-2-pyrolydinone and 0.7 ml dichloromethane. The solution was cooled to 0° C. and 26 mg of 75% 3-chloroperoxybenzoic acid was added. The solution was stirred for 2 hours at room temperature, then concentrated under high vacuum. The resultant residue was triturated with ethyl acetate to provide 32 mg of the product as a white solid; MS (−) m/z 369.08 (M−1)

Example D-118

[(1-Benzenesulfonyl-4-hydroxy-isoquinoline-3-carbonyl)-amino]-acetic acid

The title compound was prepared as follows: 50 mg of [(4-hydroxy-1-phenylsulfanyl-isoquinoline-3-carbonyl)-amino]-acetic acid, Example D-110, was dissolved in 0.1 ml 1-methyl-2-pyrolydinone and 0.7 ml dichloromethane. To the solution was added 72 mg of 75% 3-chloroperoxybenzoic acid. The solution was stirred for 6 hours at room temperature. The mixture was partitioned between ethyl acetate and water. The organic fraction was dried over anhydrous magnesium sulfate, and concentrated to a residue. The resultant residue was triturated with ethyl acetate to provide 28 mg of the product as a white solid; MS (−) m/z 385.09 (M−1)

Example D-119

{[4-Hydroxy-7-(pyridin-2-ylsulfanyl)-isoquinoline-3-carbonyl]-amino}-acetic acid a) 4-(pyridin-2-ylsulfanyl)-phthalonitrile 10 g of 2-mercaptopyridine, 14.2 g of 4-nitrophthalonitrile, and 22.6 g of potassium carbonate were suspended in 250 ml of acetone and heated at reflux temperature for 4 hours. The solution was filtered through a pad of celite and a course glass filter to remove residual solids. The solution was concentrated to a crude residue and purified by column chromatography on silica gel eluting the product with a gradient of 0-10% ethyl acetate in dichloromethane. 6.4 g of product was recovered; $^1$H NMR (200 Mz, CDCl$_3$) δ=8.49-8.53 (m, 1H), 7.84-7.83 (dd, 1H), 7.76-7.71 (m, 2H), 7.68-7.64 (dd, 1H), 7.40-7.36 (dt, 1H), 7.27-7.20 (m, 1H).

b) {[4-Hydroxy-7-(pyridin-2-ylsulfanyl)-isoquinoline-3-carbonyl]-amino}-acetic acid The title compound was prepared from 4-(pyridin-2-ylsulfanyl)-phthalonitrile in analogy to Example D-1; MS (+): m/z 356.01 (M+1).

Example D-120

{[4-Hydroxy-6-(pyridin-2-ylsulfanyl)-isoquinoline-3-carbonyl]-amino}-acetic acid The title compound was prepared from 4-(pyridin-2-ylsulfanyl)-phthalonitrile in analogy to Example D-119; MS (+): m/z 356.02 (M+1).

Example D-121

[(1-Chloro-4-hydroxy-6,7-diphenoxy-isoquinoline-3-carbonyl)-amino]-acetic acid a) 4,5-diphenoxyphthalonitrile 5.0 g of 4,5-dichlorophthalonitrile was dissolved in 50 ml of DMSO. 14.3 g of phenol was added and the solution was heated to 90° C. Portions of 6.9 g of potassium carbonate was added every five minutes until a total of 55.2 g had been added. The mixture was stirred at 90° C. for thirty minutes then cooled and poured into 500 ml of ice-water. The resulting solid precipitate was collected and crystallized from methanol to produce 3.6 g of product; $^1$H NMR (200 Mz, CDCl$_3$) δ=7.49-7.38 (m, 4H), 7.32-7.25 (m, 2H), 7.15 (s, 2H), 7.10-7.02 (m, 4H)

b) [(1-Chloro-4-hydroxy-6,7-diphenoxy-isoquinoline-3-carbonyl)-amino]-acetic acid The title compound was synthesized from 4,5-diphenoxyphthalonitrile in analogy to Example D-7a-d and Example D-9a-b; MS (+): m/z 465.05 (M+1).

Example D-122

[(4-Hydroxy-6,7-diphenoxy-isoquinoline-3-carbonyl)-amino]-acetic acid

The title compound was synthesized from 4,5-diphenoxyphthalonitrile, Example D-121a, in analogy to Example D-7; MS (+): m/z 431.07 (M+1).

Example D-123

({4-Hydroxy-7-[4-(toluene-4-sulfonylamino)-phenoxy]-isoquinoline-3-carbonyl}-amino)-acetic acid a) 1-Chloro-4-hydroxy-6-(4-nitro-phenoxy)-isoquinoline-3-carboxylic acid butyl ester 200 mg of 1-Chloro-4-hydroxy-6-phenoxy-isoquinoline-3-carboxylic acid butyl ester, Example D-10a, was dissolved in 3 ml of concentrated sulfuric acid. The reaction mixture was cooled to −20° C. and 60 mg of potassium nitrate was added slowly to the stirring solution. The reaction was kept between −10 to −20° C. while stirring for 15 min, and poured into ice-water. The aqueous mixture was extracted twice with ethyl acetate. The organic fractions were washed successively with saturated bicarbonate and brine solutions, dried over anhydrous magnesium sulfate, and concentrated to a residue under reduced pressure. The resultant solid was triturated with ethyl acetate followed by methanol to produce 103 mg of white solid; MS (+): m/z 417.07 (M+1).

b) 6-(4-Amino-phenoxy)-4-hydroxy-isoquinoline-3-carboxylic acid butyl ester 100 mg of 1-chloro-4-hydroxy-6-(4-nitro-phenoxy)-isoquinoline-3-carboxylic acid butyl ester was dissolved in 3 ml THF and 3 ml methanol. 20 mg of sodium acetate and 25 mg of 10% palladium on carbon were added to the mixture, and the stirring reaction was placed under hydrogen atmosphere (balloon) overnight. The resultant solution was filtered through a pad of celite and concentrated to a residue. The crude material was purified by column chromatography on silica gel, eluting the product with a gradient of 0-20% ethyl acetate in dichloromethane, to produce 59 mg of product; MS (−): m/z 351.27 (M−1).

c) 4-Hydroxy-7-[4-(toluene-4-sulfonylamino)-phenoxy]-isoquinoline-3-carboxylic acid butyl ester 58 mg of 6-(4-Amino-phenoxy)-4-hydroxy-isoquinoline-3-carboxylic acid butyl ester, 15.8 mg of pyridine, and 34 mg of p-toluenesulfonyl chloride were dissolved in 0.3 ml of dry dichloromethane. The mixture was stirred for 16 hours, and then partitioned between 0.25 N HCl and ethyl acetate. The organic fraction was successively washed with water, saturated bicarbonate, and brine solutions, then dried over anhydrous sodium sulfate, and concentrated to 84 mg of a crude solid. The crude material was tirturated with ethyl acetate to produce 42 mg of a white solid; $^1$H NMR (200 Mz, CDCl$_3$) δ=11.7 (s, 1H), 8.72 (d, 1H), 7.93-7.88 (d, 1H), 7.69-7.65 (d, 2H), 7.56-7.54 (m, 2H), 7.44-7.39 (dd, 1H), 7.27-7.13 (m, 5H), 7.00-6.96 (d, 2H), 4.46 (t, 2H), 2.4 (s, 3H), 1.87-1.82 (quintet, 2H), 1.48-1.40 (quint, 2H), 1.00-0.95 (t, 3H).

d) ({4-Hydroxy-7-[4-(toluene-4-sulfonylamino)-phenoxy]-isoquinoline-3-carbonyl}-amino)-acetic acid To a solution of 1.85 ml of 0.5 M sodium methoxide in methanol was added 42 mg of 4-Hydroxy-7-[4-(toluene-4-sulfonylamino)-phenoxy]-isoquinoline-3-carboxylic acid butyl ester and 70 mg of glycine. The resultant mixture was heated at reflux temperature for 24 hours and then cooled to room temperature. The reaction was poured into a 0.2 N HCl aqueous solution and then extracted three times with ethyl acetate. The organic fractions were dried over anhydrous sodium sulfate and concentrated to 41 mg of a white solid; MS (+): m/z 508.10 (M+1).

Example D-124

{[4-Hydroxy-7-(4-nitro-phenoxy)-isoquinoline-3-carbonyl]-amino}-acetic acid a) 4-Hydroxy-7-(4-nitro-phenoxy)-isoquinoline-3-carboxylic acid butyl ester 2.0 g of 4-Hydroxy-7-phenoxy-isoquinoline-3-carboxylic acid butyl ester, Example D-7f, was dissolved in 15 ml of TFA. 0.375 ml of fuming nitric acid was added slowly to the solution, and the resultant mixture was stirred at room temperature for 7 hours. The reaction mixture was concentrated under vacuum, and the resultant residue was purified by column chromatography on silica gel, eluting with 0-20% ethyl acetate in dichloromethane. The crude product obtained was triturated with methanol to produce 1.0 g of white solid; MS (+): m/z 383.01 (M+1).

b) {[4-Hydroxy-7-(4-nitro-phenoxy)-isoquinoline-3-carbonyl]-amino}-acetic acid The title compound was synthesized from 4-hydroxy-7-(4-nitro-phenoxy)-isoquinoline-3-carboxylic acid butyl ester in analogy to Example D-1 g; MS (−): m/z 382.06 (M−1).

Example D-125

[(4-Mercapto-7-phenoxy-isoquinoline-3-carbonyl)-amino]-acetic acid a) 4-Dimethylthiocarbamoyloxy-7-phenoxy-isoquinoline-3-carboxylic acid butyl ester To a solution of 1.5 g of 4-hydroxy-7-phenoxy-isoquinoline-3-carboxylic acid butyl ester, Example D-7f, in 6.3 ml of anhydrous DMF was added 578 mg of dimethylthiocarbamoylchloride and 1.5 g of 1,4-diazabicyclo[2.2.2]octane. The mixture was stirred overnight at room temperature. The mixture was poured into 30 ml of 1 N HCl and extracted three times with 30 ml portions of ethyl acetate. The organic fractions were washed with water and brine, dried over anhydrous sodium sulfate, and concentrated to 1.9 g of product; MS (+) m/z 425.27 (M+1)

b) 4-Dimethylcarbamoylsulfanyl-7-phenoxy-isoquinoline-3-carboxylic acid butyl ester A solution of 1.9 g of 4-dimethylthiocarbamoyloxy-7-phenoxy-isoquinoline-3-carboxylic acid butyl ester in 22 ml of phenyl ether was heated to 190° C. for 2 hours. The solution was concentrated under vacuum to give a crude residue, which was purified by column chromatography on silica gel, eluting the product with a gradient of 30-80% ethyl acetate in hexanes to give 1.73 g; MS (+) m/z 425.07 (M+1)

c) 4-Mercapto-7-phenoxy-isoquinoline-3-carboxylic acid methyl ester

To a solution of 6.5 ml of 0.5 N sodium methoxide in methanol was added 460 mg of 4-dimethylcarbamoylsulfanyl-7-phenoxy-isoquinoline-3-carboxylic acid butyl ester. The resultant solution was heated to 50-60° C. for 8 hours, cooled to room temperature, and diluted with 10 ml water and 7.0 ml 1 N HCl. The resulting yellow precipitate was collected by filtering the solution through a (medium) porous buchner filter funnel to give 307 mg of product; MS (+) m/z 312.08 (M+1)

d) [(4-Mercapto-7-phenoxy-isoquinoline-3-carbonyl)-amino]-acetic acid

To a solution of 4.3 ml of 0.5 M sodium methoxide in methanol was added 75 mg of 4-mercapto-7-phenoxy-isoquinoline-3-carboxylic acid methyl ester and 181 mg of glycine. The mixture was heated to 150° C. for 10 minutes using a CEM Discover microwave reactor (City, State). The resultant solution was cooled, and acidified with 1 N HCl solution to produce a yellow precipitate. The precipitate was collected by filtering the solution through a (medium) porous buchner filter funnel, and triturated with methanol to give 68 mg of product; MS (−): m/z 353.02 (M−1).

Example D-126

[(4-Mercapto-7-trifluoromethyl-isoquinoline-3-carbonyl)-amino]-acetic acid a) 4-Hydroxy-7-trifluoromethyl-isoquinoline-3-carboxylic acid butyl ester The title compound was prepared from was prepared from 4-trifluoromethylphthalic acid under conditions analogous to Example D-7a-f; MS (+) m/z 314.1 (M+1)

b) [(4-Mercapto-7-trifluoromethyl-isoquinoline-3-carbonyl)-amino]-acetic acid

The title compound was prepared from 4-Hydroxy-7-trifluoromethyl-isoquinoline-3-carboxylic acid butyl ester under conditions analogous to Example D-125; MS (−) m/z 328.33 (M−1)

Example D-127

{[7-(4-Benzenesulfonylamino-phenoxy)-4-hydroxy-isoquinoline-3-carbonyl]-amino}-acetic acid The title compound was synthesized from 4-Hydroxy-7-(4-nitro-phenoxy)-isoquinoline-3-carboxylic acid butyl ester, Example D-124a, in analogy to examples D-123b-d substituting benzenesulfonyl chloride for p-toluenesulfonyl chloride in step c; MS (+): m/z 494.09 (M+1).

Example D-128

{[4-Hydroxy-7-(4-methanesulfonylamino-phenoxy)-isoquinoline-3-carbonyl]-amino}-acetic acid The title compound was synthesized from 4-hydroxy-7-(4-nitro-phenoxy)-isoquinoline-3-carboxylic acid butyl ester, Example D-124a, in analogy to examples D-123b-d substituting methanesulfonyl chloride for p-toluenesulfonyl chloride in step c; MS (−): m/z 430.03 (M−1).

Example D-129

{[7-(4-Chloro-phenoxy)-4-hydroxy-isoquinoline-3-carbonyl]-amino}-acetic acid a) 4-(4-Chloro-phenoxy)-phthalonitrile Prepared in analogy to Example D-88 a). $^1$H NMR (200 MHz, DMSO) δ8.09 (d, J=9 Hz, 1H), 7.83 (d, J=2.6, 1H), 7.53 (d, J=8.6 Hz, 2H), 7.42 (dd, J=2.8, 8.6 Hz, 1H), 7.24 (d, J=8.6, 2H).

b) 4-(4-Chloro-phenoxy)-phthalic acid

Prepared in analogy to Example D-1 a). MS-(−)-ion: M−1=291.0.

c) [5-(4-Chloro-phenoxy)-1,3-dioxo-1,3-dihydro-isoindol-2-yl]-acetic acid butyl ester Prepared in analogy to Example D-100 c). $^1$H NMR (200 MHz, DMSO) δ7.48 (d, J=8.6 Hz, 1H), 7.59 (d, J=9.0 Hz, 2H), 7.46 (m, 2H), 7.29 (d, J=9.0 Hz, 2H), 4.46 (s, 2H), 4.16 (t, J=6.2 Hz, 2H), 1.61 (m, 2H), 1.38 (m, 2H), 0.92 (t, J=7.0 Hz, 3H).

d) 6- and 7-(4-Chloro-phenoxy)-1,4-dihydroxy-isoquinoline-3-carboxylic acid butyl ester Prepared in analogy to Example D-1d). Mixture of two isomers. MS-(−)-ion: M−1=386.1.

e) 1-Chloro-6- and 7-(4-chloro-phenoxy)-4-hydroxy-isoquinoline-3-carboxylic acid butyl ester Prepared in analogy to Example D-43 d). Mixture of two isomers. MS-(−)-ion: M−1=404.2.

f) 6- and 7-(4-Chloro-phenoxy)-4-hydroxy-isoquinoline-3-carboxylic acid butyl ester Prepared in analogy to Example D-1 f). The two isomers were separated to give 7-(4-chloro-phenoxy)-4-hydroxy-isoquinoline-3-carboxylic acid butyl ester (Compound D-129A): MS-(−)-ion: M−1=370.3 and 6-(4-chloro-phenoxy)-4-hydroxy-isoquinoline-3-carboxylic acid butyl ester (Compound D-129B): MS-(−)-ion: M−1=370.3.

g) {[7-(4-Chloro-phenoxy)-4-hydroxy-isoquinoline-3-carbonyl]-amino}-acetic acid

Prepared in analogy to Example D-37 e) starting from 7-(4-chloro-phenoxy)-4-hydroxy-isoquinoline-3-carboxylic acid butyl ester (compound D-129A). MS-(−)-ion: M−1=371.0.

Example D-130

{[6-(4-Chloro-phenoxy)-4-hydroxy-isoquinoline-3-carbonyl]-amino}-acetic acid a) {[6-(4-Chloro-phenoxy)-4-hydroxy-isoquinoline-3-carbonyl]-amino}-acetic acid Prepared in analogy to Example D-37 e) starting from 6-(4-Chloro-phenoxy)-4-hydroxy-isoquinoline-3-carboxylic acid butyl ester (compound D-129B). MS-(−)-ion: M−1=371.1.

Example D-131

{[6-(3-Fluoro-5-methoxy-phenoxy)-4-hydroxy-isoquinoline-3-carbonyl]-amino}-acetic acid a) 4-(3,4-Difluoro-phenoxy)-phthalonitrile Prepared in analogy to Example D-88 a). $^1$H NMR (200 MHz, DMSO) δ8.14 (d, J=9 Hz, 1H), 7.95 (d, J=2.6, 1H), 7.56 (dd, J=2.6, 8.6 Hz, 1H), 7.19 (dt, J=2.4, 9.2 Hz, 1H), 7.04 (m, 2H).

b) 4-(3-Fluoro-5-methoxy-phenoxy)-phthalic acid

Prepared in analogy to Example D-1 a). One of the fluoro group is substituted by a methoxy group during the hydrolysis. MS-(−)-ion: M−1=305.0.

c) [5-(3-Fluoro-5-methoxy-phenoxy)-1,3-dioxo-1,3-dihydro-isoindol-2-yl]-acetic acid butyl ester Prepared in analogy to Example D-100 c). $^1$H NMR (200 MHz, DMSO) δ7.93 (d, J=8.6 Hz, 1H), 7.43 (m, 2H), 6.79-6.63 (m, 3H), 4.41 (s, 2H), 4.10 (t, J=6.2, 2H), 1.54 (m, 2H), 1.30 (m, 2H), 0.86 (t, J=7.0, 3H).

d) 6- and 7-(3-Fluoro-5-methoxy-phenoxy)-1,4-dihydroxy-isoquinoline-3-carboxylic acid butyl ester Prepared in analogy to Example D-1d). Mixture of two isomers. MS-(−)-ion:
M−1=400.1.

e) 1-Chloro-6- and 7-(3-fluoro-5-methoxy-phenoxy)-4-hydroxy-isoquinoline-3-carboxylic acid butyl ester Prepared in analogy to Example D-43 d). Mixture of two isomers. MS-(−)-ion:
M−1=418.3.

f) 6- and 7-(3-Fluoro-5-methoxy-phenoxy)-4-hydroxy-isoquinoline-3-carboxylic acid butyl ester To a solution of 1-chloro-6- and 7-(3-fluoro-5-methoxy-phenoxy)-4-hydroxy-isoquinoline-3-carboxylic acid butyl ester (176 mg) in ethyl acetate (3 ml) was added 10% Pd/C (50% wet, 70 mg) and then ammonium formate (264 mg). Resulting mixture was heated to reflux for 0.5 h. After cooling, the reaction mixture was diluted with ethyl acetate and filtered through a pad of Celite. Filtrate was concentrated and separated by chromatography to give 64 mg 7-(3-fluoro-5-methoxy-phenoxy)-4-hydroxy-isoquinoline-3-carboxylic acid butyl ester (Compound D-131A) and 74 mg 6-(3-fluoro-5-methoxy-phenoxy)-4-hydroxy-isoquinoline-3-carboxylic acid butyl ester (Compound D-131B): $^1$H NMR (200 MHz, CD3OD) δ8.73 (s, 1H), 8.15 (d, J=9.0 Hz, 1H), 7.71 (s, 1H), 7.59 (m, 1H), 6.65-6.47 (m, 3H), 4.49 (t, J=6.6 Hz, 2H), 3.81 (s, 3H), 1.87 (m, 2H), 1.56 (m, 2H), 1.03 (t, J=7.4. 3H).

g) {[6-(3-Fluoro-5-methoxy-phenoxy)-4-hydroxy-isoquinoline-3-carbonyl]-amino}-acetic acid Prepared in analogy to Example D-37 e) starting from 6-(3-fluoro-5-methoxy-phenoxy)-4-hydroxy-isoquinoline-3-carboxylic acid butyl ester (compound D-131B). MS-(−)-ion: M−1=385.1.

Example D-132

{[7-(3-Fluoro-5-methoxy-phenoxy)-4-hydroxy-isoquinoline-3-carbonyl]-amino}-acetic acid Prepared in analogy to Example D-37 e) starting from 7-(3-fluoro-5-methoxy-phenoxy)-4-hydroxy-isoquinoline-3-carboxylic acid butyl ester (compound D-131A). MS-(−)-ion: M−1=385.1.

Example D-133

{[7-(3,4-Difluoro-phenoxy)-4-hydroxy-isoquinoline-3-carbonyl]-amino}-acetic acid a) 5-(3,4-Difluoro-phenoxy)-isoindole-1,3-dione 3,4-Difluorophenol (650 mg) was azeotroped with benzene and dissolved in sodium methoxide solution in methanol (0.5 M, 10 ml). The methanol was then removed under reduced pressure under nitrogen. Then an anhydrous DMF (10 ml) solution of 4-nitrophthalimide (769 mg) was added to the previous mixture. The resulting mixture was refluxed under nitrogen for 23 h. The reaction was cooled down and added 80 ml water. The resulting precipitate was filtered, washed with water (4×) and dried to give the title compound 685 mg. MS-(−)-ion: M−1=274.3.

b) [5-(3,4-Difluoro-phenoxy)-1,3-dioxo-1,3-dihydro-isoindol-2-yl]-acetic acid methyl ester To a pressure tube was added 5-(3,4-difluoro-phenoxy)-isoindole-1,3-dione (680 mg), potassium carbonate (1 g), 3-pentanone (20 ml), and methyl bromoacetate (295 µL). The resulting mixture was heated to 105° C. for 17 h. The reaction was diluted with 20 ml water and extracted with ethyl acetate (2×). The organic layer was dried and concentrated. The mixture was purified through silica gel chromatography with 4:1 hexanes/ethyl acetate and 3:1 hexanes/ethyl acetate to give 657 mg of the title compound.): $^1$H NMR (200 MHz, DMSO) δ7.95 (d, J=9.0 Hz, 1H), 7.64-7.41 (m, 4H), 7.15-7.08 (m, 1H), 4.44 (s, 2H), 3.70 (s, 3H).

c) 6- and 7-(3,4-Difluoro-phenoxy)-1,4-dihydroxy-isoquinoline-3-carboxylic acid butyl ester Prepared in analogy to Example D-1d). Mixture of two isomers. MS-(−)-ion:
M−1=388.1.

d) 1-Chloro-6- and 7-(3,4-difluoro-phenoxy)-4-hydroxy-isoquinoline-3-carboxylic acid butyl ester Prepared in analogy to Example D-43 d). Mixture of two isomers was directly carried on to next step.

e) 6- and 7-(3,4-Difluoro-phenoxy)-4-hydroxy-isoquinoline-3-carboxylic acid butyl ester Prepared in analogy to Example D-131 f). The two isomers were separated to give 7-(3,4-difluoro-phenoxy)-4-hydroxy-isoquinoline-3-carboxylic acid butyl ester (Compound D-133A) and 6-(3,4-difluoro-phenoxy)-4-hydroxy-isoquinoline-3-carboxylic acid butyl ester (Compound 133B).

f) {[7-(3,4-Difluoro-phenoxy)-4-hydroxy-isoquinoline-3-carbonyl]-amino}-acetic acid Prepared in analogy to Example D-37 e) starting from 7-(3,4-difluoro-phenoxy)-4-hydroxy-isoquinoline-3-carboxylic acid butyl ester (compound D-133A). MS-(−)-ion: M−1=373.2.

Example D-134

{[6-(3,4-Difluoro-phenoxy)-4-hydroxy-isoquinoline-3-carbonyl]-amino}-acetic acid a) {[6-(3,4-Difluoro-phenoxy)-4-hydroxy-isoquinoline-3-carbonyl]-amino}-acetic acid Prepared in analogy to Example D-37 e) starting from 6-(3,4-difluoro-phenoxy)-4-hydroxy-isoquinoline-3-carboxylic acid butyl ester (compound D-133B). MS-(−)-ion: M−1=373.2.

Example D-135

{[4-Hydroxy-7-(4-trifluoromethoxy-phenoxy)-isoquinoline-3-carbonyl]-amino}-acetic acid a)
5-(4-Trifluoromethoxy-phenoxy)-isoindole-1,3-dione Prepared in analogy to Example D-133 a). MS-(−)-ion: M−1=322.3.

b) [1,3-Dioxo-5-(4-trifluoromethoxy-phenoxy)-1,3-dihydro-isoindol-2-yl]-acetic acid methyl ester Prepared in analogy to Example D-133 b) by refluxing overnight. $^1$H NMR (200 MHz, CDCl$_3$) δ7.83 (d, J=8.6, 1H), 7.34-7.24 (m, 4H), 7.09 (d, J=8.6, 2H), 4.42 (s, 2H), 3.76 (s, 3H).

c) 1,4-Dihydroxy-6- and 7-(3-trifluoromethoxy-phenoxy)-isoquinoline-3-carboxylic acid butyl ester Prepared in analogy to Example D-1d). Mixture of two isomers. MS-(−)-ion: M−1=436.2.

d) 1-Chloro-4-hydroxy-6- and 7-(3-trifluoromethoxy-phenoxy)-isoquinoline-3-carboxylic acid butyl ester Prepared in analogy to Example D-43 d) by using microwave reactor with toluene as solvent and with 1.5 equivalent of POCl$_3$. Mixture of two isomers was directly carried on to next step.

e) 4-Hydroxy-6- and 7-(3-trifluoromethoxy-phenoxy)-isoquinoline-3-carboxylic acid butyl ester Prepared in analogy to Example D-131 f). The two isomers were separated to give 4-hydroxy-7-(3-trifluoromethoxy-phenoxy)-isoquinoline-3-carboxylic acid butyl ester (Compound D-135A): MS-(+)-ion: M+1=422.2 and 4-hydroxy-6-(3-trifluoromethoxy-phenoxy)-isoquinoline-3-carboxylic acid butyl ester (Compound D-135B): MS-(−)-ion: M−1=420.6.

f) {[4-Hydroxy-7-(4-trifluoromethoxy-phenoxy)-isoquinoline-3-carbonyl]-amino}-acetic acid Prepared in analogy to Example D-37 e) starting from 4-hydroxy-7-(3-trifluoromethoxy-phenoxy)-isoquinoline-3-carboxylic acid butyl ester (compound D-135A). MS-(−)-ion: M−1=421.2.

Example D-136

{[4-Hydroxy-6-(4-trifluoromethoxy-phenoxy)-isoquinoline-3-carbonyl]-amino}-acetic acid Prepared in analogy to Example D-37 e) starting from 4-hydroxy-6-(3-trifluoromethoxy-phenoxy)-isoquinoline-3-carboxylic acid butyl ester (Compound D-135B). MS-(−)-ion: M−1=421.1.

Example D-137

{[7-(3,5-Difluoro-phenoxy)-4-hydroxy-isoquinoline-3-carbonyl]-amino}-acetic acid a) [5-(3,5-Difluoro-phenoxy)-1,3-dioxo-1,3-dihydro-isoindol-2-yl]-acetic acid ethyl ester To an 80 mL microwave reaction vessel was added (5-nitro-1,3-dioxo-1,3-dihydro-isoindol-2-yl)-acetic acid ethyl ester (2 g), 3,5-difluorophenol (1.12 g), potassium carbonate (1.39 g), and dimethyl acetamide (27 mL). The resulting mixture was reacted in the microwave at 100° C. for 10 min. Water (280 mL) was added and the resulting precipitate was filtered, washed with water and dried. Further purification by silica gel chromatography generated 0.94 g of the title compound. $^1$H NMR (200 MHz, CDCl$_3$) δ7.86 (d, J=8.2 Hz, 1H), 7.41-7.31 (m, 2H), 6.67-6.57 (m, 3H), 4.41 (s, 2H), 4.22 (q, J=7.1 Hz, 2H), 1.29 (t, J=7.0 Hz, 3H).

b) 6- and 7-(3,5-Difluoro-phenoxy)-1,4-dihydroxy-isoquinoline-3-carboxylic acid butyl ester The title product was prepared in analogy to Example D-1d). Mixture of two isomers resulted. MS-(+)-ion: M+1=390.1.

c) 1-Chloro-6- and 7-(3,5-difluoro-phenoxy)-4-hydroxy-isoquinoline-3-carboxylic acid butyl ester Prepared in analogy to Example D-43 d) except that reaction was carried out in microwave reactor at 135° C. for 10 min, using toluene as solvent and 1.5 eq. POCl$_3$. Mixture of two isomers resulted. MS-(−)-ion: M−1=406.2.

d) 6- and 7-(3,5-Difluoro-phenoxy)-4-hydroxy-isoquinoline-3-carboxylic acid butyl ester Prepared in analogy to Example D-131 f). The two isomers were separated to give 7-(3,5-Difluoro-phenoxy)-4-hydroxy-isoquinoline-3-carboxylic acid butyl ester (Compound D-137A): MS-(−)-ion: M−1=372.2 and 6-(3,5-Difluoro-phenoxy)-4-hydroxy-isoquinoline-3-carboxylic acid butyl ester (Compound D-137B): MS-(+)-ion: M+1=374.1.

e) {[7-(3,5-Difluoro-phenoxy)-4-hydroxy-isoquinoline-3-carbonyl]-amino}-acetic acid Prepared in analogy to Example D-37 e) starting from 7-(3,5-Difluoro-phenoxy)-4-hydroxy-isoquinoline-3-carboxylic acid butyl ester (compound D-137A). MS-(−)-ion: M−1=373.1.

Example D-138

{[6-(3,5-Difluoro-phenoxy)-4-hydroxy-isoquinoline-3-carbonyl]-amino}-acetic acid a) {[6-(3,5-Difluoro-phenoxy)-4-hydroxy-isoquinoline-3-carbonyl]-amino}-acetic acid Prepared in analogy to Example D-37 e) starting from 6-(3,5-difluoro-phenoxy)-4-hydroxy-isoquinoline-3-carboxylic acid butyl ester (compound D-137B). MS-(−)-ion: M−1=373.1.

Example D-139

({7-[4-(4-Fluoro-phenoxy]-phenoxyl-4-hydroxy-isoquinoline-3-carbonyl}-amino)-acetic acid a) {5-[4-(4-Fluoro-phenoxy)-phenoxy]-1,3-dioxo-1,3-dihydro-isoindol-2-yl}-acetic acid ethyl ester Prepared in analogy to Example D-137 a) by reacting (5-nitro-1,3-dioxo-1,3-dihydro-isoindol-2-yl)-acetic acid ethyl ester with 4-(4-fluoro-phenoxy)-phenol. $^1$H NMR (200 MHz, CDCl$_3$) δ7.80 (d, J=8.0 Hz, 1H), 7.31 (m, 2H), 7.06-7.01 (m, 8H), 4.39 (s, 2H), 4.21 (q, J=7.2, 2H), 1.30 (t, J=7.3, 3H).

b) 6- and 7-[4-(4-Fluoro-phenoxy)-phenoxy]-1,4-dihydroxy-isoquinoline-3-carboxylic acid butyl ester Prepared in analogy to Example D-1d). Mixture of two isomers resulted. MS-(−)-ion:
M−1=462.1.

c) 1-Chloro-6- and 7-[4-(4-fluoro-phenoxy)-phenoxy]-4-hydroxy-isoquinoline-3-carboxylic acid butyl ester Prepared in analogy to Example D-137 c). Mixture of two isomers resulted. MS-(+)-ion: M+1=482.1.

d) 6- and 7-[4-(4-Fluoro-phenoxy)-phenoxy]-4-hydroxy-isoquinoline-3-carboxylic acid butyl ester Prepared in analogy to Example D-131 f). The two isomers were separated to give 7-[4-(4-Fluoro-phenoxy)-phenoxy]-4-hydroxy-isoquinoline-3-carboxylic acid butyl ester (Compound D-139A): MS-(+)-ion: M+1=448.1 and 6-[4-(4-fluoro-phenoxy)-phenoxy]-4-hydroxy-isoquinoline-3-carboxylic acid butyl ester (Compound D-139B): MS-(+)-ion: M+1=448.2.

e) ({7-[4-(4-Fluoro-phenoxy)-phenoxy]-4-hydroxy-isoquinoline-3-carbonyl}-amino)-acetic acid The title product was prepared in analogy to Example D-37 e) starting from 7-[4-(4-fluoro-phenoxy)-phenoxy]-4-hydroxy-isoquinoline-3-carboxylic acid butyl ester (compound D-139A). MS-(−)-ion: M−1=447.1.

Example D-140

({6-[4-(4-Fluoro-phenoxy)-phenoxy]-4-hydroxy-isoquinoline-3-carbonyl}-amino)-acetic acid a) ({7-[4-(4-Fluoro-phenoxy)-phenoxy]-4-hydroxy-isoquinoline-3-carbonyl}-amino)-acetic acid The title product was prepared in analogy to Example D-37 e) starting from and 6-[4-(4-fluoro-phenoxy)-phenoxy]-4-hydroxy-isoquinoline-3-carboxylic acid butyl ester (Compound D-139B): MS-(−)-ion: M−1=447.1.

Example D-141

{[7-(3-Chloro-4-fluoro-phenoxy)-4-hydroxy-isoquinoline-3-carbonyl]-amino}-acetic acid a) 5-(3-Chloro-4-fluoro-phenoxy)-isoindole-1,3-dione The title product was prepared in analogy to Example D-133 a). MS-(−)-ion: M−1=290.5.

b) [5-(3-Chloro-4-fluoro-phenoxy)-1,3-dioxo-1,3-dihydro-isoindol-2-yl]-acetic acid methyl ester The title product was prepared in analogy to Example D-133 b). $^1$H NMR (200 MHz, CDCl$_3$) δ7.83 (d, J=8.2 Hz, 1H), 7.32-7.14 (m, 4H), 6.99 (m, 1H), 4.42 (s, 2H), 3.77 (s, 3H).

c) 6- and 7-(3-Chloro-4-fluoro-phenoxy)-1,4-dihydroxy-isoquinoline-3-carboxylic acid butyl ester Prepared in analogy to Example D-1d). Mixture of two isomers. MS-(−)-ion: M−1=404.1.

d) 1-Chloro-7-(3-chloro-4-fluoro-phenoxy)-4-hydroxy-isoquinoline-3-carboxylic acid butyl ester Prepared in analogy to Example D-137 c). Mixture of two isomers. MS-(−)-ion: M−1=422.2.

e) 6- and 7-(3-Chloro-4-fluoro-phenoxy)-4-hydroxy-isoquinoline-3-carboxylic acid butyl ester Prepared in analogy to Example D-1 f). The two isomers were separated to give 7-(3-chloro-4-fluoro-phenoxy)-4-hydroxy-isoquinoline-3-carboxylic acid butyl ester (Compound D-141A): $^1$H NMR (200 MHz, CDCl$_3$) δ11.91 (s, 1H), 8.64 (s, 1H), 8.38 (d, J=9.0 Hz, 1H), 7.46 (d, J=9.4, 1H), 7.24-7.16 (m, 3H), 7.04-6.98 (m, 1H), 4.50 (t, J=6.8, 2H), 1.88 (q, J=7.2, 2H), 1.58-1.40 (m, 2H), 0.99 (t, J=7.2, 3H); and 6-(3-Chloro-4-fluoro-phenoxy)-4-hydroxy-isoquinoline-3-carboxylic acid butyl ester (Compound D-141B). MS-(+)-ion: M+1=390.1.

{[7-(3,4-Difluoro-phenoxy)-4-hydroxy-isoquinoline-3-carbonyl]-amino}-acetic acid Prepared in analogy to Example D-37 e) starting from 7-(3-chloro-4-fluoro-phenoxy)-4-hydroxy-isoquinoline-3-carboxylic acid butyl ester (Compound D-141A). MS-(−)-ion: M−1=389.0.

Example D-142

{[6-(3-Chloro-4-fluoro-phenoxy)-4-hydroxy-isoquinoline-3-carbonyl]-amino}-acetic acid a) {[6-(3,4-Difluoro-phenoxy)-4-hydroxy-isoquinoline-3-carbonyl]-amino}-acetic acid Prepared in analogy to Example D-37 e) starting from 6-(3-chloro-4-fluoro-phenoxy)-4-hydroxy-isoquinoline-3-carboxylic acid butyl ester (Compound D-141B). MS-(−)-ion: M−1=389.0.

Example D-143

{[7-(4-Chloro-phenoxy)-4-hydroxy-1-methyl-isoquinoline-3-carbonyl]-amino}-acetic acid a) 6- and 7-(4-Chloro-phenoxy)-4-hydroxy-1-methyl-isoquinoline-3-carboxylic acid butyl ester Prepared in analogy to Example D-87 b) starting from a mixture of 1-chloro-6- and 7-(4-chloro-phenoxy)-4-hydroxy-isoquinoline-3-carboxylic acid butyl ester (prepared as in example D-129 e). However, the pH adjustment was omitted. The two isomers were separated to give 7-(4-chloro-phenoxy)-4-hydroxy-1-methyl-isoquinoline-3-carboxylic acid butyl ester (compound of example D-143 a) MS-(+)-ion M−1=386.1 and 6-(4-chloro-phenoxy)-4-hydroxy-1-methyl-isoquinoline-3-carboxylic acid butyl ester (compound of example D-143 b) MS-(+)-ion M−1=386.1.

b) {[7-(4-Chloro-phenoxy)-4-hydroxy-1-methyl-isoquinoline-3-carbonyl]-amino}-acetic acid Prepared in analogy to Example D-37 e) starting from 7-(4-chloro-phenoxy)-4-hydroxy-1-methyl-isoquinoline-3-carboxylic acid butyl ester (compound of example D-143 a) and reacting in a pressure tube overnight at 90 degree. MS-(−)-ion M−1=385.0.

Example D-144

{[6-(4-Chloro-phenoxy)-4-hydroxy-1-methyl-isoquinoline-3-carbonyl]-amino}-acetic acid a) {[6-(4-Chloro-phenoxy)-4-hydroxy-1-methyl-isoquinoline-3-carbonyl]-amino}-acetic acid Prepared in analogy to Example D-37 e) starting from 6-(4-chloro-phenoxy)-4-hydroxy-1-methyl-isoquinoline-3-carboxylic acid butyl ester (compound of example D-143 b) and reacting in a pressure tube overnight at 90 degree. MS-(−)-ion M−1=385.0.

Example D-145

{[7-(3,5-Difluoro-phenoxy)-4-hydroxy-1-methyl-isoquinoline-3-carbonyl]-amino}-acetic acid a) 6- and 7-(3,5-Difluoro-phenoxy)-4-hydroxy-1-methyl-isoquinoline-3-carboxylic acid butyl ester Prepared in analogy to Example D-87 b) starting from a mixture of 1-chloro-6- and 7-(3,5-difluoro-phenoxy)-4-hydroxy-isoquinoline-3-carboxylic acid butyl ester (prepared as in example D-137 c). The work-up procedure was slightly different in omitting the pH adjustment. The two isomers were separated to give 7-(3,5-difluoro-phenoxy)-4-hydroxy-1-methyl-isoquinoline-3-carboxylic acid butyl ester (compound D-145 a1) MS-(−)-ion M−1=386.3 and 6-(3,5-difluoro-phenoxy)-4-hydroxy-1-methyl-isoquinoline-3-carboxylic acid butyl ester (compound D-145 a2) MS-(−)-ion M−1=386.3.

b) {[7-(3,5-Difluoro-phenoxy)-4-hydroxy-1-methyl-isoquinoline-3-carbonyl]-amino}-acetic acid Prepared in analogy to Example D-37 e) starting from 7-(3,5-difluoro-phenoxy)-4-hydroxy-1-methyl-isoquinoline-3-carboxylic acid butyl ester (compound D-145 a1) and reacting in a pressure tube overnight at 90 degree. MS-(−)-ion M−1=387.1.

Example D-146

{[4-Hydroxy-7-(4-methoxy-phenoxy)-1-methyl-isoquinoline-3-carbonyl]-amino}-acetic acid a. 6- and 7-(4-Methoxy-phenoxy)-1-bromo-4-hydroxy-isoquinoline-3-carboxylic acid butyl ester A mixture of 6- and 7-(4-methoxy-phenoxy)-1,4-dihydroxy-isoquinoline-3-carboxylic acid butyl ester (Compound D-88 d) (3.0 g) and phosphorus oxybromide (3.4 g) in anhydrous toluene (40 ml) was heated in a microwave reactor (sealed tube) for 15 min at 130° C. After cooling, reaction mixture was concentrated and saturated sodium bicarbonate aqueous solution (100 ml) was added. Stirred for 20 min and then extracted with ethyl acetate (2×100 ml). Combined organic layers were washed with water, brine, dried over magnesium sulfate, filtered and concentrated to give the title compound (3.1 g). MS-(+)-ion M+1=446.05, 448.05.

b. 6- and 7-(4-Methoxy-phenoxy)-4-hydroxy-1-methyl-isoquinoline-3-carboxylic acid butyl ester A mixture of 6- and 7-(4-methoxy-phenoxy)-1-bromo-4-hydroxy-isoquinoline-3-carboxylic acid butyl ester (232 mg), Pd(PPh$_3$)$_4$ (60 mg), trimethylboroxine (65 mg) and potassium carbonate (216 mg) in dioxane (4 ml) was heated in a microwave reactor (sealed tube) for 10 min at 120° C. After cooling, the reaction mixture was diluted with water (15 ml). Acidified by 2 N HCl to pH=4. Extracted with ethyl acetate. Organic layer was washed with brine, dried over magnesium sulfate and filtered. Filtrated was concentrated and separated by silica gel chromatography (eluting with 25% to 50% ethyl acetate in hexanes) to give 7-(4-methoxy-phenoxy)-4-hydroxy-1-methyl-isoquinoline-3-carboxylic acid butyl ester (35 mg) (Compound D-146 b1) (MS-(+)-ion M+1=382.18) and 6-(4-methoxy-phenoxy)-4-hydroxy-1-methyl-isoquinoline-3-carboxylic acid butyl ester (61 mg) (Compound D-146 b2) (MS-(+)-ion M+1=382.16).

c) {[4-Hydroxy-7-(4-methoxy-phenoxy)-1-methyl-isoquinoline-3-carbonyl]-amino}-acetic acid Prepared from 7-(4-methoxy-phenoxy)-4-hydroxy-1-methyl-isoquinoline-3-carboxylic acid butyl ester (Compound D-146 b1) in analogy to Example D-107 b) (microwave reaction temperature 120° C., reaction time 10 min). MS-(−)-ion M−1=381.09.

Example D-147

{[4-Hydroxy-6-(4-methoxy-phenoxy)-1-methyl-isoquinoline-3-carbonyl]-amino}-acetic acid Prepared from 6-(4-methoxy-phenoxy)-4-hydroxy-1-methyl-isoquinoline-3-carboxylic acid butyl ester (Compound D-146 b2) in analogy to Example D-146 c). MS-(−)-ion M−1=381.10.

Example D-148

[(6-Cyclohexyloxy-4-hydroxy-isoquinoline-3-carbonyl)-amino]-acetic acid a. (5-Hydroxy-1,3-dioxo-1,3-dihydro-isoindol-2-yl)-acetic acid ethyl ester

Prepared in analogy to example D-100 c) from 4-hydroxy-phthalic acid and glycine ethyl ester HCl salt. $^1$H NMR (200 MHz, DMSO-d6) δ11.0 (br s, 1H), 7.74 (d, J=7.8 Hz, 1H), 7.17 (m, 2H), 4.35 (s, 2H), 4.13 (q, J=7.0 Hz, 2H), 1.20 (t, J=7.0 Hz, 3H).

b. (5-Cyclohexyloxy-1,3-dioxo-1,3-dihydro-isoindol-2-yl)-acetic acid ethyl ester To a mixture of (5-hydroxy-1,3-dioxo-1,3-dihydro-isoindol-2-yl)-acetic acid ethyl ester (8.0 g) in anhydrous tetrahydrofuran (160 ml) was added cyclohexanol (3.2 g), diethylazadicarboxylate (6.9 g) and then triphenyl phosphine (12.6 g). Resulting mixture was stirred at room temperature overnight and concentrated. Residue was partitioned between water and ethyl acetate. Aqueous layer was extracted with ethyl acetate. Combined organic layers were washed with brine, dried over magnesium sulfate and filtered. Filtrate was concentrated and purified by silica gel chromatography (eluting with 5% ethyl acetate in methylene chloride) to give the title compound (6.2 g). $^1$H NMR (200 MHz, CDCl$_3$) δ7.73 (dd, J=8.2, 0.8 Hz, 1H), 7.30 (br s, 1H), 7.12 (m, 1H), 4.38 (m, 3H), 4.21 (q, J=7.1 Hz, 2H), 2.02 (m, 2H), 1.82-1.25 (m, 13H).

c. 6- and 7-Cyclohexyloxy-1,4-dihydroxy-isoquinoline-3-carboxylic acid butyl ester Prepared in analogy to Example D-1 d) to give 7-cyclohexyloxy-1,4-dihydroxy-isoquinoline-3-carboxylic acid butyl ester (Compound D-148 c1) (MS-(+)-ion M+1=360.16) and 6-cyclohexyloxy-1,4-dihydroxy-isoquinoline-3-carboxylic acid butyl ester (Compound D-148 c2) (MS-(+)-ion M+1=360.18).

d. 1-Bromo-6-cyclohexyloxy-4-hydroxy-isoquinoline-3-carboxylic acid butyl ester Prepared in analogy to Example D-146 a) from 6-cyclohexyloxy-1,4-dihydroxy-isoquinoline-3-carboxylic acid butyl ester (Compound D-148 c2). MS-(+)-ion M+1=422.10, 424.10.

e. 6-Cyclohexyloxy-4-hydroxy-isoquinoline-3-carboxylic acid butyl ester

To a mixture of 1-bromo-6-cyclohexyloxy-4-hydroxy-isoquinoline-3-carboxylic acid butyl ester (1.0 g) in ethyl acetate (20 ml) was added 10% Pd/C (50% wet) (460 mg) and then ammonium formate (1.5 g). Resulting mixture was refluxed for 4 h. After cooling, reaction mixture was filtered and concentrated. The residue was purified by silica gel chromatography (5%-10% ethyl acetate in methylene chloride) to give the title compound (640 mg). MS-(+)-ion M+1=344.22.

f. [(6-Cyclohexyloxy-4-hydroxy-isoquinoline-3-carbonyl)-amino]-acetic acid

Prepared in analogy to Example D-146 c). MS-(−)-ion M−1=343.15.

Example D-149

[(7-Cyclohexyloxy-4-hydroxy-isoquinoline-3-carbonyl)-amino]-acetic acid a. 1-Bromo-7-cyclohexyloxy-4-hydroxy-isoquinoline-3-carboxylic acid butyl ester Prepared in analogy to Example D-146 a) from 7-cyclohexyloxy-1,4-dihydroxy-isoquinoline-3-carboxylic acid butyl ester (Compound D-148 c1). MS-(+)-ion M+1=422.12, 424.12.

b. 7-Cyclohexyloxy-4-hydroxy-isoquinoline-3-carboxylic acid butyl ester

Prepared in analogy to Example D-148 e). MS-(+)-ion M+1=344.22.

c. [(7-Cyclohexyloxy-4-hydroxy-isoquinoline-3-carbonyl)-amino]-acetic acid

Prepared in analogy to Example D-146 c). MS-(−)-ion M−1=343.17.

Example D-150

[(7-Cyclohexyloxy-4-hydroxy-1-methyl-isoquinoline-3-carbonyl)-amino]-acetic acid a. 7-Cyclohexyloxy-4-hydroxy-1-methyl-isoquinoline-3-carboxylic acid butyl ester Prepared in analogy to Example D-146 b). MS-(+)-ion M+1=358.21.

b. [(7-Cyclohexyloxy-4-hydroxy-1-methyl-isoquinoline-3-carbonyl)-amino]-acetic acid Prepared in analogy to Example D-146 c). MS-(+)-ion M+1=359.15.

Example D-151

[(7-Cyclohexylsulfanyl-4-hydroxy-isoquinoline-3-carbonyl)-amino]-acetic acid a. (5-Cyclohexylsulfanyl-1,3-dioxo-1,3-dihydro-isoindol-2-yl)-acetic acid ethyl ester A mixture of 5-nitro-isoindole-1,3-dione (10.0 g), cyclohexanethiol (9.1 g) and potassium carbonate (18.7 g) in acetone (260 ml) was heated to reflux overnight. After cooling, the mixture was diluted with water (250 ml) and then acidified by 6 N HCl to pH=4. Precipitate was collected and dried in vacuo to give the intermediate 5-cyclohexylsulfanyl-isoindole-1,3-dione (15.6 g). This intermediate was dissolved in acetone (170 ml) and to the mixture was added bromo ethylacetate (10.6 g) and potassium carbonate (23.8 g). The mixture was refluxed overnight. After cooling, reaction mixture was filtered and rinsed with ethyl acetate.

Filtrate was concentrated and purified by silica gel chromatography (10%-50% ethyl acetate in methylene chloride) to give the title compound (13.1 g). $^1$H NMR (200 MHz, CDCl$_3$) δ7.73 (m, 2H), 7.56 (dd, J=7.8, 1.6 Hz, 1H), 4.40 (s, 2H), 4.21 (q, J=7.0 Hz, 2H), 3.37 (m, 1H), 2.07-1.28 (m, 13H).

b. 6- and 7-Cyclohexylsulfanyl-1,4-dihydroxy-isoquinoline-3-carboxylic acid butyl ester Prepared in analogy to Example D-21 b). MS-(+)-ion M+1=376.20.

c. 6- and 7-Cyclohexylsulfanyl-1-chloro-4-hydroxy-isoquinoline-3-carboxylic acid butyl ester A mixture of 6- and 7-cyclohexylsulfanyl-1,4-dihydroxy-isoquinoline-3-carboxylic acid butyl ester (1.0 g) and phosphorus oxychloride (491 mg) in anhydrous toluene (14 ml) was heated in a microwave reactor (sealed tube) (180° C., 30 min). After cooling, reaction mixture was quenched with saturated sodium bicarbonate. Stirred at room temperature for 20 min. and extracted with ethyl acetate twice. Combined organic layers were washed with water, brine, dried over magnesium sulfate, filtered, and concentrated to give the title compound (0.5 g). MS-(+)-ion M+1=394.12.

d. 6- and 7-Cyclohexylsulfanyl-4-hydroxy-isoquinoline-3-carboxylic acid butyl ester Prepared in analogy to Example D-1 f) to give 7-cyclohexylsulfanyl-4-hydroxy-isoquinoline-3-carboxylic acid butyl ester (128 mg) (Compound D-151 d1) (MS-(+)-ion M+1=360.15) and 6-cyclohexylsulfanyl-4-hydroxy-isoquinoline-3-carboxylic acid butyl ester (130 mg) (Compound D-151 d2) (MS-(+)-ion M+1=360.17).

e) [(7-Cyclohexylsulfanyl-4-hydroxy-isoquinoline-3-carbonyl)-amino]-acetic acid Prepared in analogy to Example D-1 g) from 7-cyclohexylsulfanyl-4-hydroxy-isoquinoline-3-carboxylic acid butyl ester (Compound D-151 d1). MS-(−)-ion M−1=359.11.

Example D-152

[(7-Cyclohexanesulfonyl-4-hydroxy-isoquinoline-3-carbonyl)-amino]-acetic acid a) 7-Cyclohexanesulfonyl-4-hydroxy-isoquinoline-3-carboxylic acid butyl ester A mixture of 7-cyclohexylsulfanyl-4-hydroxy-isoquinoline-3-carboxylic acid butyl ester (Compound D-151 d1) (64 mg) and m-chloroperoxybenzoic acid (111 mg) in methylene chloride (2 ml) was stirred at room temperature overnight. It was diluted with methylene chloride (50 ml) and washed successively with saturated sodium bicarbonate aqueous solution (2×50 ml), water, and brine. The organic layer was dried over magnesium sulfate and filtered. Filtrate was concentrated and purified by silica gel chromatography (eluting with 3%-15% ethyl acetate in methylene chloride) to give the title compound (70 mg). MS-(+)-ion M+1=392.20.

b. [(7-Cyclohexanesulfonyl-4-hydroxy-isoquinoline-3-carbonyl)-amino]-acetic acid Prepared in analogy to Example D-146 c). MS-(−)-ion M−1=391.05.

Example D-153

[(4-Hydroxy-1-isobutyl-isoquinoline-3-carbonyl)-amino]-acetic acid a. 4-Benzyloxy-1-isobutyl-isoquinoline-3-carboxylic acid butyl ester

A mixture of 4-Benzyloxy-1-bromo-isoquinoline-3-carboxylic acid butyl ester (207 mg, 0.5 mmol, see example D-86a), Pd(PPh$_3$)$_4$ (58 mg, 0.05 mmol), 2-methylpropylboronic acid (78 mg, 0.75 mmol), K$_2$CO$_3$ (207 mg, 1.5 mmol), and 1,4-dioxane (4 ml) was refluxed with stirring for 48 h. Subsequently, the mixture was concentrated in vacuo. To the residue was added water (5 ml) and the mixture was extracted with EtOAc (2×20 ml). The organic phase was dried over MgSO$_4$ and evaporated in vacuo. Purification of the residue by flash column chromatography on silica gel using hexanes EtOAc=88 12 as the eluent gave the title compound as a yellowish oil (136 mg); MS-(+)-ion M+1=392.3.

b) 4-Hydroxy-1-isobutyl-isoquinoline-3-carboxylic acid butyl ester

A mixture of 4-Benzyloxy-1-isobutyl-isoquinoline-3-carboxylic acid butyl ester (125 mg, 0.32 mmol), Pd/C (50 mg, Aldrich, 10 wt % Pd) and EtOAc (15 ml) were stirred at ambient pressure and temperature under an H$_2$ atmosphere for 24 h. The mixture was then filtered through a pad of celite. Concentration of the filtrate in vacuo yielded the title compound as a yellowish oil (87 mg); MS-(+)-ion M+1=302.2.

c) [(4-Hydroxy-1-isobutyl-isoquinoline-3-carbonyl)-amino]-acetic acid

Synthesized from 4-Hydroxy-1-isobutyl-isoquinoline-3-carboxylic acid butyl ester in analogy to example D-1 g); MS-(+)-ion M+1=303.2.

Example D-154

[(4-Hydroxy-1-pyridin-2-yl-isoquinoline-3-carbonyl)-amino]-acetic acid a. 4-Benzyloxy-1-pyridin-2-yl-isoquinoline-3-carboxylic acid butyl ester

To a solution of Pyridin-2-ylboronic acid (323 mg, 2.5 mmol) in EtOH (2.5 ml) was added subsequently toluene (15 ml), 4-Benzyloxy-1-bromo-isoquinoline-3-carboxylic acid butyl ester (1.035 mg, 2.5 mmol, see example D-86a), Pd(PPh$_3$)$_4$ (292 mg, 0.25 mmol), and aq. 2 M Na$_2$CO$_3$ solution (2.5 ml, 5 mmol). The mixture was then refluxed with stirring under N$_2$ protection for 24 h. Subsequently, the mixture was concentrated in vacuo. To the residue was added water (15 ml) and the mixture was extracted with EtOAc (30 ml). The organic phase was dried over MgSO$_4$ and evaporated in vacuo. Purification of the residue by flash column chromatography on silica gel using $CH_2Cl_2$ MeOH=98 2 as the eluent gave a dark oil that was further purified by flash column chromatography on silica gel using $CH_2Cl_2$ MeOH=99 1 as the eluent and subsequently by preparative TLC using $CH_2Cl_2$ MeOH=98 2 as the eluent (had to be repeated several times) to give the title compound as a yellow oil (19 mg); MS-(+)-ion M+1=413.2.

b) 4-Hydroxy-1-pyridin-2-yl-isoquinoline-3-carboxylic acid butyl ester

Synthesized from 4-Benzyloxy-1-pyridin-2-yl-isoquinoline-3-carboxylic acid butyl ester in analogy to example D-153b); MS-(−)-ion M−1=321.4.

c) [(4-Hydroxy-1-pyridin-2-yl-isoquinoline-3-carbonyl)-amino]-acetic acid

Synthesized from 4-Hydroxy-1-pyridin-2-yl-isoquinoline-3-carboxylic acid butyl ester in analogy to example D-1 g); MS-(+)-ion M+1=324.1.

Example D-155

[(1-Ethyl-4-hydroxy-7-phenoxy-isoquinoline-3-carbonyl)-amino]-acetic acid a. 4-Hydroxy-7-phenoxy-1-vinyl-isoquinoline-3-carboxylic acid butyl ester A mixture of 1-Bromo-4-hydroxy-7-phenoxy-isoquinoline-3-carboxylic acid butyl ester (416 mg, 1 mmol, see example D-28a), $Pd(PPh_3)_4$ (118 mg, 0.1 mmol), 2,4,6-Trivinylcyclotriboroxane-pyridine complex (241 mg, 1 mmol), $K_2CO_3$ (414 mg, 3 mmol), and 1,4-dioxane (8 ml) was refluxed with stirring under $N_2$ protection for 3 h. Subsequently, the mixture was concentrated in vacuo. To the residue was added water (5 ml) and the mixture was extracted with EtOAc (20 ml). The organic phase was dried over $MgSO_4$ and evaporated in vacuo. Purification of the residue by flash column chromatography on silica gel using hexanes EtOAc=98 2 as the eluent gave the title compound as a yellowish solid (65 mg); MS-(+)-ion M+1=364.1.

b) 1-Ethyl-4-hydroxy-7-phenoxy-isoquinoline-3-carboxylic acid butyl ester

Synthesized from 4-Hydroxy-7-phenoxy-1-vinyl-isoquinoline-3-carboxylic acid butyl ester in analogy to example D-153b); MS-(+)-ion M+1=366.1.

c) [(1-Ethyl-4-hydroxy-7-phenoxy-isoquinoline-3-carbonyl)-amino]-acetic acid

Synthesized from 1-Ethyl-4-hydroxy-7-phenoxy-isoquinoline-3-carboxylic acid butyl ester in analogy to example D-1 g); MS-(+)-ion M+1=367.1.

Example D-156

[(1-Dimethylaminomethyl-4-hydroxy-7-phenylsulfanyl-isoquinoline-3-carbonyl)-amino]-acetic acid a. 1-Dimethylaminomethyl-4-hydroxy-7-phenylsulfanyl-isoquinoline-3-carboxylic acid butyl ester A mixture of 4-Hydroxy-7-phenylsulfanyl-isoquinoline-3-carboxylic acid butyl ester (177 mg, 0.5 mmol; see example D-1f), N,N-dimethylmethyleneammonium iodide (94 mg, 0.5 mmol), $K_2CO_3$ (104 mg, 0.75 mmol), and anhydrous $CH_2Cl_2$ (3 ml) was stirred at ambient temperature for 2.5 d before the mixture was concentrated in vacuo. To the residue was added water (15 ml), the mixture was acidified by addition of 6 N HCl and then washed with $Et_2O$ (3×30 ml). Subsequently, the mixture was neutralized by the addition of concentrated aqueous $NaHCO_3$ and extracted with EtOAc (20 ml). The organic phase was dried over $MgSO_4$ and concentrated in vacuo to give the title compound as a dark oil (34 mg); MS-(+)-ion M+1=411.1.

b) [(1-Dimethylaminomethyl-4-hydroxy-7-phenylsulfanyl-isoquinoline-3-carbonyl)-amino]-acetic acid Synthesized from 1-Dimethylaminomethyl-4-hydroxy-7-phenylsulfanyl-isoquinoline-3-carboxylic acid butyl ester in analogy to example D-1 g); MS-(+)-ion M+1=412.0.

Example D-157

[(4-Hydroxy-1-methyl-7-phenylsulfanyl-isoquinoline-3-carbonyl)-amino]-acetic acid a) 1-Bromo-4-hydroxy-7-phenylsulfanyl-isoquinoline-3-carboxylic acid 1,4-Dihydroxy-7-phenylsulfanyl-isoquinoline-3-carboxylic acid butyl ester (Example D-1 d) Compound A) (29.0 g) and phosphorous oxybromide (67.5 g) in 600 ml anhydrous acetonitrile was stirred at reflux for 4 hours. After cooling the reaction mixture was concentrated and saturated sodium bicarbonate solution and ethyl acetate were added to the residue and stirred overnight. Precipitate that formed between layers was collected and washed with water to give the title compound (10.2 g). MS-(+)-ion M+1=376.0, 378.1.

b) 1-Bromo-4-hydroxy-7-phenylsulfanyl-isoquinoline-3-carboxylic acid methyl ester 1-Bromo-4-hydroxy-7-phenylsulfanyl-isoquinoline-3-carboxylic acid (10.0 g), potassium carbonate (3.7 g) and methyl sulfate (3.4 g) were suspended in 500 ml acetone and stirred at reflux overnight. Reaction mixture was concentrated and residue partitioned between 1 N hydrochloric acid and ethyl acetate. Organic layer was dried over magnesium sulfate and filtered. Filtrate concentrated to give title compound (9.6 g). MS-(+)-ion M+1=389.9, 391.9.

c) 4-Hydroxy-1-methyl-7-phenylsulfanyl-isoquinoline-3-carboxylic acid methyl ester 1-Bromo-4-hydroxy-7-phenylsulfanyl-isoquinoline-3-carboxylic acid methyl ester (0.2 g), tetrakis(triphenylphos phine)palladium (60 mg), trimethyl boroxine (65 mg), and potassium carbonate in 1,4-dioxane (4 ml) were heated in a microwave reactor (sealed tube) for 10 min at 140° C. After cooling reaction mixture was concentrated and partitioned between 1 N hydrochloric acid and ethyl acetate. Organic layer dried over magnesium sulfate and filtered. Filtrate concentrated and separated by silica gel chromatography (eluting with 2% ethyl acetate in methylene chloride) to give the title compound (47 mg). MS-(+)-ion M+1=326.1.

d) [(4-Hydroxy-1-methyl-7-phenylsulfanyl-isoquinoline-3-carbonyl)-amino]-acetic acid Prepared in analogy to Example D-146 c). MS-(+)-ion M+1=369.1.

Example D-158

{[4-Hydroxy-1-methyl-7-(4-trifluoromethyl-phenoxy)-isoquinoline-3-carbonyl]-amino}-acetic acid a. 4-Hydroxy-1-methyl-7-(4-trifluoromethyl-phenoxy)-isoquinoline-3-carboxylic acid butyl ester Prepared in analogy to Example D-157 d) from 4-hydroxy-1-chloro-7-(4-trifluoromethyl-phenoxy)-isoquinoline-3-carboxylic acid butyl ester (of Example D-92 f). MS-(+)-ion M+1=420.2.

b) {[4-Hydroxy-1-methyl-7-(4-trifluoromethyl-phenoxy)-isoquinoline-3-carbonyl]-amino}-acetic acid Prepared in analogy to Example D-146 c). MS-(+)-ion M+1=421.2.

What is claimed is:

1. A method of treating anemia associated with chronic kidney disease in a patient undergoing dialysis, comprising administering to the patient a therapeutically effective amount of a compound of formula:

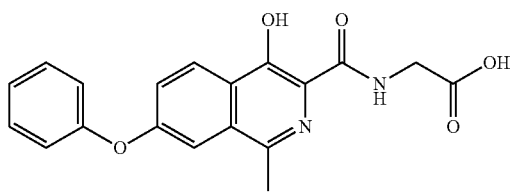 [SMILES: Cc1nc(C(=O)NCC(=O)O)c(O)c2ccc(Oc3ccccc3)cc12]

or a pharmaceutically acceptable salt thereof.

2. The method of claim 1, wherein the patient has been diagnosed with hypertension.

3. The method of claim 1, wherein the patient has been diagnosed with diabetes.

4. A method of treating anemia associated with chronic kidney disease in a patient undergoing dialysis, comprising administering to the patient a therapeutically effective amount of a compound of formula:

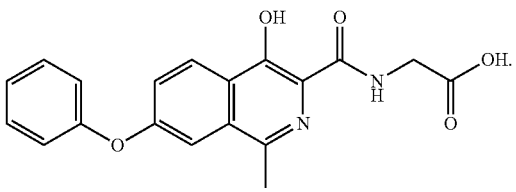 [SMILES: Cc1nc(C(=O)NCC(=O)O)c(O)c2ccc(Oc3ccccc3)cc12]

5. The method of claim 4, wherein the patient has been diagnosed with hypertension.

6. The method of claim 4, wherein the patient has been diagnosed with diabetes.

7. A method of treating anemia associated with chronic kidney disease in a patient who is not undergoing dialysis, comprising administering to the patient a therapeutically effective amount of a compound of formula:

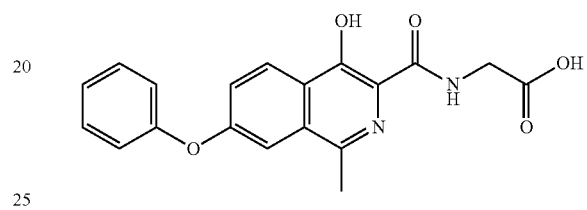

or a pharmaceutically acceptable salt thereof.

8. The method of claim 7, wherein the patient has been diagnosed with hypertension.

9. The method of claim 7, wherein the patient has been diagnosed with diabetes.

10. A method of treating anemia associated with chronic kidney disease in a patient who is not undergoing dialysis, comprising administering to the patient a therapeutically effective amount of a compound of formula:

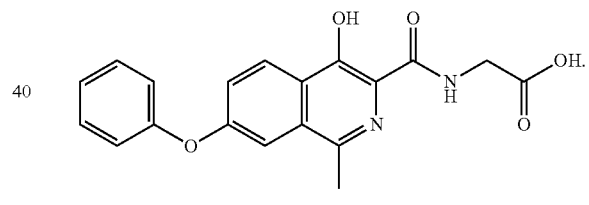

11. The method of claim 10, wherein the patient has been diagnosed with hypertension.

12. The method of claim 10, wherein the patient has been diagnosed with diabetes.

* * * * *

SEQUENCE LISTING

```
<160> NUMBER OF SEQ ID NOS: 4

<210> SEQ ID NO 1
<211> LENGTH: 6
<212> TYPE: PRT
<213> ORGANISM: Unknown
<220> FEATURE:
<223> OTHER INFORMATION: Description of Unknown:
      HIF-alpha sequence
<220> FEATURE:
<221> NAME/KEY: MOD_RES
<222> LOCATION: (2)..(3)
<223> OTHER INFORMATION: Any amino acid

<400> SEQUENCE: 1

Leu Xaa Xaa Leu Ala Pro
1               5

<210> SEQ ID NO 2
<211> LENGTH: 6
<212> TYPE: PRT
<213> ORGANISM: Homo sapiens

<400> SEQUENCE: 2

Leu Thr Leu Leu Ala Pro
1               5

<210> SEQ ID NO 3
<211> LENGTH: 6
<212> TYPE: PRT
<213> ORGANISM: Homo sapiens

<400> SEQUENCE: 3

Leu Glu Met Leu Ala Pro
1               5

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetyl
```

```
<220> FEATURE:
<223> OTHER INFORMATION: C-term CONH2

<400> SEQUENCE: 4

Asp Leu Asp Leu Glu Met Leu Ala Pro Tyr Ile Pro Met Asp Asp Asp
1               5                   10                  15

Phe Gln Leu
```